(12) United States Patent
Wang

(10) Patent No.: US 11,180,555 B2
(45) Date of Patent: Nov. 23, 2021

(54) ANTIBODIES DIRECTED AGAINST CD4 FOR THE TREATMENT AND FUNCTIONAL CURE OF HIV

(71) Applicant: UBI US HOLDINGS, LLC., Hauppauge, NY (US)

(72) Inventor: Chang Yi Wang, New York, NY (US)

(73) Assignee: UBI US HOLDINGS, LLC., Hauppauge, NY (US)

( * ) Notice: Subject to any disclaimer, the term of this patent is extended or adjusted under 35 U.S.C. 154(b) by 0 days.

(21) Appl. No.: 15/512,043

(22) PCT Filed: Nov. 11, 2014

(86) PCT No.: PCT/US2014/065048
§ 371 (c)(1),
(2) Date: Mar. 16, 2017

(87) PCT Pub. No.: WO2016/043788
PCT Pub. Date: Mar. 24, 2016

(65) Prior Publication Data
US 2017/0369576 A1     Dec. 28, 2017

Related U.S. Application Data

(60) Provisional application No. 62/051,200, filed on Sep. 16, 2014.

(51) Int. Cl.
*C07K 16/28* (2006.01)
*A61K 39/00* (2006.01)

(52) U.S. Cl.
CPC .... *C07K 16/2812* (2013.01); *A61K 2039/505* (2013.01); *C07K 2317/24* (2013.01); *C07K 2317/34* (2013.01); *C07K 2317/56* (2013.01); *C07K 2317/71* (2013.01); *C07K 2317/73* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,171,838 A | 12/1992 | Chiba | |
| 5,912,176 A | 6/1999 | Wang | |
| 5,961,976 A | 10/1999 | Wang | |
| 5,962,319 A | 10/1999 | Ogawa et al. | |
| 6,090,388 A | 7/2000 | Wang | |
| 7,501,494 B2 * | 3/2009 | Lynn | C07K 16/2812 424/130.1 |
| 2003/0186900 A1 | 10/2003 | Omura et al. | |
| 2003/0211470 A1 | 11/2003 | Olson et al. | |
| 2004/0137000 A1 | 7/2004 | Lynn et al. | |
| 2009/0053220 A1 | 2/2009 | Duensing et al. | |
| 2009/0060914 A1 * | 3/2009 | Lynn | C07K 16/2812 424/133.1 |
| 2011/0300069 A1 | 12/2011 | Emmrich et al. | |

FOREIGN PATENT DOCUMENTS

| | | |
|---|---|---|
| AU | 629847 | 3/1990 |
| EP | 0018794 | 11/1980 |
| EP | 0365209 | 4/1990 |
| EP | 1034790 | 9/2000 |
| EP | 1083226 | 3/2001 |
| JP | H02238883 | 9/1990 |
| JP | H06125783 | 5/1994 |
| JP | H1070986 | 3/1998 |
| JP | H10155489 | 6/1998 |
| RU | 2250770 | 4/2005 |
| WO | 1990002199 | 3/1990 |
| WO | 1992/009305 | 6/1992 |
| WO | 1993012227 | 6/1993 |
| WO | 1995024483 | 9/1995 |
| WO | 1998052976 | 11/1998 |

OTHER PUBLICATIONS

International Search Report and Written Opinion issued in corresponding International Application No. PCT/US2014/065048, dated Mar. 10, 2015, 9pp.
Phogat et al. "Inhibition of HIV-1 entry by antibodies: potential viral and cellular targets," Journal of Internal Medicine, Jun. 19, 2007, vol. 262, Issue 1, pp. 26-43.
Robinson et al., "High frequencies of antibody responses to CD4 induced epitopes in HIV infected patients started on HAART during acute infection," Human Antibodies, May 17, 2006 (May 17, 2006), vol. 14, pp. 115-121.
International Preliminary Report on Patentability (IPRP) issued in corresponding International Application No. PCT/US2014/065048, dated Nov. 29, 2016, 7pp.
Jiao, Y.M., et al., "CD4+CD25+CD127 regulatory cells play multiple roles in maintaining HIV-1 p24 production in patients on long-term treatment: HIV-1 p24-producing cells and suppression of anti-HIV immunity." Int. J. Infect. Dis., 37:42-49(2015).

(Continued)

*Primary Examiner* — Nicole Kinsey White
(74) *Attorney, Agent, or Firm* — Locke Lord LLP; Peter N. Fill; Nicholas J. DiCeglie, Jr.

(57) ABSTRACT

The present disclosure is directed to antibodies directed against CD4, compositions thereof, and methods employing such compositions for the prevention, treatment, and/or functional cure of HIV infection. The disclosed antibodies exert potent competitive HIV entry inhibition by binding to domain 1 of CD4 in both cell-free and cell-to-cell systems. The disclosed antibodies also inhibit antigen induced T cell proliferation and cytokine production (IL2 and IFN-gamma) of CD4+ T cells, which is implicated in the pathogenic cycle of pyroptosis. The disclosed antibodies also have the ability to reactivate resting CD4+ T cells, which is particularly useful for reactivating latent reservoirs of HIV in resting T cells to make these cells susceptible to treatment with antiretroviral agents. Reactivation of HIV infected resting CD4+ T cells allows combinational treatment incorporating antibodies of the current invention with HAART in HIV infected patients leading to the functional cure of HIV.

65 Claims, 36 Drawing Sheets

Figure 1B:
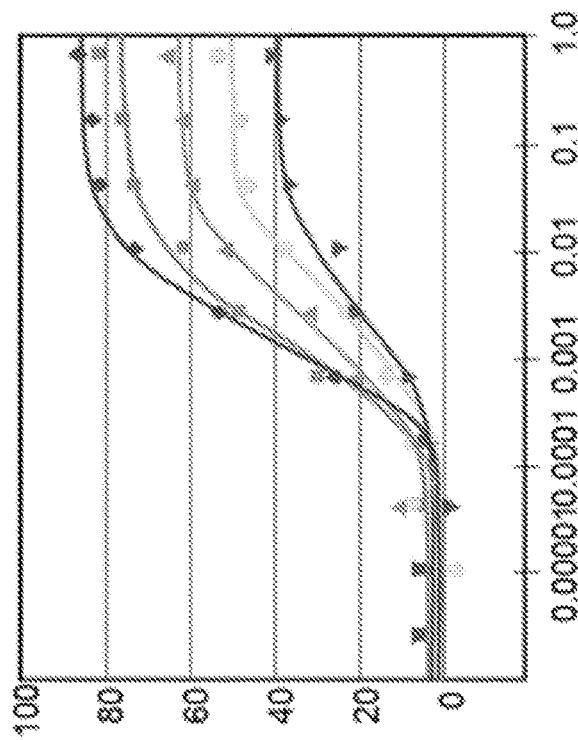

Specification includes a Sequence Listing.

(56) References Cited

OTHER PUBLICATIONS

Jones, T.D., et al., "Deimmunization of Monoclonal Antibodies." Methods Mol. Bio., 525: 405-423 (2009).
Kabat, E.A., "AbCheck—How it works." The Kabat database of sequences of proteins of immunological interest (website: immuno.bme.nwu.edu), dated Jan. 31, 2003.
König, R., et al., "Involvement of both major histocompatibility complex class II alpha and beta chains in CD4 function indicates a role for ordered oligomerization in T cell activation." J. Exp. Med., 182: 779-787 (1995).
Moore, J.P., et al., "Genetic subtypes, humoral immunity, and human immunodeficiency virus type 1 vaccine development." J. Virol., 75(13), 5721-5729 (2001).
Moore, J.P., "AIDS vaccines: On the trail of two trials." Nature 415: 365-366 (2002).
Morrison, S.L., et al., "Chimeric human antibody molecules: mouse antigen-binding domains with human constant region domains." PNAS, 81(21): 6851-6855 (1984).
Motto, M., et al., "Genetic manipulations of protein quality in maize grain." Field Crops Research, 45: 37-48 (1996).
Mulligan, R.C., et al., "Synthesis of rabbit beta-globin in cultured monkey kidney cells following infection with a SV40 beta-globin recombinant genome." Nature, 277(5692): 108-114 (1979).
Myszka, D.G., et al., "Energetics of the HIV gp120-CD4 binding reaction." PNAS, 97(16): 9026-9031 (2000).
Norderhaug, L., et al., "Versatile vectors for transient and stable expression of recombinant antibody molecules in mammalian cells." J. Immunol. Methods, 204(1): 77-87 (1997).
Pace, C., et al., "Anti-CD4 monoclonal antibody ibalizumab exhibits exceptional breadth and potency against HIV, which adopts a unique pathway to resistance " 18th CROI—Boston, Abstract 585 (2011).
Pace, C.S., et al.,"Anti-CD4 Monoclonal Antibody ibalizumab Exhibits Breadth and Potency Against HIV-1, with Natural Resistance Medicated by the loss of a V5 Glycan in Envelope." J. AIDS, 62:1-9 (2013).
Padlan, E.A., "A possible procedure for reducing the immunogenicity of antibody variable domains while preserving their ligand-binding properties." Mol. Immunol., 28(4-5): 489-498 (1991).
Page, M.J., et al., "High level expression of the humanized monoclonal antibody Campath-1H in Chinese hamster ovary cells " Boptechnology, 9(1): 64-68 (1991).
Reimann, K.A., et al., "In vivo administration of CD4-specific monoclonal antibody: Effect on provirus load in rhesus monkeys chronically infected with the simian immunodeficiency virus of macaques." AIDS Res. Hum. Retroviruses, 11 (4): 517-525 (1995).
Reimann, K.A., et al., "A humanized form of a CD4-specific monoclonal antibody exhibits decreased antigenicity and prolonged plasma half-life in rhesus monkeys while retaining its unique biological and antiviral properties." AIDS Res. Hum. Retroviruses, 13(11): 933-943 (1997).
Reiter, C., et al., "Treatment of rheumatoid arthritis with monoclonal CD4 antibody M-T151." Arthritis Rheum., 34(5) 525-536(1991).
Remington's Pharmaceutical Sciences, Mack Publishing Company, Easton, Pa., 19th Edition, pp. 1524-1532 (1995).
Rieber, E.P., et al., "Monoclonal CD4 antibodies after accidental HIV infection." Lancet, 336: 1007-1008 (1990).
Riechmann, L., et al., "Reshaping human antibodies." Nature, 332: 323-327 (1988).
Russell, D.A., "Feasibility of antibody production in plants for human therapeutic use." Curr. Top. Microbiol. Imunol., 240: 119-138(1999).
Sattentau, Q.J., et al., "Epitopes of the CD4 antigen and HIV infection." Science, 234: 1120-1123 (1986).
Sawyer, L.S.W., et al., "Neutralization sensitivity of human immunodeficiency virus type 1 is determined in part by the cell in which the virus is propagated." J. Virol., 68(3): 1342-1349 (1994).

Saxena, A., et al., "Advances in Therapeutic Fc Engineering—Modulation of IgG-Associated Effector Functions and Serum Half-life " Front. Immunol, 7(580): 1-11 (2016).
Sigal, A., et al., "Cell-to-Cell spread of HIV permits ongoing replication despite antiretroviral therapy." Nature, 477: 95-98 (2011).
Song, R., et al., "Strategic addition of an N-linked glycan to a monoclonal antibody improves its HIV-1-neutralizing activity." Nature Biotechnology, 31: 1047-1052 (2013).
Stiegler, G., et al., "Antiviral activity of the neutralizing antibodies 2F5 and 2G12 in asymptomatic HIV-1-infected humans: a phase I evaluation." AIDS, 16: 2019-2025 (2002).
Stott, E.J., "Anti-cell antibody in macaques." Nature, 353(6343): 393 (1991).
Takahashi, N., et al., "Structure of human immunoglobulin gamma genes: Implications for evolution of a gene family." Cell, 29: 671-679 (1982).
Tao, M.H., et al., "Studies of aglycosylated chimeric mouse-human IgG. Role of carbohydrate in the structure and effector functions mediated by the human IgG constant region." J. Immunol., 143(8): 2595-2601 (1989).
Than, S., et al., "Upregulation of human immunodeficiency virus (HIV) replication by CD4 cross-linking on peripheral blood mononuclear cells of HIV-infected adults." J. Virol, 71(8): 6230-6232 (1997).
Toma, T., et al., "Loss of Asparagine-linked glycosylation sites in variable region 5 of human immunodeficiency virus type 1 envelope is associated with resistance to CD4 antibody ibalizumab." J Virol, 85: 3872-3880 (2011).
Tomlinson, I.M., et al., "The repertoire of human germline VH sequences reveals about fifty groups of VH segments with different hypervariable loops." J. Mol. Biol., 227: 776-798 (1992).
Van De Winkel, J., "Antibody therapeutic approaches for inflammation. " in EULAR 2002 Annual European Congress of Rheumatology, Stockholm, Sweden, (2002).
Wang, C.Y., et al., "Postexposure immunoprophylaxis of primary isolates by an antibody to HIV receptor complex." PNAS, 96: 10367-10372 (1999).
Wang, C.Y., et al., "Synthetic AIDS vaccine by targeting HIV receptor." Vaccine, 21: 89-97 (2002).
Weissenhorn, W., et al., "Combinatorial Functions of Two Chimeric Antibodies Directed to Human CD4 and One Directed to the α-Chai of the Human Interleukin-2 Receptor." Gene, 121(2): 271-278 (1992).
Wikipedia, The free encyclopedia, "HIV/AIDS", available at website: en.wikipedia.org/wiki/HIV/AIDS. Accessed Aug. 12, 2014.
Wikipedia, The free encyclopedia, "CD4", available at website: en.wikipedia.org/wiki/CD4. Accessed Aug. 10, 2016.
World Health Organization, "Global Health Observatory (GHO) HIV/AIDS", available at website:: www.who.int/gho/hiv/en. Accessed Aug. 12, 2014.
Wright, A., et al., "Effect of glycosylation on antibody function: implications for genetic engineering." Trends Biotechnol., 15(1): 26-32 (1997).
Yuan, R., et al., "Anti-CD4: An Alternative Way to Inhibit HIV Infection." J. HIV Retrovirus., 2(1:1): 1-6 (2016).
Supplementary European Search Report issued in corresponding EP Patent Application No. 14902149, dated Apr. 17, 2018.
Office Action and Search Report (translated into English) issued in corresponding Indonesian Patent Application No. P00201605747, dated Feb. 12, 2019.
Search Report (translated into English) issued in corresponding Russian Patent Application No. 2017112967, dated Jul. 24, 2018.
First Written Opinion and Search Report issued in corresponding Singapore Patent Application No. 11201702056Y, dated Nov. 1, 2017.
Second Written Opinion and Search Report issued in corresponding Singapore Patent Application No. 11201702056Y, dated Nov. 7, 2018.
Search Report issued in corresponding Taiwan Patent Application No. 104130548, dated Jun. 1, 2016.
Adair, F., "Immunogenicity—The last hurdle for clinically successful therapeutic antibodies." BioPharm, 42-46 (2000).

(56) References Cited

OTHER PUBLICATIONS

Altuvia, Y., et al., "Ranking potential binding peptides to MHC molecules by a computational threading approach." J. Mol. Biol., 249(2): 244-250 (1995).
Arthos et al., "Identification of the Residues in Human CD4 Critical for the Binding of HIV." Cell, 57: 469-481 (1989).
Baltimore, D., "The Enigma of HIV Infection." Cell, 82: 175-176 (1995).
Bebbington, C.R., et al., "High-level expression of a recombinant antibody from myeloma cells using a glutamine synthetase gene as an amplifiable selectable marker." Biotechnology, 10(2): 169-175 (1992).
Belshe, R.B., et al., "Neutralizing antibodies to HIV-1 in seronegative volunteers immunized with recombinant gp120 from the MN strain of HIV-1." JAMA, 272(6): 475-480 (1994).
Benkirane, M., et al., "Functional epitope analysis of the human CD4 molecule: antibodies that inhibit human immunodeficiency virus type 1 gene expression bind to the immunoglobulin CDR3-like region of CD4." Journal of Virology, 69(11): 6898-6903 (1995).
Briant, L., et al., "HIV-1 Reactivation in resting peripheral blood mononuclear cells of infected Adults upon in vitro CD4 cross-linking by ligands of the CDR2-loop in extracellular domain 1." J. AIDS. 21: 9-19 (1999).
Burkly, L.C., et al., "Inhibition of HIV infection by a novel CD4 domain 2-specific monoclonal antibody. Dissecting the basis for its inhibitory effect on HIV-induced cell fusion." J. Immunol., 149: 1779-87 (1992).
Burton, D.R., et al., "Effective Neutralization of Primary Isolates of HIV-1 by a Recombinant Human Monoclonal Antibody." Science, 266: 1024-1027 (1994).
Celada, F., et al., "Antibody raised against soluble CD4-rgp120 complex recognizes the CD4 moiety and blocks membrane fusion without inhibiting CD4-gp120 binding." J. Exp. Med., 172(4): 1143-1150 (1990).
Cheng-Mayer, C., et al., "Biologic features of HIV-1 that correlate with virulence in the host." Science, 240: 80-82 (1988).
Clinical Trials Update. Genetic Engineering News, 21, 3 (2001).
Clinicaltrials.gov—"Study to Evaluate Safety and Pharmacokinetics of UB-421 Antibody in HIV-1 Infected Adults." dated Jul. 11, 2011 (available at website: clinicaltrials.gov/ct2/show/NCT01140126).
Co, M.S., et al., "Humanized antibodies for antiviral therapy." PNAS, 88: 2869-2873 (1991).
Coloma, M.J., et al., "The role of carbohydrate in the assembly and function of polymeric IgG." Mol Immunol., 37(17): 1081-1090(2000).
Cox, J.P.L., et al., "A directory of human germ-line Vk segments reveals a strong bias in their usage." Eur. J. Immunol., 24(4): 827-836 (1994).
Daar, E.S., et al., "High concentrations of recombinant soluble CD4 are required to neutralize primary human immunodeficiency virus type 1 isolates." PNAS, 87(17): 6574-6578 (1990).
Dall'Acqua, W.F., et al., "Properties of human IgG1s engineered for enhanced binding to the neonatal Fc receptor (FcRn)." The Journal of Biological Chemistry, 281(33): 23514-23524 (2006).
Deeks, S.G., et al., "International AIDS Society global scientific strategy: towards an HIV cure 2016." Nature Medicine, 22: 839-850 (2016).
Desrosiers, R.C., et al., "Vaccine protection against simian immunodeficiency virus infection." PNAS, 86: 6353-6357 (1989).
Dimitrov, D.S. "Fusin—a place for HIV-1 and T4 Cells to Meet." Nature Medicine, 2: 640-641 (1996).
Doitsh, G., et al., "Cell Death by pyroptosis derives CD4 T-cell depletion in HIV infection." Nature, 505: 509-514 (2014).
Doms, R.W., et al., "The plasma membrane as a combat zone in the HIV battlefield." Genes Dev., 14: 2677-2688 (2000).
Donahue, R.E. et al., "Helper Virus Induced T Cell Lymphoma in Nonhuman Primates After Retroviral Mediated Gene Transfer." J. of Experimental Medicine, 176(4): 1125-1135 (1992).

Eloit, M., "Risks of virus transmission associated with animal sera or substitutes and methods of control." Dev Biol Stand, 99: 9-16 (1999).
Emini, E.A., et al., "Antibody-Mediated In Vitro Neutralization of Human Immunodeficiency Virus Type 1 Abolishes Infectivity for Chimpanzees." J. Virol., 64: 3674-3678 (1990).
Feng, Y., et al., "HIV-1 Entry Cofactor: Functional cDNA Cloning of a Seven-Transmembrane, G Protein-Coupled Receptor." Science, 272: 873-877 (1996).
Gardner, M., et al., "Passive immunization of rhesus macaques against SIV infection and disease." AIDS Res Hum Retroviruses, 11(7): 843-854 (1995).
Gutin, S., "Perinatal Tranmission of HIV is Preventable." CAPS/Community Health Systems—UCSF School of Nursing, Fact Sheet 34ER (2015) (available at website: prevention.ucsf.edu/sites/prevention.ucsf.edu/files/MTCT-Revised-Sept-2015.pdf).
Hanson, C.V., et al., "Application of a rapid microplaque assay for determination of human immunodeficiency virus neutralizing titers." J. Clin. Microbiol., 28(9): 2030-2034 (1990).
Hanson, C.V., "Measuring vaccine-induced HIV neutralization: Report of a workshop." AIDS Res Hum Retroviruses, 10(6), 645-648 (1994).
Hieter, P.A., et al., "Cloned human and mouse kappa immunoglobulin constant and J region genes conserve homology in functional segments " Cell, 22(1 Pt 1), 197-207 (1980).
Hieter, P.A., et al., "Evolution of human immunoglobulin kappa J region genes." J. Biol. Chem., 257(3): 1516-1522 (1982).
Ho, D.D., et al., "Conformational Epitope on gp120 Important in CD4 Binding and Human Immunodeficiency Virus Type 1 Neutralization Identified by a Human Monoclonal Antibody" J. of Virology, 65: 489-493 (1991).
Hofmann-Lehmann, R., et al., "Postnatal passive immunization of neonatal macaques with a triple combination of human monoclonal antibodies against oral simian-human immunodeficency virus challenge." J. Virol., 75(16), 7470-7480 (2001).
Hunt, P.W., et al., "A low T regulatory Cell Response May Contribute to Both Viral Control and Generalized Immune Activation in HIV Controllers" PLoS One, 6: e15924 (2011).
Jacobson, J.M., et al., "Safety, Pharmacokinetics, and Antiretroviral Activity of Multiple Doses of Ibalizumab (formerly TNX-355), an Anti-CD4 Monoclonal Antibody, in Human Immunodeficiency Virus Type-1-Infected Adults." Antimicrob. Agents Chemother., 53:450457 (2009).
Jameson, B.D., et al., "Location and chemical synthesis of a binding site for HIV-1 on the CD4 protein." Science, 240: 1335-1339(1988).
Jeffrey, A.M., et al., "A model based analysis of anti-CD4 therapy as adjuvant to HAART interruption." IFAC Proceedings vols. 38,(1): 131-136 (2005).
Keefer, M.C., et al., "Studies of high doses of a human immunodeficiency virus type 1 recombinant glycoprotein 160 candidate vaccine in HIV type 1-seronegative humans." AIDS Res Hum Retroviruses, 10(12): 1713-1723 (1994).
Kim, S.J., et al., "Characterization of chimeric antibody producing CHO cells in the course of dihydrofolate reductase-mediated gene amplification and their stability in the absence of selective pressure." Biotechnol. Bioeng., 58(1): 73-84 (1998).
Kuritzkes, D.R., et al., "Antiretroviral activity of the anti-CD4 monoclonal antibody TNX-355 in patients infected with HIV type I" J. Infect Dis., 189: 286-291 (2004).
Leatherbarrow, R.J., et al., "Effector functions of a monoclonal aglycosylated mouse IgG2a: binding and activation of complement C1 and interaction with human monocyte Fc receptor." Mol. Immunol. 22(4): 407-415 (1985).
Li, Y., et al., "Three-dimensional structures of the free and antigen-bound Fab from monoclonal antilysozyme antibody HyHEL-63(,)." Biochemistry, 39: 6296-6309 (2000).
Lu, L., et.aL, "A bivalent recombinant protein inactivates HIV-1 by targeting the gp41 prehairpin fusion intermediate induced by CD4 D1D2 domains, 1." Retrovirology, 104(9): 1-14 (2012).
Ma, J.K-C., et al., "Assembly of monoclonal antibodies with IgG1 and IgA heavy chain domains in transgenic tobacco plants." Eur J. Immunol, 24(1): 131-138 (1994).

(56) References Cited

OTHER PUBLICATIONS

Mascola, J.R., et al., "Human immunodeficiency virus type 1 neutralizing antibody serotyping using serum pools and an infectivity reduction assay." AIDS Res. Hum. Retroviruses, 12(14): 1319-1328 (1996).
Mascola, J.R., et al., "Immunization with envelope subunit vaccine products elicits neutralizing antibodies against laboratory-adapted but not primary isolates of human immunodeficiency virus type 1." J. Infect. Dis., 173(2): 340-348 (1996).
Meloen, R.H., et al., "The Use of Peptides to Reconstruct Conformational Determinants; a Brief Review." Ann. Biol. Clin , 49: 231-242(1991).
Mizushima, S., et al., "pEF-BOS, a powerful mammalian expression vector." Nucleic Acids Res., 18(17), 5322 (1990).
Monossi, M., et al., "Improved analysis of promotor activity in biolistically transformed plant cells." BioTechniques, 28 (1): 54-58 (2000).
Monroe, K.M., et al., "IFI16 DNA sensor is required for death of lymphoid CD4 T cells abortively infected with HIV." Science, 343(6169): 428-32 (2014), Epub (2013).
Moore, J.P. AIDS vaccines: On the trail of two trials. Nature 2002, 415, 365-366.
Loetscher, et al. "Cloning of a Human Seven-Transmembrane Domain Receptor, LESTR, That Is Highly Expressed in Leukocytes " J. of Biological Chemistry, 264:232-237 (1994).
Monroe, K.M., et al. "IFI16 DNA Sensor Is Required for Death of Lymphoid CD4 T-cells Abortively Infected with HIV", Science, 343(6169):428-432 (2014).
Attanasio, R., et al., "Monoclonal Anti-CD4 as Immunoprophylactic Agents for Human Immunodeficiency Virus Infection." J. Infect. Dis., 168:515-516 (1993).
Briant, L., et al., "Binding of HIV virions or gp120-anti-gp120 immune complexes to HIV-1 infected quiescent peripheral blood mononuclear cells reveals latent infection." J. Immunol., 156(10):3994-4004 (1996).
Corbeau, P., et al., "Ig CDR3-Like Region of the CD4 Molecule is Involved in HIV-Induced Syncytia Formation but not in Viral Entry." J. Immunol., 150:290-301 (1993).
Hasunuma, T., et al., "Regions of the CD4 Molecule not involved in Virus Binding or Syncytia Formation are Required for HIV-1 Infection of Lymphocytes." J. of Immunology, 148:1841-1846 (1992).
Jones, P.T., et al., "Replacing the Complementarily-Determining Regions in a Human Antibody with those from a Mouse." Nature, 321:522-525 (1986).
Kalyanaraman, V.S., et al., "Evidence by Peptide Mapping that the Region CD4 (81-92) is Involved in gp120/CD4 Interaction Leading of HIV Infection and HIV-Induced Syncytium Formation." J. of Immunology, 145:4072-4078 (1990).
Kennett, R.H., et al. (editors)., Appendix "Method for Production and Characterization of Monoclonal Antibodies." In Monoclonal Antibodies, Hybridomas: A New Dimension in Biological Analyses, pp. 363-419 (1980).
Wilson, M.B., et al., "Recent developments in the periodate method of conjugating horseradish peroxidase (HRPO) to antibodies." In Knapp, W., et al. (editors), Immunofluorescence and Related Staining Techniques, Elsevier/North Holland Biomedical Press, pp. 215-224 (1978).
Walfield, A.M., et al., "High-Titer Neutralization of Multiple HIV-1 Isolates by Radially Branched Immunogens" In Koff, W.C., et al. (editors), AIDS Research Reviews vol. 3, Chapter 18, New York: Marcel Dekker, Inc., pp. 345-361 (1993).
Anonymous, NIH AIDS and Research and Reference Reagent Program, Catalog No. 207 Data Sheet, (available at website: aidsreagent. org/reagentdetail.cfm?t=molecular_clones&id=116) (accessed Jan. 12, 2021) (1988).

Anonymous, ThermoFisher Scientific Product Catalog, Cat. No. 21221: Pierce™ Avidin, Fluorescein (FITC) Conjugated, Pierce Chemical Co., Rockford IL,. (available at website: thermofisher. com/order/catalog/product/21221?us&en#/21221?us&en) (accessed Jan. 8, 2021) (2012).
Putkonen, P., et al., "Prevention of HIV-2 and SIVsm Infection by Passive Immunization in Cynomolgus Monkeys." Nature, 352:436-438 (1991).
Rieber, E.P., et al., "The Monoclonal CD4 Antibodies M-T413 Inhibits Cellular Infection with Human Immunodeficiency Virus after Viral attachment to the Cell Membrane: An Approach to Postexposure Prophylaxis." Proc. Nat'l. Acad. Sci. U.S.A., 89:10792-10796 (1992).
Rowe, P.M., "A Cofactor for HIV-1 Entry into Cells is Identified." The Lancet Science and Medicine, 347:1395 (1996).
Sattentau, Q.J., et al., "Structure Analysis of the Human Immunodeficiency Virus-Binding Domain of CD4." J. Exp. Med., 170:1319-1334 (1989).
Smith, S.D., et al., "Monoclonal Antibody and Enzymatic Profiles of Human Malignant T-Lymphoid Cells and Derived Cell Lines." Cancer Research, 44:5657-5660 (1984).
Wang, J., et al., "Atomic Structure of a Fragment of Human CD4 Containing Two Immunoglobulin-Like Domains." Nature, 348:411-418 (1990).
Watson, S., et al. (editors), "Chemokines" in The G-Protein Linked Receptor Facts Book, Academic Press, pp. 83-88 (1994).
Wrin, T., et al., "Adaptation to Persistent Growth in the H9 Cell Line Renders a Primary Isolate of Human Immunodeficiency Virus Type 1 Sensitive to neutralization by Vaccine Sera" J. of Virology, 69(1):39-48 (1995).
Arthur, L.O., et al., "Cellular Proteins Bound to Immunodeficiency Viruses: Implications for Pathogenesis and Vaccines" Science 258:1935-1938 (1991).
Brady, R.L., et al., "Crystal Structure of Domains 3 and 4 of Rat CD4: Relation to the NH.sub.2-Terminal Domains" Science 260:979-983 (1993).
Camerini, D., et al., "A CD4 Domain Important for HIV-Mediated Syncytium Formation Lies outside the Virus Binding Site" Cell 60:747-754 (1990).
Clayton, L.K., et al., "Substitution of Murine for Human CD4 Residues Identifies Amino Acids Critical for HIV-gp120 Binding" Nature 335:363-366 (1988).
Cocchi, F., et al., "Identification of RANTES, MIP-1 Alpha, and MIP-1 Beta as the Major HIV-suppressive Factors Produced by CD8+ T Cells" Science 270:1811-1815 (1995).
Dalgleish, A.G., et al., "The CD4 (T4) Antigen is an Essential Component of the Receptor for the AIDS Retrovirus" Nature 312:763-766 (1984).
Davis, S.J., et al., "Antibody and HIV-1 gp120 Recognition of CD4 Undermines the Concept of Mimicry between Antibodies and Receptors" Nature 358:76-79 (1992).
Emini, E.A., et al., "Prevention of HIV-1 Infection in Chimpanzees by gp120 V3 Domain-Specific Monoclonal Antibody" Nature 355:728-730 (1992).
Gauduin, M.C., et al., "Pre-and Postexposure Protection against Human Immunodeficiency Virus Type 1 Infection Mediated by a Monoclonal Antibody" J. of Infectious Diseases 171l203-1209 (1995).
Ho, D.D., et al., "Quantitation of Human Immunodeficiency Virus Type 1 in the Blood of Infected Persons" The New England Journal of Medicine 321:1621-1625 (1989).
Kohler, G., et al., "Continuous Cultures of Fused Cells Secreting Antibody of Predefined Specificity" Nature 256:495-497 (1975).
Landau, N.R., et al., "The Envelope Glycoprotein of the Human Immunodeficiency Virus Binds to the Immunoglobulin-Like Domain of CD4" Nature 334:159-162 (1988).
Lewis, M.G., et al., "Passively Transferred Antibodies Directed Against Conserved Regions of SIV Envelope Protect Macaques from SIV Infection" Vaccine 11:1347-1355 (1993).

(56) References Cited

OTHER PUBLICATIONS

Montefiori, D.C., et al., "Complement Control Proteins, CD46, CD55, and CD59 as Common Surface Constituents of Human and Simian Immunodeficiency Viruses and Possible Targets for Vaccine Protection" Virology 205:82-92 (1994).

Montefiori, D.C., et al., "New Insights into the Role of Host Cell Proteins in Antiviral Vaccine Protection" AIDS Research and Human Retroviruses 11:1429-1431 (1995).

Murphey-Corb, M., et al., "A Formalin-Inactivated Whole SIV Vaccine Confers Protection in Macaques" Science 246:1293-1297 (1989).

Petterson, A., et al., "Genetic Analysis of Monoclonal Antibody and HIV Binding Sites on the Human Lymphocyte Antigen CD4" Cell 54:65-72 (1988).

Prince, A.M., et al., "Prevention of HIV Infection by Passive Immunization with HIV Immunoglobulin" AIDS Research and Human Retroviruses 7:971-973 (1991).

Ryu, S.E., et al., "Crystal Structure of an HIV-Binding Recombinant Fragment of Human CD4" Nature 348:419-426 (1990).

Safrit, J.T., et al., "hu-PBL-SCID Mice can be Protected from HIV-1 Infection by Passive Transfer of Monoclonal Antibody to the Principal Neutralizing Determinant of Envelope gp120" AIDS 7:15-21 (1993).

Sastry, L., et al., "Cloning of the Immunological Repertoire in *Escherichia coli* for Generation of Monoclonal Catalytic Antibodies: Construction of a Heavy Chain Variable Region-Specific cDNA Library" Proc. Nat'l. Acad. Sci. U. S.A. 86:5728-5732 (1989).

Wang, C.Y., et al., "Stimulation and Expansion of a Human T-Cell Subpopulation by a Monoclonal Antibody to T-Cell Receptor Molecule" Hybridoma 5:179-190 (1986).

Wang, et al., "Long-Term High-Titer Neutralizing Activity Induced by Octameric Synthetic HIV-1 Antigen" Science 254:285-288 (1991).

White-Scharf, M.E., et al. "Broadly Neutralizing Monoclonal Antibodies to the V3 Region of HIV-1 Can Be Elicited by Peptide Immunization" Virology 192:197-206 (1993).

Menossi, M. et al., "Improved analysis of promotor activity in biolistically transformed plant cells." BioTechniques, 28 (1), 54-58 (2000).

Moore, J.P., et al., "A monoclonal antibody to CD4 domain 2 blocks soluble CD4-induced conformational changes in the envelope glycoproteins of human immunodeficiency virus type 1 (HIV-1) and HIV-1 infection of CD4+ cells." J. VVirol., 66(8)14784-93 (1992).

Yang, H-C, et al., "Isolation of a cellular factor that can reactivate latent HIV-1 without T cell activation." Proc Natl. Acad. Sci. U.S A., 106(15):6321-6 (2009).

\* cited by examiner

Figure 2.

Full Heavy Chain Fv Region of mAb dBAC7/UB-421 (SEQ ID NO: 7):

Figure 5.

Full Light Chain Fv Region of mAb dB4C7/UB-421 (SEQ ID NO: 8):

DIVLTQSPASLAVSLGQRATITCKAGQSVDYDGDSYMNWYQQKPGQPPKLLIYVASNLESGIPARFSGSGS
                             CDR1                                  CDR2

GTDFTLNIHPVEENDAATYYCQQSYKDPLTFGQGTKLEIKRTVAAPSVFIFPPSDEQLKSGTASVVCLLNN
                      CDR3

FYPREAKVQWKVDNALQSGNSQESVTEQDSKDSTYSLSSTLTLSKADYEKHKLYACEVTHQGLSSPVTKSF

NRGEC

Variable region (SEQ ID NO: 13)
Constant region (SEQ ID NO: 14)

Figure 6.

Full Heavy Chain Fv Region of Improved Humanized Antibody (SEQ ID NO: 9):

QVQLVQSGPELKKPGASVKVSCKASGYTFTDIYIHWVKQATGQLEWIGELYPGSGSAYSNAKFKDRVTMT
                                                      CDR1                  CDR2

ADKSSNTAYMELSSLISDDTAVYFCARRGNGTGFAYWGQGTLVTVSSASTKGPSVFPLAPSSKSTSGGTAA
                      101 →
                             CDR3

AALGCLVKDYFPEPVTVSWNSGALTSGVHTPAVLQSSGLYSLSSVVTVPSSSLGTQTYICNVNHKPSNTK

VDKKVEPKSCDKTHTCPPCPAPELLGGPSVFLFPPKPKDTLYITREPEVTCVVVDVSHEDPEVKFNWYVDG
                                       253 255 257

VEVHNAKTKPREEQYHSTYRVVSVLTVLHQDWLNGKEYKCKVSNKALPAPIEKTISKAKGQPREPQVYTLP
      298 →

PSRDELTKNQVSLTCLVKGFYPSDIAVEWESNGQPENNYKTTPPVLDSDGSFFLYSKLTVDKSRWQQGNVF

SCSVMHEALHNHYTQKSLSLSPGK

Legend:
☐ : Variable region (SEQ ID NO: 11)
▓ : Constant region (SEQ ID NO: 12)

N101: N-glycosylation site

M253Y/S255T/T257E: Mutations based on SEQ ID NO:7

N298H: Avoids ADCC or CDC

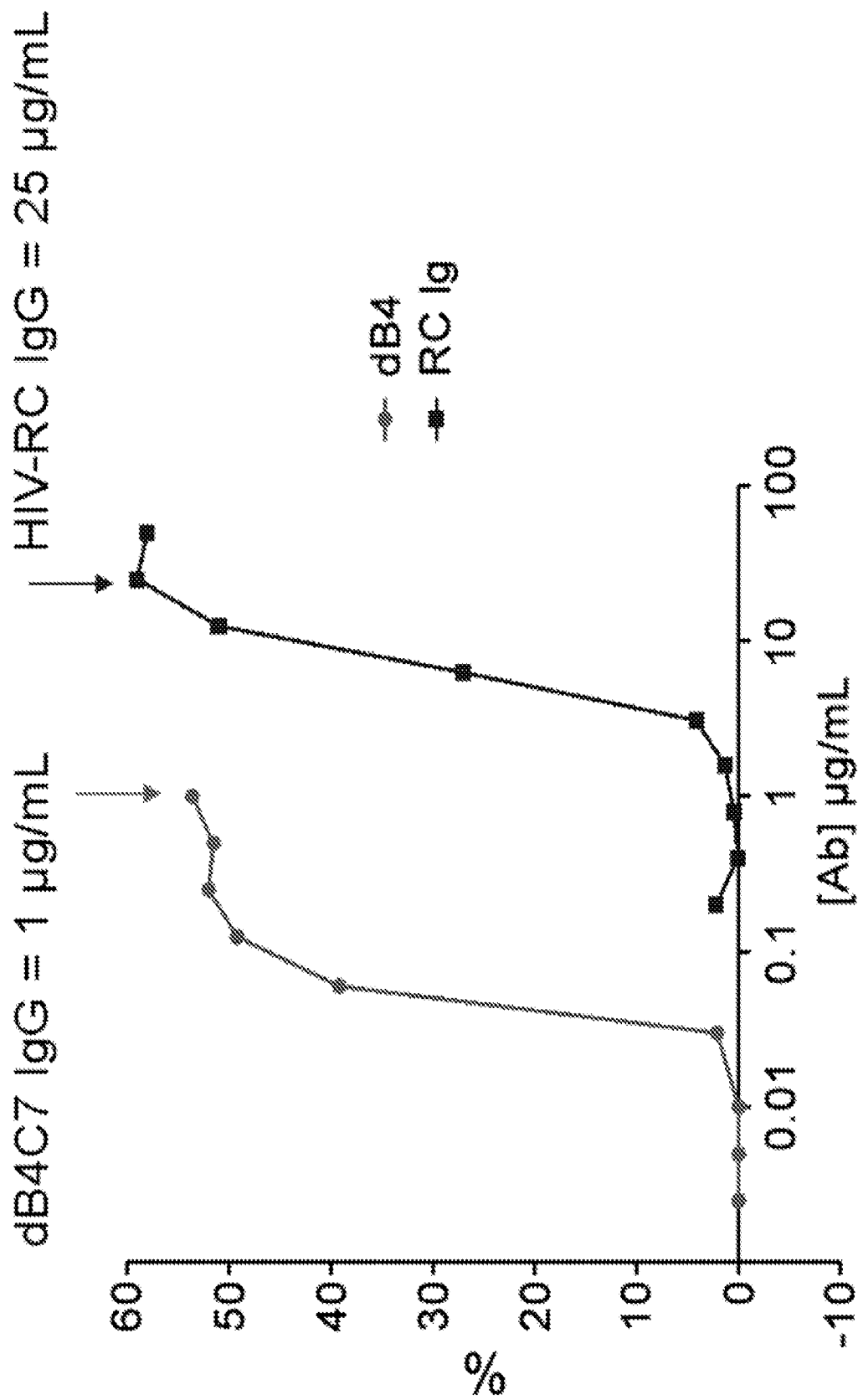

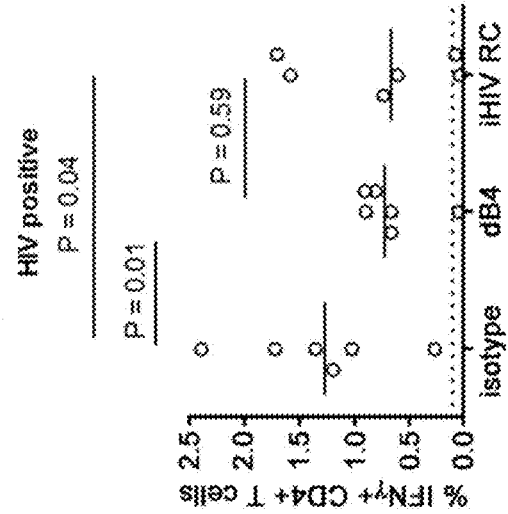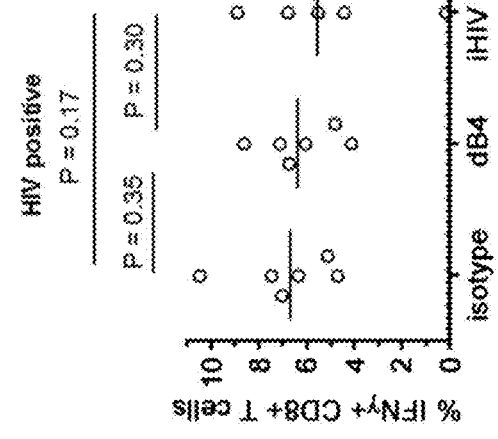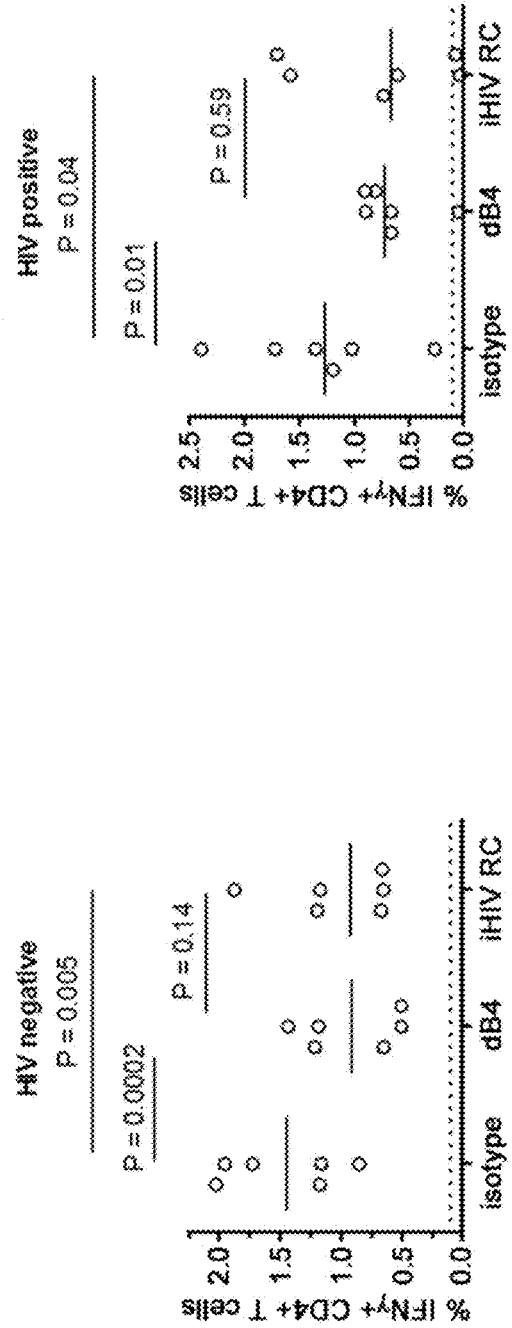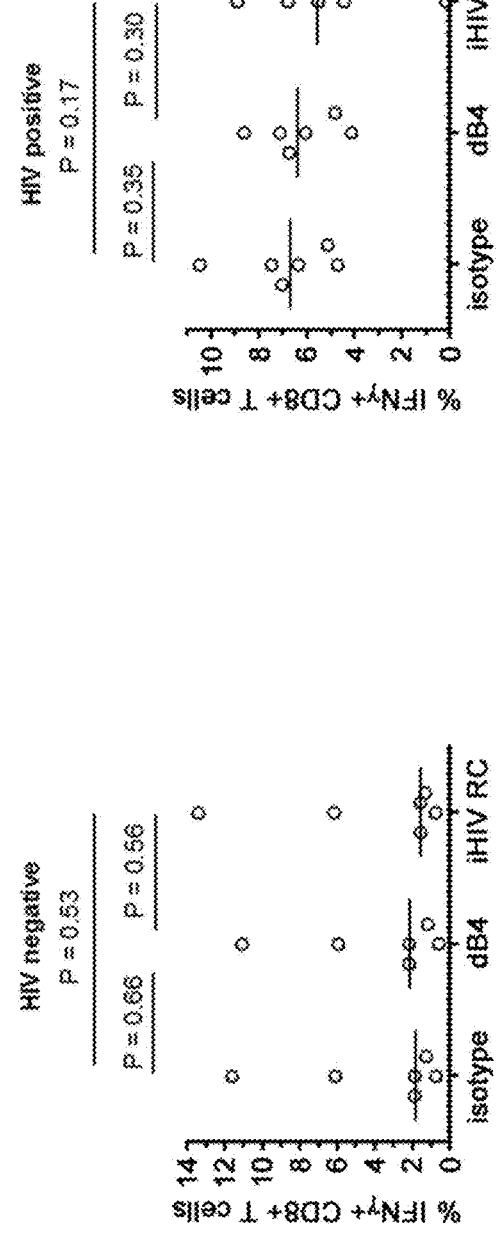

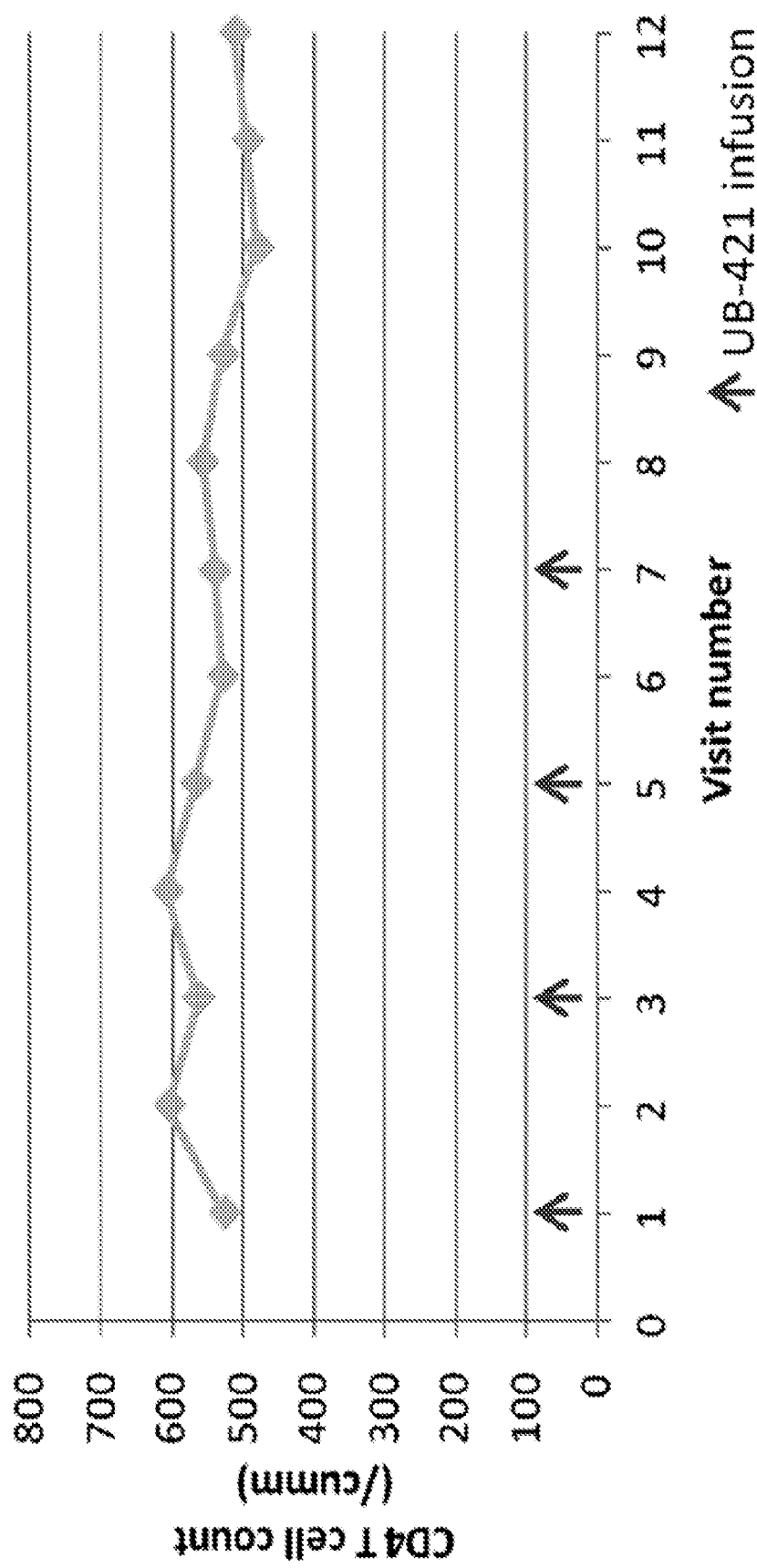

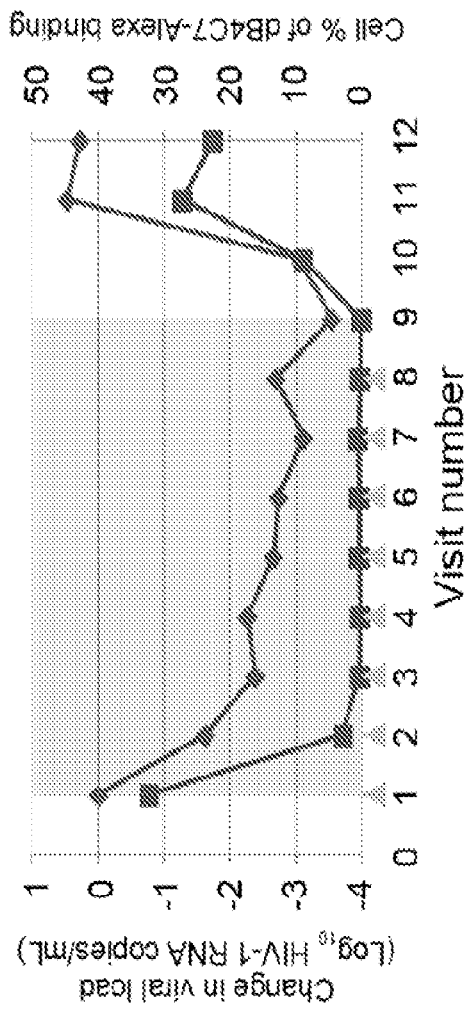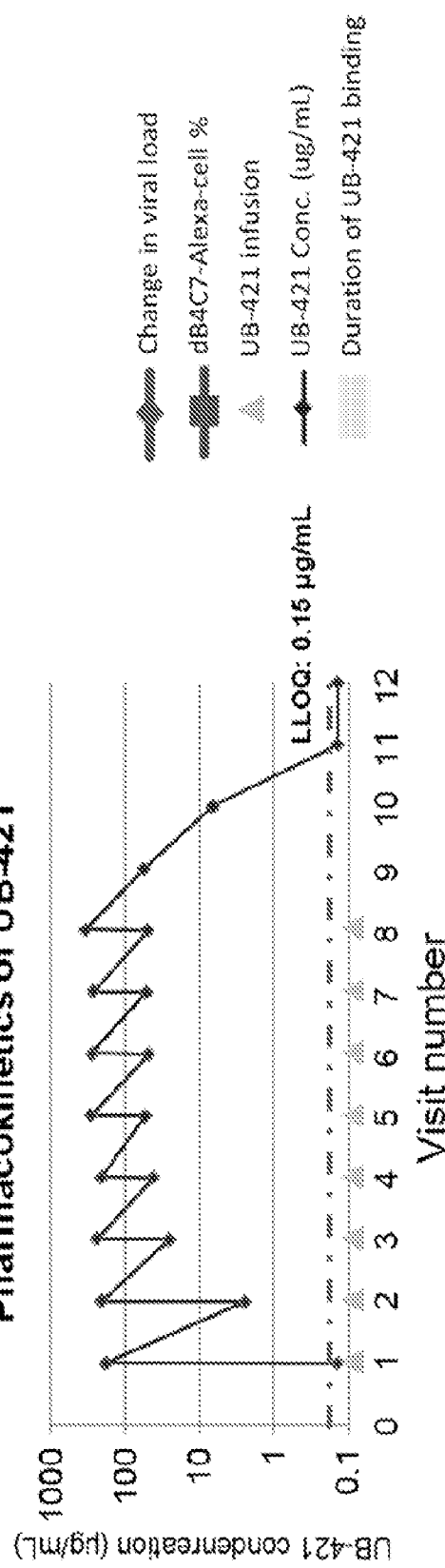
Figure 25b.

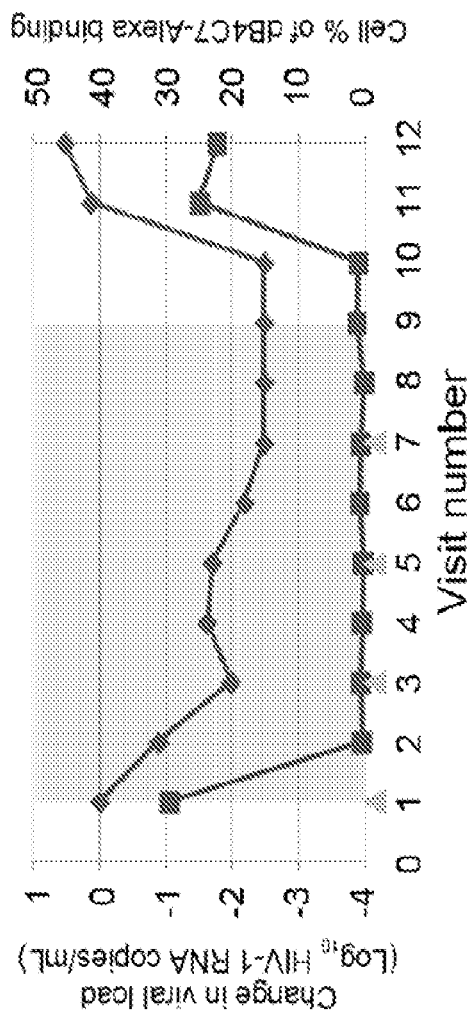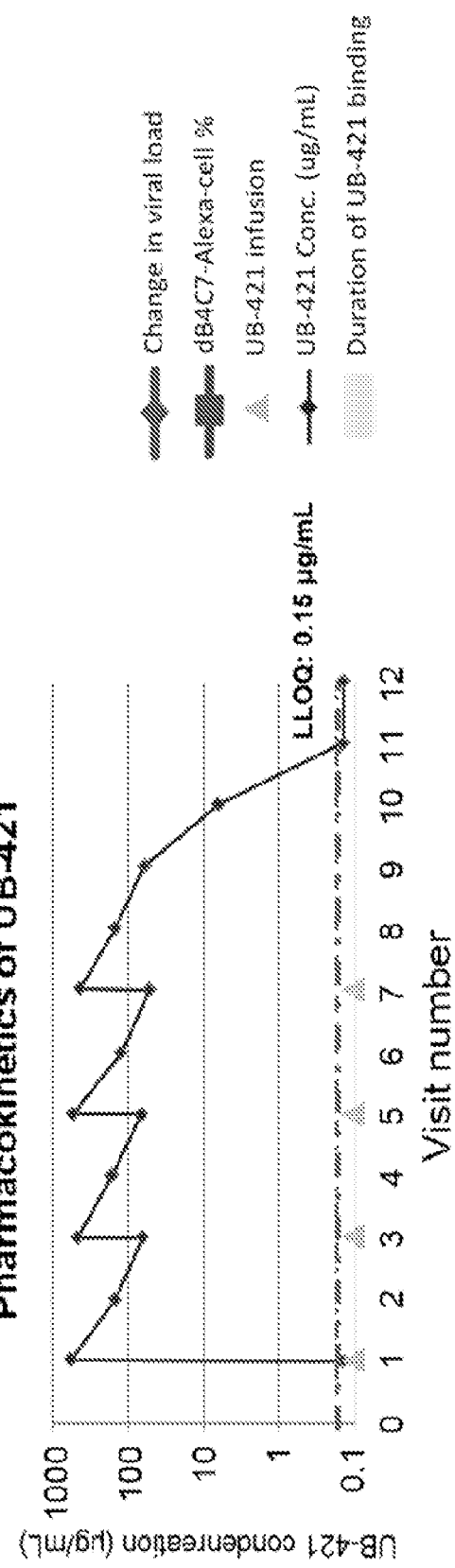
Figure 25c.

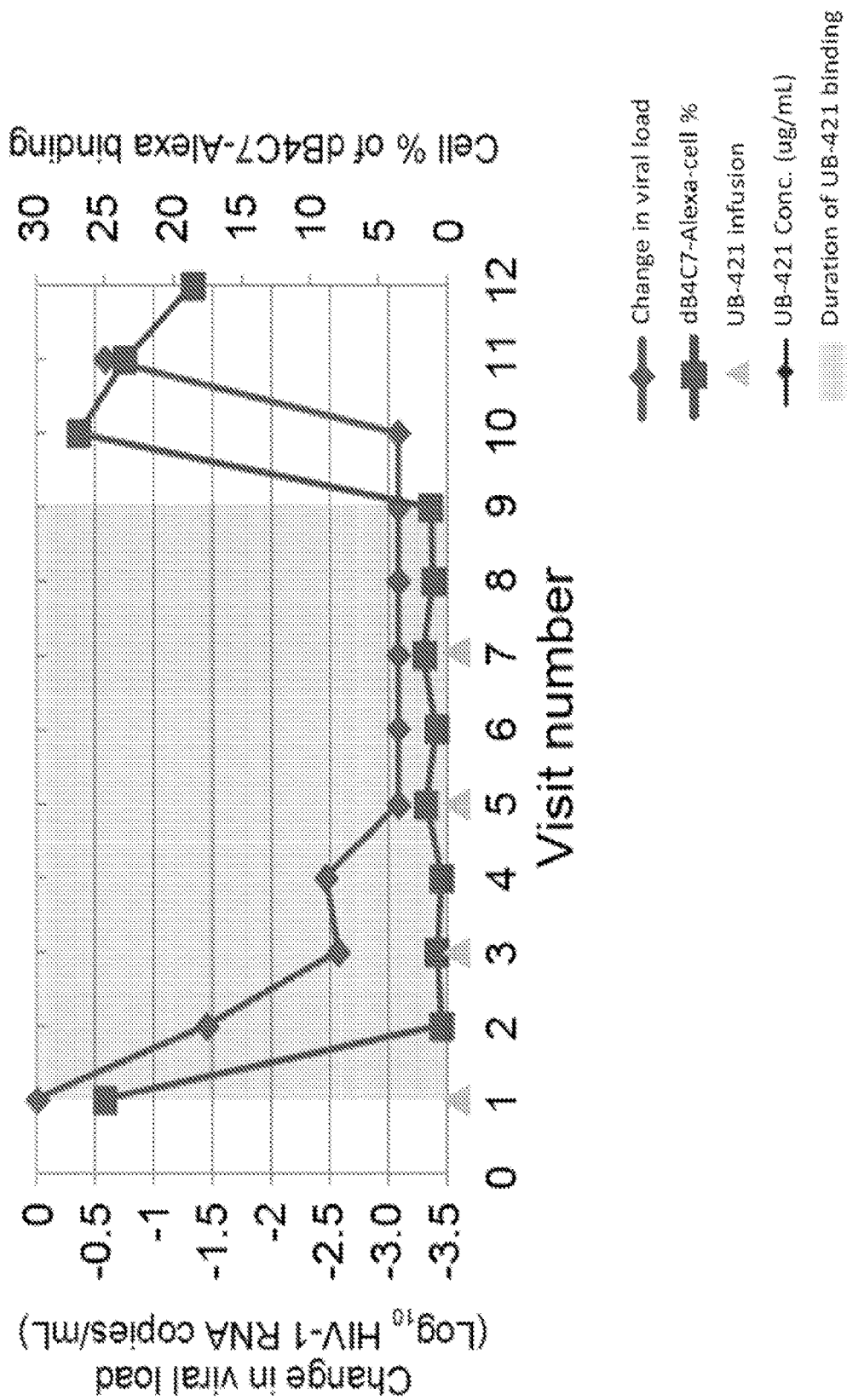

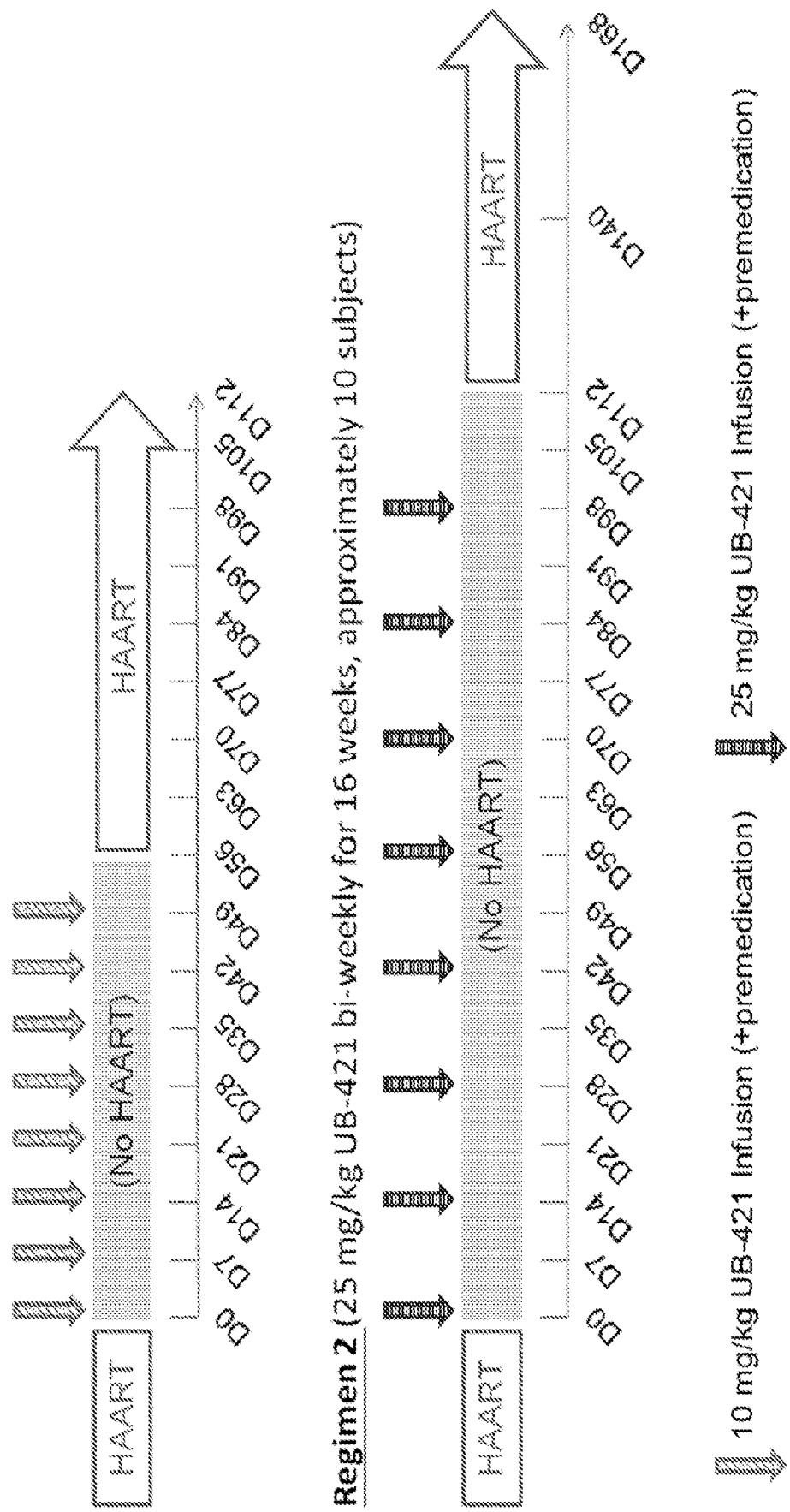
Figure 27. UB421 monotherapy as HAART Replacement Therapy

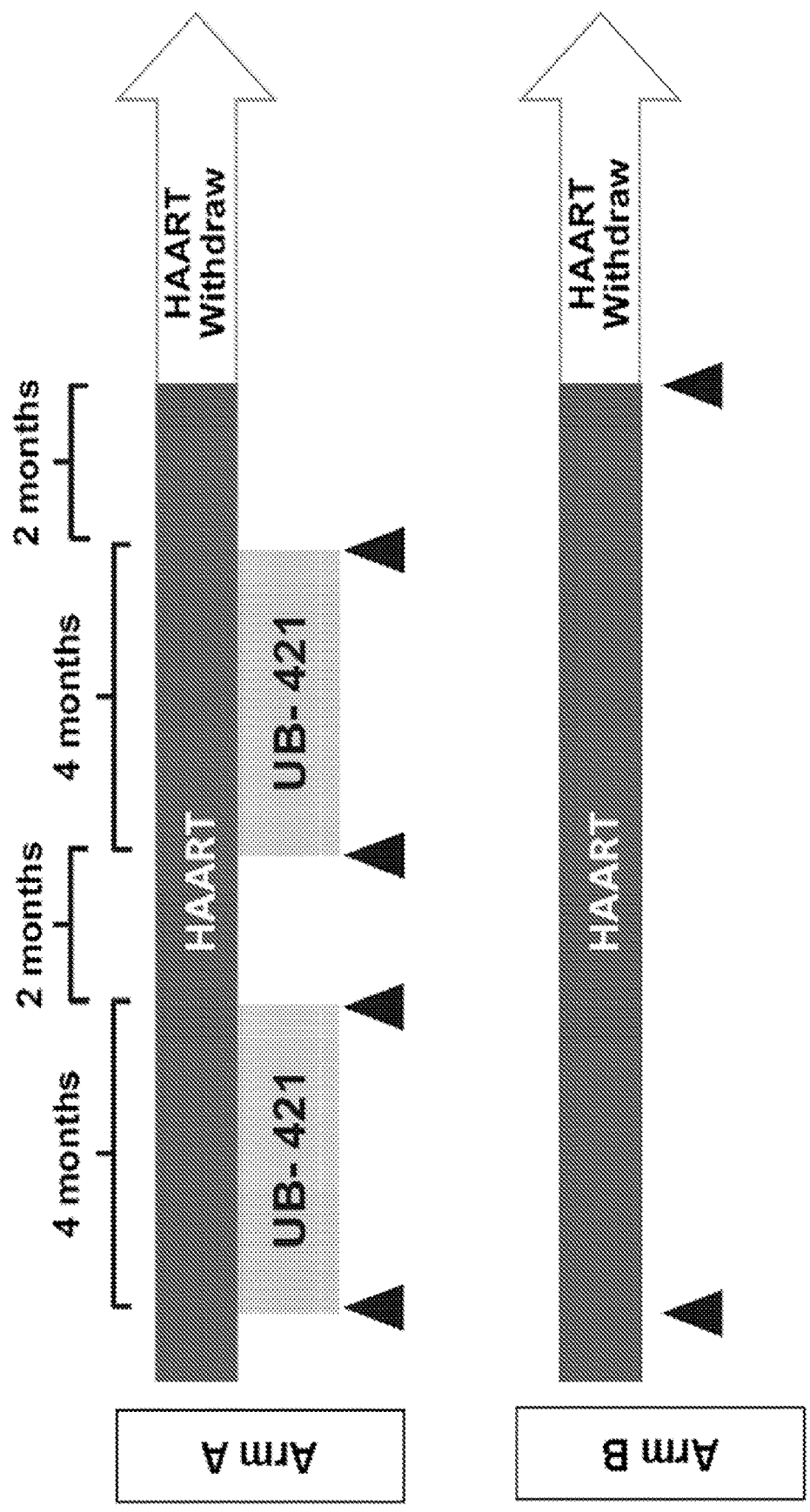
Figure 28. Combination of UB421 and HAART for Functional Cure of HIV Infection

ANTIBODIES DIRECTED AGAINST CD4 FOR THE TREATMENT AND FUNCTIONAL CURE OF HIV

This application is a national phase entry under 35 U.S.C. § 371 of International Application Number PCT/US2014/065048, filed Nov. 11, 2014, entitled "TREATMENT AND FUNCTIONAL CURE OF HIV INFECTION BY MONOCLONAL ANTIBODIES TO CD4 MEDIATING COMPETITIVE HIV ENTRY INHIBITION", which claims the benefit of U.S. Provisional Application Ser. No. 62/051,200, filed Sep. 16, 2014, the entire contents of these prior applications are hereby incorporated by reference as if fully set forth herein.

FIELD OF THE INVENTION

The invention relates to monoclonal antibodies directed against CD4 mediating competitive HIV entry inhibition, compositions thereof, and methods employing such compositions for treatment and functional cure of HIV infection.

BACKGROUND OF THE INVENTION

Acquired immune deficiency syndrome (AIDS) is a disease of the human immune system caused by the human immunodeficiency virus (HIV) (website: en.wikipedia.org/wiki/HIV/AIDS). Genetic research indicates that HIV originated in west-central Africa during the late nineteenth or early twentieth century. AIDS was first recognized by the U.S. Centers for Disease Control and Prevention in 1981 and its cause, HIV, identified in the early 1980s. Since the beginning of the epidemic, over 70 million people have been infected with the HIV and 35 million people have died of AIDS. Globally, 34.0 million people were living with HIV at the end of 2011 (website: www.who.int/gho/hiv/en/).

HIV infection progressively reduces the effectiveness of the immune system and leaves individuals susceptible to opportunistic infections and tumors. HIV is transmitted through direct contact of a mucous membrane or the bloodstream with a bodily fluid containing HIV, such as blood, semen, vaginal fluid, pre seminal fluid, and breast milk. This transmission can involve anal, vaginal or oral sex, blood transfusion, contaminated hypodermic needles, exchange between mother and baby during pregnancy, childbirth, breastfeeding or other exposure to one of the above bodily fluids.

For 30 years, scientists have thought that AIDS was brought on by the "virus-producing" CD4 T-cells, rather than the resting T-cells. But there were not enough of these "virus producing" infected cells to explain the huge swaths of T-cells being wiped out in patients developing AIDS. Greene and his colleagues reported that 95 percent of the quiescent (resting) lymphoid CD4 T-cells die by pyroptosis, triggered by abortive viral infection (Doitsh, G. et al. 2014). These cells have cytosolic viral DNA, but unlike the T-cells that become virus-replicating units, these "HIV-infected" resting T-cells self-destruct by a highly inflammatory form of programmed cell death (pyroptosis) that involves the release of pro-inflammatory cytokines. The cellular protein, interferon-gamma-inducible protein 16 (IFI16), recognizes the viral DNA and triggers a series of responses in the T-cells, including caspase-1 enzyme activation that mediates pyroptosis and causes cell swelling, plasma membrane permeabilization, and leaky cytoplasmic contents. The resting T-cells self-destruct in a vain attempt to kill the virus. This process ultimately leads to HIV pathogenesis that propels disease progression to AIDS.

Current treatments for HIV infection delaying the onset of AIDS consist of highly active antiretroviral therapy, or HAART to prevent viral replication. Current optimal HAART options consist of combinations (or "cocktails") consisting of at least three drugs belonging to at least two classes of antiretroviral agents (cART). Typical regimens consist of two nucleoside analogue reverse transcriptase inhibitors (NARTIs or NRTIs) plus either a protease inhibitor or a non-nucleoside reverse transcriptase inhibitor (NNRTI).

In developed countries, doctors assess the viral load, CD4 T-cell counts, rapidity of CD4-positive cell decline and patient readiness while deciding when to recommend initiating HAART treatment. Traditionally, treatment has been recommended for asymptomatic patients when CD4 T-cell counts fall to 200-250 cells per microliter of blood. However, beginning treatment earlier (at a CD4 level of 350 cells/microliter) may significantly reduce the risk of AIDS and death.

Without treatment, the net median survival time after infection with HIV is estimated to be 9 to 11 years, depending on the HIV subtype; and the median survival rate after diagnosis of AIDS ranges between 6 and 19 months. In areas where HAART treatment is widely available, the death rate of this disease is reduced by 80% which in turn raises the life expectancy for a newly diagnosed HIV-infected person to about 20 years.

Standard goals of HAART include improvement in the patient's quality of life, reduction in complications, and reduction of HIV viremia below the limit of detection.

However, there are several issues with HAART treatment. First, it does not cure the patient of HIV infection nor does it prevent the return of high blood levels of mostly "HAART resistant" HIV once treatment is stopped. Second, HAART can have unpleasant side effects including malaise, fatigue, diarrhea, headache, nausea and vomiting. Over the long term, HIV-infected patients may experience neurocognitive disorders, osteoporosis, neuropathy, cancers, nephropathy, and cardiovascular disease. While newer antiretroviral drugs have fewer side effects than older ones, lifetime use can still take its toll. Non-adherence can mean HIV rebound, drug resistance, and disease progression. Third, for up to more than 50% of patients, HAART achieves far less than optimal results, due to medication intolerance, prior ineffective antiretroviral therapy and infection with a drug-resistant strain of HIV.

Researchers are increasingly investigating how to cure HIV infection, or at least achieve long-term or permanent remission without anti-retrovirals.

Two curative strategies, sterilizing (i.e., eradication) and functional cures, as shown in Table 1, are currently being investigated for HIV infection. The sterilizing cure method aims to eliminate all HIV-infected cells, completely purging HIV from the body and is defined as one that reduces viral loads to less than 1 copy per milliliter of blood. A functional cure aims for a remission state and long-term control of HIV, including low viral loads in the absence of antiretroviral therapy and in one that reduces viral loads to less than 50 copies per milliliter of blood, either permanently or for an extended period of time.

The only current example of a "sterilizing cure" is from a case study of a man nicknamed "The Berlin Patient" with HIV infection, who had acute myeloid leukemia and received a bone marrow transplant from a donor with a mutated or alternate form of the CCR5 gene. After 45 months without treatment, doctors have been unable to detect HIV in his system. Nonetheless, a strategy of using bone marrow transplantation with a CCR5 mutant donor is not a realistic cure for HIV given the toxicity and complexity of the treatment. One natural example of a "functional cure" can be found in elite controllers. Elite controllers are individuals infected with HIV whose immune systems are able to naturally control the virus without antiretroviral drugs. These individuals successfully maintain stable CD4 (white blood) cell counts, low or undetectable viral loads and a significantly smaller amount of "latent HIV" in their cells.

One major obstacle to a cure is the fact that there are "latent HIV reservoirs" that lie dormant in immune system cells, such as memory cells, with long life-spans during anti-retroviral drug treatment as such treatment can work on active viral infection by blocking replication but not on latent HIV. However, if such anti-retroviral drug treatment is stopped, latent HIV may be activated, renewing the HIV infection process.

Current strategies to target these "problematic" latent HIV reservoirs include efforts to deplete latent reservoirs through activation of virus expression in the presence of HAART treatment resulting in the killing-off of infected cells leaving only uninfected cells behind. One group of activators is histone deacetylase (HDAC) inhibitors as illustrated in Table 2. Currently, HDAC inhibitors are used as mood stabilizers, anti-epileptic drugs and anti-cancer treatments. The long-term impact of HDAC inhibitors on enhancing the risk of malignancy and/or reactivation of oncogenes remains a major concern. This strategy is viable if active viral replication is completely inhibited with combination anti-retroviral therapy (cART). So far, these efforts have not yielded long term virus suppression or functional cures.

Two plans for restricting or reducing the size of latent HIV reservoirs in people with HIV infection involve (1) intensification treatment by addition of new ART drug to a person's regimen and (2) early treatment by starting ART immediately after infection. Results from several studies have shown that the number of HIV-infected cells decreases significantly when cART is initiated during the early acute stage rather than the chronic late stage of HIV infection.

In summary, potent and safe agents would be highly desirable for use in HIV treatment either alone or as an adjunct to cART provided that they can (1) block HIV entry, in both cell-free and cell-to-cell transmission modes, leading to significant reduction of HIV infection in activated or resting CD4 T-cells including those long-lived memory T cells; (2) specifically reactivate HIV infected resting CD4 T-cells to release HIV leading to apoptosis in latently infected cells; and/or (3) inhibit HIV infected resting CD4 T-cell activation/inflammation upon antigen/cytokine stimulation, when such activation can cause pyroptosis and massive depletion of normal CD4 positive T-cells leading to AIDS. A concerted effort towards a functional or sterilizing cure for HIV infection leading to long-term or permanent remission in the subsequent absence of cART is high on the global public health agenda and is being actively explored worldwide and, when available, will revolutionize the treatment of HIV infection.

REFERENCES

1. Briant, L., Reynes, J., Coudronniere, N., et al. "HIV Reactivation in resting peripheral blood mononuclear cells of infected Adults upon in vitro CD4 cross-linking by ligands of the CDR2-loop in extracellular domain 1." *J. AIDS.* 1999. 21:9-19.
2. Briant, L., Coudronniere, N., Robert-Hebmann, V., et al. "Binding of HIV virions or gp120-anti-gp120 immune complexes to HIV-1 infected quiescent peripheral blood mononuclear cells reveals latent infection." *J. Immunol.*, 1996. 156:3994-4004.
3. Burkly, L. C., Olson, D., Shapiro, R., et al. "Inhibition of HIV infection by a novel CD4 domain 2-specific monoclonal antibody. Dissecting the basis for its inhibitory effect on HIV-induced cell fusion." *J. Immunol.* 1992; 149: 1779-87.
4. Carr, F. J., Carter, G., Hamilton, A. A. & Adair, F. S. "Reducing immunogenicity of proteins—by modifying the amino acid sequence of the protein to eliminate potential epitopes for T-cells of a given species." PCT Publication WO 1998-052976.
5. Chiba, Y., "Leu3A Binding Peptides." U.S. Pat. No. 5,171,838 (1992).
6. Doitsh, G. Galloway, K., Geng, X., et al. "Cell Death by pyroptosis derives CD4 T-cell depletion in HIV infection." *Nature.* 2014. 505:509-514.
7. Global Health Observatory (GHO) HIV/AIDS. (website: www.who.int/gho/hiv/en/)
8. HIV—Wikepedia, The free encyclopedia. (website: en.wikipedia.org/wiki/HIV/AIDS)
9. Jacobson, J. M. Kuritzkes, D. R., Godofsky, E., et al. "Safety, Pharmacokinetics, and Antiretroviral Activity of Multiple Doses of Ibalizumab (formerly TNX-355), an Anti-CD4 Monoclonal Antibody, in Human Immunodeficiency Virus Type-1-Infected Adults." *Antimicrob. Agents Chemother.* 2009. 53:450457.
10. Jameson, B. D., Rao, P. E., Kong, L. L. et al. Location and chemical synthesis of a binding site for HIV-1 on the CD4 protein. *Science.* 1988, 240, 1335-1339.
11. Jones, T. D., et al. "Deimmunization of Monoclonal Antibodies."*Methods Mol. Bio.* 2009. 525:405-423.
12. Kuritzkes, D. R., Jacobson, J. L., Powderly, W. G., et al. "Antiretroviral activity of the anti-CD4 monoclonal antibody TNX-355 in patients infected with HIV type I." *J. Infect. Dis.* 2004. 189:286-291.
13. Lynn, S. and Wang, C. Y. "Designed deimmunized monoclonal antibodies for protection against HIV exposure and treatment of HIV infection." U.S. Pat. No. 7,501,494 (Issued Mar. 10, 2009).
14. Pace, C. S., Fordyce, M. W., Franco, D., et al. "Anti-CD4 Monoclonal Antibody ibalizumab Exhibits Breadth and Potency Against HIV-1, with Natural Resistance Medicated by the loss of a V5 Glycan in Envelope." *J. AIDS.* 2013. 62:1-9.
15. Pace G, Fordyce M, Franco D. "Anti-CD4 monoclonal antibody ibalizumab exhibits exceptional breadth and potency against HIV, which adopts a unique pathway to resistance." Abstract 585, 18th CROI 2011, Boston.
16. Sawyer, L. S. W., Wrin, M. T., Crawford-Miksza, L., et al. "Neutralization sensitivity of human immunodeficiency virus type 1 is determined in part by the cell in which the virus is propagated." *J. Virol.* 1994, 68(3), 1342-1349.
17. Sigal, A., Kim, J. T., Balazs, A. B., et al. "Cell-to-Cell spread of HIV permits ongoing replication despite antiretroviral therapy." *Nature.* 2011. 477:95-98.
18. Than, S., Oyaizu, N., Tetali, S., et al. "Upregulation of human immunodeficiency virus (HIV) replication by CD4 cross-linking on peripheral blood mononuclear cells of HIV-infected adults."*J. Virol.* 1997: 71(8):6230-6232.

19. Toma, T., Weinheimer, S. P., Stawiski, E., et al. "Loss of Asparagine-linked glycosylation sites in variable region 5 of human immunodeficiency virus type 1 envelope is associated with resistance to CD4 antibody ibalizumab." *J. Virol.* 2011. 85:3872-3880
20. Wang, C. Y. "Antibodies against a host cell antigen complex for pre and post exposure protection from infection by HIV." U.S. Pat. No. 5,912,176, 1999.
21. Wang, C. Y., Sawyer, L. S. W., Murthy, K. K., et al. "Postexposure immunoprophylaxis of primary isolates by an antibody to HIV receptor complex." *Proc. Nat. Acad. Sci. USA.* 1999, 96, 10367-10372.

BRIEF SUMMARY OF THE INVENTION

The present disclosure is directed to compositions and methods for the prevention, treatment, and/or functional cure of HIV infection. One aspect of the present disclosure relates to monoclonal antibodies directed against CD4, compositions thereof, and methods employing such compositions for the prevention, treatment, and functional cure of HIV infection.

One aspect of the present disclosure relates to an antibody directed against CD4, compositions thereof, and methods employing such compositions for the prevention, treatment, and/or functional cure of HIV infection. In certain embodiments, the antibody specifically binds to the CDR2 region in domain 1 of CD4. The disclosed antibody exerts potent competitive HIV entry inhibition through its binding to domain 1 of CD4 in both cell-free and cell-to-cell systems. The disclosed antibody also inhibits antigen induced T cell proliferation and cytokine production (IL2 and IFN-gamma) of CD4 positive T cells, which is implicated in the pathogenic cycle of pyroptosis. The disclosed antibody also has the ability to reactivate resting CD4 positive T cells. This property is particularly useful for reactivating latent reservoirs of HIV in resting T cells to make these cells susceptible to treatment with antiretroviral agents. Such high affinity antibodies to CD4 are capable of activating resting HIV infected cells for the release of HIV. Reactivation of HIV infected resting CD4+ T cells allows combinational treatment incorporating antibody of the current invention with HAART in HIV infected patients leading to functional cure.

The present disclosure is directed to methods for the treatment, prevention, and functional cure of HIV infection. In certain embodiments, the formulations contain antibodies directed against CD4. The present disclosure also includes antiviral agents that can be used in the methods for the treatment, prevention, and functional cure of HIV infection.

In certain embodiments, the present invention relates to pharmaceutical compositions comprising monoclonal human, humanized or chimeric, anti-CD4 antibodies with the above described binding characteristics that when given, at a dose of about 10 mg/kg or higher on a weekly or biweekly schedule, as a monotherapy, such treatment can reduce viral load down to non-detectable level in treated subjects with no viral load rebound as long the serum antibody level is higher than 10 μg/mL.

In another embodiment, the present invention relates to pharmaceutical compositions comprising a monoclonal humanized anti-CD4 antibody with the above described binding characteristics as the key ingredient in an adjunct therapy with HAART, that when given, at about 10 mg/kg or higher on a weekly or biweekly schedule, to treatment naïve HIV patients, will lead to functional cure of the patients.

BRIEF DESCRIPTION OF THE DRAWINGS

FIG. 1. Competitive vs. Non Competitive HIV Entry Inhibition mechanisms. FIG. 1*a* is a graph showing theoretical results obtained in a competitive HIV entry inhibition model, where HIV envelope protein gp120 and an inhibitor (e.g., antibody drug) compete for binding on the same portion of a common target surface molecule (i.e., CDR2 of CD4 domain 1). In this model, 100% inhibition of HIV binding/entry can be achieved when the concentration of the inhibitor reaches a certain threshold. In comparison, FIG. 1*b* is a graph showing theoretical results obtained in a non-competitive HIV entry inhibition model, where HIV and an inhibitor bind to different sites on the same target molecule (e.g. domain 2 of CD4 for TMB-355). In this non-competitive inhibition model, HIV binding/entry can be reduced by the inhibitor, but complete inhibition is not achieved regardless of the concentration of the inhibitor. Resistance of HIV to the antibody drug is reflected as a "plateau" in % inhibition regardless of drug concentration.

FIG. 2. HIV-1 entry inhibition results from a panel of 118 diverse HIV-1 Env pseudovirus strains covering 11 clades using TMB-355 (Pace, G., et al., 2011). For each virus, black lines indicate maximum percent inhibition (MPI) when treated at TMB-355 concentrations up to 10 μg/mL (left Y axis); and grey lines indicate the corresponding $IC_{50}$ (right Y axis). TMB-355 neutralized 92% of the viral strains with ≥50% inhibition and only neutralized 31% of the viral strains with ≥95% inhibition.

FIG. 3. HIV-1 entry inhibition from a panel of over 850 Env pseudotype HIV viruses collected over a 10 year period using mAb B4. MAb B4 offers both breadth and potency in HIV entry inhibition with nearly 100% maximum percent inhibition (MPI) in all 850 Env pseudotype viruses with $IC_{50}$ clustered around two concentrations one between 0.01 to 1 μg/mL and the second one around 10 μg/mL.

FIG. 4. Full amino acid sequence for the heavy chain of the Fv region of mAb dB4C7 antibody (SEQ ID NO: 7), which is used in UB-421. Sequences representing the corresponding CDR1, 2 and 3 regions derived from its parental murine B4 antibody are underlined (Table 4, SEQ ID NOs: 1 to 3). Variable and constant regions are respectively shaded in light grey and heavy grey colors (SEQ ID NOs: 11 and 12, respectively). Amino acid residue Asn (N) at aa101 of the heavy chain serves as an N-glycosylation site, which is unusual for its Fv region location, is critical to B4 antibody binding. For the substituted human $IgG_1$ Fc region sequence, the N-glycosylation site at amino acid residue Asn (N) at aa298 was removed by substituting the amino acid with His (H), i.e. N298H. This mutation has been found to eliminate IgG mediated complement dependent cytotoxicity (CdC) and depletion of CD4 positive T cells in the presence of antibody B4.

FIG. 5. Full amino acid sequence for the light chain of the Fv region of dB4C7 antibody (SEQ ID NO: 8), which is used in UB-421. Sequences representing the corresponding CDR1, 2 and 3 regions derived from its parental murine B4 antibody are underlined (Table 4, SEQ ID NOs: 4 to 6). Variable and constant regions are respectively shaded in light grey and heavy grey colors (SEQ ID NOs: 13 and 14, respectively).

FIG. 6. Full amino acid sequence for the heavy chain of a further improved humanized antibody (SEQ ID NO: 9) with longer half-life, due to amino acid substitution at the Fc region of the heavy chain positions aa253, aa255 and aa257 from Met (M) to Tyr (Y), i.e. M253Y, Ser (S) to Thr (T), i.e. S255T, and Thr (T) to Glu (E), i.e. T257E respectively.

FIG. 7. Full amino acid sequence for the heavy chain of humanized antibody mAb dB4 (SEQ ID NO: 10) encompassing the variable amino acids discussed in FIGS. 4 and 6.

Figure 8:
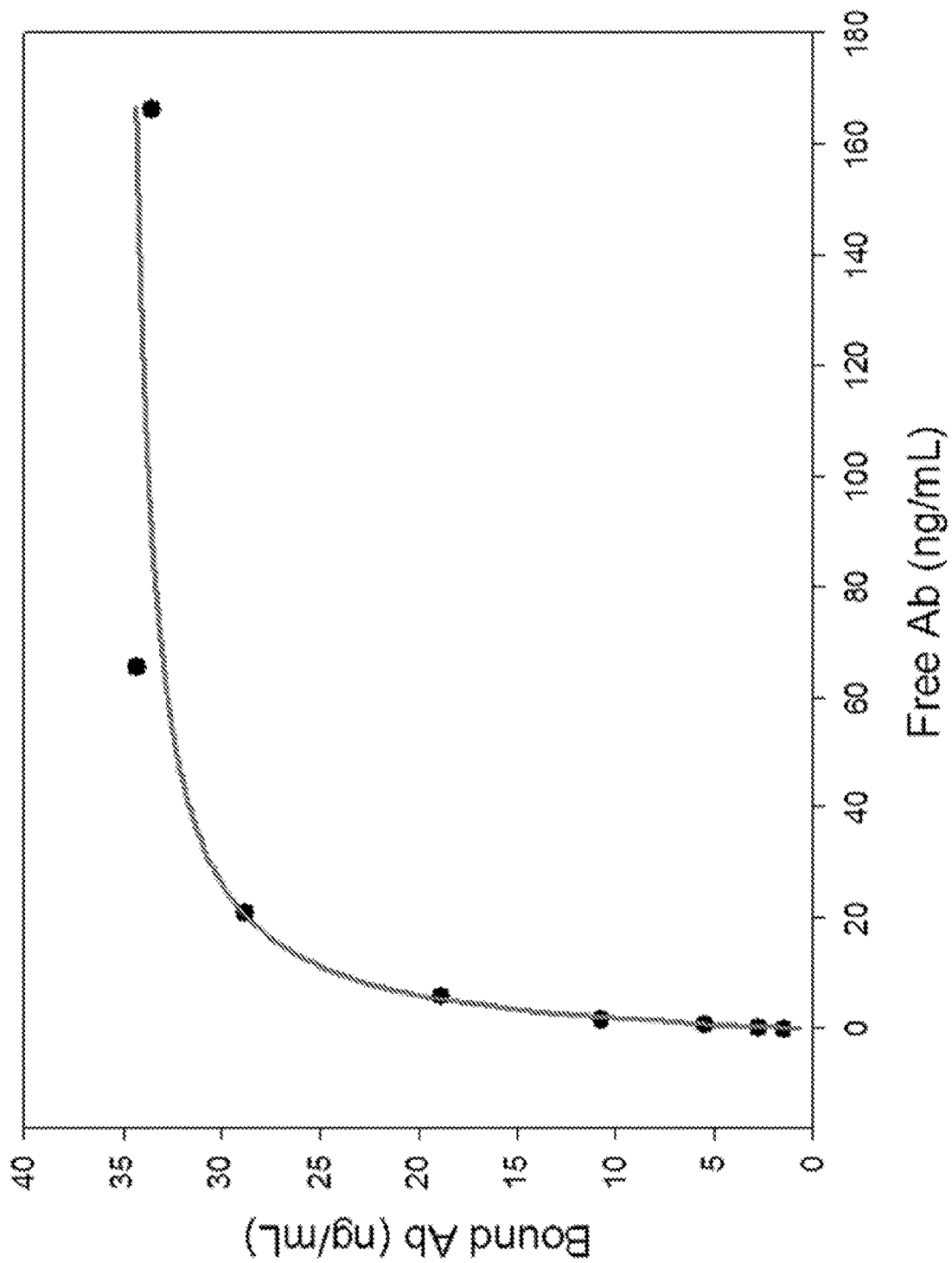

FIG. 8. Graph showing the binding affinity (antibody concentration) and binding capacity (free and bound antibody) of mAb B4 to surface CD4 on HPB-ALL cells after three passages of the antibody over the cells.

Figure 9:
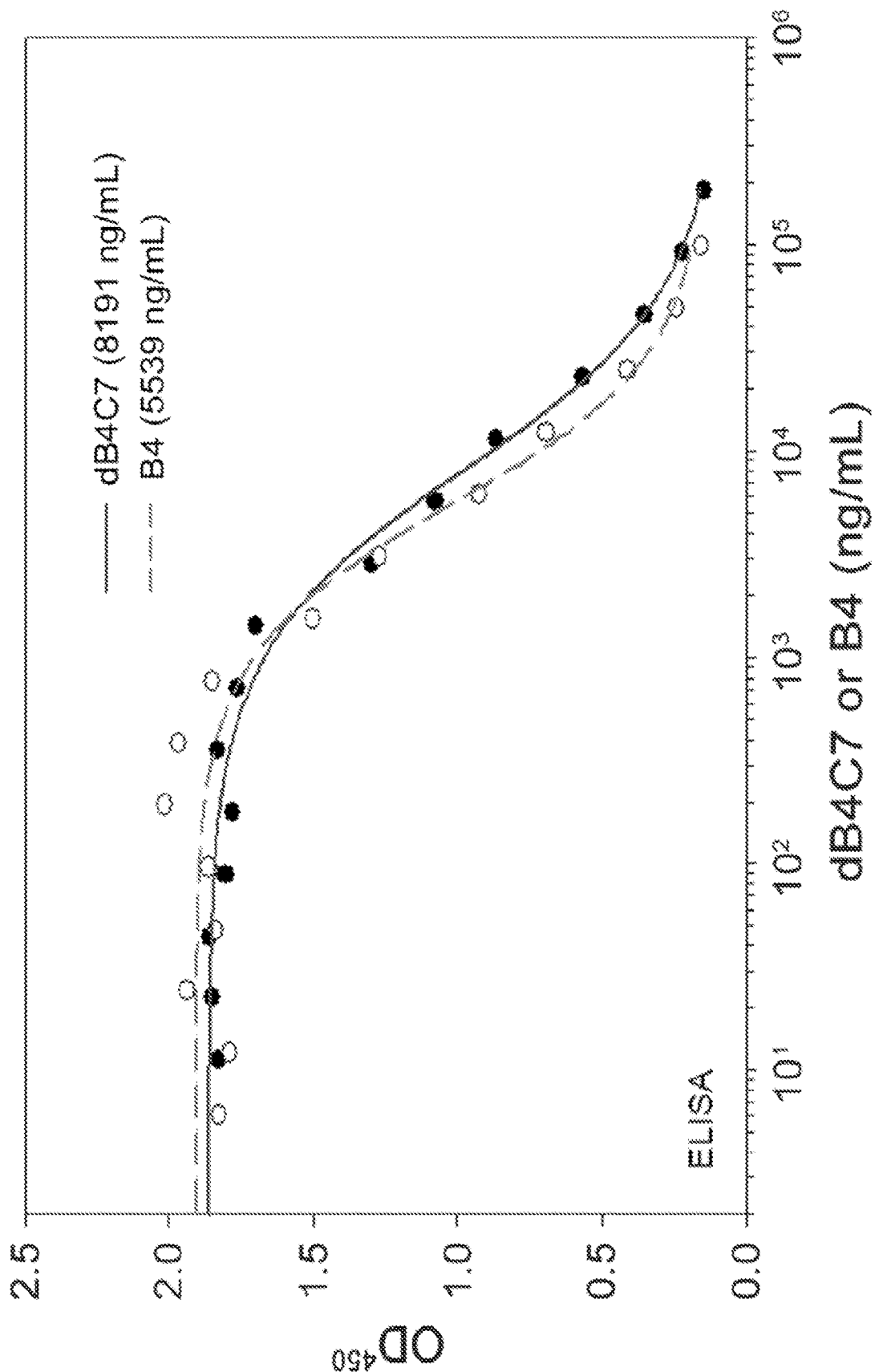

FIG. 9. Graph comparing the binding affinities of mAb B4 ( - - - ) and mAb dB4 (_____) to a capturing mixture of soluble CD4 (sCD4) and p2704a peptide coated on ELISA plates. Binding affinities were determined using mAb B4 and mAb dB4 to competitively inhibit the binding of B4-biotin and dB4C7-Alexa, respectively, to the capturing mixture.

Figure 10:
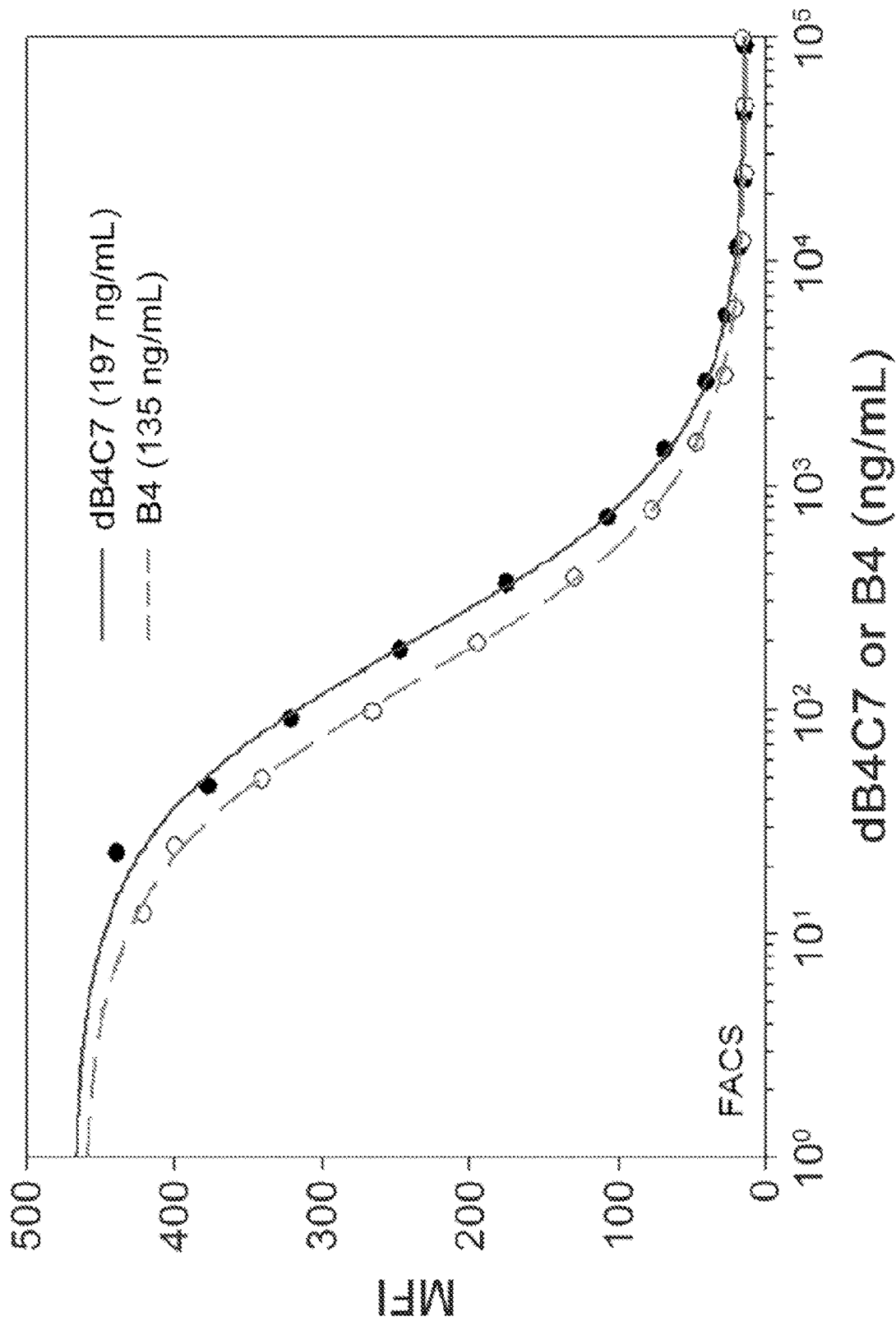

FIG. 10. Graph comparing the binding affinities of mAb B4 ( - - - ) and mAb dB4 (_____) to CD4 on HPB-ALL cells. Binding affinities were determined by FACS using mAb B4 and mAb dB4 to competitively inhibit the binding of B4-biotin and dB4C7-Alexa, respectively, to surface CD4 on HPB-ALL cells.

Figure 11:
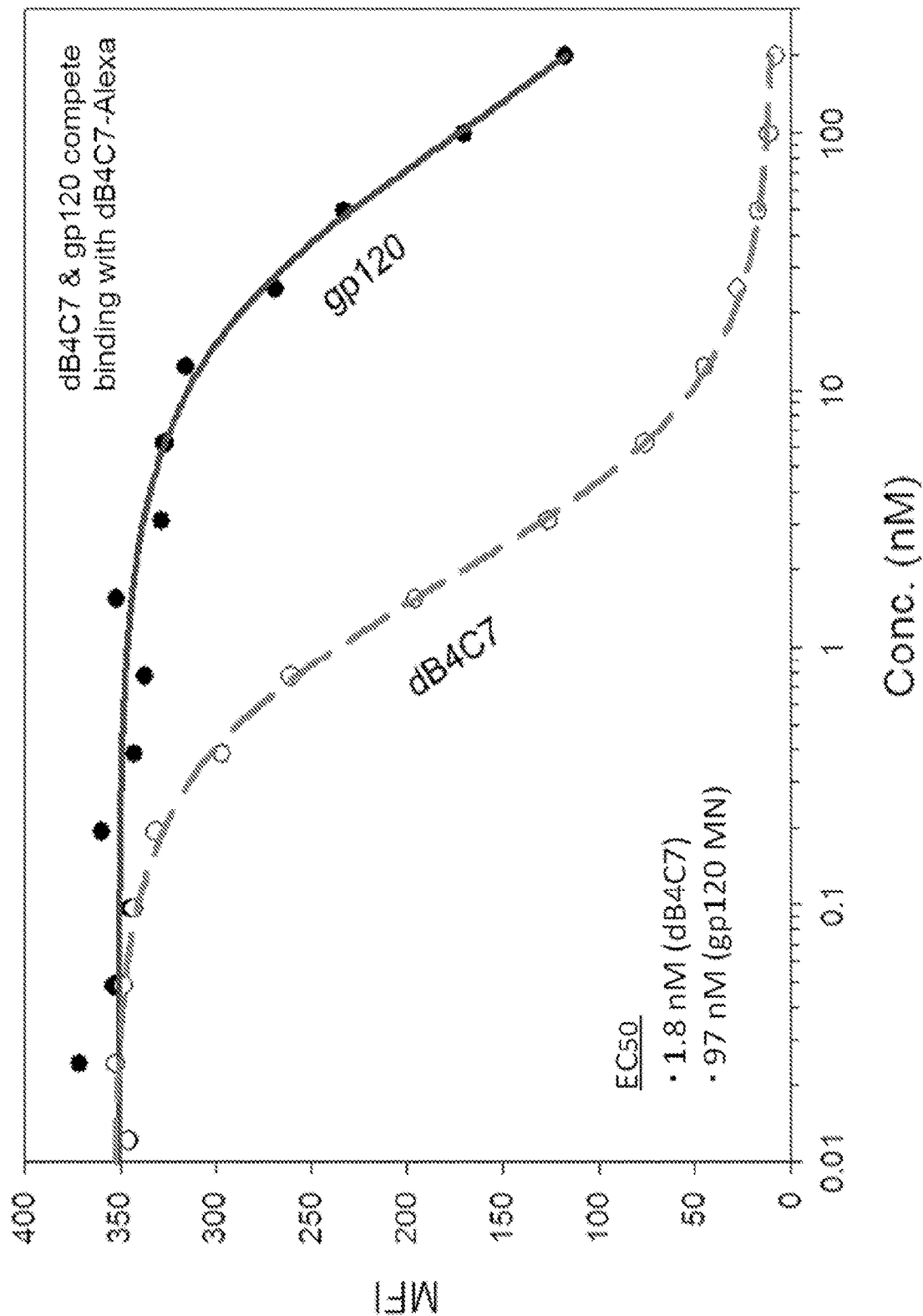

FIG. 11. Graph comparing the binding affinities of mAb dB4 ( - - - ) and gp120MN (_____) to CD4 on HPB-ALL cells. Binding affinities were determined by FACS using mAb dB4 and gp120MN to competitively inhibit the binding of dB4C7-Alexa to surface CD4 on HPB-ALL cells.

Figure 12:
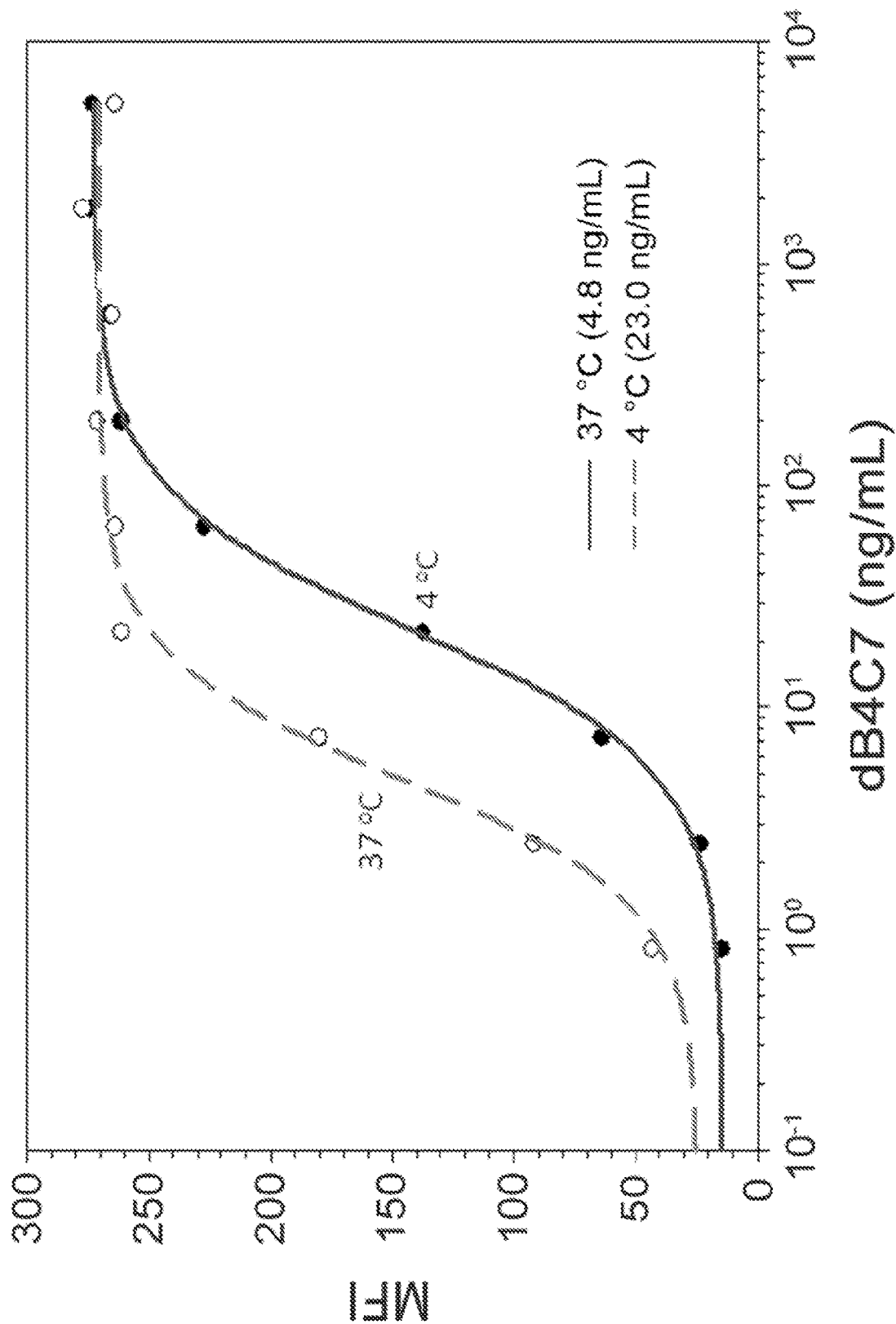

FIG. 12. Graph showing temperature-dependent binding (MFI) of mAb dB4C7 to PBMC CD4+ T cells.

Figure 13:
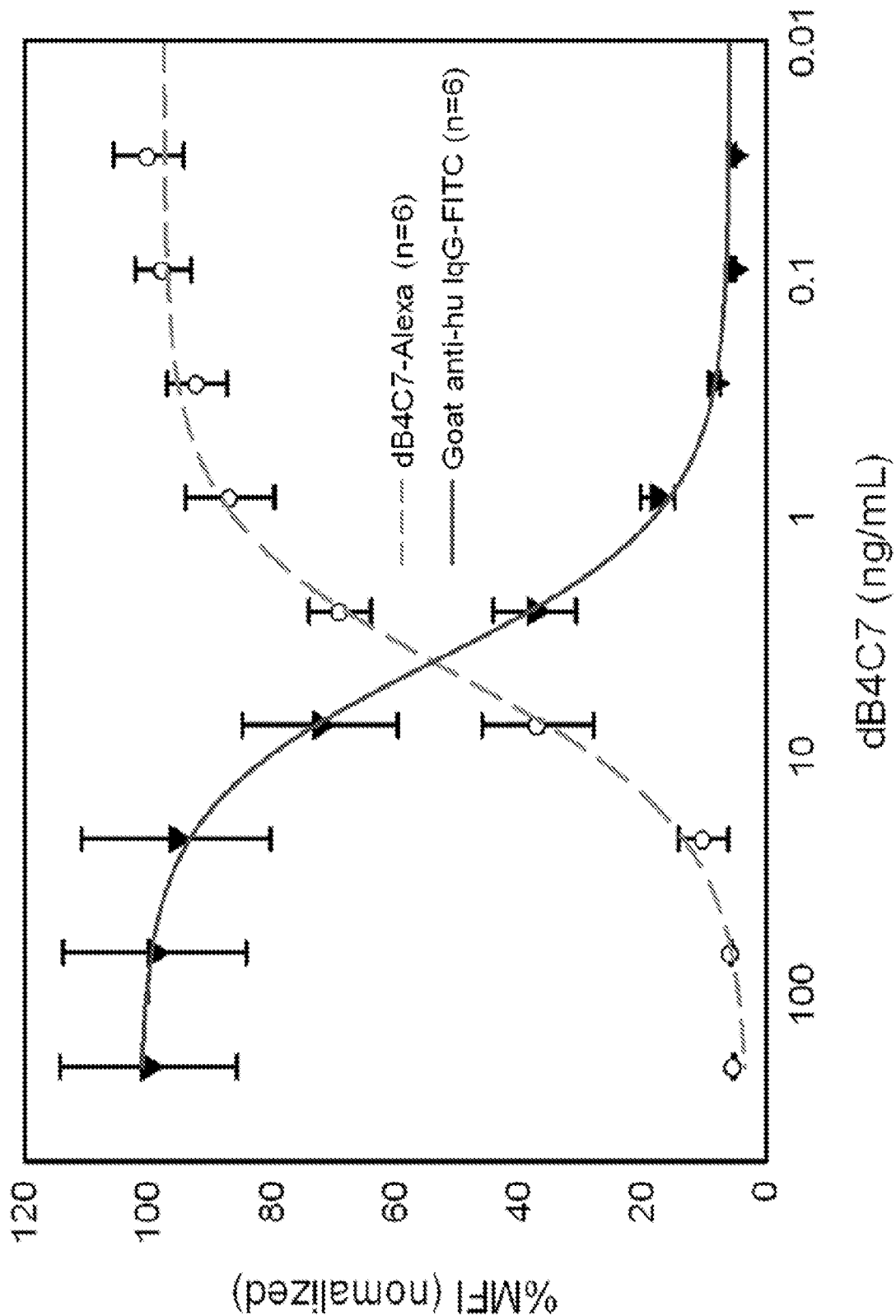

FIG. 13. Graph showing mean percentages (±SD) of unoccupied CD4 receptors (_____) and CD4 receptors occupied/bound with mAb dB4 ( - - - ) from blood samples of six non-infected individuals and as a function of mAb dB4 concentration. Unoccupied receptors were detected by the binding of dB4C7-Alexa to the free binding sites on the surface of blood CD4+ T cells while mAb dB4 occupied receptors were detected by goat anti-huIgG-FITC.

Figure 14:
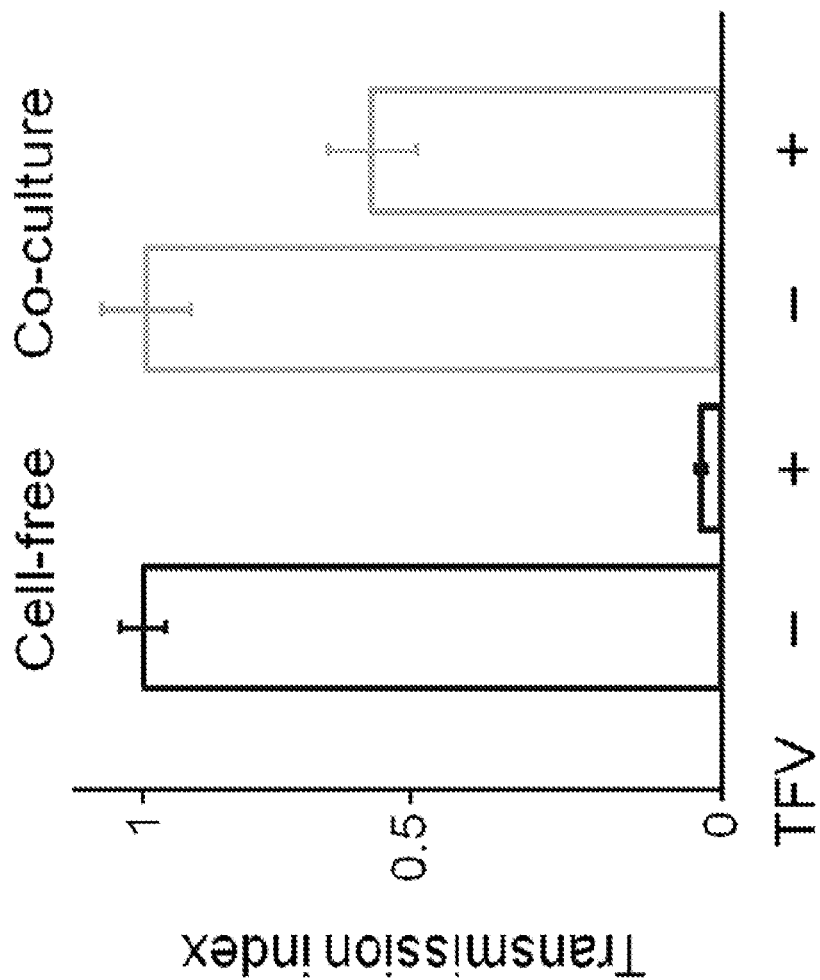

FIG. 14. Bar graph showing the effect of the current antiretroviral therapy (cART) drug Tenofovir on cell-free and cell-to-cell transmission of HIV (Sigal, A., et al., 2011). The Y-axis represents the transmission index from Peripheral Blood Mononuclear Cells (PBMCs) isolated from different infection sources in the presence or absence of tenofovir (Sigal, A. et al., 2011).

Figure 15:
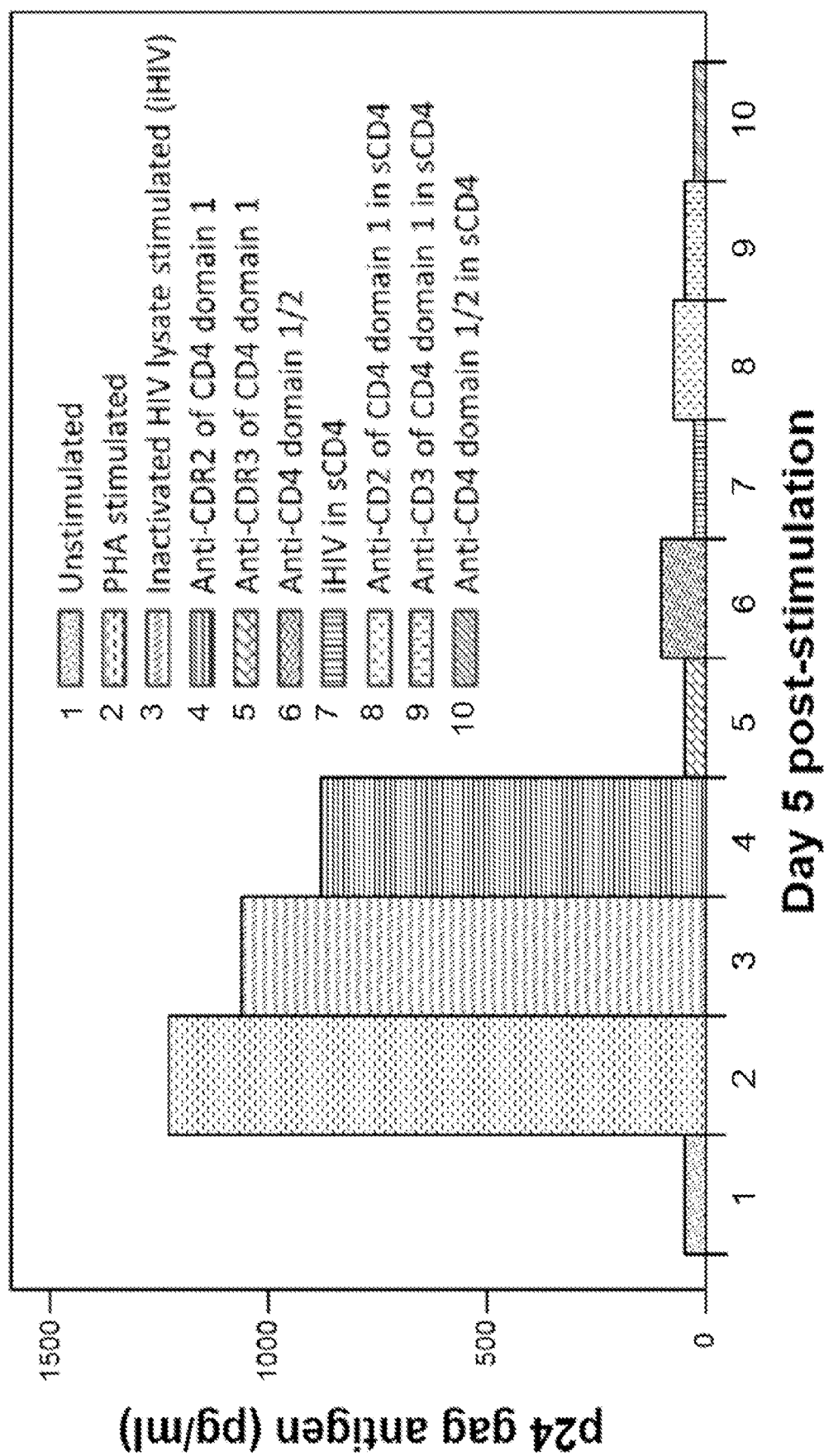

FIG. 15. Bar graph showing virus reactivation in resting PBMCs (as measured by HIV-1 p24 gag production) induced by the following stimuli: unstimulated (lane 1), PHA (lane 2), inactivated HIV (iHIV) lysate (lane 3), monoclonal antibody directed at CDR2 region of CD4 domain 1 (lane 4), monoclonal antibody directed at CDR3 region of CD4 domain (lane 5), monoclonal antibody directed at CD4 domains 1/2 (lane 6), iHIV in the presence of soluble CD4 (lane 7), monoclonal antibody directed at CDR2 region of CD4 domain 1 in the presence of soluble CD4 (lane 8), monoclonal antibody directed at CDR3 region of CD4 domain 1 in the presence of soluble CD4 (lane 9), and monoclonal antibody directed at CD4 domains 1/2 in the presence of soluble CD4 (lane 10), as depicted in the figure legend (adapted from Briant L., et al., 1999).

Figure 16:
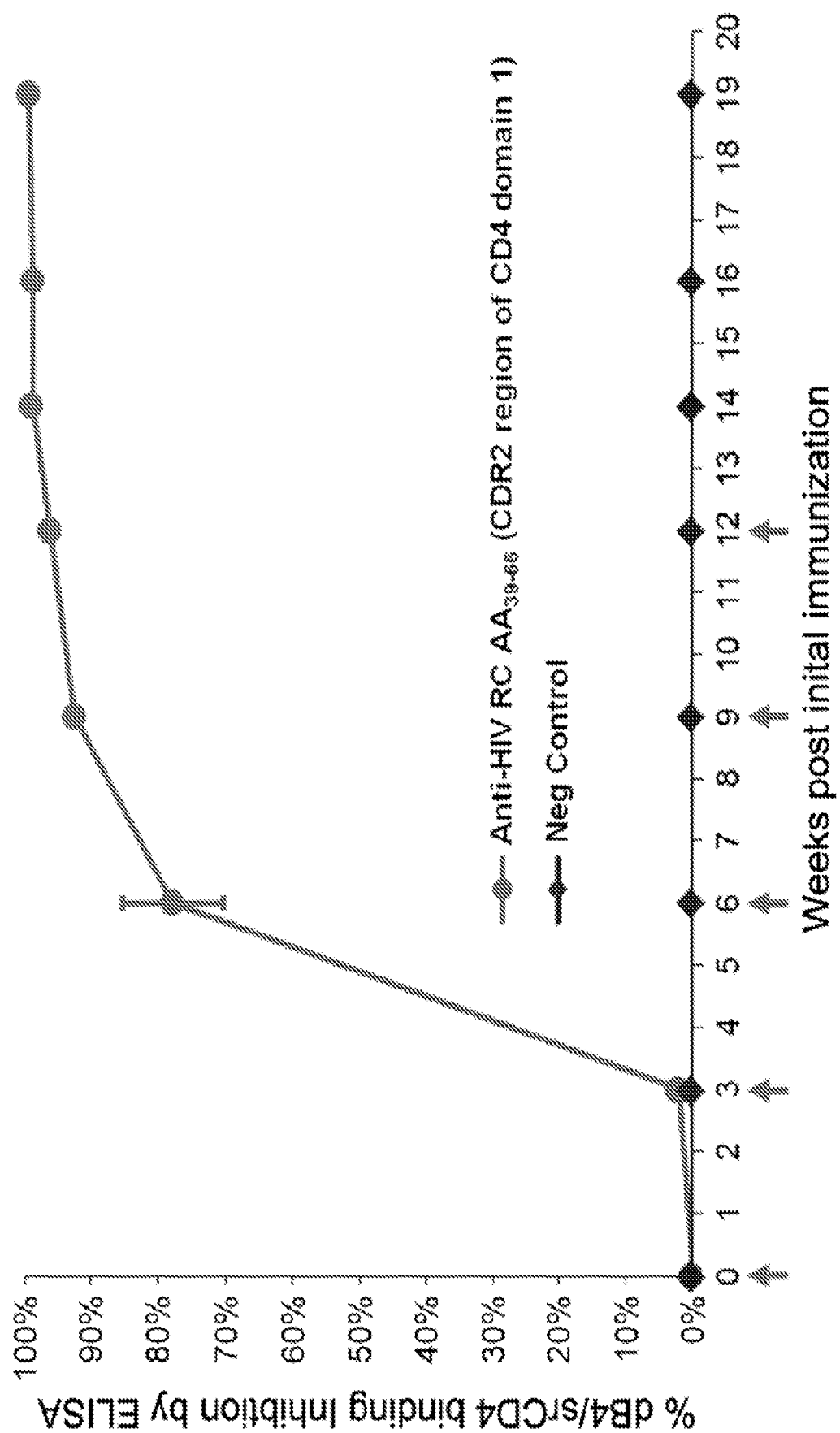

FIG. 16. Graph showing competitive inhibition of biotinylated-B4 binding to rsCD4 by anti-HIV RC polyclonal antibodies, as measured by ELISA.

FIG. 17. Graph showing antibody titration of mAb dB4 and anti-HIV RC polyclonal antibodies to surface CD4 on PBMCs. The antibody titration was determined as % CD4 binding vs antibody concentration in µg/mL.

FIGS. 18a to 18g. Analysis of mAb dB4 and anti-HIV RC polyclonal antibody inhibition of superantigen SEB induced production of cytokines IL2 and IFN-γ by proliferating CD4+ and CD8+ T cells in treatment naïve HIV positive and HIV negative subjects. MAb dB4 and anti-HIV RC polyclonal antibody inhibition of IL2 production by superantigen induced proliferating CD4+ T cells for HIV negative (FIG. 18a) and HIV positive (FIG. 18b) subjects are shown. MAb dB4 and anti-HIV RC polyclonal antibody inhibition of IL2 production by superantigen induced proliferating CD8+ T cells for HIV negative subjects and age-matched HIV positive subjects (FIG. 18c) are also shown. MAb dB4 and anti-HIV RC polyclonal antibody inhibition of IFN-γ production by superantigen induced proliferating CD4+ T cells for HIV negative (FIG. 18d) and HIV positive (FIG. 18e) subjects are shown. MAb dB4 and anti-HIV RC polyclonal antibody inhibition of IFN-γ production by superantigen induced proliferating CD8+ T cells for HIV negative (FIG. 19l) and HIV positive (FIG. 19g) subjects are also shown.

Figure 19A:
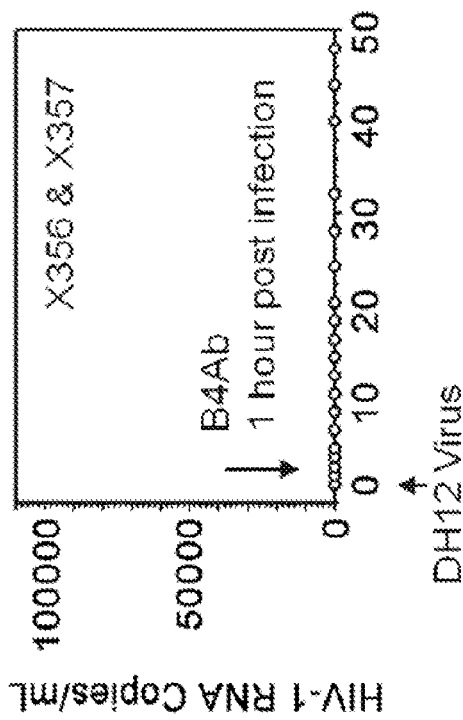
Figure 19B:
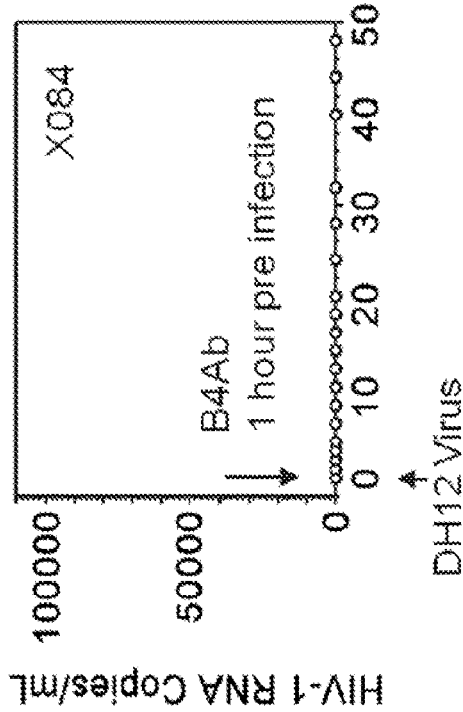
Figure 19C:
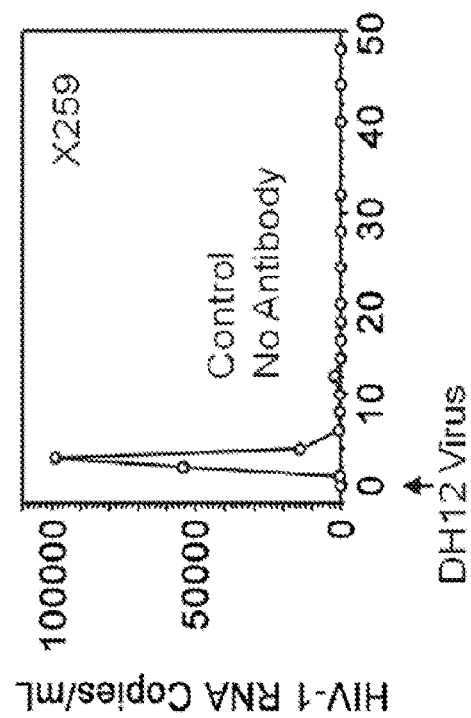

FIGS. 19a to 19c. Graphs showing protection of chimpanzees from HIV infection by administration of mAb B4 pre-exposure (FIG. 19a) and post-exposure (FIG. 19b) to HIV-1 primary isolate DH12 (HIV-1DH12), as measured by HIV-1 RNA copies/mL in PBMCs over time post infection. Graph showing the results of the control animal exposed to HIV-1DH12 without antibody administration (FIG. 19c) is also shown. Down Arrows mark the beginning of the study when mAb B4 was administered either prior to or one hour after the HIV-1DH12 challenge.

Figure 20B:
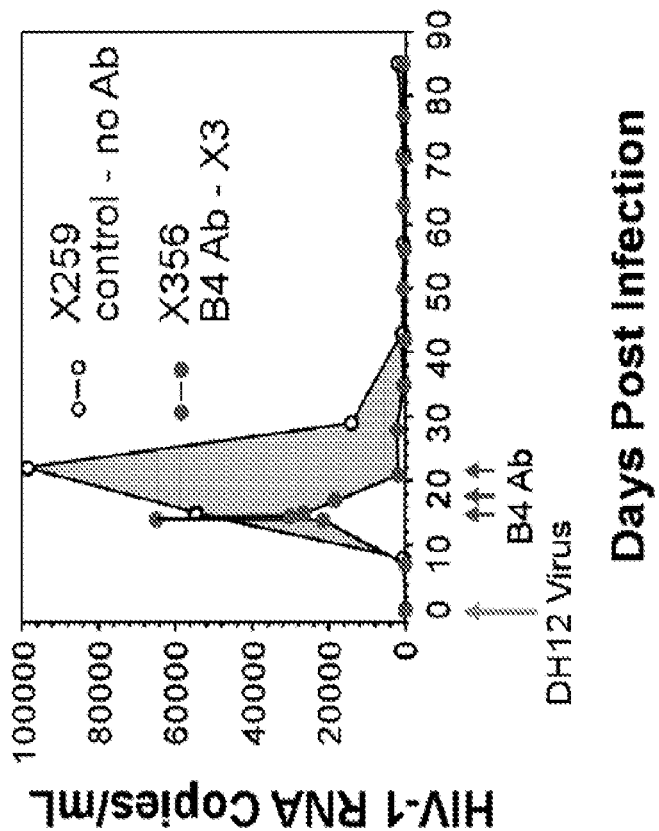
Figure 20A:
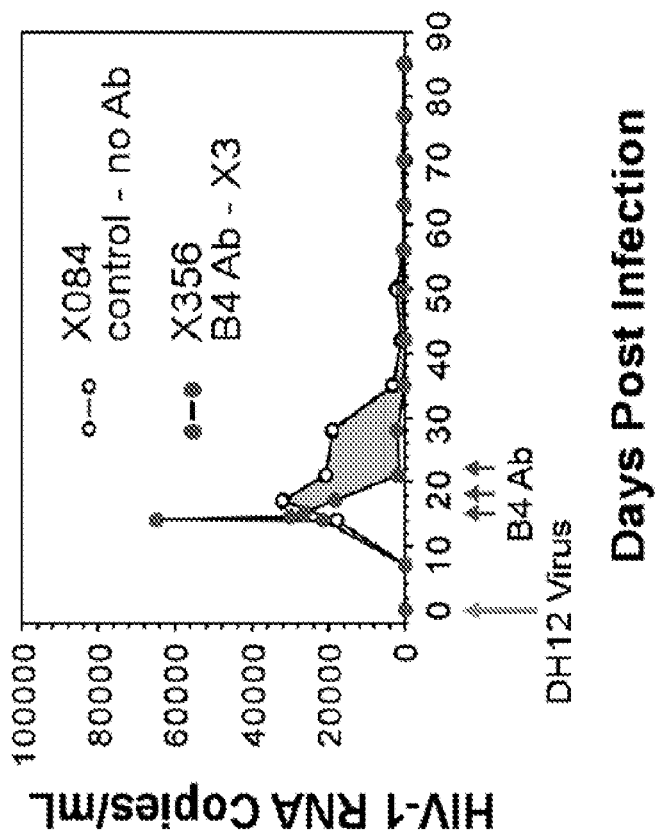

FIGS. 20a and 20b. Graphs showing the HIV viral load of untreated and mAb B4 treated HIV-1 infected chimpanzees, as measured by HIV-1 RNA copies/mL over time. FIG. 20a compares the duration of plasma viremia in chimpanzee X356 receiving three infusions of mAb B4 (closed circles) with untreated control chimpanzee X084 that previously received a single dose of mAb B4 in a prior study (open circles). FIG. 20b compares the duration of plasma viremia in chimpanzee X356 receiving three infusions of mAb B4 (closed circles) with untreated control chimpanzee X259 that did not receive a previous dose of mAb B4 in (open circles).

Figure 21:
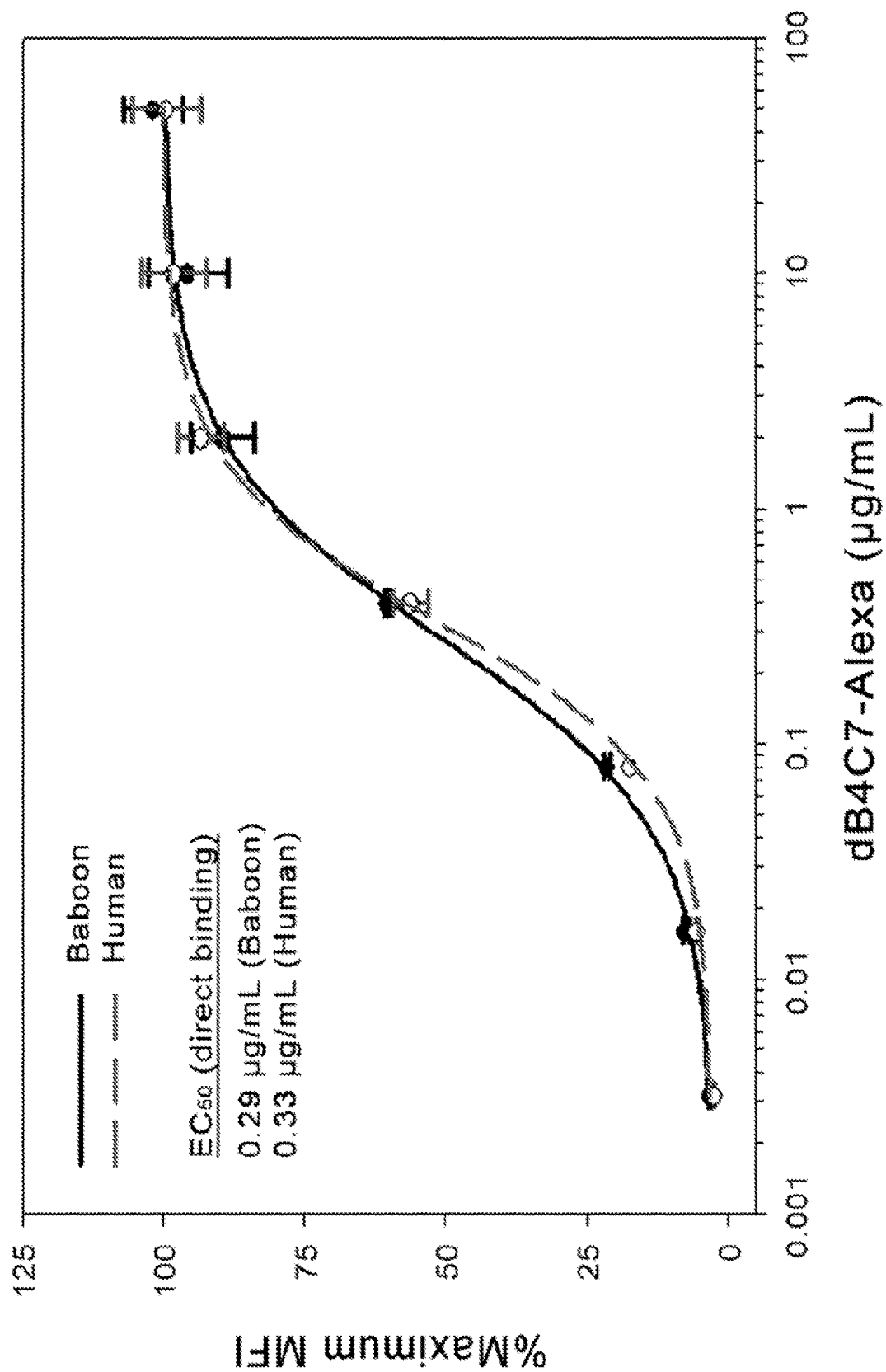

FIG. 21. Graph comparing the binding affinity of mAb dB4 to human ( - - - ) and baboon (_____) CD4 positive T cells.

Figure 22B:
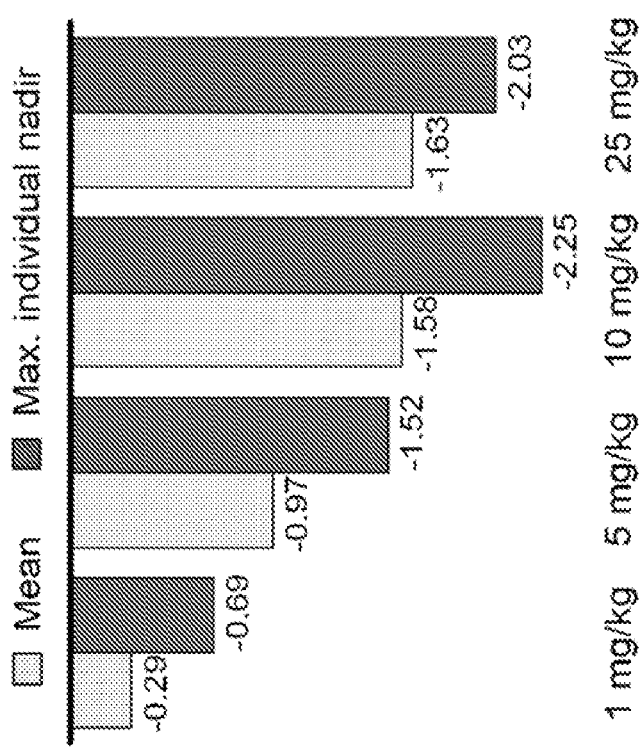
Figure 22A:
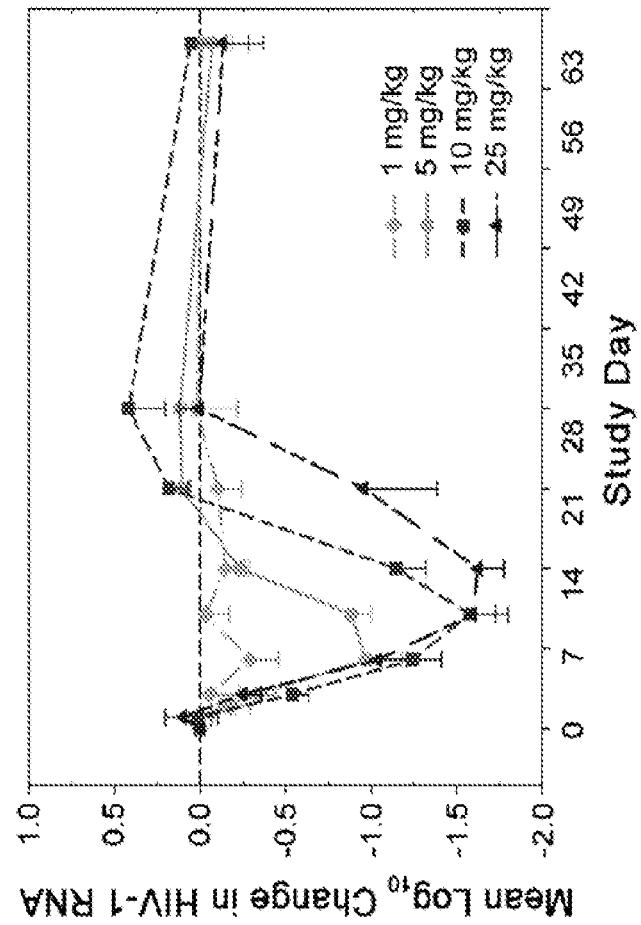

FIGS. 22a and 22b. Graphs showing the mean $Log_{10}$ change in HIV-1 RNA vs study day for patients receiving single administration of antibody drug UB-421 (mAb dB4C7) in a dose escalation (1, 5, 10, and 25 mg/kg) Phase I clinical study. FIG. 22a is a graph showing the viral reduction exhibited by each of the doses over the course of the study. FIG. 22b is a graph showing the mean and max individual nadir for each of the doses.

Figure 23A:
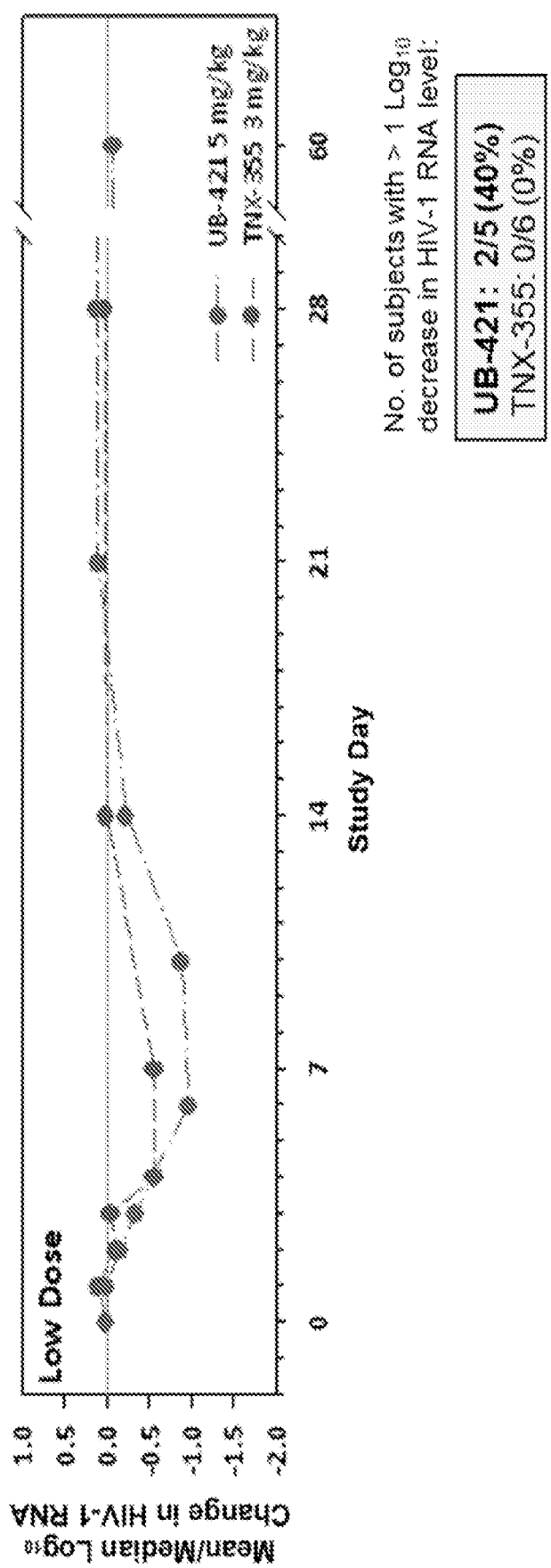
Figure 23B:
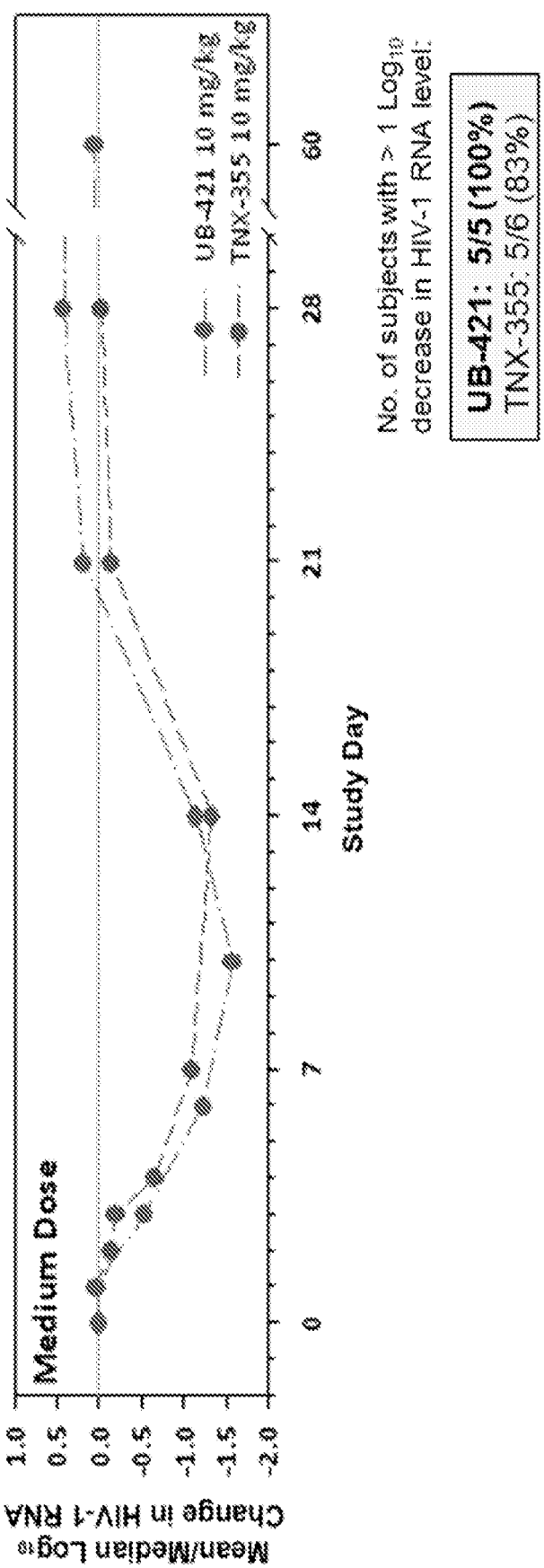
Figure 23C:
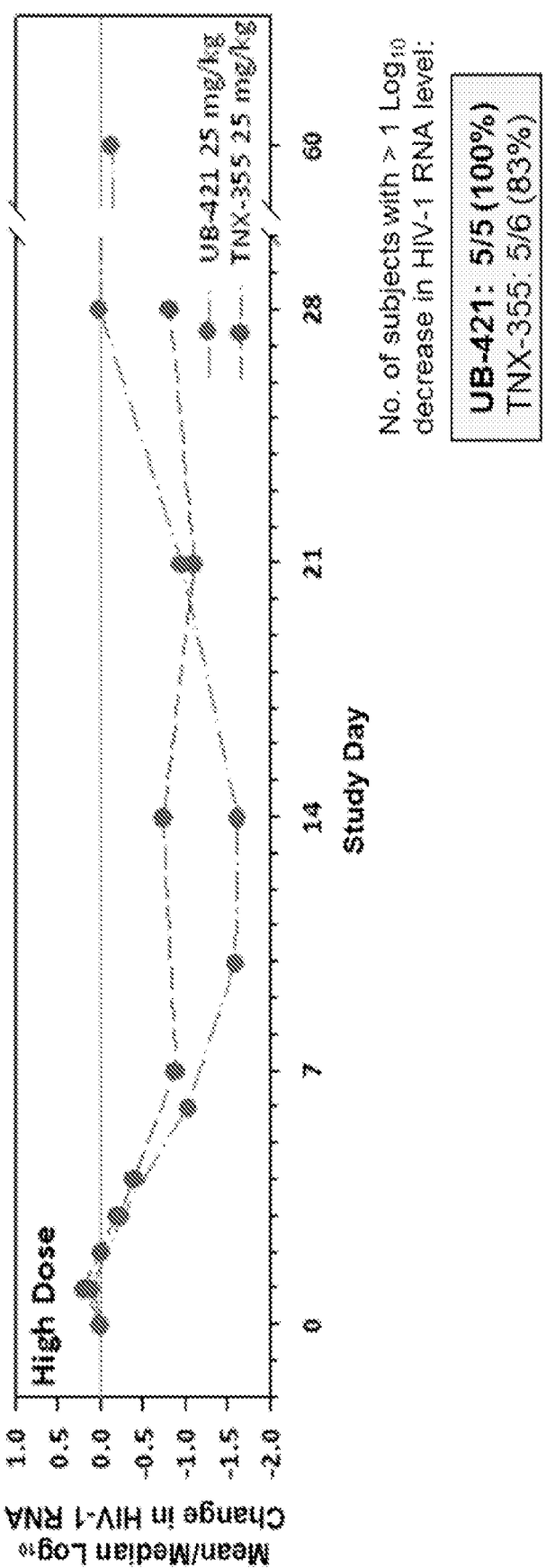

FIGS. 23a to 23c. Graphs showing a theoretical comparison of the efficacy of UB-421 (mAb dB4C7) and the efficacy data previously reported for TMB-355 (previously known as TNX-355; Kuritzkes, D. R., et al., 2004, FIG. 1). FIG. 23a is a graph comparing the viral load reduction observed after a single administration of 5 mg/kg of UB-421 and 3 mg/kg of TMB-355. FIG. 23b is a graph comparing the viral load reduction observed after a single administration of 10 mg/kg of UB-421 or TMB-355. FIG. 23c is a graph comparing the viral load reduction observed after a single administration of 25 mg/kg of UB-421 or TMB-355.

Figure 24A:
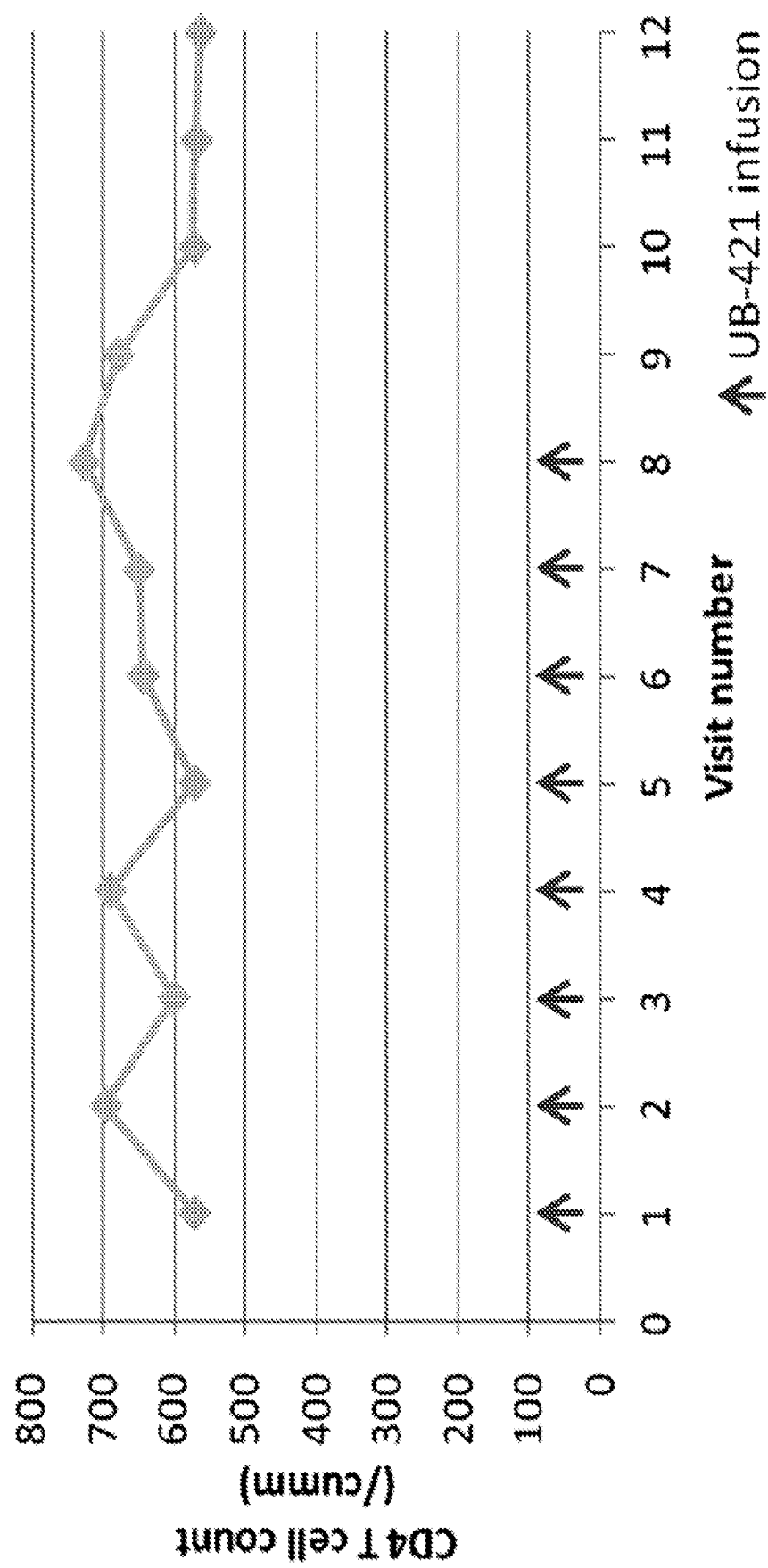

FIGS. 24a and 24b. Graphs showing mean PBMC CD4 T cell counts/mm³ in subjects receiving 10 mg/kg weekly (FIG. 24a) or 25 mg/kg bi-weekly (FIG. 24b) administrations of UB-421 (mAb dB4C7) over an eight-week treatment period. Stable CD4 T cell counts were detected in UB-421 treated patients by biotinylated antibody directed against domain 2 of CD4.

Figure 25A:
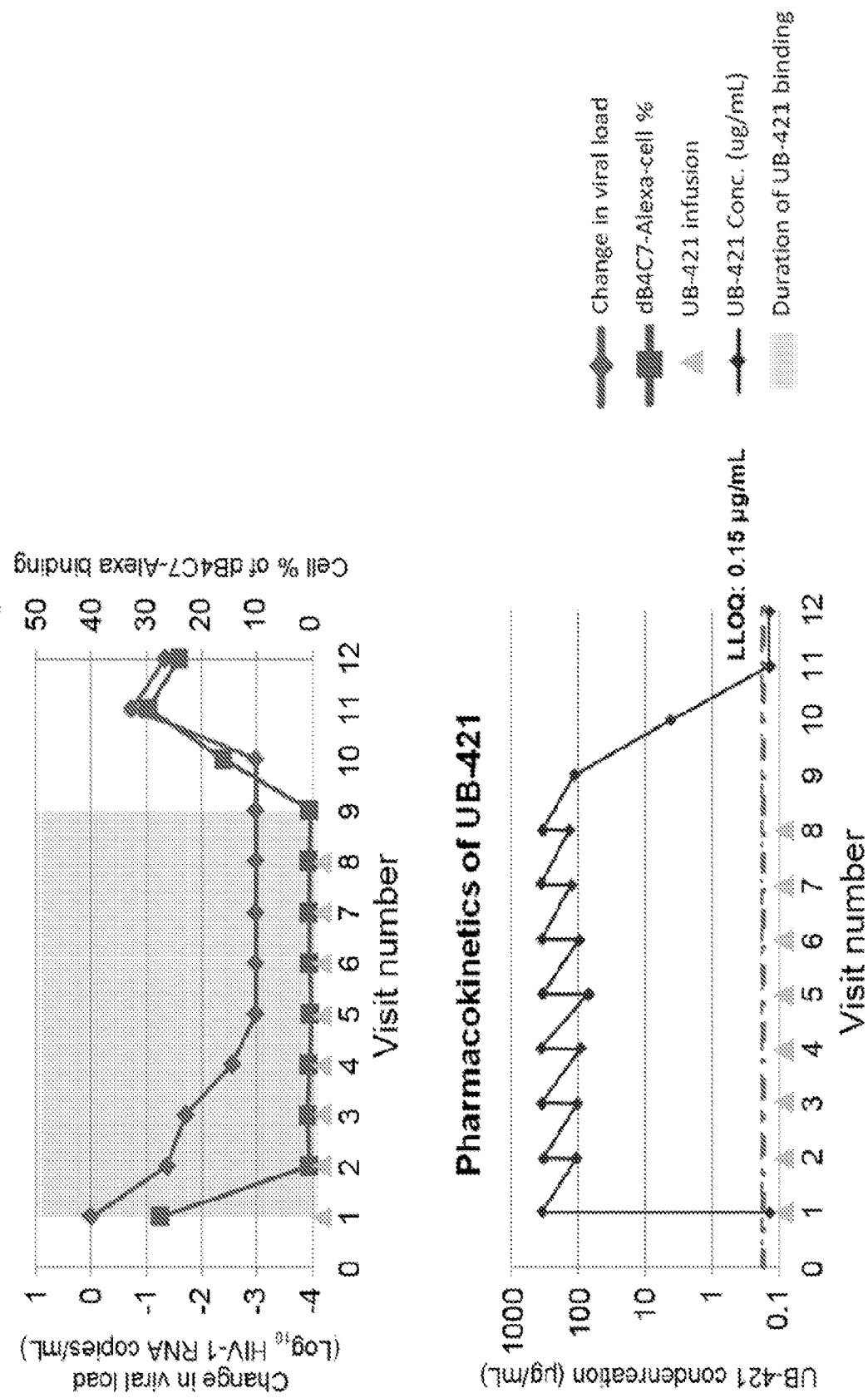

FIGS. 25a to 25d. Graphs showing the clinical efficacy of UB-421 treatment, as measured by viral load reduction (upper panels), and pharmacokinetics of UB-421, as measured by μg/mL serum concentration (lower panels), over the course of a Phase IIa clinical trial. The relevant data are provided for the following representative patients: Patient 1-1-01 receiving 10 mg/kg weekly administrations of UB-421 (FIG. 25a); Patient 1-1-02 receiving 10 mg/kg weekly administrations of UB-421 (FIG. 25b); Patient 1-2-03 receiving 25 mg/kg bi-weekly administrations of UB-421 (FIG. 25c); and Patient 1-2-06 receiving 25 mg/kg bi-weekly administrations of UB-421 (FIG. 25d). Duration of UB-421 binding on PBMC CD4+ cells indicative of full coating of the cells is shaded in grey.

Figure 26A:
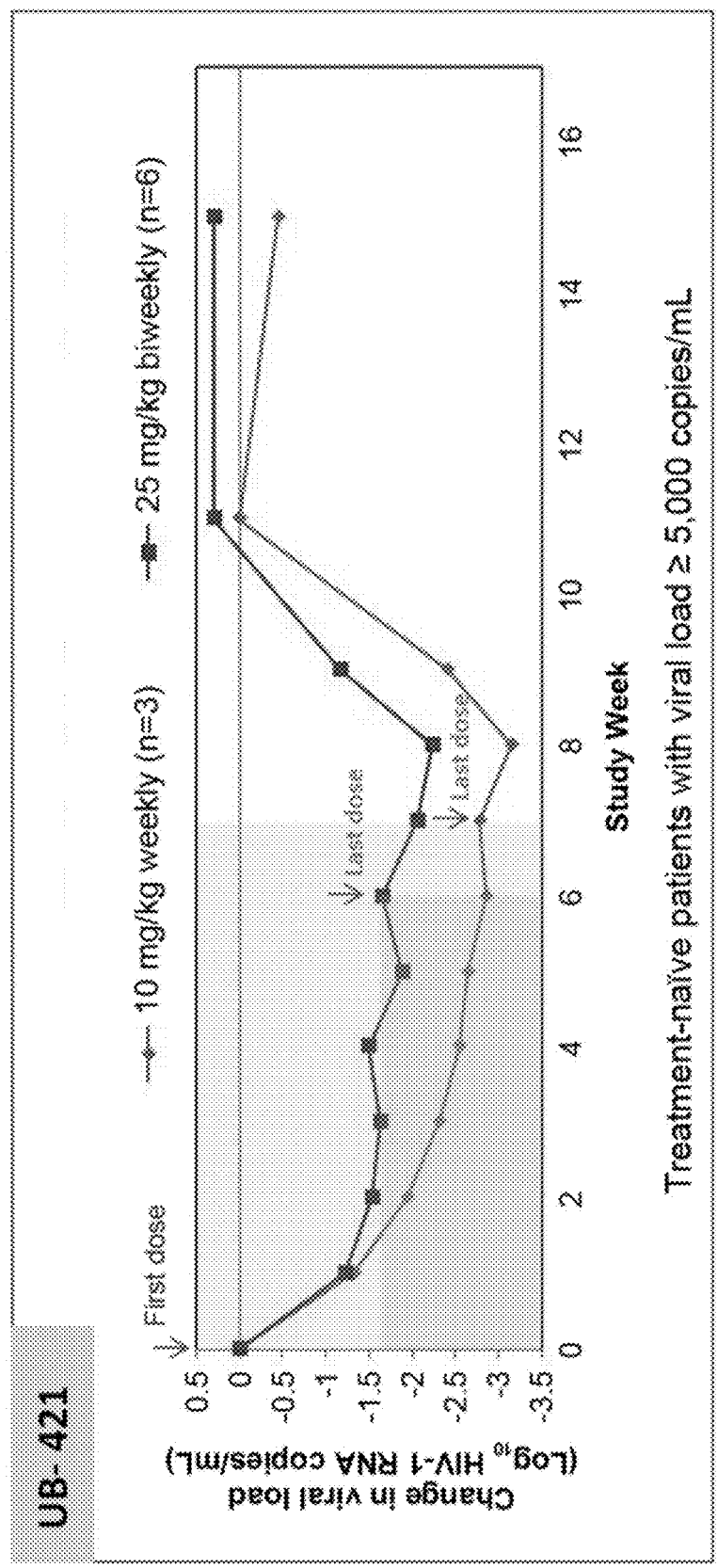
Figure 26B:
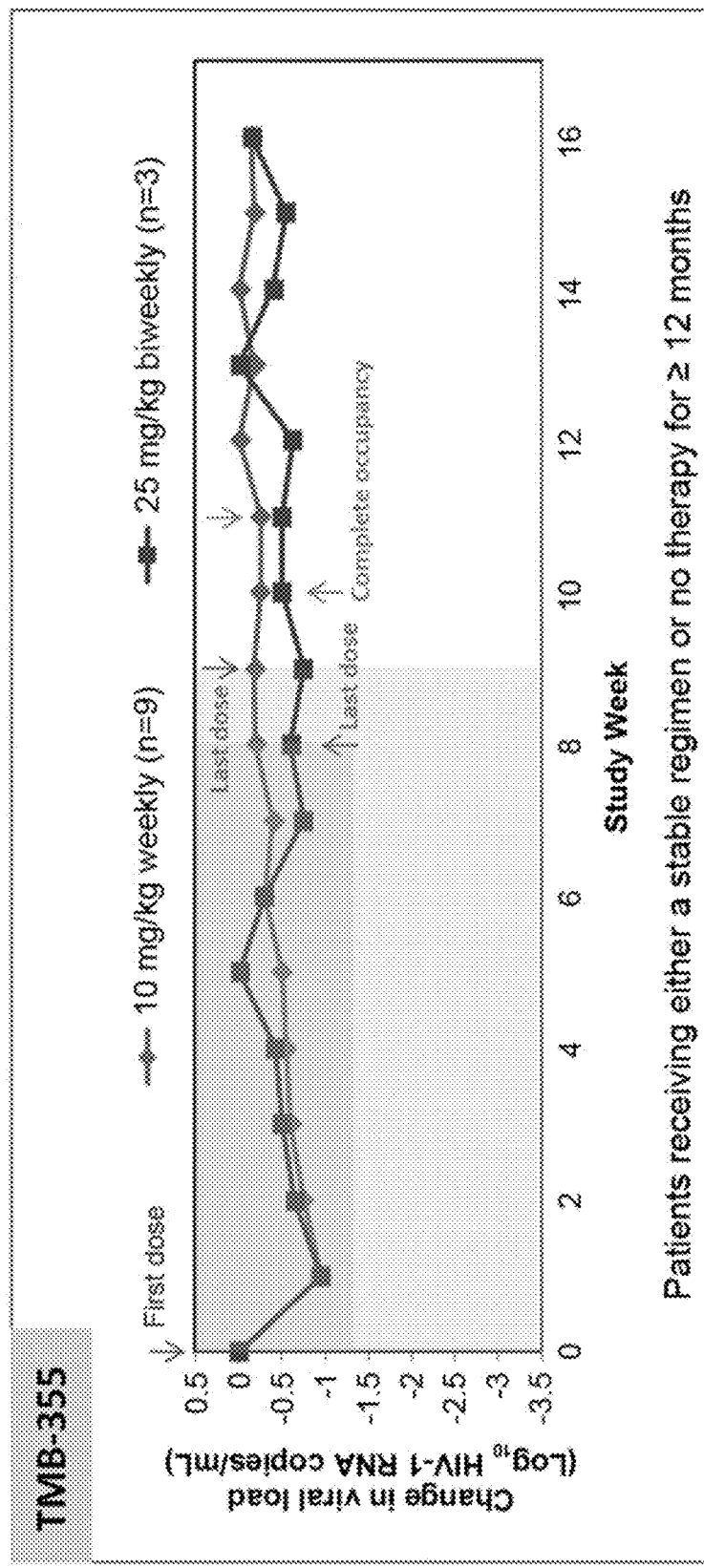

FIGS. 26a and 26b. Graphs showing a theoretical comparison of viral load reduction observed in a Phase IIa clinical trial using UB-421 against the viral load reduction observed in similar studies for TMB-355 (ibalizumab, formerly TNX-355) performed by others (Jacobson, J. L., et al., 2009; Toma, J., et al., 2011; and Pace, C. S., et al., 2013). FIG. 26a summarizes the viral load changes observed in subjects treated with 10 mg/kg and 25 mg/kg of UB-421, while FIG. 26b summarizes the viral load changes observed in subjects treated with the same dosage levels of TMB-355.

FIG. 27. Schematic showing a treatment modality in HIV patient populations employing UB-421 monotherapy as a replacement to HAART therapy in treatment naïve HIV patients and HAART treatment stabilized HIV patients.

FIG. 28. Schematic showing a treatment modality in HIV patient populations employing UB-421 in combination with HAART therapy for a functional cure of HIV infection in treatment naïve HIV patients; HAART treatment stabilized HIV patients; and HIV patients who failed HAART treatment.

DETAILED DESCRIPTION OF THE INVENTION

The present disclosure is directed to compositions and methods for the prevention, treatment, and/or functional cure of HIV infection. One aspect of the present disclosure relates to antibodies directed against CD4, formulations thereof, and methods employing such formulations for the prevention, treatment, and/or functional cure of HIV infection.

The section headings used herein are for organizational purposes only and are not to be construed as limiting the subject matter described. All references or portions of references cited in this application are expressly incorporated by reference herein in their entirety for any purpose.

CD4

CD4 (cluster of differentiation 4) is a glycoprotein (UniProtKB/Swiss-Prot: P01730.1) found on the surface of immune cells such as T helper cells, monocytes, macrophages, and dendritic cells (website: en.wikipedia.org/wiki/CD4). CD4 is a member of the immunoglobulin superfamily and has four immunoglobulin domains (D1 to D4) that are exposed on the extracellular surface of the cell. CD4 domains D1 and D3 resemble immunoglobulin variable (IgV) domains; whereas D2 and D4 resemble immunoglobulin constant (IgC) domains. CD4 uses its D1 domain to interact with the β2-domain of MHC class II molecules. T cells expressing CD4 molecules on their surface, therefore, are specific for antigens presented by MHC II. The short cytoplasmic/intracellular tail of CD4 contains a special sequence of amino acids that allow it to interact with the lck molecule.

The first extracellular domain of CD4 shares homologies with immunoglobulin at three complimentarity determining regions (CDRs) similar to that of immunoglobulin chains. Both domain 1 and domain 2 of the extracellular region of the CD4 molecule were found to contribute to the binding sites for class II MHC molecules; however, domain 1 alone was found to be involved with HIV binding and syncytia formation. In particular, the binding site for the HIV envelope glycoprotein gp120 was found to be localized to the CDR2-like loop of domain 1.

HIV-1 uses CD4 to gain entry into host T-cells and achieves this through its viral envelope protein known as gp120. The binding to CD4 creates a shift in the conformation of gp120 allowing HIV-1 to bind to chemokine receptors CCR5 or CXCR4 expressed on the host cell. Following a structural change in another viral protein (gp41), HIV inserts a fusion peptide into the host cell that allows the outer membrane of the virus to fuse with the cell membrane. HIV infection leads to a progressive reduction in the number of T cells expressing CD4.

Antibody

One aspect of the present disclosure relates to an antibody directed against CD4, compositions thereof, and methods employing such compositions for the prevention, treatment, and/or functional cure of HIV infection.

The antibody of the present disclosure broadly encompasses intact antibody molecules, which include intact polyclonal, monoclonal, monospecific, polyspecific, chimeric, deimmunized, humanized, human, primatized, single-chain, single-domain, synthetic and recombinant antibodies, and antibody fragments that have a desired activity or function.

The antibody of the present disclosure recognizes domain 1 of CD4. In certain embodiments, the antibody specifically binds to the CDR2 region in domain 1 of CD4.

The antibody of the present disclosure can be produced by any standard method. In some embodiments, the disclosed antibody is produced by immunizing an animal (e.g., mouse, dog, guinea pig, pig, goat, horse, etc.) with a recombinant CD4 protein, fragments of recombinant CD4 protein, or cells expressing CD4 on the surface. Alternatively, the antibody can be chemically synthesized.

In certain embodiments, the antibody is produced by immunizing an animal with a peptide containing the amino acid sequence of domain 1 of CD4. For example, polyclonal antibodies can be produced by immunizing an animal with a peptide or combination of peptides containing the amino acid sequence of the CDR2 region of CD4 domain 1. In some embodiments, the peptide contains aa39-66 of CD4, which is also known to as the HIV receptor complex ("HIV RC"), as HIV binds to this portion of CD4. In a specific embodiment, the HIV RC peptide is made cyclic through a disulfide bond.

In some embodiments, polyclonal antibodies are produced by immunizing an animal with the cyclic HIV RC peptide. The term "anti-HIV RC polyclonal antibodies", as used herein, refers to immune sera directed against a cyclic peptide containing aa39-66 of the CDR2 region of CD4 domain 1.

In other embodiments, the antibody is produced by immunizing an animal with CD4 positive cells. For example, in certain embodiments, the antibody was produced by immunizing BALB/c mice with intact, uninfected CD4+ human HPB-ALL cells, a T-acute lymphoblastic leukemia cell line. This antibody is discussed in further detail in U.S. Pat. Nos. 5,912,176 and 6,090,388 by Wang and the journal article by Wang et al., 1999, all of which are incorporated by reference in their entireties.

In other embodiments, the antibody contains heavy and light chain amino acid sequences of those contained in the Sequence Listing. The present disclosure encompasses homologues and functional analogues of an antibody containing the amino acid sequences contained in the Sequence Listing.

A functional analogue of the disclosed antibody includes sequence variants and homologues that retain substantially the same functional characteristics (binding recognition, binding affinity, etc.) as the original antibody. For example, an antibody variant that is a functional analogue or homologue can have a conservative substitution in an amino acid position; a change in overall charge; a covalent attachment to another moiety; or small additions, insertions, deletions or conservative substitutions and/or any combination thereof. Thus, variant antibodies functional analogues and homologues of the antibodies will recognize and bind to CD4 and can be used to treat HIV in subjects.

In one embodiment, a functional analogue or homologue of the antibody generally has at least about 50% sequence identity to an antibody containing an amino acid sequence disclosed in the Sequence Listing. In variations of this embodiment, a functional analogue or homologue of the antibody has at least about 50%, about 75%, about 80%, about 85%, about 90%, about 95%, or about 99% identity to an antibody containing an amino acid sequence disclosed in the Sequence Listing.

Conservative substitutions are when one amino acid residue is substituted for another amino acid residue with similar chemical properties. For example, the nonpolar (hydrophobic) amino acids include alanine, leucine, isoleucine, valine, proline, phenylalanine, tryptophan and methionine; the polar neutral amino acids include glycine, serine, threonine, cysteine, tyrosine, asparagine, and glutamine; the positively charged (basic) amino acids include arginine, lysine and histidine; and the negatively charged (acidic) amino acids include aspartic acid and glutamic acid.

In another embodiment, a functional analogue of the antibody can be modified by amino acid additions or deletions to the N-terminus, C-terminus, and/or by insertions into the middle of the sequence. In various embodiments of the invention, additions or deletions are to the N-terminus or C-terminus of the peptide. Additions or deletions can be of 1, 2, 3, 4, 5, 6, 7, 8, 9, 10, 11, 12, 13, 14, 15, 16, 17, 18, 19, or 20 amino acid residues. Such additions or deletions may constitute amino acid sequences that are not present in the sequences contained in the Sequence Listing do not alter the general functional properties of the antibody.

In certain embodiments, the antibody of the present disclosure is tagged or labeled with a chemical. For example, the antibody can be labeled with biotin, spacer arms, probes (e.g., FITC, PE, TRITC, DyLight Fluors, Alexa, GFP, R-Phycoerythrin, quantum dots, etc.), enzyme conjugates, and combinations thereof. In a specific embodiment, the antibody is labeled with a biotin or fluorescent probe.

In specific embodiments, the antibody can be modified through a process known as deimmunization. The term "deimmunization", as used herein, generally refers to a process for modifying portions of an antibody so that it can be administered to an animal without triggering an immune response within the animal. Specifically, deimmunization involves a process for locating and removing portions of the amino acid sequence of the antibody that would be immunogenic (e.g., T-cell epitopes) in the particular animal that is being administered the antibody. This process can be accomplished through the combined use of immunological and molecular biology techniques. This process has been described previously (e.g., Jones, T. D., et al. 2009). In the case of deimmunization of antibodies, mutations to remove T-cell epitopes can generally be introduced without significantly reducing the binding affinity of the antibody.

The term "humanized", as used herein, refers to an antibody that was originally produced by a non-human species whose protein sequence has been modified (deimmunized), in a manner that removes the immunogenicity of the antibody when it is administered to a human. In certain embodiments, the disclosed antibody is deimmunized for human use by replacing the constant regions with human constant regions and/or by expression of genes encoding these antibodies in mammalian cells.

In certain embodiments, the disclosed antibody has heavy and light chain amino acid sequences of those shown in Table 4.

The term "mAb B4" or "B4" or "murine B4" as used herein, refers to a murine monoclonal antibody having amino acid sequences of the CDR1, 2, 3 regions for the heavy and light chains of SEQ ID NOs: 1-6, respectively (Table 4). This murine monoclonal antibody has been shown to recognize CD4 and can inhibit HIV entry. The structural and functional characteristics of this antibody are discussed in further detailed in the Examples that follow.

Figure 4:
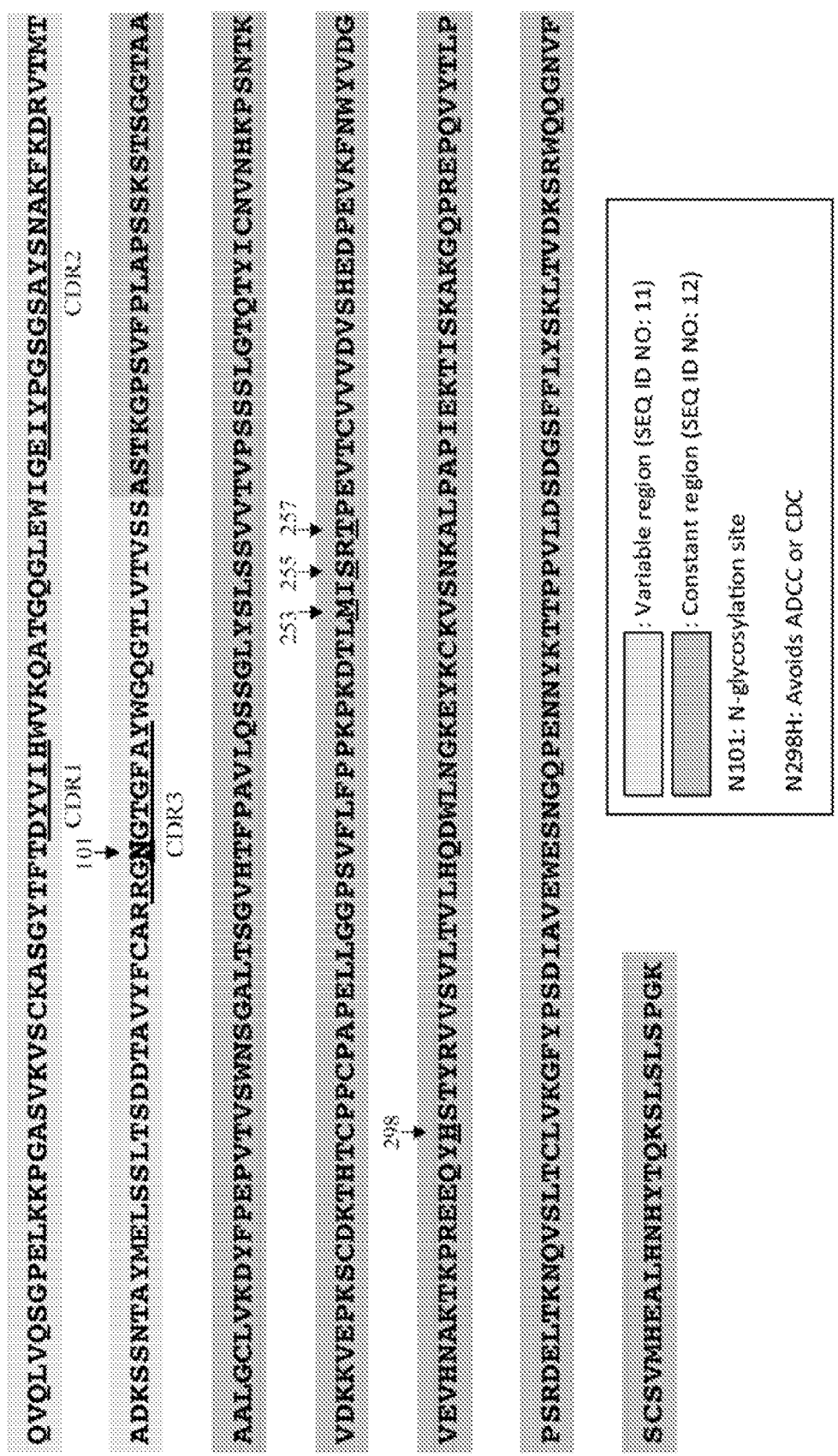

The term "mAb dB4" or "dB4", as used herein, refers to the human deimmunized antibody derived from mAb B4. The human deimmunized mAb dB4 has the amino acid sequences of the CDR1, 2, 3 regions for the heavy and light chains of SEQ ID NOs: 1-6, respectively (Table 4). In some embodiments, the light chain of mAb dB4 has the amino acid sequence of SEQ ID NO: 8, as depicted in FIG. 5. In some embodiments, the heavy chain of mAb dB4 has the amino acid sequence of SEQ ID NO: 7, as depicted in FIG. 4. In variant embodiments, the heavy chain of mAb dB4 has the amino acid sequence of SEQ ID NO: 9, as depicted in FIG. 6. MAb B4 can be deimmunized by any appropriate method known in the field. In one embodiment, mAb B4 is deimmunized for human use according to the method described in U.S. Pat. Nos. 7,501,494 and 7,872,110, which are incorporated by references in their entireties. In a particular embodiment, the human deimmunized mAb dB4 is produced by removing and replacing the constant regions of the murine antibody ($C_H$ and $C_\kappa$) of mAb B4 and with the constant regions of human IgG1. MAb dB4 encompasses the dB4 produced by any suitable cellular clone. In a specific embodiment, mAb dB4 is produced by clone 7.

The term "mAb dB4C7" or "dB4C7", as used herein, refers to mAb dB4 expressed by clone 7 containing the recombinant genes B4DIVHv1/VK1CHO#7 that was described previously in U.S. Pat. Nos. 7,501,494 and 7,872,110, which are incorporated by references in their entireties. The C7 clone has been shown to produce high quantities of mAb dB4 antibody. In particular, mAb B4C7 is a human deimmunized antibody with a light chain having the amino acid sequence of SEQ ID NO: 8 (FIG. 5) and a heavy chain having the amino acid sequence of SEQ ID NO: 7 (FIG. 4). Additionally, the Asn (N) residue at position 298 in mAb dB4C7 has been substituted with His (H), to remove the N-glycosylation site, thus eliminating the IgG mediated complement dependent cytotoxicity (CdC) to prevent depletion of CD4 positive T cells in the presence of antibody B4.

The term "UB-421", as used herein, refers to the mAb dB4C7 that is used in a suitable form to be administered to human subjects.

The antibody of the present disclosure can also be described by its interesting and unique functional characteristics.

For example, the disclosed antibody exerts potent competitive HIV entry inhibition through its binding to domain 1 of CD4. In particular, the disclosed antibody has nearly 100% maximum percent inhibition (MPI) in all Env pseudotype viruses tested, with $IC_{50}$s clustered around two concentrations; one between 0.01 to 1 µg/mL and the second one around 10 µg/mL. The binding activity of the disclosed antibody is about two logs higher (i.e. 100× tighter binding) than the CD4 binding affinity exhibited by HIV gp120 envelope protein. Additionally, the mean Kd of the disclosed antibody was estimated to be $5.6 \times 10^{-11}$ M (range: 3.1 to $8.1 \times 10^{-11}$ M), and the Bmax was estimated to be $1.2 \times 10^6$ Ab per cell (range: $0.93-1.4 \times 10^6$).

The competitive inhibition property for the disclosed antibody has been shown in both cell-free and cell-to-cell systems. The disclosed antibody binds to CD4 receptors with an affinity at least 50-fold higher than that for HIV-1 envelope protein gp120 MN. Also, the disclosed antibody binds to CD4 with greater affinity and specificity compared to other commercially available antibodies, such as Leu3a.

The disclosed antibody can also inhibit antigen induced T cell proliferation and cytokine production (IL2 and IFN-gamma) of CD4 positive T cells, which is implicated in the pathogenic cycle of pyroptosis. Such high affinity monoclonal antibodies to CD4 inhibit antigen such as superantigen SEB (staphylococcal enterotoxin B, SEB) induced CD4 positive T cell activation and cytokine (e.g. IL2 and IFN-γ) production. Such antigen induced activation leading to cytokine production in quiescent CD4+ T cells having abortive HIV infection would lead to pyroptosis of these quiescent CD4+ T cells and nearby normal resting CD4 positive cells resulting in ensuing mass depletion of CD4+ T cells, thus AIDS.

The disclosed antibody also has the ability to reactivate resting CD4 positive T cells. This property is particularly useful for reactivating latent reservoirs of HIV in resting T cells to make these cells susceptible to treatment with antiretroviral agents. Such high affinity antibodies to CD4 are capable of activating resting HIV infected cells for the release of HIV. Reactivation of HIV infected resting CD4+ T cells allows combinational treatment incorporating antibody of the current invention with HAART in HIV infected patients leading to functional cure.

Additional structural and functional characteristics of the disclosed antibodies are provided in the Examples that follow.

Formulation

The present disclosure is also directed to pharmaceutical formulations that can be used for the prevention, treatment, and/or functional cure of HIV infection. In certain embodiments, the formulations contain antibodies directed against CD4. In specific embodiments, the present disclosure relates to pharmaceutical compositions comprising high affinity monoclonal antibodies to CD4 that are directed to sites within or nearby CDR2 region of CD4 domain 1. The binding activity ($EC_{50}$) of such antibodies is about two logs higher (i.e. 100× tighter binding) than the CD4 binding affinity exhibited by HIV gp120 envelope protein ($EC_{50}$ for gp120=97 nM).

Pharmaceutical formulations of the antibody proteins disclosed can be prepared by mixing an antibody protein with optional pharmaceutically acceptable carriers. Pharmaceutically acceptable carriers include solvents, dispersion media, isotonic agents and the like. The carrier can be liquid, semi-solid, e.g. pastes, or solid carriers. Examples of carriers include water, saline solutions or other buffers (such as phosphate, citrate buffers), oil, alcohol, proteins (such as serum albumin, gelatin), carbohydrates (such as monosaccharides, disaccharides, and other carbohydrates including glucose, sucrose, trehalose, mannose, mannitol, sorbitol or dextrins), gel, lipids, liposomes, resins, porous matrices, binders, fillers, coatings, stabilizers, preservatives, antioxidants including ascorbic acid and methionine, chelating agents such as EDTA; salt forming counter-ions such as sodium; non-ionic surfactants such as TWEEN™, PLURONICS™ or polyethylene glycol (PEG), or combinations thereof.

The formulation can contain more than one active compound. For example, the formulation can contain one or more antibody and/or one or more additional beneficial compound for preventing and treating HIV infections. The active ingredients can be combined with the carrier in any convenient and practical manner, e.g., by admixture, solution, suspension, emulsification, encapsulation, absorption and the like, and can be made in formulations such as tablets, capsules, powder (including lyophilized powder), syrup, suspensions that are suitable for injections, ingestions, infusion, or the like. Sustained-release preparations can also be prepared.

In certain embodiments, the pharmaceutical formulation contains mAb dB4C7 for human use. The pharmaceutical formulation containing mAb dB4C7 can be prepared in an appropriate buffer including, but not limited to, citrate, phosphate, Tris, BIS-Tris, etc. at a pH between 6.0 to 7.0 and can also contain excipients such as sugars (50 mM to 500 mM of sucrose, trehalose, mannitol, or mixtures thereof), surfactants (e.g., 0.025%-0.5% of TWEEN 20 or TWEEN 80), and/or other reagents. In a specific embodiment, the formulation contains mAb dB4C7 in 20 mM glycine, and 0.05% (v/v) TWEEN (polysorbate 20) in phosphate buffer saline (PBS), pH 6.5. In another specific embodiment, high concentration formulations of mAb dB4 were also prepared for use in certain applications including subcutaneous injections, which included 10 mM histidine.

The formulation can be prepared to contain various amounts of antibody. In general, formulations for administration to a subject contain between about 0.1 mg/mL to about 200 mg/mL. In certain embodiments, the formulations can contain between about 0.5 mg/mL to about 50 mg/mL; between about 1.0 mg/mL to about 50 mg/mL; between about 1 mg/mL to about 25 mg/mL; or between about 10 mg/mL to about 25 mg/mL of antibody. In specific embodiments, the formulations contain about 1.0 mg/mL, about 5.0 mg/mL, about 10.0 mg/mL, or about 25.0 mg/mL of antibody.

In specific embodiments, the present invention relates to pharmaceutical compositions comprising human, humanized or chimeric, monoclonal anti-CD4 antibodies targeting CDR2 region of domain 1 of CD4, with the above described binding characteristics which exhibit competitive HIV entry inhibition as well as activation of CD4+ T cells, as an immunotherapy in patients with HIV infection.

In another embodiment, the present invention relates to pharmaceutical compositions comprising monoclonal human, humanized or chimeric, anti-CD4 antibodies with the above described binding characteristics that serve as a monotherapy that can reduce viral load down to non-detectable level in treated subjects at a serum antibody level higher than 10 µg/mL.

In another embodiment, the present invention relates to pharmaceutical compositions comprising monoclonal human, humanized or chimeric, anti-CD4 antibodies with the above described binding characteristics that serve as a monotherapy that can reduce viral load down to nondetectable level in treated subjects at a serum antibody level higher than 10 µg/mL and maintained stable CD4 T cell counts during a 12-weeks treatment period.

In certain embodiments, the present invention relates to pharmaceutical compositions comprising monoclonal human, humanized or chimeric) anti-CD4 antibodies with the above described binding characteristics that when given, at a dose of about 10 mg/kg or higher on a weekly or biweekly schedule, as a monotherapy, such treatment can reduce viral load down to non-detectable level in treated subjects during a 12-weeks treatment period.

In yet another preferred embodiment, the present invention relates to pharmaceutical compositions comprising a monoclonal humanized anti-CD4 antibody with the above described binding characteristics as the key ingredient in an adjunct therapy with HAART, that when given, at about 10 mg/kg or higher on a weekly or biweekly schedule, to treatment naïve HIV patients, will lead to functional cure of the patients.

In yet another preferred embodiment, the present invention relates to pharmaceutical compositions comprising a monoclonal humanized anti-CD4 antibody with the above described binding characteristics as the key ingredient in an adjunct therapy with HAART, that when given, at about 10 mg/kg or higher on a weekly or biweekly schedule, to patients with stabilized viral load under HAART, will lead to functional cure of the patients.

Antiviral Agents

The present disclosure also includes antiviral agents that can be used in the methods for the treatment, prevention, and functional cure of HIV infection.

Antiviral agents include any agent (compound or biological) that is effective to inhibit the formation and/or replication of HIV in a mammal. Examples of antiviral agents include, but are not limited to, entry/fusion inhibitors (e.g., maraviroc, enfuvirtide); nucleoside reverse transcriptase inhibitors (NRTI) and nucleotide reverse transcriptase inhibitors (NtRTI) (e.g., zidovudine, abacavir, lamivudine, emtricitabine, and tenofovir); non-nucleoside reverse transcriptase inhibitors (NNRTI) (e.g., nevirapine, efavirenz, etravirine, and rilpivirine); integrase inhibitors also known as integrase nuclear strand transfer inhibitors or INSTIs (e.g., raltegravir, dolutegravir); protease inhibitors (e.g., saquinavir, saquinavir mesylate, fosamprenavir, tipranavir, lopinavir, indinavir, nelfinavir, amprenavir, ritonavir, darunavir, atazanavir, bevirimat, vivecon); viral maturation inhibitors; agents targeting the expression of HIV genes; agents targeting key host cell genes and gene products involved in HIV replication; and other anti-HIV agents; iRNA agents; antisense RNA; vectors expressing iRNA agents or antisense RNA; PNA and antiviral antibodies; and combinations thereof.

The antiviral agents can be used individually or in combination. Use of antiviral agents in combination is known as anti-retroviral therapy (ART), combination anti-retroviral therapy (cART) or highly active anti-retroviral therapy (HAART). Anti-retroviral (ARV) drugs are broadly classified by the phase of the retrovirus life-cycle that the drug inhibits. Typical combinations include 2 NRTIs as a "backbone" along with 1 NNRTI, PI or INSTI as a "base". In certain embodiments combinations of antiviral agents are used, such as COMBIVIR® (a combination of zidovudine and lamivudine), TRIZIVIR® (a combination of abacavir, lamivudine, and zidovudine), KALETRA® (a combination of lopinavir and ritonavir), EPIZCOM™ (a combination of abacavir and lamivudine), TRUVADA® (a combination of emtricitabine and tenofovir), ATRIPLA® (a combination of efavirenz, emtricitabine, and tenofovir), COMPLERA® (a combination of emtricitabine, rilpivirine, and tenofovir), STRIBILD® (a combination of dolutegravir and lamivudine), and TRIUMEQ® (a combination of abacavir, dolutegravir, and lamivudine).

Methods of Treatment, Prevention, and Functional Cure

The present disclosure is also directed to methods for the treatment, prevention, and functional cure of HIV infection. In certain embodiments, the formulations contain antibodies directed against CD4.

In a further aspect, the antibody disclosed herein, optionally provided in pharmaceutically acceptable carrier, can be employed for the treatment, prevention, and/or functional cure of HIV infection in a subject, as well as prevention of HIV transmission.

The term "treatment" of HIV infection refers to effective inhibition of the HIV infection so as to delay the onset, slow down the progression, reduce viral load, and/or ameliorate the symptoms caused by HIV infection. Treatment include both pre- and post-exposure to HIV.

The term "prevention" of HIV infection means the onset of HIV infection is delayed, and/or the incidence or likelihood of HIV infection is reduced or eliminated. The term "prevention" of HIV transmission means the incidence or likelihood of HIV being transmitted from one individual to another (e.g., from an HIV-positive woman to the child during pregnancy, labor or delivery, or breastfeeding) is reduced or eliminated.

The term "subject" refers to any primate subject, including human, rhesus, baboon, and chimpanzee subjects.

To treat and/or prevent HIV infection, a therapeutic amount of an antibody disclosed herein is administered to a subject in need.

The term "therapeutically effective amount" means the dosage required to effect an inhibition of HIV infection so as to treat and/or prevent HIV infection. The dosage of antibody depends on the disease state and other clinical factors, such as weight and condition of the subject, the subject's response to the therapy, the type of formulations and the route of administration. The precise dosage to be therapeutically effective and non-detrimental can be determined by those skilled in the art.

Generally, a suitable dose of an antibody for the administration to adult humans is in the range of about 3 to 50 mg/kg of the subject's body weight, with the typical initial range used being in the range of about 5 to 25 mg/kg of the subject's body weight. Suitable dosages also include about 5.0 mg/kg, about 10.0 mg/kg, or about 25.0 mg/kg of the patient's body weight.

The therapeutic compositions containing a human monoclonal antibody of this invention are conventionally administered intravenously, as by injection of a unit dose, for example. A unit dose generally refers to a therapeutic composition of the present invention which further refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

The method for the treatment, prevention, and/or functional cure of HIV infection in a subject includes administering to the subject an effective amount of a formulation containing the antibody. In certain embodiments, the formulation is provided to the subject in a single administration. In other embodiments, the formulation is provided to the subject in multiple administrations. When the formulation is provided in multiple administrations, the formulation can be administered once per day, once a week, bi-weekly (every other week), or once a month. In a specific embodiment, when the treatment schedule is once a week, the formulation is administered to the subject in a dosage of about 5.0 mg/kg of the subject's body weight. In another embodiment, when the treatment schedule is bi-weekly, the formulation is administered to the subject in a dosage of about 25.0 mg/kg of the subject's body weight.

In certain embodiments, formulations containing the monoclonal antibody show high safety factor and was well tolerated when subjects were given repeatedly on a weekly basis at 5 mg/kg or 25 mg/kg for a total of 8 weeks. In specific embodiments, the monoclonal antibody can be given to subjects within hours of HIV infection at 5 mg/kg to provide sterilizing cure of HIV infection. In other embodiments, the monoclonal antibody can be given to a subject within days after HIV infection at 5 mg/kg to provide a functional cure of HIV infection.

In certain embodiments, the present invention relates to pharmaceutical compositions comprising monoclonal human, humanized or chimeric, anti-CD4 antibodies with the above described binding characteristics that can be administered to HIV patients through IV or SC route as an immunotherapy for reduction of viral load. In specific embodiments, the present invention relates to pharmaceutical compositions comprising human, humanized or chimeric, monoclonal anti-CD4 antibodies targeting CDR2 region of domain 1 of CD4, with the above described binding characteristics which exhibit competitive HIV entry inhibition as well as activation of CD4+ T cells, as an immunotherapy in patients with HIV infection.

In other certain embodiments, the present invention relates to pharmaceutical compositions comprising monoclonal human, humanized or chimeric, anti-CD4 antibodies with the above described binding characteristics that can be administered to HIV patients through IV or SC route as an immunotherapy for reduction of viral load at a dose of about 10 mg/kg or higher on a weekly or biweekly schedule.

In another embodiment, the present invention relates to pharmaceutical compositions comprising monoclonal human, humanized or chimeric, anti-CD4 antibodies with the above described binding characteristics that serve as a monotherapy that can reduce viral load down to non-detectable level in treated subjects at a serum antibody level higher than 10 μg/mL.

In another embodiment, the present invention relates to pharmaceutical compositions comprising monoclonal human, humanized or chimeric, anti-CD4 antibodies with the above described binding characteristics that serve as a monotherapy that can reduce viral load down to non-detectable level in treated subjects at a serum antibody level higher than 10 μg/mL and maintained stable CD4 T cell counts during a 12-weeks treatment period.

In another embodiment, the present invention relates to pharmaceutical compositions comprising monoclonal human, humanized or chimeric) anti-CD4 antibodies with the above described binding characteristics that when given, at a dose of about 10 mg/kg or higher on a weekly or biweekly schedule, as a monotherapy, such treatment can reduce viral load down to non-detectable level in treated subjects during a 12-weeks treatment period.

In another embodiment, the present invention relates to pharmaceutical compositions comprising monoclonal human, humanized or chimeric, anti-CD4 antibodies with the above described binding characteristics that when given, at a dose of about 10 mg/kg or higher on a weekly or biweekly schedule, as a monotherapy, such treatment can reduce viral load down to non-detectable level in treated subjects with no viral load rebound as long the serum antibody level is higher than 10 μg/mL.

In another embodiment, the present invention relates to pharmaceutical compositions comprising a monoclonal humanized anti-CD4 antibody with the above described binding characteristics as the key ingredient in an adjunct therapy with HAART, that when given, at about 10 mg/kg or higher on a weekly or biweekly schedule, to treatment naïve HIV patients, will lead to functional cure of the patients.

In another embodiment, the present invention relates to pharmaceutical compositions comprising a monoclonal humanized anti-CD4 antibody with the above described binding characteristics as the key ingredient in an adjunct therapy with HAART, that when given, at about 10 mg/kg or higher on a weekly or biweekly schedule, to patients with stabilized viral load under HAART, will lead to functional cure of the patients.

In another embodiment, the present invention relates to pharmaceutical compositions comprising a monoclonal humanized anti-CD4 antibody with the above described binding characteristics that can be administered in either IV or SC route, to patients who failed HAART treatment in an adjunct therapy to HAART at a dose of about 10 mg/kg or higher on a weekly or biweekly schedule, leading to further viral reduction.

In another embodiment, the present invention relates to pharmaceutical compositions comprising a monoclonal humanized anti-CD4 antibody with the above described binding characteristics that can be administered, in either IV or SC route, as the key ingredient in an HAART replacement therapy, whereby each treatment cycle begins with anti-CD4 antibody treatment for 2 to 4 months as a treatment holiday for patients experiencing stabilized undetectable viral load under HAART followed by HAART treatment over one to four or more cycles leading to functional cure.

In another embodiment, the present invention relates to pharmaceutical compositions comprising a monoclonal humanized anti-CD4 antibody with the above described binding characteristics that can be administered, in either IV or SC route, as the key ingredient in an HAART replacement therapy, whereby each treatment cycle begins with anti-CD4 antibody treatment for 2 to 4 months for treatment naïve HIV patients followed by 2 to 4 months of HAART treatment over one to four or more cycles leading to functional cure.

In another embodiment, the present invention relates to pharmaceutical compositions comprising a monoclonal humanized anti-CD4 antibody with the above described binding characteristics that can be administered, in either IV or SC route, as the key ingredient in an HAART replacement therapy, whereby each treatment cycle begins with anti-CD4 antibody treatment for 2 to 4 months as a treatment holiday for patients experiencing stabilized undetectable viral load under HAART followed by HAART treatment over one to four or more cycles at a dose of about 5 mg/kg or higher on a weekly or biweekly schedule, leading to functional cure.

In another embodiment, the present invention relates to pharmaceutical compositions comprising a monoclonal humanized anti-CD4 antibody with the above described binding characteristics that can be administered, in either IV or SC route, as the key ingredient in an HAART replacement therapy, whereby each treatment cycle begins with anti-CD4 antibody treatment for 2 to 4 months for treatment naïve HIV patients followed by 2 to 4 months of HAART treatment over one to four or more cycles at a dose of about 5 mg/kg or higher on a weekly or biweekly schedule, leading to functional cure.

In another embodiment, the present invention relates to pharmaceutical compositions comprising a monoclonal humanized anti-CD4 antibody with the above described binding characteristics as the key ingredient in an adjunct therapy with HAART, that when given, at about 10 mg/kg or higher on a weekly or biweekly schedule, to treatment naïve HIV patients, will lead to functional cure of the patients.

In another embodiment, the present invention relates to pharmaceutical compositions comprising a monoclonal humanized anti-CD4 antibody with the above described binding characteristics as the key ingredient in an adjunct therapy with HAART, that when given, at about 10 mg/kg or higher on a weekly or biweekly schedule, to patients with stabilized viral load under HAART, will lead to functional cure of the patients.

In another embodiment, the present invention relates to pharmaceutical compositions comprising a monoclonal humanized anti-CD4 antibody with the above described binding characteristics that can be administered in either IV or SC route, to patients who failed HAART treatment in an adjunct therapy to HAART at a dose of about 10 mg/kg or higher on a weekly or biweekly schedule, leading to further viral reduction.

In another embodiment, the present invention relates to pharmaceutical compositions comprising a monoclonal humanized anti-CD4 antibody with the above described binding characteristics that can be administered, in either IV or SC route, as the key ingredient in an adjunct therapy with HAART, in an intermittent mode beginning with a treatment period for 2 to 4 months and a treatment holiday for 1 to 2 months per cycle over one to four or more cycles, to treatment naïve HIV patients as an adjunct therapy in an intensive HAART treatment mode, leading to functional cure of the patients.

In another embodiment, the present invention relates to pharmaceutical compositions comprising a monoclonal humanized anti-CD4 antibody with the above described binding characteristics that can be administered, in either IV or SC route, as the key ingredient in an adjunct therapy with HAART, in an intermittent mode beginning with a treatment period for 2 to 4 months and a treatment holiday for 1 to 2 months per cycle over one to four or more cycles, at a dose of about 5 mg/kg or higher on a weekly or biweekly schedule, to treatment naïve HIV patients as an adjunct therapy in an intensive HAART treatment mode, leading to functional cure of the patients.

In another embodiment, the present invention relates to pharmaceutical compositions comprising a monoclonal humanized anti-CD4 antibody with the above described binding characteristics that can be administered, in either IV or SC route, as the key ingredient in an adjunct therapy with HAART, in an intermittent mode beginning with a treatment period for 2 to 4 months and a treatment holiday for 1 to 2 months per cycle over one to four or more cycles, at a dose of about 5 mg/kg or higher on a weekly or biweekly schedule, to patients experiencing stabilized undetectable viral load under HAART, as an adjunct therapy in an intensive HAART treatment mode, leading to functional cure of the patients.

In another embodiment, the present invention relates to pharmaceutical compositions comprising monoclonal human, humanized or chimeric, anti-CD4 antibodies with the above described binding characteristics that can be administered to HIV patients through IV or SC route as an immunotherapy for reduction of viral load.

In another embodiment, the present invention relates to pharmaceutical compositions comprising monoclonal human, humanized, or chimeric anti-CD4 antibodies with the above described binding characteristics that can be administered to HIV patients through IV or SC route as an immunotherapy for reduction of viral load at a dose of about 5 mg/kg or higher on a weekly or biweekly schedule.

Specific Embodiments

The present disclosure encompasses the following specific embodiments:

(1) A method of treating a subject exposed to HIV infection comprising: a) administering a pharmacologically effective amount of a monoclonal antibody to CD4 comprising: a CDR1 of heavy chain of murine antibody B4 of SEQ ID NO: 1, a CDR2 of heavy chain of murine antibody B4 of SEQ ID NO: 2, a CDR3 of heavy chain of murine antibody B4 of SEQ ID NO: 3, a CDR1 of light chain of murine antibody B4 of SEQ ID NO: 4, a CDR2 of light chain of murine antibody B4 of SEQ ID NO: 5, and a CDR3 of light chain of murine antibody B4 of SEQ ID NO: 6; b) evaluating the HIV RNA level per milliliter of blood of the subject after step (a).

(2) The method of (1), wherein the heavy chain sequence of the antibody comprises SEQ ID NO: 7.

(3) The method of (1), wherein the heavy chain sequence of the antibody comprises SEQ ID NO: 9.

(4) The method of (1), wherein the light chain sequence of the antibody comprises SEQ ID NO: 8.

(5) The method of (1), wherein the heavy chain sequence of the antibody comprises SEQ ID NO: 7 and the light chain sequence of the antibody comprises SEQ ID NO: 8.

(6) The method of (1), wherein the heavy chain sequence of the antibody comprises SEQ ID NO: 9 and the light chain sequence of the antibody comprises SEQ ID NO: 8.

(7) The method of (1), wherein the administering step (a) is performed within 24 hours of exposure to HIV infection.

(8) The method of (1), wherein the administering step (a) is performed within 48 days of exposure to HIV infection.

(9) The method of (1), wherein the pharmacologically effective amount of the monoclonal antibody is administered at serum level of about 10 µg/ml or more on a weekly or biweekly schedule during a 12-week period.

(10) The method of (1), wherein an HIV RNA level per milliliter value of less than 1 copy/ml is considered eradication of the virus.

(11) The method of (1), wherein an HIV RNA level per milliliter value between 1 to less than 50 copy/ml is considered a functional cure of the virus.

(12) A method of treating a patient having HIV comprising: a) administering a pharmacologically effective amount of a composition comprising: a monoclonal antibody to CD4 comprising: a CDR1 of heavy chain of murine antibody B4 of SEQ ID NO: 1, a CDR2 of heavy chain of murine antibody B4 of SEQ ID NO: 2, a CDR3 of heavy chain of murine antibody B4 of SEQ ID NO: 3, a CDR1 of light chain of murine antibody B4 of SEQ ID NO: 4, a CDR2 of light chain of murine antibody B4 of SEQ ID NO: 5, and a CDR3 of light chain of murine antibody B4 of SEQ ID NO: 6; and a highly active antiretroviral therapy (HAART); and b) evaluating the HIV RNA level per milliliter of blood of the subject after step (a).

(13) The method of (12), wherein the heavy chain sequence of the antibody comprises SEQ ID NO: 7.

(14) The method of (12), wherein the heavy chain sequence of the antibody comprises SEQ ID NO: 9.

(15) The method of (12), wherein the light chain sequence of the antibody comprises SEQ ID NO: 8.

(16) The method of (12), wherein the heavy chain sequence of the antibody comprises SEQ ID NO: 7 and the light chain sequence of the antibody comprises SEQ ID NO: 8.

(17) The method of (12), wherein the heavy chain sequence of the antibody comprises SEQ ID NO: 9 and the light chain sequence of the antibody comprises SEQ ID NO: 8.

(18) The method of (12), wherein the pharmacologically effective amount of the antibody is administered at a dose of 10 mg/kg or higher on a weekly or biweekly basis.

(19) The method of (12), wherein the antibody is administered in an intermittent mode as an adjunct therapy in HAART treatment mode.

(20) The method of (19), wherein the antibody is administered for a period of about 2 to 4 months as an adjunct therapy in HAART treatment mode followed by an antibody treatment holiday for 1 to 2 months in HAART treatment mode per cycle.

(21) The method of (20), wherein the intermediate mode continues over one to four cycles.

(22) A method of treating a patient having HIV comprising: a) reducing latent HIV reservoirs in a patient infected with HIV by activating HIV virus expression and apoptosis of latently infected cells in the patient; and b) administering a pharmacologically effective amount of HAART to the patient.

(23) The method of (22), wherein the activating HIV virus expression and apoptosis of latently infected cells in the patient is performed by administering a pharmacologically effective amount of a monoclonal antibody to CD4 to the patient comprising: a CDR1 of heavy chain of murine antibody B4 of SEQ ID NO: 1, a CDR2 of heavy chain of murine antibody B4 of SEQ ID NO: 2, a CDR3 of heavy chain of murine antibody B4 of SEQ ID NO: 3, a CDR1 of light chain of murine antibody B4 of SEQ ID NO: 4, a CDR2 of light chain of murine antibody B4 of SEQ ID NO: 5, and a CDR3 of light chain of murine antibody B4 of SEQ ID NO: 6.

(24) The method of (22), wherein the activating HIV virus expression and apoptosis of latently infected cells in the patient is performed by administering a histone deacetylase (HDAC) inhibitor to the patient.

(25) A method of treating a subject exposed to HIV infection comprising: a) administering a pharmacologically effective amount of a monoclonal antibody having a high affinity to a CDR2-like domain region of CD4; and b) evaluating the HIV RNA level per milliliter of blood of the subject after step (a).

(26) The method of (25), wherein the heavy chain sequence of the antibody comprises SEQ ID NO: 7.

(27) The method of (25), wherein the heavy chain sequence of the antibody comprises SEQ ID NO: 9.

(28) The method of (25), wherein the light chain sequence of the antibody comprises SEQ ID NO: 8.

(29) The method of (25), wherein the heavy chain sequence of the antibody comprises SEQ ID NO: 7 and the light chain sequence of the antibody comprises SEQ ID NO: 8.

(30) The method of (25), wherein the heavy chain sequence of the antibody comprises SEQ ID NO: 9 and the light chain sequence of the antibody comprises SEQ ID NO: 8.

(31) The method of (25), wherein the administering step (a) is performed within 24 hours of exposure to HIV infection.

(32) The method of (25), wherein the administering step (a) is performed within 48 days of exposure to HIV infection.

(33) The method of (25), wherein the pharmacologically effective amount of the monoclonal antibody is administered at serum level of about 10 µg/ml or more on a weekly or biweekly schedule during a 12-week period.

(34) The method of (25), wherein an HIV RNA level per milliliter value of less than 1 copy/ml is considered eradication of the virus.

(35) The method of (25), wherein an HIV RNA level per milliliter value between 1 to less than 50 copy/ml is considered a functional cure of the virus.

Additional Specific Embodiments (1) A method for treating a subject exposed to HIV comprising: administering to the subject a pharmacologically effective amount of an antibody directed against domain 1 of CD4.

(2) The method according to (1), wherein the antibody specifically binds to the CDR2 region in domain 1 of CD4.

(3) The method according to (2), wherein the antibody is a monoclonal antibody, a polyclonal antibody, or a combination thereof.

(4) The method according to (2), wherein the antibody is a humanized monoclonal antibody.

(5) The method according to (4), wherein the humanized monoclonal antibody comprises:
a heavy chain amino acid sequence comprising: CDR1 of SEQ ID NO: 1, CDR2 of SEQ ID NO: 2, and CDR3 of SEQ ID NO: 3; and a light chain amino acid sequence comprising: CDR1 of SEQ ID NO: 4, CDR2 of SEQ ID NO: 5, and CDR3 of SEQ ID NO: 6.

(6) The method according to (4), wherein the humanized monoclonal antibody comprises: a heavy chain comprising an amino acid sequence of SEQ ID NO: 11; and a light chain comprising an amino acid sequence of SEQ ID NO: 13.

(7) The method according to (4), wherein the humanized monoclonal antibody comprises: a heavy chain comprising an amino acid sequence of SEQ ID NO: 10; and a light chain comprising an amino acid sequence of SEQ ID NO: 8.

(8) The method according to (7), wherein the heavy chain comprising an amino acid sequence of SEQ ID NO: 7.

(9) The method according to (8), wherein the humanized antibody is administered to the subject prior to exposure to HIV.

(10) The method according to (8), wherein the humanized antibody is administered to the subject after exposure to HIV.

(11) The method according to (10), wherein the humanized antibody is administered within 48 hours after exposure to HIV.

(12) The method according to (8), wherein the humanized antibody is administered to the subject at a dosage of at least about 5 mg/kg body weight.

(13) The method according to (12), wherein the humanized antibody is administered to the subject multiple times.

(14) The method according to (13), wherein the humanized antibody is administered to the subject in a weekly or bi-weekly interval.

(15) The method according to (13), further comprising a step of administering an antiviral agent to the subject.

(16) The method according to (15), wherein the antiviral agent is a highly active antiretroviral therapy (HAART).

(17) The method according to (16), wherein HAART comprises a nucleoside analogue reverse transcriptase inhibitor in combination with a protease inhibitor or a non-nucleoside reverse transcriptase inhibitor.

(18) The method according to (16), wherein the humanized antibody is administered concurrently with HAART.

(19) The method according to (16), wherein the humanized antibody and HAART are administered to the subject over the course of a cycle, wherein the cycle comprises: (i) administering the humanized antibody to the subject for a period of four months in a weekly or bi-weekly interval followed by a two month treatment holiday; and (ii) administering HAART to the subject continuously during the six-month period in (i).

(20) The method according to (19), wherein the subject is treated over the course of two cycles.

(21) A method for treating a subject with HIV infection, comprising administering to the subject a treatment regimen comprising: (a) a pharmacologically effective amount of an antibody directed against domain 1 of CD4; and (b) a highly active antiretroviral therapy (HAART).

(22) The method according to (21), wherein the antibody specifically binds to the CDR2 region in domain 1 of CD4.

(23) The method according to (22), wherein the antibody is a monoclonal antibody, a polyclonal antibody, or a combination thereof.

(24) The method according to (22), wherein the antibody is a humanized monoclonal antibody.

(25) The method according to (24), wherein the humanized monoclonal antibody comprises: a heavy chain amino acid sequence comprising: CDR1 of SEQ ID NO: 1, CDR2 of SEQ ID NO: 2, and CDR3 of SEQ ID NO: 3; and a light chain amino acid sequence comprising: CDR1 of SEQ ID NO: 4, CDR2 of SEQ ID NO: 5, and CDR3 of SEQ ID NO: 6.

(26) The method according to (24), wherein the humanized monoclonal antibody comprises: a heavy chain comprising an amino acid sequence of SEQ ID NO: 11; and a light chain comprising an amino acid sequence of SEQ ID NO: 13.

(27) The method according to (24), wherein the humanized monoclonal antibody comprises: a heavy chain comprising an amino acid sequence of SEQ ID NO: 10; and a light chain comprising an amino acid sequence of SEQ ID NO: 8.

(28) The method according to (27), wherein the humanized antibody is administered to the subject at a dosage of at least about 5 mg/kg body weight.

(29) The method according to (21), wherein the treatment regimen is administered to the subject over the course of a cycle, wherein the cycle comprises: (i) administering the humanized antibody to the subject for a period of four months in a weekly or bi-weekly interval followed by a two month treatment holiday; and (ii) administering HAART to the subject continuously during the six-month period in (i).

(30) The method according to (29), wherein the subject is treated with two cycles.

Further Specific Embodiments (1) A composition for treating a subject exposed to HIV comprising: a pharmacologically effective amount of an antibody directed against domain 1 of CD4.

(2) The composition according to (1), wherein the antibody specifically binds to the CDR2 region in domain 1 of CD4.

(3) The composition according to (2), wherein the antibody is a monoclonal antibody, a polyclonal antibody, or a combination thereof.

(4) The composition according to (2), wherein the antibody is a humanized monoclonal antibody.

(5) The composition according to (4), wherein the humanized monoclonal antibody comprises:
a heavy chain amino acid sequence comprising: CDR1 of SEQ ID NO: 1, CDR2 of SEQ ID NO: 2, and CDR3 of SEQ ID NO: 3; and a light chain amino acid sequence comprising: CDR1 of SEQ ID NO: 4, CDR2 of SEQ ID NO: 5, and CDR3 of SEQ ID NO: 6.

(6) The composition according to (4), wherein the humanized monoclonal antibody comprises: a heavy chain comprising an amino acid sequence of SEQ ID NO: 11; and a light chain comprising an amino acid sequence of SEQ ID NO: 13.

(7) The composition according to (4), wherein the humanized monoclonal antibody comprises: a heavy chain comprising an amino acid sequence of SEQ ID NO: 10; and a light chain comprising an amino acid sequence of SEQ ID NO: 8.

(8) The composition according to (7), wherein the heavy chain comprising an amino acid sequence of SEQ ID NO: 7.

(9) The composition according to (8), wherein the humanized antibody is administered to the subject prior to exposure to HIV.

(10) The composition according to (8), wherein the humanized antibody is administered to the subject after exposure to HIV.

(11) The composition according to (10), wherein the humanized antibody is administered within 48 hours after exposure to HIV.

(12) The composition according to (8), wherein the humanized antibody is administered to the subject at a dosage of at least about 5 mg/kg body weight.

(13) The composition according to (12), wherein the humanized antibody is administered to the subject multiple times.

(14) The composition according to (13), wherein the humanized antibody is administered to the subject in a weekly or bi-weekly interval.

(15) The composition according to (13), wherein the subject is treated (or administered) with an antiviral agent.

(16) The composition according to (15), wherein the antiviral agent is a highly active antiretroviral therapy (HAART).

(17) The composition according to (16), wherein HAART comprises a nucleoside analogue reverse transcriptase inhibitor in combination with a protease inhibitor or a non-nucleoside reverse transcriptase inhibitor.

(18) The composition according to (16), wherein the humanized antibody is administered concurrently with HAART.

(19) The composition according to (16), wherein the humanized antibody and HAART are administered to the subject over the course of a cycle, wherein the cycle comprises: (i) administering the humanized antibody to the subject for a period of four months in a weekly or bi-weekly interval followed by a two month treatment holiday; and (ii) administering HAART to the subject continuously during the six-month period in (i).

(20) The composition according to (18), wherein the subject is treated over the course of two cycles.

(21) A composition for treating a subject with HIV infection, comprising: (a) a pharmacologically effective amount of an antibody directed against domain 1 of CD4; and (b) a highly active antiretroviral therapy (HAART).

(22) The composition according to (21), wherein the antibody specifically binds to the CDR2 region in domain 1 of CD4.

(23) The composition according to (22), wherein the antibody is a monoclonal antibody, a polyclonal antibody, or a combination thereof.

(24) The composition according to (22), wherein the antibody is a humanized monoclonal antibody.

(25) The composition according to (24), wherein the humanized monoclonal antibody comprises: a heavy chain amino acid sequence comprising: CDR1 of SEQ ID NO: 1, CDR2 of SEQ ID NO: 2, and CDR3 of SEQ ID NO: 3; and a light chain amino acid sequence comprising: CDR1 of SEQ ID NO: 4, CDR2 of SEQ ID NO: 5, and CDR3 of SEQ ID NO: 6.

(26) The composition according to (24), wherein the humanized monoclonal antibody comprises: a heavy chain comprising an amino acid sequence of SEQ ID NO: 11; and a light chain comprising an amino acid sequence of SEQ ID NO: 13.

(27) The composition according to (24), wherein the humanized monoclonal antibody comprises: a heavy chain comprising an amino acid sequence of SEQ ID NO: 10; and a light chain comprising an amino acid sequence of SEQ ID NO: 8.

(28) The composition according to (27), wherein the humanized antibody is administered to the subject at a dosage of at least about 5 mg/kg body weight.

(29) The composition according to (21), wherein the treatment regimen is administered to the subject over the course of a cycle, wherein the cycle comprises: (i) administering the humanized antibody to the subject for a period of four months in a weekly or bi-weekly interval followed by a two month treatment holiday; and (ii) administering HAART to the subject continuously during the six-month period in (i).

(30) The composition according to (18), wherein the subject is treated with two cycles.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all amino acid sizes, and all molecular weight or molecular mass values, given for polypeptides are approximate, and are provided for description. Although methods and materials similar or equivalent to those described herein can be used in the practice or testing of the disclosed method, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

The following illustrative explanations of the figures and related examples are provided to facilitate understanding of certain terms used frequently herein, particularly in the examples. The explanations are provided as a convenience and are not limitative of the invention.

Example 1

Immunological and Functional Properties of MAb B4

Monoclonal antibody B4 (mAb B4) is a monoclonal antibody that recognizes a complex HIV receptor site on the T cell surface (CD4). MAb B4 can influence and interfere with CD4's interaction with HIV co-receptors. MAb B4 preferentially neutralized primary HIV-1 isolates.

The information below summarizes the discovery and preliminary characterization studies of murine mAb B4 including data excerpted from two US patents (U.S. Pat. Nos. 5,912,176 and 6,090,388 by Wang) and the journal article by Wang et al., 1999, all of which are incorporated by reference in their entireties.

1. Murine Monoclonal Antibody Derived from HPB-ALL Immunization

MAb B4 was obtained by immunizing BALB/c mice with intact, uninfected CD4+ human HPB-ALL cells, a T-acute lymphoblastic leukemia cell line.

A novel class of anti-CD4 antibodies, represented by mAb B4, were obtained having specificity for CD4 on the cell surface and with broad neutralizing activity against primary isolates of HIV-1.

2. Characterization of the mAb B4 Recognition Site

MAb B4 has been found to preferentially recognize membrane-bound CD4 on the surface of cells compared to recombinant soluble CD4 (rsCD4).

MAb B4 binding to membrane-bound CD4 prior to exposure of HIV has been shown to block subsequent attachment of gp120 and whole virus to CD4. However, membrane-bound CD4 that has been bound to gp120 prior to exposure to the antibody can still bind mAb B4. Thus, mAb B4 can affect the binding of gp120 to membrane-bound CD4, but gp120 does not affect the binding of mAb B4 to CD4.

The recognition site of mAb B4 is distinctive from that of other well-studied anti-CD4 monoclonal antibodies, including mAbs Leu3a and OKT4A, which recognize CD4 domain 1 (Chiba, Y. 1992; Jameson, B. D., et al., 1988) and mAb 5A8, which recognizes CD4 domain 2 (Burkly, et al., 1992).

3. In Vitro Neutralization Activity of mAb B4

Murine mAb B4 is not, by common definition, a neutralizing antibody. Instead, mAb B4 inhibits viral entry by coating the host cell receptor rather than by attaching to the virus. MAb B4's effect on HIV infection can be readily observed by viral neutralization assays used in the field (e.g., MT-2 Microplaque Neutralization Assay (Sawyer et al., 1994)). The neutralization activity of murine mAb B4 was evaluated by our collaborator Dr. Carl Hanson (California Department of Health Services) and was also independently evaluated in the laboratories of Dr. John Mascola, (Henry Jackson Foundation, WRAIR), Dr. David Montefiori (Duke University) and Dr. Malcolm Martin (NIAID). The following HIV neutralizing features, extensively characterized from 1995 to 2010, are associated with mAb B4:

1. PBMC-grown primary isolates are more sensitive to neutralization by mAb B4 than T cell line-adapted isolates HIV-1$_{IIIB}$ and HIV-1$_{MN}$.
2. mAb B4 neutralizes infection by primary isolates of co-receptor usage CCR5/CXCR4 (dual) and CCR5.
3. mAb B4 has low activity against T cell line-adapted HIV-1 isolates of CXCR4 co-receptor usage.
4. mAb B4 neutralizes a diverse range of Syncytial Inducing (SI) and Non-Syncytial Inducing (NSI) primary isolates representing HIV-1 subtypes A-G, to 90% endpoints and up to 3 logs of infectivity.
5. mAb B4 neutralizes HIV-2, SIV, and SHIV having a dual co-receptor HIV-1 envelope.
6. In the tonsil histoculture system, mAb B4 reduces the infectivity of HIV-1 primary isolate VL135 (HIV-1$_{VL135}$) by two logs. As little as 12.5 µg/mL of mAb B4 completely neutralizes >100 TID$_{50}$ (50% tonsil infectious doses) of the monocytotropic isolate JR-CSF in the presence of active human complement, which is a condition under which many anti-viral antibodies show antibody-dependent enhancement.
7. mAb B4 exerts neutralizing activity on HIV-1$_{VL135}$ when added up to 48 hours post-infection, with significant anti-viral effect when added up to 72 hours later.
    a. it is equally effective whether pre-incubated with cells or virus.
    b. it acts by blocking foci of infection from spreading to new cells rather than by a post-entry mechanism.
    c. in these assays, mAb B4 did not contribute to cytotoxicity.

Example 2

HIV-1 Neutralization and Resistance Assays

The following viral neutralization and resistance assays were performed at the laboratories of Dr. Carl Hanson and MONOGRAM BIOSCIENCES, INC. for multiple HIV isolates of various clades during the period 1998 to 2011. Detailed descriptions of the assays are described below.

1. HIV-1 Neutralization Assays.

Blood or antibody samples were collected as indicated in each of the studies. Serum or antibody samples were evaluated on a multi-clade panel of HIV-1 isolates using either MT-2 microplaque assay or mitogen (PHA)-stimulated PBMC assay.

1.1. MT-2 microplaque Assay

The MT-2 microplaque assay was limited to syncytium-inducing isolates of HIV. The assay was performed in 96-well plates, in which up to 25 small plaques per well could be enumerated by fluorescence staining of the syncytia on the microplaques. In this assay, infected MT-2 cells formed into monolayers by centrifugation through molten agarose, which gels during centrifugation. The assay was found to be sensitive and has a dynamic range extending over many orders of magnitude. The assay has also been found to be uniquely efficient for processing large number of specimens. The use of computerized statistical analysis, made possible by the large number of replicate wells, was found to provide a degree of quality control and standardization that has been difficult to achieve using other formats.

1.2 the PBMC Assay

The PBMC assay is a standard antigen-reduction assay in which expression of p24 antigen in PBMCs is quantified by antigen-capture ELISA following growth of infected cells in 96-well microtiter plates. An advantage of this assay is its applicability to all HIV strains and isolates.

1.3 Virus Stocks.

HIV-1 stocks for neutralization, ex vivo and in vivo studies are listed in Tables 3, 5, and 6 as well as in FIGS. 1$a$, 1$b$, 3, 22 and 23. Primary HIV-1 viruses from subtypes A to G and H were: (a) isolated from homosexual men participating in the San Francisco Men's Health Study of the California Department of Health Services, Viral and Rickettsial Disease Laboratory, VRDL; (b) acquired from the World Health Organization Network for HIV Isolation and Characterization, (c) supplied by the U.S. Military HIV Research Program, and (d) as gifts from National Institute of Allergy and Infectious Diseases AIDS Research and Reference Reagent Program. DH-12, a patient isolate passaged in chimpanzee peripheral blood mononuclear cells (PBMCs) was also supplied by the National Institute of Allergy and Infectious Diseases AIDS Research and Reference Reagent Program.

1.4. B4 or dB4 Neutralizing Activity

B4 or dB4 neutralizing activity was defined as the antibody concentration that provided the indicated percentage of reduction (50-95%) in virus when compared to controls containing no antibody. Antibody concentrations for the 50% and 90% endpoints were derived by interpolation between antibody dilutions.

2. The PHENOSENSE™ HIV Entry Assay

The PHENOSENSE™ HIV Entry Assay for determination of drug resistance was performed at MONOGRAM BIOSCIENCES, INC. (South San Francisco, Calif.).

Recombinant virus generated from vector pools was used to infect cells in the presence of varying concentrations of a drug or antibody (e.g. B4 or dB4). The amount of drug needed to inhibit viral replication of the test vector by 50% (IC$_{50}$) or 90% (IC$_{90}$) was determined.

2.1 Generation of Recombinant Viruses Used in the PHENOSENSE™ HIV Assay

Recombinant viruses used in the PHENOSENSE™ HIV Assay were generated from samples collected from patients screened in longitudinal studies of HIV infection and identified as HIV seropositive. For individuals with incident HIV infection, clinical and plasma samples were collected for laboratory assessment including HIV viral load and CD4 cell counts. For individuals who were initially seronegative, but became seropositive after approximately 1 year of follow-up, HIV infection was confirmed by two enzyme immunoassays with western blot confirmation.

Samples from participants who had subtype A, BF, C, D, E, EA, F, G, or J at the time of seroconversion (based on previous HIV subtyping using a multiple hybridization assay) were collected for construction of recombinant viruses, as shown in Table 3. The HIV env, pol regions were amplified from a test sample and the amplified DNAs were cloned into a test vector. In the GENESEQ® HIV, vector pools were sequenced to determine the HIV genotype. In the PHENOSENSE™ HIV assay, recombinant virus generated from the vector pools was used to infect cells in the presence of varying concentrations of a drug.

Example 3

Neutralizing Activities of mAb B4 by Monogram Bioscience PHENOSENSE™ Assay Against HIV Isolates of all Clades It has been well documented that mAb B4 neutralizes all HIV viruses of the B clade. In one study a total of 73 representative non-B clade HIV isolates from clades A (n=8), BF (n=1), C (n=18), D (n=18), E (n=4), EA (n=10), F (n=8), G (n=4), J (N=2), plus three control viruses 92HT594, JRCSF, JRFL were made into recombinant viruses and tested in a PHENOSENSE™ HIV assay for their sensitivity to mAb B4 (Table 3). It was found that all of the recombinant viruses were highly sensitive to mAb B4 with an unprecedented low $IC_{50}$ and $IC_{90}$ concentrations, with an average $IC_{50}$=0.018 µg/mL and $IC_{90}$=0.062 µg/mL. It was noteworthy to find that many of these HIV isolates were derived from multi-drug resistant patients, a clear indication that mAb B4 or its human counterpart would be highly efficient in treating patients who are already HIV drug resistant.

Example 4

Figure 1A:
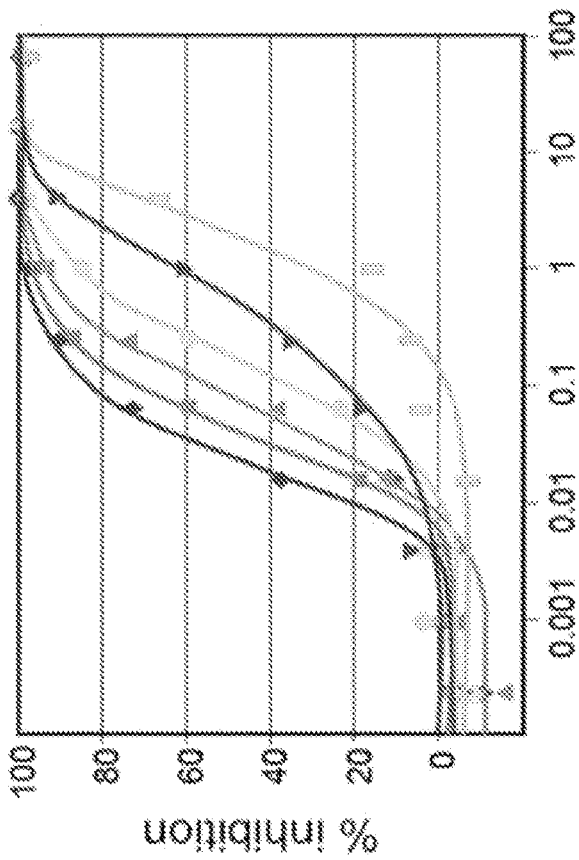

Monoclonal Antibody B4 Mediates Competitive HIV Entry Inhibition: An Unexpected Feature which Predicts the Prevention of HIV Resistant Mutants Upon Treatment Competitive inhibition studies can evaluate the ability and efficacy of an inhibitor (e.g., entry inhibitor antibody) to compete with HIV envelope proteins for the same receptor binding site on CD4, thereby, inhibiting entry of HIV into the cell. In a theoretical study, mAb B4 competes with HIV envelope protein (gp120) for binding of CD4. FIG. 1a shows the predicted results of this study, where each line represents a different viral isolate. Specifically, the expected results from this theoretical study demonstrate that, although different viral isolates would have different sensitivities ($IC_{50}$) to mAb B4, entry of all viral isolates would be inhibited by 100% as long as mAb B4 was present in a sufficient concentration.

By comparison, noncompetitive inhibition studies can evaluate the ability and efficacy of an inhibitor (e.g., co-receptor antagonist or antibody that binds to a different portion of CD4) to inhibit or reduce the ability of HIV envelope proteins to bind to CD4, thereby, inhibiting entry of HIV into the cell. In a theoretical study, the ability of a noncompetitive inhibitor (e.g., TMB-355) to inhibit HIV envelope protein (gp120) from binding CD4 is analyzed. FIG. 1b shows the predicted results of this study, where each line represents a different viral isolate. Specifically, the expected results from this theoretical study demonstrate that different viral isolates would have different sensitivities ($IC_{50}$) to TMB-355 and at least some portion of the viral isolates would enter the cell regardless of the amount of TMB-355 present. Based on this theoretical study, it would be expected that HIV resistance would be observed as a "plateau" in maximal percent inhibition regardless of $IC_{50}$.

TMB-355 (formerly TNX-355, also called Ibalizumab) is a humanized IgG4 monoclonal antibody that was designed to bind to extracellular domain 2 of rhesus and human CD4 to prevent post-binding entry of HIV into CD4+ cells (e.g., Burkly, L C, et al., 1992; and Kurizkes, D R, et al., 2004). The TMB-355 antibody binding site on CD4 is distinct from the site required for the binding of HIV-1 envelope gp120 and is distinct from the site needed for interaction with major histocompatibility complex proteins. Accordingly, TMB-355 mediates non-competitive HIV entry inhibition.

Figure 2:
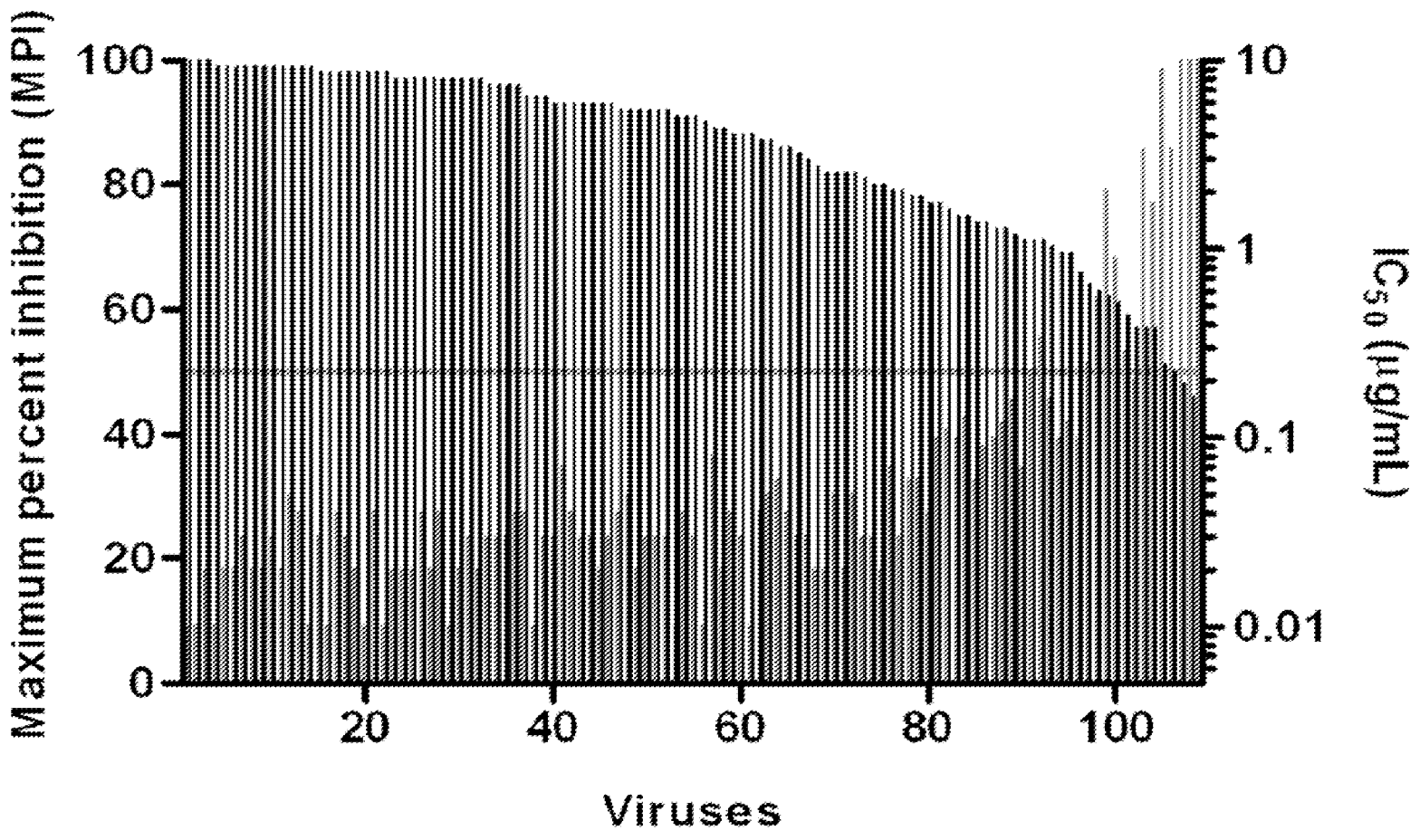

TMB-355 has been shown to have a strong neutralization activity against some HIV-1 viruses but its inhibitory activity is inconsistent when a broad panel of HIV strains is evaluated. FIG. 2 shows that the MPI of TMB-355 ranges between 100% to 15% (left Y axis), coupled with an increasing $IC_{50}$ from 0.01 µg/mL to 10 µg/mL (right Y axis), against a panel of 118 Env pseudotype HIV viruses with each bar representing one virus isolate (Song, R., et al., 2013). Of all clades analyzed, clade A and E viruses were significantly more susceptible to TMB-355 than non-clade A and E viruses. In addition, viral resistant mutants were found with mutations identified in the V5 region of gp120 from patients receiving TMB-355 treatment for viral load reduction (Toma, J., et al., 2011; Pace, C. S., et al., 2013). The non-competitive inhibitory effect demonstrated by TMB-355 (Ibalizumab) suggests that there would be a high likelihood for development of resistant HIV mutants during the antibody treatment period because viral replication will take place for isolates that have less than 100% inhibition.

Figure 3:
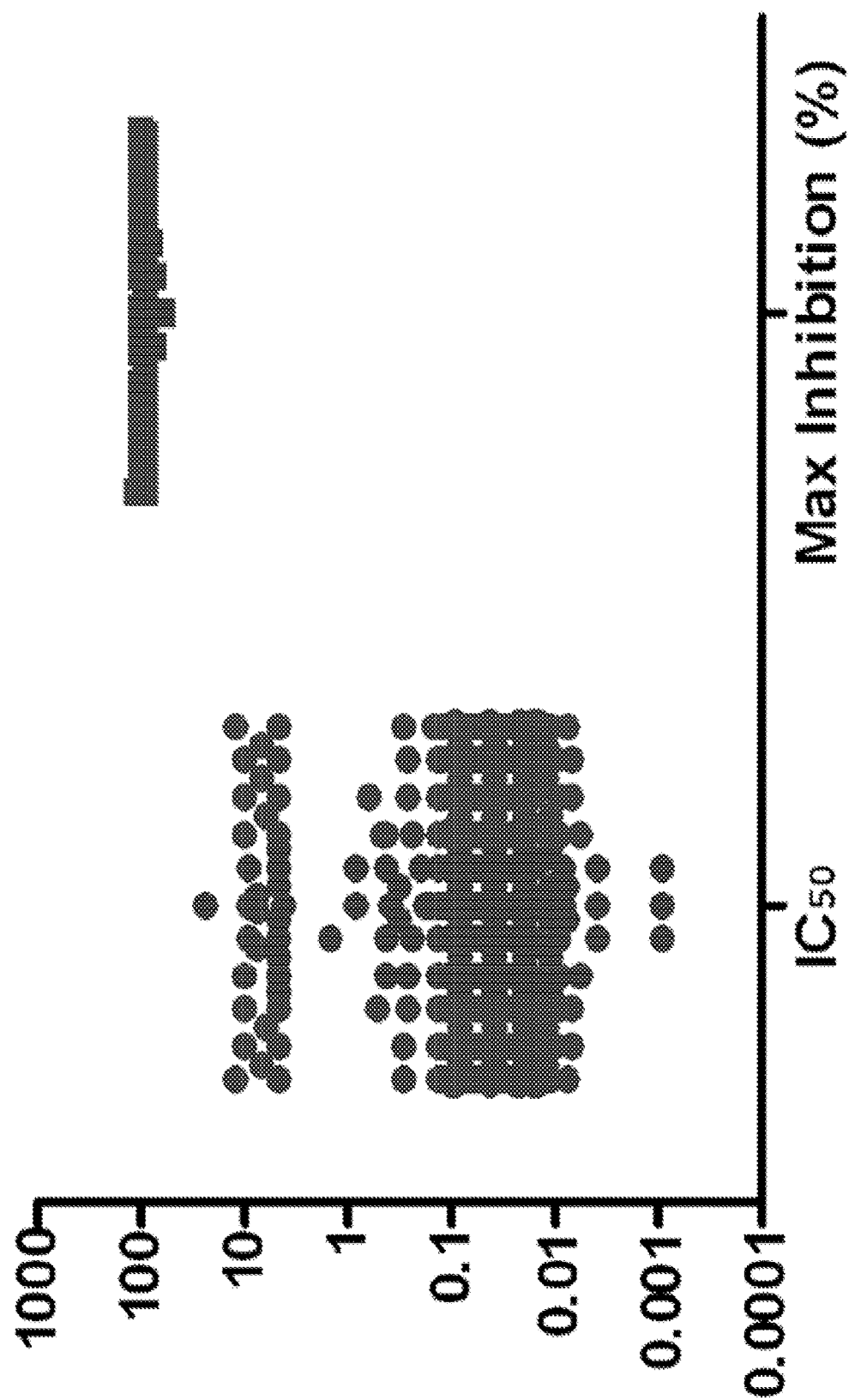

In contrast, data collected over a 10 year period from a panel of over 850 Env pseudotype HIV viruses shows that mAb B4 offers an unexpected breadth and potency in HIV entry inhibition (FIG. 3). From this collection of data, it can be seen that mAb B4 has nearly 100% MPI with an $IC_{50}$ clustered around two concentrations, one between 0.01 to 1 µg/mL, and the other around 10 µg/mL. The HIV entry inhibition profile for mAb B4 has the typical characteristics of a competitive inhibition mechanism with an MPI for each of the HIV viruses at ~100% regardless of $IC_{50}$. In view of mAb B4's notably strong competitive HIV entry inhibition characteristics, viral resistant mutants are unlikely to develop during the mAb B4 treatment period. Such tight competitive inhibition, as exerted by mAb B4, has never been observed with any other HIV inhibitor tested thus far.

The MPI and $IC_{50}$ data from this Example, combined with the data showing that many of the HIV isolates derived from multi-drug resistant patients were highly sensitive to mAb B4 discussed in Example 3, suggested that mAb B4 or its human counterpart would be highly efficient in treating drug resistant HIV patients who are failing HAART treatment. The mode of neutralization mediated by mAb B4 offers a unique HIV drug that would prevent the generation of drug resistant viral mutants in HIV patients receiving treatment with mAb B4 or its human counterpart analogues carrying similar Fv regions.

Example 5

Humanization of Monoclonal Antibody B4

As a murine antibody, mAb B4 is immunogenic in humans. Humanization of murine antibodies can be achieved through a process that is now known as deimmunization technology (Jones, T. D., et al. 2009). The deimmunization of mAb B4 is described in detail in U.S. Pat. No. 7,501,494 by Lynn., S. and Wang, C. Y. (both of which are incorporated by reference in their entireties) as summarized below.

First, the constant regions of murine antibody B4 ($C_H$ and $C_\kappa$) were entirely removed and replaced with the constant regions of human $IgG_1$ (SEQ ID NOs: 12 and 14, respectively), while the Fv portions were retained, thereby producing a chimeric B4 antibody. Next, deimmunization of the Fv fragment of murine mAb B4 for human use was accomplished by the identification and elimination of potentially immunogenic murine T and B-cell epitopes. Removal of the T cell epitopes was achieved following the identification of such epitopes from the variable regions of mAb B4. The amino acid sequences of the variable region were analyzed for the presence of MHC class II-binding motifs by a 3-dimensional "peptide threading" method. Removal of the B cell epitopes from the variable region was achieved by the 'veneering' of surface residues that do not interfere with antibody recognition. The deimmunized, humanized version of mAb B4 is designated mAb dB4.

U.S. Pat. No. 7,501,494 by Lynn., S. and Wang, C. Y. discussed that $IgG_1$ contains a biantennary complex N-linked carbohydrate within CH2 that is important for effector functions, such as complement fixation and antigen-dependent-cellular-cytotoxicity (ADCC), which result in elimination of the target antigen. Since mAb B4 is targeted to the CD4 receptor complex, it could cause the destruction of CD4+ cells and immunosuppression of CD4+ cell function through the effector functions of $IgG_1$ that are responsible for binding complement. Thus, removing the N-glycosylation site in the Fc region of $IgG_1$ abolishes the ability of $IgG_1$ to bind the human FcR1, to activate complement, or to bind C1 q, thereby eliminating the $IgG_1$ mediated complement dependent cytotoxicity (CdC). Removal of the N-glycosylation site in the Fc region of $IgG_1$ was accomplished by substituting one amino acid residue Asn (N) with His (H) (i.e., N298H).

The amino acid numbering/positions discussed in this description are based on the sequences contained in the Sequence Listing that is part of this specification. It is noted that the glycosylation site at aa298 discussed above corresponds to the glycosylation site found at aa297 of the native $IgG_1$ molecule, which is numbered according to the European numbering system for $IgG_1$. Thus, aa298 in this application corresponds to the glycosylation site at aa297 discussed in U.S. Pat. No. 7,501,494.

The CDR1, 2, and 3 regions of the deimmunized mAb dB4 heavy (FIG. 4) and light (FIG. 5) chains of the Fv domain contain the amino acid sequences of SEQ ID NOs: 1 to 6, respectively (Table 4). The full length sequences for the heavy and light chains of mAb dB4 are shown in FIGS. 4 and 5 as SEQ ID NOs: 7 and 8, respectively.

The half-life of mAb dB4 was found to be improved (extended) when certain amino acids in the heavy chain of the antibody were mutated. Specifically, the half-life of the humanized antibody was improved when the heavy chain Fc amino acids at positions aa253(Met), aa255(Ser), and aa257 (Thr) were substituted with Tyr, Thr and Glu, respectively. The full length sequence for the improved heavy chain of the humanized mAb dB4 antibody is shown in FIG. 6 as SEQ ID NO: 9. Accordingly, the improved humanized antibody mAb dB4 contains a light chain having the sequence of SEQ ID NO: 8 and a heavy chain having the sequence of SEQ ID NO: 9.

A unique feature of the sequence and structure of the murine mAb B4 and the humanized mAb dB4 is the presence of a sugar binding residue Asn at amino acid position 101 (Asn101), in the heavy chain of the Fv. This sugar binding site is unusual for its Fv region location and is unexpectedly hidden inside the Fv domain and can only be exposed for enzymatic cleavage of the sugar by the denaturation of the full antibody molecule. The presence of this sugar in the Fv region initially complicated the characterization of the antibody. However, modifications to the sugar chain or binding site destroyed the binding affinity of the antibody to CD4. Therefore, this unusual N-glycosylation site in the Fv region is critical to the antibody binding to CD4.

Figure 7:
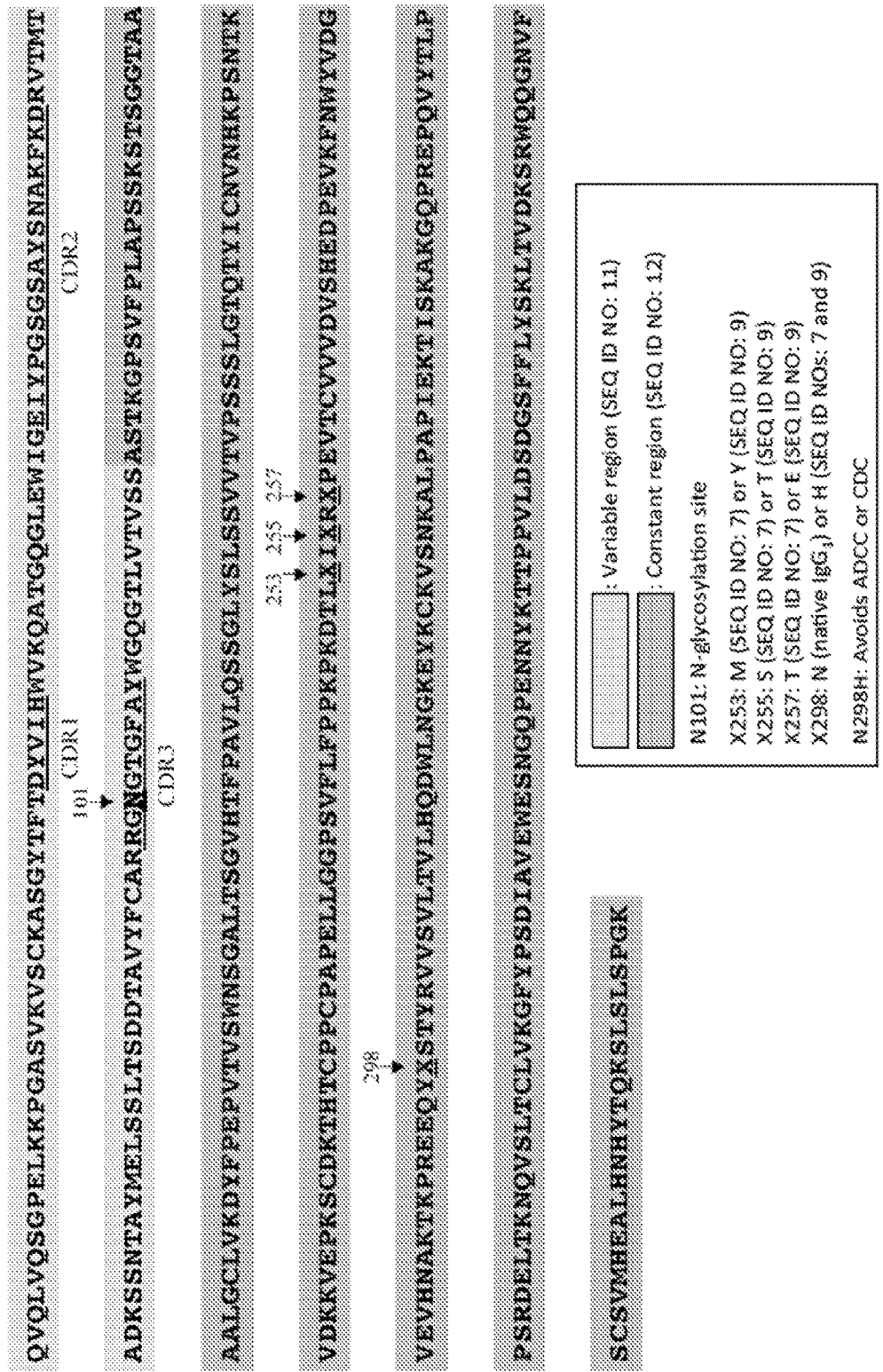

FIG. 7 illustrates the full length heavy chain amino acid sequence of mAb dB4 highlighting the glycosylation, substitution, and mutation sites discussed above for FIGS. 4 and 6.

Example 6

Demonstration of Bioequivalence Between mAb DB4 and its Parental mAb B4 by Mt-2 Microplaque, PBMC Neutralizing Assays and PHENOSENSE™ Entry Assay Extensive comparative studies were conducted to assess the bioequivalence of the deimmunized/humanized, Fc-aglycosylated mAb dB4 and the parental murine mAb B4 to ensure that the humanized version could be utilized for further toxicity/safety and efficacy studies in primate animals and humans. Results from these comparative studies are summarized below.

1. Highly sensitive HIV-1 neutralization assays performed in both MT-2 microplaque and mitogen-stimulated PBMC assays with representative HIV isolates from clades A, B, C, D and E and clades C and E, respectively. There was no loss of HIV neutralization activity after humanization of the murine mAb B4 to mAb dB4 antibody by deimmunization technology. The comparable results are shown in MT-2 microplaque (Table 5) and PBMC-based assay (Table 6).
2. Bioequivalence is therefore demonstrated between murine mAb B4 and mAb dB4 since the $IC_{50}$s and $IC_{90}$s for all HIV isolates from all clades measured are within two fold of each other.
3. HIV entry inhibition by mAb B4, mAb dB4, as well as two other well-known HIV-env directed monoclonal neutralizing antibodies, 2F5 and 2G12, was evaluated on a dual-receptor (CXCR4 and CCR5 or X4/R5) expressing cell line U87 with selected HIV isolates of varied tropisms including JRCSF (R5), HXB2 (X4), 92TH594 (R5/X4), primary isolate #5 (R5), primary isolate #6 (R5), and primary isolate #7 (R5). In this study, inhibition of HIV entry was evaluated by MONOGRAM BIOSCIENCES, INC. using pseudotype viruses that carried the envelope glycoprotein from any one of hundreds of HIV strains and a luciferase. Neutralization by antibody is measured by quantitating bioluminescence produced in U87-CD4+/CCR5+/CXCR4+ cells engineered to express luciferase under the control of HIV tat. The results from this study are shown in Table 7, which demonstrate that:
   a. Murine mAb B4 (MuB4; row 4) is far more potent in HIV entry inhibition, when compared to the two most potent anti-HIV Env antibodies 2F5 (row 1) and 2G12 (row 2). The corresponding $IC_{50}$s for the different HIV isolates being 0.04 vs 4 and 0.8; 0.4 vs 0.07 and 0.5; 0.05 vs 3 and 1.3; 0.05 vs 50 and 20; 0.05 vs 2 and 3; 0.03 vs >100 and 2 respectively; and
   b. Murine mAb B4 (MuB4; row 4) and mAb dB4 (row 3) are surprisingly equivalent in their $IC_{50}$s when tested with the same representative HIV isolates of varied types of tropism.

It is therefore well documented that the murine mAb B4 and the deimmunized mAb dB4, which share the same CDRs for both heavy and light chains, are bioequivalent and the functional properties of the two antibodies are representative of each other in various in vitro and in vivo studies.

Example 7

Characterization of (A) DB4 and mAb B4 Binding Activities to HPB-all Cells; (B) DB4 Binding Activity to PBMC CD4 Positive Cells; (C) DB4 Binding Activity to Recombinant CD4, and (D) DB4 and Gp120 Binding Activities to HPB-all Cells 1. Background While the qualitative aspect of antigenic binding and functional properties are known, as demonstrated by neutralizing assays, for mAb dB4 and its parental murine mAb B4 as shown in previous Examples, the quantitative cellular binding profiles of mAb B4 and mAb dB4 in CD4+T lymphocytes have not been previously investigated.

Both murine mAb B4 and its humanized, Fc-aglycosylated $IgG_1$ monoclonal antibody mAb dB4 were tested for cellular binding profiles on normal human blood CD4+T lymphocytes and also on CD4+T-leukemic HPB-ALL cells. HPB-ALL cells were used since mAb B4 was selected through immunization of mice with HPB-ALL cells as discussed in Example 1. General cellular binding was evaluated by FACS analysis and the results were reported as $EC_{50}$ or $IC_{50}$ values based on mean fluorescence intensity (MFI). In addition to evaluating general cellular binding of the antibodies, the absolute binding affinity (Kd) and capacity (Bmax) of the native dB4 $IgG_1$ molecule to HPB-ALL cells were also studied.

2. Materials 2.1 Culture Medium and Reagents.

RPMI-1640 medium and fetal bovine serum for culturing HPB-ALL cells were from Gibco (Cat. 11875-093 and 10091-148, respectively). Bovine serum albumin was from ApplicChem (Cat. A-0850). Incubation of cells with test antibodies was performed on NUNC V-bottomed 96-well plates (Cat. 249662). Microdilution tubes (1.2 mL) for sample preparation were from Bertec (Cat. 1710-00). Cell fixation was made with 2% formaldehyde; samples were dilution with PBS (pH 7.4) containing 0.05% BSA and 0.05% sodium azide; and washing buffer was PBS (pH 7.4) with 0.05% sodium azide.

The binding of murine mAb B4 and humanized mAb dB4 was tracked by goat anti-mouse IgG-FITC (Sigma, Cat. F8264) and Goat F(ab')2 anti-human IgG Fcγ-FITC (Jackson ImmunoResearch, Cat. 109-096-098), respectively. The dB4-Alexa 488 conjugate (shown as the abbreviated "dB4-Alexa" throughout the text) was made in-house at United Biomedical, Inc. ("UBI") (UBI Lot. 0102143). B4-biotin conjugate was from UBI (Lot 051807). Sheep anti-hIgG-HRP was from The Binding Site (Cat. AP004); Extravidin-HRP from Sigma Aldrich, Cat. E2886; and soluble rCD4 was from R & D System (Cat. 514-CD-050). Peptide p2704a HIV envelope was from UBI, recombinant gp120 MN was from ImmunoDiagnostics (Cat. 1021-2). Blood CD4+ T cells gated for tracking of binding was done with anti-CD4 (D2)-FITC antibody (Ancell, Cat. 148-020). The fluorescence beads from LINEARFLOW™ Green Flow Cytometry Intensity Calibration Kits (Molecular Probe) were used as reference standards, to quantify the relative fluorescence of labeled cells. Other fluorescence detectors used were: FITC-ChromPure Goat IgG, $F(ab')_2$ fragment (Jackson ImmunoResearch, Cat. 005-090-006); CD3 PE (ASR) (BD Biosciences, Cat. 340662); CD45 PerCP (ASR) (BD Biosciences, Cat. 340665).

2.2 HPB-ALL Cells and Peripheral Blood CD4+ T Cells.

The HPB-ALL cell line, a human thymic acute lymphocytic leukemia cell line, was obtained from DSMZ ACC. PBMC CD4+ T cells (blood freshly drawn from healthy donors into EDTA-vacutainers) were derived from peripheral blood leukocytes (PBL) after lysis of red blood cells with $NH_4Cl$-containing hypotonic solution (a mixture of 8.3 g/L ammonium chloride, 0.84 g/L sodium bicarbonate, and 29.4 mg/L EDTA at pH 7.4)

2.3 Murine mAb B4 and Humanized dB4 mAb.

The murine monoclonal B4 $IgG_1$ (UBI Lot 120197) was obtained through hybridoma operation using HPB-ALL cells as immunogen. The B4-derived humanized dB4 $IgG_1$ (UBI Asia Reference Lot) was rendered Fc-aglycosylated by N298H (Examples 5).

2.4 Detection on ELISA & FACS.

The 96-well microplate was from Nalge NUNC International, flat-bottomed (Cat. 442404) for optical reading and V-bottomed for cells incubation (Cat. 249570). Optical density was read on VERSAMAX® microplate reader (Molecular Devices). Fluorescencing stainers were detected by BD FACSCalibur scanner (DB Biosciences); and the resultant data were acquired by the associated Cell Quest software. Binding data from ELISA & FACS were imported to SIGMAPLOT® 11 software for quantitative analysis.

3. Methods 3.1 Binding of dB4 To HPB-ALL Cells 3.1.1 Equilibrium Time Study.

On V-bottomed microplates, aliquots of $2 \times 10^5$ cells in 0.1 mL per well were added, centrifuged, and liquid discarded. For various time durations up to 180 minutes, the cells were incubated on ice with aliquots of 100 μL of dB7 at various concentrations up to 100 ng/mL. At indicated times, the supernatants were collected for determination of free, unbound antibody drug. The bound fraction was calculated by subtraction of the free fraction from the total drug concentration added.

The free dB4 concentrations in binding solution were quantitated by ELISA. Briefly, the assay involved the use of a mixture of sheep anti-hIgL (0.5 μg/mL) coated on the NUNC Maxisorp microplates, and the sheep anti-huIgG-HRP (1/1000 dilution) as detector protein. Concentrations in the unknown samples were measured based on calibration standards in the range of 0.14-18.5 ng/mL.

3.1.2 Direct Binding Study with dB4.

On V-bottomed microplates, aliquots of $2 \times 10^5$ cells in 0.1 mL per well were added, centrifuged, and liquid discarded. The cells were incubated on ice for 1 hr with aliquots of 100 μL of dB4 at various concentrations up to 2000 ng/mL. After incubation, the dB4 was removed and a fresh aliquot of dB4 was added to the cells at the same concentration used for the initial incubation, and the cells were incubated on ice for another hour. This step was repeated one more time. The cells from the three incubations (passages) were investigated. After the third incubation, the cells were washed once, centrifuged at 300 g for 5 min, and stained on ice for 30 min with 100 μL of goat $F(ab)_2$ anti-huIgG Fc-FITC (250 ng/mL). The cells were washed once and the liquid discarded after centrifugation. To each well, aliquots of 200 μL of binding buffer were added and transferred to microdilution tubes for flow cytometric analysis. The binding intensity (mean fluorescence intensity, MFI), based on an inlet of 5,000 cells per sample, was read on FACS.

3.1.3 Binding Affinity (Kd) Study of dB4.

In EPPENDORF® tubes, the dB4 antibody at 3.1-2000 ng/mL (0.5 mL) was added to HPB-ALL cells at $4 \times 10^5$ cells (0.5 mL) and incubated for 1 hr on ice under gentle shaking. The absolute binding affinity was determined at saturating binding where the free dB4 concentrations ([F]) in the solution were quantitated by ELISA and the bound fraction ([B]) calculated as described in the equilibrium study above. The resultant saturating free-vs.-bound concentration profiles were analyzed on SigmaPlot by curve-fitting based on the equation, $[B]=Bmax \cdot \{[F]/([F]+Kd)\}$, where the respective [B] and [F] stand for the bound and free concentrations.

3.1.4 Competition of dB4 and B4 with B4-Biotin.

On flat-bottomed microplates coated with a mixture of sCD4 (0.5 μg/mL) and p2704a peptide (2.0 μg/mL), aliquots of 0.1 mL dB4 or B4 at 0.78-100 μg/mL in the presence of B4-biotin (10 μg/mL) were added and incubated at room temperature for 1 hr. Following the competitive binding to the capturing mixture, the bound B4-biotin was detected with Extravidin-HRP and measured on ELISA reader.

3.1.5 Competition of dB4 and B4 with dB4-Alexa.

On V-bottomed microplates, aliquots of $2 \times 10^5$ cells in 0.1 mL per well were added, centrifuged, and liquid discarded. The cells were incubated on ice for 1 hr with aliquots of 100 μL of dB4 or B4 (up to 2000 ng/mL) in the presence of dB4-Alexa (250 ng/mL). The cells were washed once and the liquid discarded after centrifugation. To each well, aliquots of 200 µL of binding buffer were added and transferred to microdilution tubes for flow cytometric analysis. The binding intensity (mean fluorescence intensity, MFI), based on an inlet of 5,000 cells per sample, was read on FACS.

3.1.6 Competition of dB4C7 and gp120 MN with dB4C7-Alexa.

On V-bottomed microplates, aliquots of $2 \times 10^5$ cells in 0.1 mL per well were added, centrifuged, and liquid discarded. The cells were incubated on ice for 1 hr with aliquots of 100 µL of dB4C7 or gp120 MN (up to 200 nM, ~30 µg/mL) in the presence of dB4-Alexa (250 ng/mL). The cells were washed once and the liquid discarded after centrifugation. To each well, aliquots of 200 µL of binding buffer were added and transferred to microdilution tubes for flow cytometric analysis. The binding intensity (mean fluorescence intensity, MFI), based on an inlet of 5,000 cells per sample, was read on FACS.

3.2 Binding of dB4 to Blood CD4+T Lymphocytes 3.2.1 Temperature-Dependent Binding Study of dB4.

To mimic the physiological setting where dB4 (UB-421) after IV administration would bind (coat or occupy) CD4 receptors on CD4+ T cells, aliquots of freshly drawn EDTA-blood from lab personnel were incubated at 37° C. with equal volume of dB4 in dilution buffer at concentrations up to 100 µg/mL. For comparison, another sample set was incubated in parallel on ice. After incubation for 1 hr., the samples were lysed with 20-fold volume of RBC lysis buffer for 10 min. at room temperature to yield a fraction of peripheral blood leukocytes (PBL).

The PBL fractions were centrifuged, washed and then reconstituted with equal volume of PBS buffer containing 1.0% BSA and sodium azide (e.g., 0.1 mL blood with 0.1 mL dilution buffer). The PBL samples were stained on ice for 30 min. with 0.1 mL mixture of goat $F(ab)_2$ anti-hIgG Fc-FITC, anti-CD3-PE, and anti-CD45 perCP. After wash, the samples were fixed with 2% formaldehyde and subjected to FACS analysis based on an inlet of 10,000 cells. The T lymphocyte population was gated with anti-CD3-PE.

3.2.2 Direct Binding.

The direct binding of dB4 to blood CD4+ T cells was defined in three male and three female subjects, in which their freshly drawn EDTA-blood was incubated with dB4 at 37° C. for 1 hr. MAb dB4 was bound to CD4+ T cells and found to reach an apparent saturation at a concentration range of 0.2-200 ng/mL. The T lymphocyte population was gated with anti-CD3-PE. The experimental procedures were the same as that described above in the temperature-dependent binding study, where the cells were stained with goat $F(ab)_2$ anti-hIgG Fcγ-FITC to track dB4 binding.

3.2.3 Free Binding Sites.

In parallel to the above definitive direct binding study, the level of free binding sites left behind dB4 binding (before a complete receptor occupancy) was investigated on the same occasion for each of the individual three male and three female subjects. The experimental procedures were the same as described above for direct binding, except that a fixed amount of dB4-Alexa at 250 ng/mL was used to reveal the levels of unoccupied, free binding sites.

3.2.4 Calibration Beads.

For simultaneous investigation on direct binding and free binding sites, a log(MFI)-vs.-log(bead %) standard curve was generated on each of six different occasions using a combination of two Molecular Probes's LINEARFLOW™ Kits (Cat. L14821 and L14823). The kit combination provides a wide calibrated range of high and low intensity standards for use in flow cytometry experiments. As reference standards, these fluorescent beads were used to quantitate the relative fluorescence on cells labeled by goat $F(ab)_2$ anti-hIgG FcR-FITC or dB4-Alexa.

4. Results and Discussion 4.1 Binding Profile of dB4 and Determination of its Absolute Binding Affinity (Kd) in CD4-Positive HPB-ALL Cells.

4.1.1 Equilibrium of Binding Activity to HPB-ALL Cells.

Prior to a full characterization on ligand-receptor binding reaction, the time length to reach equilibrium was defined for the ligand at various concentrations, i.e., a plateau status where the on-rate is equal to the off-rate. It is generally known that the lower the concentration, the longer the time it would take to reach equilibrium.

In the case of dB4-CD4 interaction in CD4-positive HPB-ALL cells incubated on ice, it took approximately 60 min. for the 2.0 ng/mL concentration and approximately 15 min. for the 50 ng/mL concentration to reach a plateau in % bound value. An almost instant plateau was observed for a dB4 concentration at 100 ng/mL (0.1 µg/mL) and higher levels.

These results indicate that the dB4 binding reaction can be carried out for 1 hr. for a wide range of concentrations (e.g., concentrations ≥2.0 ng/mL). The binding study was conducted at cold and/or under 0.05% azide to avoid a potential endocytosis of the ligand-receptor complexes. Incubation at room temperature or 37° C. could allow a reaction plateau to be reached sooner. Under this above worked out condition, HPB-ALL cells, with three different cell passages, were incubated on ice for 1 hr with dB4. The supernatants were collected for determination by ELISA of the free drug concentrations, and the bound fractions were obtained by subtraction from the total. The absolute binding affinity and capacity were calculated with the binding curve shown in FIG. 8.

4.1.2 Direct Binding to HPB-ALL Cells.

On three different occasions (cell passages), $2 \times 10^5$ HPB-ALL cells were incubated for 1 hr. on ice with dB4 up to ~2000 ng/mL, the antibody exhibited a saturating binding profile characterized by a 4-parameter logit function, where the extent of binding was detected by goat $F(ab)_2$ anti-huIgG Fc-FITC and expressed as the mean fluorescence intensity (MFI). The binding approached saturation at 200 ng/mL (0.2 µg/mL) and beyond. The mean binding $EC_{50}$ was estimated to be 42.2 ng/mL (Table 8) with little between-passage variation (n=3). The absolute MFI values were also normalized to % MFI for purpose of between-passage comparison. The standard deviation was thus minimized, and the $EC_{50}$ values essentially remained the same; the overall mean binding $EC_{50}$ values for both mean curves were estimated to be 42.9 ng/mL (Table 8).

4.1.3 Binding Affinity (Kd) and Capacity (Bmax) in HPB-ALL Cells.

Collection of post-incubation supernatants (on ice for 1 hour) allowed determination by ELISA of the free (unbound) dB4 concentration [F] and thus the bound concentration [B] through subtraction from the added (total) concentration. Estimation of the absolute binding affinity for dB4 was made using the free drug-vs.-bound drug profile as shown in Table 9. The mean Kd was estimated to be $5.6 \times 10^{-11}$ M (range: 3.1 to $8.1 \times 10^{-11}$ M), and the Bmax was estimated to be $1.2 \times 10^6$ Ab per cell (range: 0.93-$1.4 \times 10^6$). These results indicated that dB4 bound to the CD4 receptors on HPB-ALL cells with an exceptionally high affinity and that HPB-ALL cells have a high density, with over a million binding sites for dB4 per cell at the maximum (Table 9). The CD4 receptor density on HPB-ALL cells was at least 20-fold higher than that of blood CD4+T lymphocytes, which was about $3.2\text{-}6.1\times10^4$ binding sites per cell.

4.2 Comparison of dB4 and B4 in Binding to HPB-ALL Cells.

The question of whether humanization by method of deimmunization of the murine B4 antibody to the dB4 altered the binding affinity was thoroughly investigated on two technical accounts using competition design.

First, the binding affinities of mAb B4 and mAb dB4 were examined on an ELISA plate coated with a capturing mixture of soluble CD4 (sCD4) and p2704a peptide. The p2704a peptide mimics the CD4-CCR5 receptor complex because it contains the epitope sequence on CCR5 that HIV-1 anchors to to enter CD4 cells. The binding of B4-biotin to the coated sCD4/p2704a mixture was inhibited in the presence of mAb B4 or mAb dB4 at various concentrations when analyzed by ELISA. When mAb B4 or mAb dB4 antibody were coexistent and competing with B4-biotin for binding to the capturing protein mixture, the binding of B4-biotin was inhibited with $IC_{50}$ values of 5539 ng/mL and 8191 ng/mL by B4 and dB4, respectively (FIG. 9). The $IC_{50}$ ratio of B4 to dB4 was 0.68, indicating that the humanized dB4 has a binding affinity relatively comparable to the murine B4 antibody.

Second, the relative binding affinity was also investigated using CD4-positive HPB-ALL cells where B4 or dB4 antibodies were co-existent and competing with dB4-Alexa for binding to the cellular CD4 receptors. Analyzed by FACS, the binding of dB4-Alexa was inhibited with $IC_{50}$ values of 135 and 197 ng/mL by B4 and dB4, respectively (FIG. 10). The $IC_{50}$ ratio of B4 to dB4 was 0.69, which was substantially the same as that demonstrated by ELISA paradigm, indicating again that the humanized dB4 binds to CD4 receptor with an affinity relatively comparable to the murine B4 antibody.

This comparative competitive binding inhibition study, using the parental antibody B4 and its humanized antibody dB4C7 (UB-421), provided an antibody binding profile against CD4 positive T cells (HPB-ALL) as measured by mean fluorescence intensity (MFI) versus antibody concentration over a series of concentrations (from 100 to 104 ng/mL). This study further validated data presented in Tables 5 and 6 that the respective neutralizing activities of both antibodies in both the MT2 and PBMC assay systems have comparable neutralizing antibody activities.

The results obtained in these comparative studies suggest that humanization by deimmunization technique did not significantly reduce binding affinity of dB4C7 (UB-421) to CD4 receptors when compared to its parental murine antibody B4.

4.3. MAb dB4's Binding Characteristics to CD4.

MAb dB4's binding characteristics to CD4 were evaluated.

4.3.1. Biding of mAb dB4 to Soluble CD4 vs. Cell-Bound CD4.

As discussed above, dB4 inhibited the binding of B4-biotin to sCD4/p2704a with an $IC_{50}$ of 8191 ng/mL, as evaluated by ELISA (FIG. 9), and dB4 inhibited the binding of dB4-Alexa to HPB-ALL cells with an $IC_{50}$ of 197 ng/mL, as examined by FACS (FIG. 10). These data interestingly demonstrate that dB4 had a much higher binding affinity to CD4-positive T cells compared to soluble CD4 (sCD4). Specifically, a comparison of the $IC_{50}$ values of the two studies showed that dB4's binding affinity was more than 40-times higher to CD4-positive T cells compared to sCD4.

4.3.2. Comparison of dB4 and Gp120 MN in Binding HPB-ALL Cells.

Competition studies were performed to compare the binding affinities of dB4 and HIV gp120 MN to CD4 bound to CD4-positive T cells. Specifically, the ability of dB4 and gp120 MN to inhibit dB4-Alexa from binding to CD4 on HPB-ALL cells were compared (FIG. 11). In the first study, dB4 inhibited the binding of dB4-Alexa to CD4 on HPB-ALL cells with an $IC_{50}$ of 1.8 nM. In the comparative study, gp120 MN inhibited the binding of dB4-Alexa to CD4 on HPB-ALL cells with an $IC_{50}$ of 97.2 nM. According to these results, dB4 was found to have a substantially higher binding affinity to CD4 on HPB-ALL T cells compared to gp120 MN. Specifically, a comparison of the $IC_{50}$ values of the two studies showed that the binding affinity of dB4 to CD4 is at least 50-fold higher than that of gp120 MN.

4.3.3. Comparison of dB4 and Gp120 MN Binding Affinities to CD4.

As discussed above, mAb dB4 binds to CD4 with a binding affinity (Kd) of about $5.6\times10^{-11}$ M (Table 9). It has previously been found by others, through a crystallography study, that HIV-1 gp120 binds around domain 1 of the CD4 molecule with a high binding affinity (Kd) of approximately $5\times10^{-9}$ M (Myszka, D. G., et al., "Energetics of the HIV gp120-CD4 binding reaction" Proc Natl Acad Sci USA. Aug. 1, 2000; 97(16): 9026-9031). Thus, a comparison of the Kd values of dB4 and gp120 shows that dB4's binding affinity to CD4 is approximately 100-fold higher than gp120's binding affinity. This result is in agreement with the above finding that dB4 binds to HPB-ALL cells at least 50-fold stronger than gp120 MN based on a comparison of $IC_{50}$ values.

The overall in vitro results suggest discussed above demonstrated that dB4 would be competent in blocking or reducing HIV-1 infection by preventing or shutting down HIV viral entry.

4.4. Temperature-Dependent Binding of dB4 (UB-421) to Blood CD4+ T Cells.

The binding of dB4 to CD4+ T cells in human blood at a normal body temperature (37° C.) was investigated to determine if dB4 could effectively be administered as a therapeutic to human subjects. To mimic the physiological setting of the human body, dB4C7 (UB-421) was incubated with freshly drawn blood at 37° C. for 1 hr. and the peripheral blood leukocyte (PBL) samples were obtained by RBC lysis procedures. Incubation on ice (4° C.) was also conducted in parallel. The PBL fractions were then stained with goat $F(ab)_2$ anti-huIgG-FITC to visualize direct binding of dB4 to the CD4 receptors on CD4-gated T cells.

It was noted that cellular incubation with dB4 for 1 hr. at 37° C. did not appear to cause endocytosis of ligand-receptor as no change in the MFI of mouse anti-CD4(D2)-FITC was observed, as compared to the incubation at 4° C. (data not shown). Mouse anti-CD4(D2)-FITC for gating of CD4+ T cells at 50-1000 ng/mL and dB4 (targeting D1 domain of the CD4 receptor) at concentrations up to 200 ng/mL did not compete for binding.

As shown in the blood sample from one female individual (FIG. 12), peripheral blood mononuclear cells (PBMC) were incubated with dB4 at two different temperatures, 37° C. or 4° C., for 1 hour. The gated CD4+ T cells were stained for observation of dB4 binding on FACS. FIG. 12 shows that dB4 bound to the CD4 receptors with an affinity 5-fold higher at 37° C. than at 4° C., based on the $IC_{50}$ values of 4.8 ng/mL and 23.0 ng/mL, respectively. As expected, dB4 reached the same maximum binding MFI under both temperature conditions. The MFI values reflect the degree of receptor occupancy, in particular when these values are normalized and expressed as % MFI.

4.4.1 Direct Binding of dB4 to Blood CD4+ T Cells.

The binding profile of dB4 to CD4+ T cells in human blood at a normal body temperature (37° C.) was also investigated. The direct binding activity of dB4 to blood CD4+ cells was evaluated on six different occasions using freshly drawn blood from six human adults (three males and three females) (Table 10). After 1 hr. incubation, the peripheral blood leukocytes were isolated, stained with goat F(ab)$_2$ anti-huIgG Fc-FITC, and the dB4-bound to the CD4-gated T cells were analyzed by FACS. The samples were calibrated with reference beads for fluorescence reading. The binding ($EC_{50}$) values were found to be between 2.6 ng/mL to 5.7 ng/mL, with the mean $EC_{50}$ being 4.1 ng/mL. Also, the maximum % MFI values ranged between 68% to 93% with the mean being 77.8% (Table 10). These results reflect that the inter-subject variation of minor significance in binding affinity and receptor density, respectively.

4.4.2 Free CD4 Binding Sites after Receptor Occupancy by mAb dB4.

In conjunction with the direct binding of dB4 to blood CD4+ cells at 4° C. (as detected by detected by goat anti-hIgG), the unoccupied, free CD4 binding sites on the CD4+ cells were assessed by dB4-Alexa.

In the absence of dB4, the dB4-Alexa conjugate alone was capable of approaching ~100% of its maximum binding at about 250 ng/mL (FIG. 13). At concentrations higher than 500 ng/mL, the dB4-Alexa conjugate could dislodge approximately 10% or more of the bound dB4 (data not shown). Specifically, when the receptors were occupied by dB4 at a saturation-approaching level of 250 ng/mL, the binding of dB4-Alexa (at 250 ng/mL) to the CD4 receptors was completely blocked.

The fall in receptor occupancy with decreasing presence of dB4 was observed to be in parallel to the rise in binding of dB4-Alexa. The degree of receptor occupancy synchronized in symmetric manner with the level of free binding sites, and both curves crossed over at approximately 4.0 ng/mL (FIG. 13), is in agreement with their binding $EC_{50}$ values (Table 10).

The overall results thus suggest that the in vitro use of dB4-Alexa at 250 ng/mL along with MFI and % MFI could be an appropriate paradigm to investigate the in vivo receptor occupancy after dB4C7 (UB-421) is administered to human subjects.

5. Conclusions

1. MAb dB4 reacts with CD4 receptors on HPB-ALL cells with an unusually high activity, reaching an instant equilibrium on ice at concentrations higher than 50 ng/mL. The absolute binding affinity (Kd) was estimated to be $5.6 \times 10^{11}$ M, and maximally $1.2 \times 10^6$ dB4 molecules (Bmax) could bind to a single HPB-ALL cell, which has a receptor density at least 20-fold higher than that of normal blood CD4+ T cells.
2. Humanization of the murine B4 to dB4 mAb does not significantly alter dB4 binding affinity to CD4 receptors. By binding inhibition design, using a molecule-based ELISA (coated with sCD4 and CCR5 epitope-containing peptide p2704a) as well as a cell-based FACS with HPB-ALL cells, both antibodies comparably block the binding of the tracers, be that B4-biotin or dB4-Alexa, as the $IC_{50}$ ratios of B4-to-dB4 was observed to be approximately 0.7 in both studies.
3. The dB4 antibody binds to CD4 receptors with an affinity at least 50-fold higher than that for HIV-1 envelope protein gp120 MN. Specifically, binding inhibition studies using HPB-ALL cells demonstrated that dB4 and gp120 MN inhibit the binding of the tracer dB4-Alexa with $IC_{50}$ values 1.8 and 97.2 nM, respectively. This result is also in agreement with dB4's high binding affinity (Kd) that is about 100-fold greater than that previously reported for recombinant gp120.
4. MAb dB4 binds to blood CD4+ T cells with a similar binding affinity to HPB-ALL cells. Under cold conditions (4° C.), dB4 has an $EC_{50}$ of approximately 23.0 ng/mL and under normal body temperature (37° C.), dB4 binds to blood CD4+ T cells with about a 5-fold higher affinity, as the binding $EC_{50}$ value estimated to be at 4.8 ng/mL.
5. Studies from blood samples taken from six human subjects confirmed that there is a direct (inversely proportional) correlation between dB4 concentration and CD4 receptor occupancy. The opposing curves, shown in FIG. 13, intersect at approximately 4.0 ng/mL, which corresponds with dB4's mean $EC_{50}$ binding value for CD4. These overall results suggest that the in-vitro use of dB4-Alexa (at 250 ng/mL) along with the measurement of fluorescence beads-calibrated % MFI can be an appropriate paradigm for investigation on the in-vivo receptor occupancy after dB4C7 (UB-421) is administered to human subjects.

Example 8

Antibody B4 Inhibits Effectively Both Cell-Free and Cell-to-Cell Transmission of HIV HIV particles classically spread throughout the body by cell-free transmission, where the virus diffuses in the bloodstream and local environment to infect cells. The virus also has the ability to transfer from infected to uninfected cells directly by a mechanism that requires intimate cell-to-cell contact. Such spread occurs when an infected cell forms a stable point of contact with an uninfected cell and transmits HIV particles directly to the uninfected cell. Cell-to-cell spread is more efficient, quicker, and does not require diffusion in the bloodstream, compared to cell-free spread.

Sigal, A., et al., 2011 reported that infections originating from cell-free virus decrease strongly in the presence of the antiretroviral drug tenofovir whereas infections involving cell-to-cell spread are markedly less sensitive to the drug in a co-culture assay (FIG. 14). The reduction in sensitivity was sufficient to keep multiple rounds of infection from terminating in the presence of drug. The authors examined replication from cell-to-cell spread in the presence of clinical drug concentrations using a stochastic infection model and found that replication was intermittent, without substantial accumulation of mutations. If cell-to-cell spread has the same properties in vivo, it may have adverse consequences for the immune system, leading to therapy failure in individuals with risk factors, and potentially contribute to viral persistence and, hence, be a barrier to curing HIV infection.

It is therefore important to assess the ability and potency of mAb B4 and mAb dB4 related antibodies to inhibit cell-to-cell transmission of HIV for assessment of its potential effect in treatment.

1. Assay to Measure Antibody Mediated Inhibition of Cell-to-Cell Transmission of HIV 1.1 Materials and Methods 1.1.1 Cells and Viruses.

The Jurkat-inGLuc clone (NIH AIDS Research and Reagents Program) with a reporter gene luciferase engineered into HIV-1 genome was selected as donor cells due to low expression of surface CD4 to minimize donor-todonor infection in co-culture experiments with target primary CD4+ T cells. The reporter gene luciferase can be expressed in infected cells and used as a marker for viral infection. These virally expressed reporters in the infected cells can be measured to quantify HIV-1 infection. Primary CD4+ T cells were used as the target cells. Viruses UG266 and UG046 of clade D were used in the study.

1.1.2 Viral Cell-to-Cell Transmission Assay.

In this assay, donors were preincubated with the antibody B4 in serial dilutions prior to mixing with the indicated HIV-1 strains and used a few days later, when ~10-75% of the cells were Gag+. Donor and CD4 positive PBMC target cells were then mixed at a 1:2 ratio in 96-well plates at a final concentration of $1.5 \times 10^6$ cells/ml in 200 µl. After 48 hrs, cells were stained for intracellular Gag and analyzed by flow cytometry. GLuc accumulated in the culture supernatant was detected using the BIOLUX® *Gaussia* Luciferase Assay Kit (New England Biolabs) and a Berthold Technologies luminometer.

1.1.3 Calculation of $IC_{50}$ and $IC_{90}$.

Dose-response inhibition curves were drawn by fitting data to sigmoid dose-response curves (variable slope). Percentage of inhibition was defined as (percent signal in nontreated target cells−percent signal in antibody-treated cells)/(percent signal in nontreated target cells)×100. The $IC_{50}$ and $IC_{90}$ were calculated accordingly.

2. Results and Discussion

Table 11 shows that antibody B4 was able to inhibit cell-to-cell and cell-free transmission of HIV (viral strains UG266 and UG046 of clade C) equivalently when measured by a stringent 90% entry inhibition criteria. Specifically, the fusion inhibition titers were found to be 1:140 and 1:245 for UG266 and UG046 viral strains in cell-to-cell transmission assays, which was comparable to the neutralization titers of 1:136 and 1:234 in cell-free transmission neutralization assays, respectively. Higher fusion inhibition titers for the two strains were observed for cell-to-cell transmission compared to the corresponding cell-free transmission when measured by a 50% entry inhibition criteria.

These results demonstrate that antibody B4 has an unusual property in its capability to inhibit both cell-to-cell and cell-free transmission of HIV when compared to all other neutralizing monoclonal antibodies targeting HIV Env proteins and other ART-drugs measured thus far. These results suggest that mAb B4 and mAb dB4 related antibodies are uniquely qualified to prevent cell-free and cell-to-cell spread of HIV virus in an individual.

Example 9

Antibody UB-421 (DB4C7 or DB4) Mediates Reactivation of Resting PBMCs for Enhanced Viral Replication in HIV Infected Individuals 1. Background HIV-1 infects resting peripheral blood mononuclear cells (PBMCs) but remains inactive until subsequent cell activation. An in vitro model using cell culture condition and a protocol that allows nonproductive infection of resting T cells mimicking latent HIV-1 harbored in quiescent PBMCs was used to investigate the stimulation effect of heat-inactivated HIV-1 (iHIV-1) or gp120-anti-gp120 immune complexes on these resting PBMCs (Briant, L., et al., 1996).

It was demonstrated that CD4 engagement with the envelope glycoproteins of heat-inactivated HIV-1 (iHIV-1) or gp120-anti-gp120 immune complexes was sufficient, through crosslinking, to stimulate a signal transduction pathway controlling activation of NF-kB (i.e. nuclear translocation) and AP-1 which in turn involves extracellular domain 1 (D1) and the intracytoplasmic domain of CD4 and several kinases (Lck, Raf-1, MEK and ERK) to induce cell cycle progression, promote cell-surface expression of activation marker CD25, and stimulate provirus integration and commit cells to produce virus.

A separate scientific finding by Than, et al. (Than, et al., 1997) further confirmed that crosslinking of CD4 molecules at the gp120 binding site by anti-CD4 monoclonal antibody induces latently infected PBMCs from HIV infected patients to promote virus replication. The anti-CD4 mAb used in this study was Leu3a which binds the CDR2-loop of D1 of CD4. Specifically, Leu3a is directed to a linear epitope represented by peptide with aa47-64 within domain 1 of CD4 (Chiba, Y. 1992).

Additionally, virus reactivation in resting PBMCs was found to be specifically induced by monoclonal antibodies directed against the CDR2-loop in domain 1 (D1) of CD4 and not by antibodies directed against other epitopes, such as CDR3 in D1 or the nearby D1/D2 junction region (Briant, L., et al., 1999) (FIG. 15, compare lane 4 with lanes 5 and 6). Such virus reactivation can be prevented by prior absorption of CDR2-loop ligands with soluble CD4 (sCD4) (FIG. 15, compare lane 4 and lane 8).

It was, therefore, important to assess whether antibody dB4C7 (UB-421) with high binding affinity with CD4 around domain 1 region can mediate reactivation of resting PBMCs for enhanced viral replication in HIV infected individuals.

2. Refinement of B4/dB4 Conformational Binding Site Around D1 of CD4

2.1 Competitive Sequential Binding Inhibition of Leu3a Binding to Chimp CD4 Positive PBMCs by mAb B4 but not in the Reverse Order Chimp PBMC cells isolated from two subjects (X282 and X301) were used in this study as well as mAb B4 (labeled by FITC) and Leu3a (labeled by PE). PBMCs were sequentially stained with the respective antibodies and analyzed by cytofluorography. The data obtained from this experiment is reported in Table 12 and discussed below.

In the single label control samples, cells stained with Leu3a only tested positive for Leu3a-PE binding; and cells stained with mAb B4 only tested positive for B4-FITC binding. Specifically, CD4+ cells (as detected by Leu3a) in non-infected chimp samples (X282 and X301) were 25.5% and 44.0% respectively, similar to those detected by mAb B4 (26.1% and 45.5%).

Prior binding of Leu3a followed by exposure to mAb B4 led to double stained (Leu3a+/B4+) PBMC cell counts similar to the single label control cells stained with Leu3a or B4 alone (i.e., 24.5% and 46.7% for X282 and X301, respectively).

In contrast, prior binding of mAb B4 followed by exposure to Leu3a led to only mAb B4 stained PBMCs with no Leu3a positive staining in either single or double staining procedure.

Collectively, these results demonstrate a one way inhibition by antibody B4-FITC against Leu3a-PE. That is, B4 binding is not blocked by prior Leu3a binding; however, Leu3a binding is blocked by prior B4 binding. These data support the conclusion that mAb B4 recognizes conformational epitopes covering the CDR2 region of CD4 domain 1 recognized by antibody Leu3a and that mAb B4 binds to this region of CD4 with a higher affinity compared to antibody Leu3a.

2.2 Competitive Inhibition by ELISA of B4 Binding to rsCD4 by Immune Sera Directed Against HIV RC Peptide (Aa39-66)

The binding affinity of mAb B4 to full-length recombinant soluble CD4 (rsCD4) was evaluated through a competitive inhibition study using immune sera directed against the CDR2 region of CD4 domain 1.

2.2.1 Anti-HIV RC Polyclonal Antibodies.

Polyclonal antibodies against the CDR2 region of CD4 domain 1 were prepared by immunizing guinea pigs with a cyclic peptide comprising aa39-66 of CD4. This cyclic peptide is referred to in this study as the HIV receptor complex peptide (HIV RC peptide) and was previously described as peptide p2240c in Wang, et al., 2002.

Specifically, guinea pig serum directed against the HIV RC peptide was obtained at the specified time points after intramuscular immunization of 4-6 week old Duncan Hartley guinea pigs with 100 µg in 0.5 ml per dose in Complete Freunds Adjuvant at week 0 and Incomplete Freunds at 3 and 6 weeks, followed by monthly boosts in Incomplete Freunds thereafter.

The polyclonal antibodies obtained are referred to as "anti-HIV RC polyclonal antibodies".

2.2.2 Competitive Inhibition of B4 Binding to rsCD4 by Anti-HIV RC Polyclonal Antibodies.

The competitive inhibition experiment was carried out using 96 well microtiter plates coated with full-length rsCD4 at 0.08 µg/mL at 0.1 mL per well. The wells were incubated with guinea pig sera collected from 0, 3, 6, 9, 12, 14, 16, and 19 weeks post immunization with immunogen directed against the HIV RC peptide (aa39-66 of CD4) at 1:30 dilutions prior to binding by biotinylated B4-antibody followed by binding with conjugated avidin-HRP as a tracer. Negative control sera (RC isotype) from unimmunized guinea pigs collected throughout the same period were tested as well.

FIG. 16 shows that biotinylated-B4 binding to rsCD4 was significantly inhibited by anti-HIV RC polyclonal antibodies obtained at 6 weeks post initial immunization, reaching near complete inhibition by 9 weeks post initial immunization.

This competitive binding inhibition study further demonstrated the binding site of mAb B4 is around the CDR2 loop of domain 1 of CD4, although direct binding by mAb B4 to this peptide was not significant due to mAb B4's preferential binding to the conformational contour of membrane-bound CD4.

2.3 Reactivation of Resting CD4 Positive T Cells for Enhanced Viral Production in HIV Infected Individual Upon Crosslinking of mAb dB4

The ability of mAb dB4 to activate resting CD4+ cells was assessed by treating cells with mAb dB4 and monitoring TNF-α production, viral load, and cell proliferation.

In this study, 8-well culture plates were coated with human IgG by incubating the plate with 200 µL of Goat anti-Human IgG (Jackson ImmunoResearch) for 1 hour at 37° C. The coated plates were kept in 4° C. refrigerator until further use in this study.

PBMC from HIV patients were thawed for 1.5 hours according to standard practice. Activation of resting CD4+ cells was evaluated by treating the PBMC with either mAb dB4 (experimental), PMA+PHA (positive control), or medium alone (negative control), as set forth below.

2.3.1 mAb dB4 Treatment.

Cells were treated with mAb dB4 at a concentration of 3 µg/106 cells/mL for 1 hour at 4° C. to initiate cross-linking of the CD4 on the cells. Cells treated with mAb dB4 were then washed and cultured on coated 48-well culture plates for 7 days with RPMI medium and 10% FBS. An uncoated well was also used as a negative control. Aliquots of the culture supernatant were frozen on day 0, day 2 and day 7 for later evaluation. The Day 0 time point for the mAb dB4 sample was obtained by removing supernatant from cells after 30 minutes of treatment at 4° C.

2.3.2 PMA+PHA Treatment.

Cells were treated with 0.1 µM phytohaemagglutinin (PHA) plus 15 µg/mL phorbol myristate acetate (PMA) (Sigma) (PMA+PHA) on coated 48-well culture plates for 7 days with RPMI medium and 10% FBS, as a positive control for reactivating resting CD4+ cells. An uncoated well was also used as a negative control. Aliquots of the culture supernatant were frozen on day 0, day 2 and day 7 for later evaluation. The Day 0 time point for the PMA+PHA sample was obtained by removing supernatant from cells after 30 minutes of treatment at 4° C.

2.3.3 Medium Alone.

As a negative control, cells were incubated on coated 48-well culture plates for 7 days with RPMI medium and 10% FBS (medium alone). An uncoated well was also used as an additional negative control. Aliquots of the culture supernatant were frozen on day 0, day 2 and day 7 for later evaluation. The Day 0 time point for the medium alone sample was obtained by removing supernatant from cells after 30 minutes of incubation in medium at 4° C.

2.3.4 Analysis of CD4+ Reactivation.

Reactivation of CD4+ cells was determined by evaluating TNF-α production, viral load, and cell proliferation. The results from this study are summarized in Table 13.

The aliquots from all samples were assayed for (1) the concentration of TNF-α by quantitative ELISA; (2) HIV viral load by RT PCR; (3) cell count; and (4) viability by trypan blue, using standard methods.

Specifically, the data show that cross-linking of mAb dB4 coated PBMC cells from HIV patients triggered moderate production of TNF-α when compared to the medium alone negative control (non-detectable) and cells stimulated with PMA+PHA (about 3 to 5 times higher than mAb dB4 coated cells).

Also, the mAb dB4 sample proliferated at a rate similar to the medium alone negative control; whereas the PMA+PHA stimulated cells proliferated at a much greater extent compared to cells cross-linked with mAb dB4 (cell counts were 5 times higher in the PMA+PHA culture than the mAb dB4 culture on day 7).

However, the HIV viral load was significantly enhanced in the cells cross-linked with mAb dB4 compared to the medium control and the PMA+PHA stimulated cells. Specifically, cells cross-linked with mAb dB4 showed a 151% and 220% increase in viral load when compared to the medium alone negative control at days 2 and 7, respectively; whereas the PMA+PHA culture displayed suboptimal viral load production (55% and 78% at days 2 and 7, respectively) despite a 5 times increase in cell proliferation.

3. Conclusions

1. Murine mAb B4 was found to recognize a conformational site on CD4 close to the site recognized by antibody Leu3a (aa47-64 in the CDR2 region). MAb dB4 is expected to have the same recognition properties as those described here for mAb B4 based on the comparative studies reported in Example 7.
2. Murine mAb B4 binding to full-length rsCD4 was inhibited by polyclonal antibodies directed against a cyclic peptide containing aa39-66 of the CDR2 region of CD4 domain 1 (HIV RC peptide). These results suggest that mAb B4 recognizes aa39-66 of CD4, which corresponds to the CDR2 loop of D1 of CD4. MAb dB4 is expected to have the same recognition properties as those described here for mAb B4 based on the comparative studies reported in Example 7.

3. CD4 cross-linking with mAb dB4 was found to activate virus production in HIV infected PBMC CD4+ T cells. Specifically, mAb dB4 lead to induction of TNF-α production and enhanced HIV production without induction of cell proliferation, as shown in Table 13.

4. Based on the results obtained in this Example, mAb dB4 (including UB-421) can mediate reactivation of resting PBMCs for enhanced viral production in HIV infected individuals.

Example 10 mAb DB4C7 and Anti-HIV RC Polyclonal Antibodies Inhibit Antigen Induced T Cell Proliferation and Cytokine (IL2 and IFN-γ) Production by CD4 Positive T Cells Thus Breaking the HIV Pathogenic Cycle of Pyroptosis 1. Background Recent reports have shown that when HIV infects permissive, activated CD4+ T cells, cell death occurs silently through caspase-3-dependent apoptosis (Doitsh, G., et al., 2014). Conversely, when either R5 or X4-tropic HIV abortively infects non-permissive, quiescent CD4+ T cells from lymphoid tissue, these cells die by caspase-1-dependent pyroptosis, an intensely inflammatory form of programmed cell death. Interferon inducing factor 16 (IFI16) has been identified as the host DNA sensor that recognizes the incomplete HIV reverse transcripts which, in turn, initiates activation of caspase-1 (Monroe, K. M., et al., 2013). In most human lymphoid tissues including tonsil, lymph node and spleen, the activated and permissive subset of cells represents 5% or less of the total CD4 T-cells, whereas the non-permissive quiescent cells represent 95% or more of the targets encountered by HIV. Thus caspase-1-mediated pyroptosis, not caspase-3-mediated apoptosis, appears predominantly responsible for driving CD4 T-cell death following HIV infection of these lymphoid tissues. These findings are further supported by analysis of fresh lymph nodes from subjects infected with R5-tropic HIV, in which caspase-1 and IL-1β are detected in the paracortical zone that is rich in resting CD4 T cells, whereas caspase-3 activity is detected in the anatomically distinct germinal centers where productively infected cells are found.

Pyroptosis most likely promotes the rapid clearance of various bacterial infections by removing intracellular replication niches and enhancing the host's defensive responses through the release of pro-inflammatory cytokines and endogenous danger signals. However, in pathogenic chronic inflammation, such as in HIV infection, pyroptosis is not a protective response and does not lead to clearance of the primary infection. In fact, pyroptosis appears to create a vicious pathogenic cycle, where dying CD4 T cells release inflammatory signals that attract more cells into the infected lymphoid tissue to die and to produce more inflammation. These events establish a chronic state of inflammation that fuels disease progression and tissue injury. Chronic inflammation might also promote maintenance of the latent HIV reservoir stimulating homeostatic proliferation of memory CD4 T cells.

The depletion of CD4 T cells and the development of chronic inflammation are signature processes in HIV pathogenesis that propel disease progression and pyroptosis provides an unexpected link between these two disease-promoting processes.

The information above suggests that pyroptosis that occurs in lymphoid tissues during HIV infection might be alleviated or reduced by a mechanism that suppresses CD4+ cell proliferation and/or inflammatory cytokine production triggered by antigenic stimulation of CD4+ cells.

2. Experiment

A study was performed to determine if mAb dB4 can break the pathogenic cycle caused by pyroptosis by inhibiting the development of chronic inflammation in HIV infected individuals. Inhibition of cytokine production triggered by antigenic stimulus would help to relieve the burden of pyroptosis by many of the resting T cells, which already have an abortive HIV infection, thus breaking the HIV pathology in CD4 positive T cell depletion due to cytokine production.

An in vitro model employing Staphylococcal Enterotoxin B (SEB) was used to assess the ability of mAb dB4C7 (UB-421) to inhibit PBMC T cell proliferation in both normal and HIV infected individuals. SEB is a superantigen that has the ability to stimulate all T cells bearing a particular T cell antigen receptor (TCR) and induces massive cytokine production.

Through collaboration with Drs. Huyen Cao and Mohamed Elrefaei, functional analyses of normal human donors (n=3) and HIV-infected donors (n=6, ART naïve, CD4+ count >200, viral load >10,000) were conducted to assess if mAb dB4C7 (UB-421) or anti-HIV RC polyclonal antibodies directed against the CDR2 region of D1 of CD4 (described in Example 9) could inhibit cell proliferation and cytokine (IL2 and IFN-γ) production.

2.1 Study Subjects and Samples.

HIV-positive ART treatment naïve volunteers (n=6) were recruited from the REACH cohort (San Francisco). Three age-matched, HIV-seronegative control volunteers were also included in the study. PBMC were separated and cryopreserved in liquid nitrogen until assay time.

2.2 Saturating Concentration of mAb dB4C7 or Purified Anti-HIV RC Polyclonal Antibodies were Used.

CD4+T lymphocytes were first stained in an indirect immunofluorescence study with mAb dB4C7 IgG or anti-HIV RC polyclonal antibodies IgG followed by Alexa-goat anti-HuIgG or Alexa-goat anti-guinea pig IgG, respectively. The resultant stained cells were analyzed by flow cytometry for the percent positive cells detected. Both mAb dB4C7 and anti-HIV RC polyclonal antibodies were titered between 50 μg/mL and 0.0025 μg/mL in a 2-fold dilution. Antibody titration for mAb dB4 and anti-HIV RC antibodies were determined as % CD4 binding vs antibody concentration in μg/mL. These titrations were assessed prior to use in T cell functional assays performed on HIV infected and normal individuals.

FIG. 17 shows that saturating concentrations for the respective reagents used in the functional studies were found to be 1 μg/mL for mAb dB4 (dB4C7) and 25 μg/mL for anti-HIV RC polyclonal antibodies.

2.3 Proliferation of CD4+ or CD8+ T Cells.

Cell proliferation was analyzed by a CFSE (carboxyfluorescein succinimidyl ester) fluorescence assay, which follows the loss of CFDA-SE (carboxy-fluorescein diacetate, succinimidyl ester) stain upon cell division. CFSE was used as a surrogate for a $^3$H-Thymidine (proliferation) assay.

PBMCs were incubated with saturating concentrations of mAb dB4C7 or purified anti-HIV RC polyclonal antibodies to coat the CD4 receptors on the surface of the cells. Cells were also incubated with anti-HIV RC isotype at 25 µg/mL and PHA (10 µg/ml; Sigma-Aldrich) as negative and positive controls, respectively.

PBMCs were labeled with CFDA-SE (Molecular Probes, Eugene, Oreg.) in PBS, then quenched with 100% FCS (Sigma-Aldrich, St. Louis, Mo.). The cells were then resuspended in RPMI 1640 (Sigma-Aldrich) with 10% FCS after washing with PBS.

Cells were then cultured in the presence of SEB Ag (1 µg/mL) for 5 days at 37° C. in 5% $CO_2$ and analyzed for the expression of surface markers.

Flow cytometry was conducted for analyses of CD3+ (Amcyan) gated CD4+(PE, D2), CD8+(PercpCY5.5) cell populations which were each further measured for % CFSE positive cells as % of proliferating cells. Forty thousand (40,000) lymphocytes per sample were acquired using an LSR II (BD Biosciences, Mountain View, Calif.), and analysis was performed by FLOWJO software (TreeStar, San Carlos, Calif.). Results were measured as % of dividing CD4 (or CD8) T cells. All study participants demonstrated significant proliferation following PHA stimulation. Proliferation of CD4 T cells without SEB Ag stimulation (negative controls) was <0.5%.

2.4 Intracellular Staining Assay for Measurement of Cytokines (IL2 and IFN-γ Production.

PBMC ($0.5 \times 10^6$ cells) were incubated for 2 hr with SEB Ag (1 µg/mL) at 37° C. in 5% $CO_2$. Cells were washed with PBS containing 0.1% FCS (wash buffer), and fixed by resuspending the cells in lysing solution (BD Biosciences) for 10 min at room temperature. Cells were washed once with wash buffer, then permeabilized by resuspension in 0.5 mL of permeabilizing solution 2 (BD Biosciences), and incubated for 10 min. at room temperature. Cells were subsequently washed with wash buffer and stained with anti-IL-2 APC, anti-IFN-γ (PE CY7), and anti-CD3 (Amcyan), anti-CD4 (PE, D2) or anti-CD8 (Percp CY5.5) (BD Pharmingen). Forty thousand (40,000) lymphocytes per sample were acquired using an LSR II (BD Biosciences), and analysis was performed by FLOWJO software (TreeStar). Percentage of cytokine-producing CD4 or CD8 T cells without Ag stimulation was <0.05% (negative control). Results were expressed as % of CD4+(or CD8+) T cells that express IFN-γ or IL2.

2.5 Statistical Analysis.

Statistical analysis and comparisons were performed with paired t test.

3. Results

The results obtained from this SEB Ag induced T cell proliferation study revealed that both mAb dB4C7 (1 µg/mL) and anti-HIV RC polyclonal antibodies (25 µg/mL), under saturating conditions, decreased CD4+ T cell proliferation but not CD8+ T cell proliferation in both HIV ART treatment naïve patients and in age-matched normal individuals (data not shown).

Figure 18A:
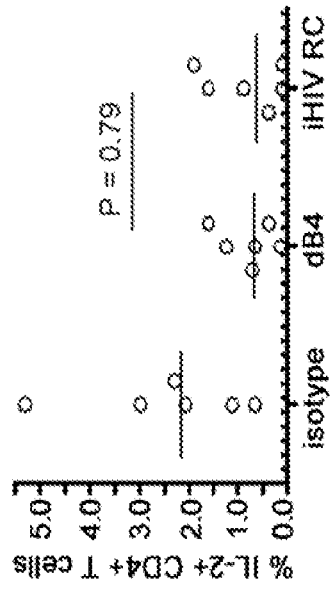
Figure 18B:
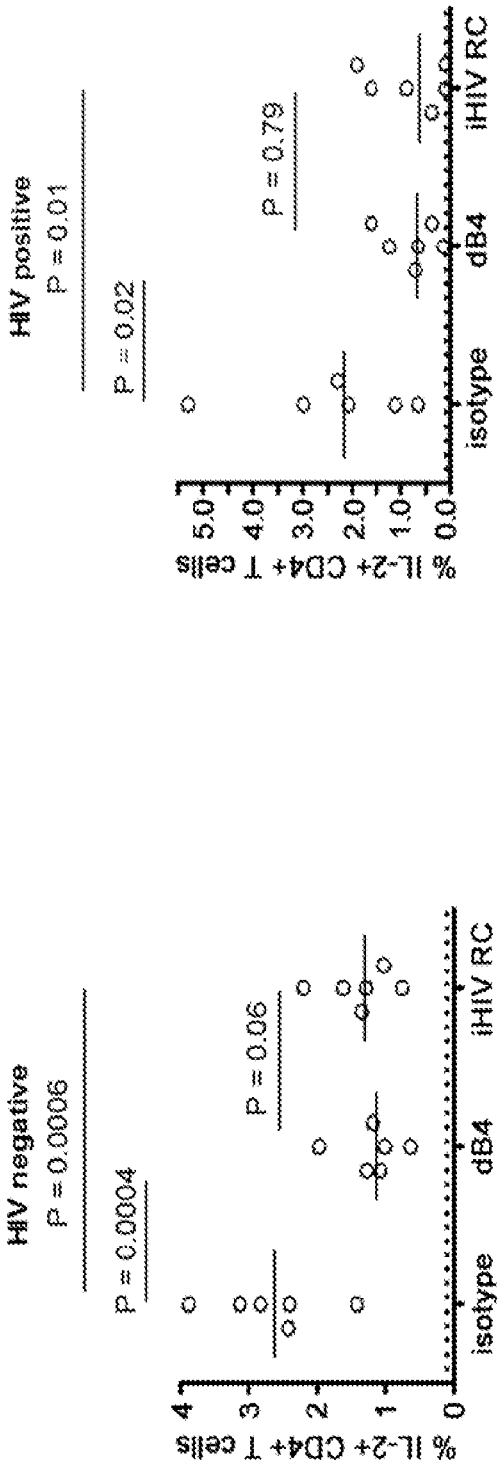
Figure 18C:
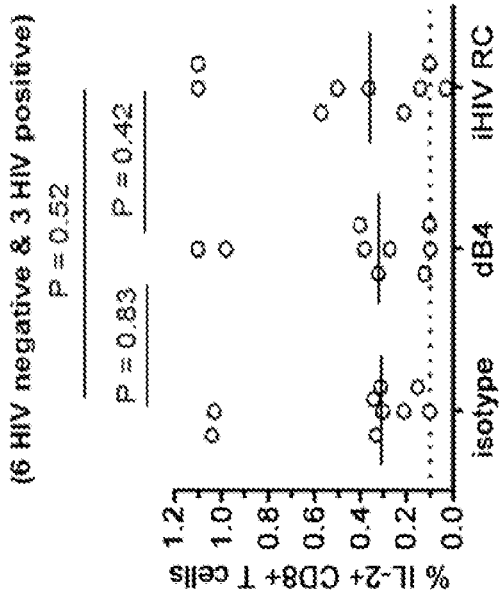

Both mAb dB4 (1 µg/mL) and purified anti-HIV RC polyclonal antibodies (25 µg/mL), at their respective saturating PBMC surface CD4 binding concentrations, suppressed IL2 production by superantigen SEB induced proliferating CD4+ T cells in HIV negative (FIG. 18a) and HIV positive (FIG. 18b) individuals. Such suppression was not found in CD8+ T cells from the same HIV positive and negative individuals (FIG. 18c).

Both mAb dB4 (1 µg/mL) and purified anti-HIV RC antibodies (25 µg/mL), at their respective saturating concentrations, also suppressed IFN-gamma production by superantigen SEB induced proliferating CD4+ T cells in HIV negative (FIG. 18d) and HIV positive (FIG. 18e) individuals. Such suppression was not found in CD8+ T cells from the same HIV negative (FIG. 18f) and positive (FIG. 18g) individuals.

4. Conclusions

Antibody mAb dB4C7 (UB-421) and anti-HIV RC polyclonal antibodies, both targeting CDR2 region of CD4 domain 1, were found to suppress super antigen SEB induced T cell proliferation and cytokine (IL2 and IFN-γ) production by CD4 positive T cells, but not T cell proliferation and cytokine (IL2 and IFN-γ) production by CD8 positive T cells. The finding that dB4C7 and anti-HIV RC polyclonal antibodies could suppress CD4+ T cell proliferation and the associated cytokine (IL2 and IFN-γ) production suggests that the antibody may exert similar suppressive effects on other CD4 positive cells related cytokine production with the potential of breaking the HIV pathogenic cycle of pyroptosis.

The suppressive effect on CD4 positive T cell proliferation and associated cytokine (IL2 and IFN-γ) production observed in this and preceding Examples is highly significant in that the CDR2 region targeting antibodies described herein may exert simultaneous opposing effects on CD4 cells, including: (1) reactivation of resting HIV infected CD4 positive T cells to trigger the release of HIV from their latent status (as discussed in Example 9); (2) competitive inhibition and prevention of HIV entry into uninfected CD4 positive T cells from new virus released by reactivation of the resting CD4+ T cells (Examples 4 and 6); and (3) inhibition of T cell proliferation and cytokine production by CD4 positive T cells upon (super)antigenic stimulation (this Example).

The unique biological features of mAb dB4 and anti-HIV RC polyclonal antibodies targeting the very site of HIV binding and initiation of immune responses (i.e., the CDR2 region of CD4 domain 1) provide properties required for functional cure of HIV infection, namely the ability (1) to prohibit HIV infection through entry inhibition; (2) to reactivate virus production in resting T cells; and (3) to directly alter cytokine production.

Example 11

Pre- and Post-Exposure Prophylaxis as Well as Treatment of HIV Infection by mAb B4 in Chimpanzees Challenged with HIV Primary Isolate HIV-1$_{DH12}$ of Clade B Having many of the unique in vitro properties demonstrated for the B4 related high affinity antibodies targeting CDR2 region of CD4 domain 1, it was important to test B4 antibody's efficacy in preventing and/or treating HIV infection in an animal model that most resembles humans. Chimpanzees have been used for over 100 years to model human viral, bacterial, and parasitic infections. With a carefully worked out challenge model in chimpanzees using HIV primary isolate HIV-1$_{DH12}$ of clade B, challenge studies were initiated to assess the potential of mAb B4 to provide passive immunity against HIV-1 infection in both Pre- and Post-Exposure modes. Specifically, mAb B4 was evaluated for its ability to provide (1) sterilizing immunity to protect an exposed subject against infection and (2) treatment to an exposed subject when antibody was given days after establishment of infection.

1. Pre- and Post-Exposure Prophylaxis of HIV Infection by mAb B4 in Chimpanzees.

The potential of mAb B4 to provide passive immunity against HIV-1 infection in both pre- and post-challenge (exposure to HIV-1) modes was evaluated.

1.1 Methods.

1.1.1 Animals Used in Study.

A total of four (4) chimpanzees were used in this study. One chimpanzee was used for as a pre-exposure treatment animal (X084), two chimpanzees were used as post-exposure treatment animals (X356 and X357), and one chimpanzee was used as a control (X259).

1.1.2 Susceptibility of Animals to Infection with HIV-$1_{DH12}$ Stock.

The susceptibility of the animals to infection with the HIV-1Dg-112 stock was determined by in vitro infection of their PBMC before treatment and infection. All cultures were infected within 3 days of exposure to virus.

1.1.3 MAb B4 Antibody.

MAb B4 for infusion was prepared as a highly purified antibody preparation at 5 mg/mL.

1.1.4 Pre-Challenge Prophylaxis/Treatment.

Chimpanzee X084 was infused intravenously with 5 mg/kg mAb B4 1 hour prior to HIV-$1_{DH12}$ challenge.

1.1.5 Post-Challenge Prophylaxis/Treatment.

Chimpanzees X356 and X357 were infused intravenously with 5 mg/kg of mAb B4 1 hour after HIV-$1_{DH12}$ challenge.

1.1.6 Control Animal.

Chimpanzee X259 was challenged with HIV-$1_{DH12}$ without being infused with mAb B4 antibody.

1.1.7 Challenge with HIV-$1_{DH12}$.

The four (4) chimpanzees were intravenously challenged with 100 TCID$_{50}$ of HIV-$1_{DH12}$ taken from a virus stock previously prepared and titered in chimpanzee PBMC at the Southwest Foundation for Biomedical Research.

1.1.8 Detection of HIV-$1_{DH12}$ Virus.

Establishment of infection in the chimpanzees was monitored by detection of plasma viremia, cell-associated viral load, and immune response to HIV by using DNA PCR amplification of gag sequence, co-culture, p24 capture ELISA, and immunoblot. Serum viremia indicative of HIV infection was measured by HIV-1 RNA copies/mL in all blood samples collected during a 50-week period of study from all chimps. HIV-$1_{DH12}$ virus was detected in chimpanzee PBMC by virus isolation and by a DNA PCR assay to detect proviral DNA corresponding to gag. Virus production was evaluated by p24 antigen capture ELISA (Coulter). Serial dilutions of $1\times10^6$ to $1\times10^2$ cells of chimpanzee PBMC and lymph node cells were prepared for co-culture with $2\times10^6$ cells from 3-day-old PHA-stimulated blasts in IL-2 medium. The well of highest dilution that resulted in the production of p24 was taken as the endpoint.

1.1.9 Animal Housing.

Chimpanzees were maintained at the Southwest Foundation for Biomedical Research in accordance with the National Research Council guidelines and with approval of the institutional IACUC.

1.2. Results

Sterilizing immunity was provided by mAb B4 to chimpanzees receiving HIV-$1_{DH12}$ challenge. No markers of infection could be detected during 32 weeks of follow-up post-challenge in the animal infused with mAb B4 antibody prior to HIV-1 challenge (X084) (FIG. 19a) or in the two animals infused with mAb B4 antibody 1 hour after HIV-1 treatment (X356 and X357) (FIG. 19b).

In contrast, virus was readily isolated from PBMC from the control animal (X259) beginning at week 1 post-challenge (FIG. 19c) and from plasma by week 2 post-challenge. Virus also was isolated from lymph node cells of X259 biopsied at weeks 4 and 20. Infected cells in the PBMC and lymph node compartments were detected at dilutions containing cell numbers that ranged from $1\times10^4$ to $1\times10^6$. Seroconversion occurred in animal X259 by week 4.

The presence of free, unbound mAb B4 found in circulation rapidly declined in chimpanzees X084, X356 and X357 treated with antibody. CD4+ and CD8+ subsets from the treated chimpanzees were monitored over 20 weeks post-challenge with no evidence of CD4+ depletion. There was no suppression of the proliferative response of chimpanzee PBMC to mitogens (PHA, Pokeweed mitogen, and Concanavalin A) through week 32.

The results from this study indicate that mAb B4 can provide a prevention or sterilizing cure against HIV infection, documented by an extensive follow-up of serum viremia and other parameters even one year from day of challenge.

1.3. Conclusion

In the chimpanzee trial, HIV infection by a virulent primary isolate was aborted by the administration of mAb B4 either prior to, or within a short interval after, exposure. The transferred immunity was sterilizing with no evidence of a transient, reduced, or delayed viremia. Complete protection was evident, despite the rapid clearance of mAb B4 antibody from plasma, by being sequestered on CD4+ cells in the peripheral blood and lymphoid tissue.

This carefully executed experiment further suggested a treatment protocol using mAb B4 or related antibodies at 5 mg/kg for (i) patients within hours from having encountered HIV or (ii) babies born to seropositive mothers upon delivery, to arrive at sterilizing cure.

1.4 Applications for Post-Exposure Prophylaxis by mAb B4.

U.S. Public Health Service Guidelines recommend post-exposure prophylaxis using antiretroviral drugs for a healthcare worker after an accidental exposure to HIV. However, the U.S. Public Health Service Guidelines express reservations regarding the toxicity of the drugs that are presently available for post-exposure prophylaxis.

The results obtained in this study demonstrate the potential of using mAb B4 as a post-exposure prophylactic treatment that can be used in place of, or in conjunction with, current post-exposure treatments. The low toxicity and efficacy of mAb B4 demonstrates a potential of the antibody to be more broadly active than antiretroviral drugs.

These results further suggest that mAb B4 can be used for the prevention of vertical transmission of HIV from mother-to-child. Mother-to-child transmission (MTCT) of HIV, also called perinatal or vertical transmission, occurs when HIV is spread from an HIV+ woman to her baby during pregnancy, labor, and/or delivery or breastfeeding. The chance of MTCT is about 25% during pregnancy, labor, and delivery for HIV+ women not receiving treatment for the virus. There is an additional 12% chance of MTCT in untreated HIV+ women who breastfeed their infants. Worldwide, in 2001, 1.8 million women became infected with HIV and approximately 800,000 children also became HIV infected, the majority of them via MTCT. A large proportion of people newly diagnosed with HIV worldwide are between 15-24 years old. A very important component of MTCT prevention must be HIV prevention for young people, especially girls and young women before they become sexually active, and treatment for those already infected. Additional information pertaining to MTCT can be found at: caps.ucsf.edu/archives/factsheets/mother-to-child-transmissionmtct#sthash.DTRyms46.dpuf. The results obtained with mAb B4 suggest that MTCT could be prevented during the labor and delivery stage by providing a single administration of 5 mg/kg or more of mAb dB4 to a newborn child of an HIV+ woman.

2. Treatment of HIV Infection by mAb B4 in Chimpanzees.

2.1 Method.

2.1.1 Animals Used in Study.

Chimpanzees X084, X356, and X357 used in the previous prophylaxis study and protected from HIV-1DH12 infection upon receiving a single administration of mAb B4 at 5 mg/kg, were reused in this challenge study in a treatment mode.

2.1.2 Susceptibility of Animals to Infection with HIV-$1_{DH12}$ Stock.

Prior to antibody treatment and HIV challenge, PBMCs were prepared from the animals in order to determine the susceptibility to infection with HIV-$1_{DH12}$. All in vitro cultures were infected within 3 days of inoculation with virus.

2.1.3 Mab B4 Antibody.

MAb B4 for infusion was prepared as a highly purified antibody preparation at 5 mg/mL.

2.1.4 Challenge with HIV-$1_{DH12}$.

All animals (X084, X356, and X357) were intravenously challenged with 100 TCID$_{50}$ of HIV-$1_{DH12}$ taken from a virus stock previously prepared and titered in chimpanzee PBMC at the Southwest Foundation for Biomedical Research.

2.1.5 Post-Challenge Treatment.

Chimpanzee X084 did not have any post-challenge treatment. Chimpanzee X357 was infused with 5 mg/kg of mAb B4 on day 14 post-challenge, when HIV viremia was highest in the challenged animal for treatment of HIV infection. Chimpanzee X356 was infused with 5 mg/kg of mAb B4 on days 14, 18, and 22 post-challenge.

2.2 Summary of Results

This passive immunotherapy study was performed with 5 mg/kg infusions of murine mAb B4 to determine the therapeutic efficacy of mAb B4 in chimpanzees with acute phase HIV infection. Three chimpanzees (X084, X356, and X357) were inoculated intravenously (i.v.) with the HIV-$1_{DH12}$ and establishment of infection was confirmed based on virus detection (not shown) and quantitative RT-PCR.

RNA from HIV-$1_{DH12}$ was detected (above baseline) by RT-PCR by 7 days post-exposure in all chimpanzees (X084, X356, and X357). Cell-associated virus was detected in PBMCs and lymph node cells from all three animals in 14 days, by virus isolation and by DNA-PCR for detection of HIV-$1_{DH12}$ integration.

At day 14 post-infection, two of the infected chimpanzees (X356 and X357) were infused with mAb B4 (5 mg/kg, i.v.). At days 18 and 22 post-infection, one animal (X356) received two additional doses of the antibody (5 mg/kg, i.v.). Viral load was monitored by RT-PCR assay at weekly intervals for the first 12 weeks and then monthly until 40 weeks post-infection. By day 14 post-infection, the day on which chimpanzees X356 and X357 were infused with mAb B4, viral RNA was already in a rapidly ascending phase. The two chimpanzees receiving antibody then experienced rapid and significant declines in their viral load of 1-2 logs by day 20, and a marked decrease in duration of primary viremic period from four weeks to one week (FIG. 20a, closed circle), in comparison to the untreated chimpanzee (X084) (FIG. 20a, open circle).

FIGS. 20a and 20b compare the duration of plasma viremia in the untreated control chimpanzee X084 (from this study, which previously received a single pre-exposure dose of mAb B4) and the untreated control X259 (from the previous study, which did not receive a dose of mAb B4) with chimpanzee X356 receiving three infusions of mAb B4. Chimps X084 (FIG. 20a, open circles) and X259 (FIG. 20b, open circles) were challenged by HIV-$1_{DH12}$ without any intervention and viremia began showing as early as day 3, detected as serum HIV-1 RNA copies, after viral challenge. The duration of serum HIV-1 viremia lasted about 42 days, characteristic for HIV-$1_{DH12}$ infection. Chimp X356 (FIGS. 20a and 20b, closed circles) received three administrations of mAb B4 and the HIV-1 viremia dropped precipitously thereafter reaching non-detectable level on or about day 21. Comparing the viral load data between X356 with X084 and X259 shows a reduction of 21 days from the characteristic viremia duration of HIV-1DH12 infection.

As noted above, the untreated control chimpanzee X084 from this study received a single pre-exposure administration of mAb B4 in the prior study; whereas the untreated control chimpanzee X259 from the previous study did not receive any administration of mAb B4. Interestingly, a comparison of the data obtained for X084 (FIG. 20a, open circles) with X259 (FIG. 20b, open circles) shows that X084 had an overall lower viral load over the study period compared to X259. Thus, although the viral load of the untreated animal in this study (X084) was significantly higher than the mAb B4 treated animal (X256), a prior exposure to mAb B4 in X084 appears to significantly reduce the overall viral load, especially during the acute phase, of HIV infection (comparing X084 with X259). Collectively, these results suggest that any administration of mAb B4 prior to HIV exposure can reduce the intensity of the viral load during the acute phase of infection, which could further reduce transmission of the virus from individual to individual post-infection.

Cell surface staining was also performed and found that mAb B4 remained bound to CD4+ cells for at least seven days in the animal given the single dose of mAb B4 at day 14 (X357), and persisted for at least 14 days in the animal given multiple doses of the antibody (X356). In contrast, free mAb B4 was detected in circulation in both animals for only three days post-infusion as measured by neutralizing activity against the HIV-1 mm isolate. As in the chimpanzee prophylaxis study, this is consistent with the mAb B4 having been removed from circulation by binding to CD4+ cells.

FACS analysis detected CD4+ cells in all samples through 40 weeks by in vitro immunostaining for the CD4/B4 epitope, without notable depletion. Immunostaining of the infused mAb B4 was done on PBMC's during the first 21 days. Mitogen-induced proliferative response (using Con A, PWM, or PHA) of PBMC samples before and after antibody treatment was variable and did not appear to be affected by infusion with mAb B4. These observations suggest that mAb B4 is capable of subverting viral infection and decreasing both the viral load and the viremic period with no evidence of undue immunotoxicity.

Example 12

UB-421 Formulation, Pre-Clinical Pharmacology/Toxicity Studies in Baboons and Cross-Reactivity in Human Tissues Introduction The data obtained from the cell culture and chimpanzee studies discussed in the previous Examples demonstrated sufficient scientific merit to justify further development of a pharmaceutical formulation containing mAb dB4 for human use. A pharmaceutical formulation containing mAb dB4C7 (UB-421) was prepared and general safety tests were performed on lots manufactured for clinical use.

A panel of pre-clinical safety studies were also performed to obtain pharmacodynamic, pharmacokinetic, toxicity, and safety information for the drug candidate UB-421.

Single- and multiple-administration as well as dose-dependent (low- and high-dose) studies were performed in baboons (*Papio* species) to facilitate the design of a Phase I clinical trial for assessing dose-dependent safety, tolerability and immunotoxicity of UB-421 in asymptomatic HIV-1 infected human subjects. Baboons were used as the animal model in the pre-clinical pharmacology/toxicity studies because CD4+ T cells in baboons have a similar binding affinity to mAb dB4C7 as humans, as shown in FIG. 21 (i.e., $EC_{50}$=0.33 µg/mL and 0.29 µg/mL for human and baboon, respectively). Non-human primate pharmacology and toxicity studies in baboons were initiated and performed in collaboration with Dr. Krishna Murthy at the Southwest Foundation for Biomedical Research, Department of Virology & Immunology, San Antonio, Tex.

In addition, cross-reactivity studies were performed to evaluate whether UB-421 has any unintentional reactivity and potential locations of cytotoxicity towards human tissues distinct from the intended target.

As discussed in further detail below, the data obtained from these pre-clinical studies demonstrate sufficient scientific merit to justify further development of UB-421 as an investigational new drug in human clinical trials.

1. Pharmaceutical Formulation

Pharmaceutical formulations containing mAb dB4C7 were prepared for human use. In general, pharmaceutical formulations containing mAb dB4C7 can be prepared in an appropriate buffer including, but not limited to, citrate, phosphate, Tris, BIS-Tris, etc. at a pH between 6.0 to 7.0 and can also contain excipients such as sugars (50 mM to 500 mM of sucrose, trehalose, mannitol, or mixtures thereof), surfactants (e.g., 0.025%-0.5% of TWEEN 20 or TWEEN 80), and/or other reagents.

UB-421 is the designation for a pharmaceutical composition containing 10 mg/mL mAb dB4C7, 20 mM glycine, and 0.05% (v/v) TWEEN (polysorbate 20) in phosphate buffer saline (PBS), pH 6.5.

High concentration formulations of mAb dB4 were also prepared for use in certain applications including subcutaneous injections, which included 10 mM histidine.

Following production, general safety and toxicity studies were performed to ensure that the manufactured drug product was safe to administer to human and animal subjects.

2. General Safety Studies 2.1 UB-421 Production Lots and Safety Criteria

Two large-scale productions of UB-421 drug product (P/N Z807, Lot Nos. 225711 and 225758) were prepared for use in clinical trials and evaluated for general safety.

Large-scale batches (lots) of UB-421 were deemed safe and acceptable for clinical use if the following criteria were met during the 7-day test period: (1) all animals survived through the test period; (2) no apparent signs of toxicity were observed; and (3) no animal had an appreciable weight loss between the time the pharmaceutical composition was administered through the end of the test period.

2.2 Test Animals

Mice:

(Albino, BALB/cByJNarl strain (*Mus musculus*), specific pathogen free, male (National Animal Research Laboratory (NLAC), Taiwan)). (Study Number BIO-003.90)

Guinea Pigs:

(Albino, Hartley strain (*Cavia porcellus*), specific pathogen free, male (National Taiwan University Hospital (NTUH), Animal Center, Taiwan)). (Study Number BIO-003.91)

2.3 Methods

Two (2) mice and two (2) guinea pigs were injected by intraperitoneal route for each lot of UB-421. Control mice and guinea pigs were injected by intraperitoneal route with the Isotonic Sodium Chloride Solution ("S.T.", Lot No. 1OC0206). Each mouse received 0.5 mL total volume and each guinea pig received 5.0 mL total volume. The animals' weights were recorded before dosing (day 0) and before termination (day 7). Each animal was observed daily for general health and clinical signs of toxicity.

2.4 Analysis and Conclusion

Results from the general safety study yielded the following satisfactory results for the criteria analyzed:

(1) All the animals used for the General Safety Test survived during the test period.

(2) No apparent signs of toxicity were observed in the UB-421-treated animals.

(3) No animal lost weight during the test period.

In view of the above, the lots were considered negative for unexpected, unacceptable extraneous contaminants.

These findings confirmed that the large-scale production lots of UB-421 (Lot Nos. 225711 and 225758) were negative for unexpected or unacceptable extraneous contaminants. Accordingly, these two lots were deemed safe and acceptable to be used in human clinical trials.

3. Study A: Single Administration Toxicity Studies of UB-421 in Baboons 3.1 Methods Study A assessed the pharmacodynamics, pharmacokinetics and safety of a single administration of either a low-dose (5 mg/kg body weight) or high-dose (25 mg/kg body weight) of UB-421 over a 42-day period, as shown in Table 14a. In this study, UB-421 was administered by intravenous infusion at either 5 mg/kg or 25 mg/kg body weight over 30 minutes. Blood samples were collected for Pharmacokinetic (PK) analysis at 0, 0.5, 1, 2, 4, 8, 12, 24 hours, and at 2, 3, 5, 7, 10, 14, 21, 28, 35, 42 days.

Blood samples were analyzed by flow cytometry analysis to monitor the presence of $CD4^+$ T lymphocytes using the following markers: CD4 domain 1 (anti-CD4+D1), and CD4 domain 2 (anti-CD4+D2). Alexa-dB4 was used both as a marker and a tracer for competitive CD4 binding by the monoclonal antibodies UB-421 and those directed against CD4 domain 1 and 2. Alexa-goat anti-huIgG was used as a tracer for monoclonal antibodies directed against CD4 domain 1 and 2. In addition, Antibodies directed against CD3 and CD14 were used to monitor the total T cell counts (CD3) and the monocytes (CD14) in the PBMC preparation.

3.2 Summary of Results

No consistent negative observations were found in the pharmacodynamics, pharmacokinetics and safety studies that would suggest that UB-421 should not proceed to phase I clinical trials in humans. For all parameters evaluated, any data point found to be significantly above or below the average ("out of normal range") was observed in both the control and experimental animals.

Initial pharmacokinetic (PK) properties of UB-421 were assessed by evaluating blood samples obtained from baboons treated with a single administration of low dose (5 mg/kg) and high dose (25 mg/kg) UB-421.

The results from this study showed that treatment with UB-421 resulted in a dramatic decrease in the detection of CD3+CD4+T lymphocytes and CD14+CD4+ monocytes isolated from either peripheral blood mononuclear cells (PBMC) or cell suspensions of lymph node biopsy samples. It was suspected that the decrease in these cells was due to "coating" of CD4+ cells with UB-421 and not due to depletion of CD4+ cells in the animals. This suspicion was confirmed when it was found that there was no change in the percentage of CD4+T-lymphocytes detected by antibody to the anti-CD4+D2 marker. The duration of such "coating" by UB-421 on CD4+ cells after the infusion was at least 3 days in animals receiving the low dose and at least 7 days in animals receiving the high dose. When UB-421 was no longer detected in the plasma of the animals, the "coating" on CD4+ cells diminished and CD4+ cells (as detected by anti-CD4+D1) returned to the same percentage as those detected by anti-CD4+D2.

In summary, this study found UB-421 to be safe and could coat CD4 positive cells fully for at least 3 days when low dose UB-421 was administered and at least 7 days when high dose UB-421 was administered. Based on the results discussed in previous Examples, when CD4+ cells are fully coated, HIV is expected to be fully excluded from entering into the cells, which will yield a reduction in viral load.

4. Study B: Multiple Administration Toxicity Studies in Baboons 4.1 Methods

Study B assessed the pharmacodynamics, pharmacokinetics and toxicology of a repeat administration of either a low-dose (5 mg/kg body weight) or high-dose (25 mg/kg body weight) of UB-421 over a 56-day (8 week) period, as shown in Table 14b. In this study, a Treatment Phase consisted of 8 total administrations of UB-421 given at weekly intervals (one administration per week). At the end of the 8-week Treatment Phase, one-half of the treated animals were necropsied and evaluated (Table 14b, Part 1). The remaining animals were followed through a 12-week Recovery Phase, in which the animals were maintained for observation and to collect blood and lymph node samples (Table 14b, Part 2). Blood samples (and lymph node biopsies*) were collected from the animals for analysis at 0*, 1, 3, 7*, 14, 21, 28, 35*, 42, 49, 56* days during the Treatment Phase and at 63*, 70, 77, 91, 105*, 133 days during Recovery Phase. Adult male (M) and female (M) baboons (n=20; age: 7 to 18 years) were used as the test system.

4.2 Summary of Results

Pharmacokinetic, pharmacodynamic, toxicity, and safety information for multiple administrations of low dose (5 mg/kg) and high dose (25 mg/kg) UB-421 was obtained from an extensive panel of pre-clinical studies.

Collectively, the data obtained from Part 1 and Part 2 of Study B indicated the UB-421 drug candidate had scientific merit for further development as an investigational new drug. No consistent negative observations were found in the pharmacodynamics, pharmacokinetics and safety studies that would suggest that UB-421 should not proceed to phase I clinical trials in humans. For all parameters evaluated, any data point found to be significantly above or below the average ("out of normal range") was observed in both the control and experimental animals.

4.2.1 Blood and Biopsy Analysis.

An extensive panel of tests were performed on samples obtained from animals treated with multiple administrations of low dose and high dose UB-421. Results from these tests are summarized in Tables 15 and 17 and discussed further below.

UB-421 was detectable in plasma for at least 3 days in the animals receiving low dose (5 mg/kg) UB-421 and for at least 7 days in animals receiving the high dose (25 mg/kg) UB-421 using both the UBI ELISA test (as discussed in Example 7) and the MT-2 assay (as discussed in Example 2). Excess UB-421 was detected in the plasma of some high dose animals for at least 14 days after the last infusion.

Baboon antibodies directed against UB-421 were not found in any of the 16 animals receiving UB-421, confirming that the drug candidate was not immunogenic in the treated animals.

All baboons were immunized with a hepatitis B virus (HBV) vaccine (Merck) at days 0 and 28. Detectible levels of baboon anti-HBsAg antibodies were observed at day 56 in 4 of 4 control (1B) animals, 6 of 8 baboons receiving the low dose (2B) UB-421, and 3 of 8 baboons receiving the high dose (3B) UB-421. These results suggest that UB-421 "coating" of CD4$^+$ cells may cause hypo-responsiveness in some animals preventing immunization to antigens. However, such hypo-responsive effect was found to be reversible, as these animals were able to develop anti-HBsAg antibodies after cessation of UB-421 treatment and an additional immunization with the HBV vaccine.

4.2.2 Observations and Necropsy Results.

Gross and microscopic analyses of baboons treated in this study are summarized in Tables 16 and 17.

In general, tissues taken from all of the baboons evaluated in this study (Parts 1 and 2) did not show any unique or consistent pathological changes that that could be attributed to the administration of UB-421 at either the low or high dose levels.

Ophthalmoscopic (eye) examinations were performed on all Group 3B (high dose) animals (n=8) at the time of enrollment before infusion and again at the end of the Treatment Phase, one week after the last infusion. The Ophthalmic Reports from these animals indicated that both eyes remained within normal limits for all tests performed at the end of the Treatment Phase.

Electrocardiogram (ECG) recordings were obtained from all animals (n=20) prior to, during, and after the completion of administering each dose. The Electrocardiogram Reports from all animals studied concluded that the ECG changes identified were within normal day-to-day variation.

4.2.3 IND-Enabling Toxicology Results

There were no significant differences in immunotoxicity results between the UB-421 treated groups (2B and 3B) and the control group (1B), except for decreased immune response to HBV vaccination. The clinical laboratory test results, ophthalmic (eye) reports, ECG recordings, and histopathology results supported a conclusion that UB-421 was safe and well tolerated in the adult baboons after receiving eight weekly infusions at dose levels up to 25 mg/kg, a treatment which effectively coated the target cells without depleting them.

5. Cross Reactivity Study in Human Tissues

As discussed in previous Examples, mAb dB4 antibodies, including mAb dB4C7 (the main component in the UB-421 drug candidate), demonstrate high biding affinity to CD4 and, in particular, membrane-bound CD4 on T cells. The following pre-clinical study evaluated whether mAb dB4C7 binds to other cell types using an array of tissues from 30 human organs. The purpose of this study was to evaluate whether mAb dB4C7 has any unintentional reactivity and potential locations of cytotoxicity towards human tissues distinct from the intended target.

5.1 Methods

An immunohistochemistry study was performed using an FDA Standard Frozen Tissue Array containing 90 total tissue cores of 30 organs, with each organ taken from 3 normal human individual donors (US BioMax Tissue Micro Array (TMA) slides, Rockville, Md.). Additional cryostat sections of individual human specimens were also included in the human tissue panel, as described in Table 18. The panel of human tissues was screened for immunoreactivity using biotinylated mAb dB4C7 and a control reagent (biotinylated goat anti-rabbit IgG) for assessment of specificity and undesirable autoreactivities.

5.2 Results

The staining patterns observed on the adult normal tissue sections were reviewed and scored for reactivity by a certified clinical pathologist at PhenoPath Laboratories (Seattle, Wash.). Strong positive surface membrane staining was observed in the thymus gland and T-cell dependent areas in the tonsil (and lymph nodes) and weak positive reactivity was noted in the spleen. Occasional mononuclear cells, consistent with lymphocytes or macrophages, stained positive in multiple tissues in an expected pattern. Focal weak Kupffer cell staining in the liver was also noted. Except for weak staining of endogenous biotin in some tissues, all other adult human tissues tested were negative. Pre-incubation of tonsil sections with unlabeled mAb dB4C7 antibody blocked the specific staining pattern. No unexpected cross-reactivity was observed.

These results confirmed that mAb dB4C7 (the main component in UB-421) does not have any unintentional cross-reactivity that could potentially lead to cytotoxicity towards human tissues distinct from the intended target.

Example 13

A Phase I, Open-Label, Single-Administration, Dose-Dependent Study to Evaluate the Safety and Pharmacokinetics of UB-421 in Asymptomatic HIV-1 Infected Adults 1. Objectives The primary objective was to evaluate the safety and tolerability of a single intravenous infusion of escalating doses of UB-421 in asymptomatic human immunodeficiency virus-1 (HIV-1) infected subjects with the secondary objective to determine the pharmacokinetics of a single intravenous infusion of escalating doses of UB-421 in asymptomatic HIV-1 infected subjects. (Clinical Trial Identifier: NCT01140126).

2. Methodology

Open-label, single-administration, dose-dependent (escalation), two-center, non-comparative.

3. Number of Subjects

A total of 20 subjects (5 subjects in each cohort) were enrolled.

4. Diagnosis and Main Criteria for Inclusion

Subjects were required to meet all of the following criteria in order to participate in this study.
1. HIV-1 seropositive;
2. Aged 20 years or older;
3. For protocol version Mar. 9, 2010: Asymptomatic, as determined by the investigator based on medical history, physical examination, electrocardiogram (ECG), and the results of coagulation tests and clinical chemistry & hematology tests at screening visit (visit 1, V1) must have been within normal range ±10%;
4. For protocol version Jul. 1, 2010: Asymptomatic, defined as patients with no acute or symptomatic viral hepatitis within 24 weeks prior to the screening visit (visit 1, V1) and no history of AIDS-defining illness, which was determined by the investigator based on the medical history, physical examination, ECG and laboratory evaluations;
5. For protocol version Mar. 9, 2010: CD4+ T cell count >350 cells/mm$^3$ and HIV-1 viral load >5,000 copies/mL obtained at screening visit (visit 1, V1);
6. For protocol version Jul. 1, 2010: CD4+ T cell count >350 cells/mm$^3$ and HIV-1 viral load >5,000 copies/mL obtained within 4 weeks prior to screening visit or at screening visit (visit 1, V1);
7. Treatment-naïve, i.e., subjects receiving no prior or current antiretroviral therapy;
8. Not breastfeeding for women;
9. Subjects must have a negative serum pregnancy test result at screening visit for women of childbearing potential;
10. Subjects must agree on using birth control barrier (female or male condom) during study period; and
11. Subjects should sign the informed consent before undergoing any study procedures.

5. Investigational Product(s) and Intervention Method

The UB-421 (dB4C7 mAb) was supplied at a concentration of 10 mg/mL (100 mg in 10 mL vial).

Subjects were separated into four (4) cohorts, containing 5 subjects each, based on the dosage of UB-421 received. Each enrolled subjects received a single intravenous infusion of UB-421 at one of the following dose levels: 1 mg/kg body weight (Cohort 1), 5 mg/kg body weight (Cohort 2), 10 mg/kg body weight (Cohort 3) or 25 mg/kg body weight (Cohort 4) at day 0 (Visit 2, V2). The appropriate volume of UB-421 was calculated based on the specified dose and the subject's body weight. The volume of each individual dose was adjusted using sterile saline so that each individual subject within a cohort was infused with an equivalent infusion volume of drug. The dose of UB-421 was then delivered with an infusion pump.

6. Duration of Treatment:

Time frame from screening, treatment, and follow-up: 62 to 90 days. Time frame from infusion to end of study: 60 days.

7. Criteria for Evaluation:

7.1 Primary Safety Endpoints:
1. Physical examination (PE)
2. Vital signs
3. Clinical Chemistry & Hematology tests
4. Incidence of adverse event (AE)/serious adverse event (SAE)
5. Electrocardiogram (ECG)

7.2 Secondary Safety Endpoints:
1. Serum concentrations of anti-UB-421 antibodies (immunogenicity of UB-421) were performed on day 0 (pre-infusion), day 14, day 28, and day 60 after dosing.
2. Initial CD4+ T cell counts were assessed at the screening visit (V1) or were based on pre-screening data obtained within 4 weeks prior to screening visit.
3. Follow-up CD4+ T cell counts were assessed on day 60 after dosing.

8. Efficacy Endpoint:

Efficacy endpoint was assessed as a change in HIV-1 viral load from baseline. Baseline HIV-1 viral load was defined as the viral load assessed at the screening visit V1.

9. Pharmacokinetics (PK)

The following pharmacokinetic (PK) parameters were evaluated for UB-421:
1. $C_{max}$: the observed maximum serum drug concentration after dosing.
2. $T_{max}$: the time at which $C_{max}$ was reached.
3. $\lambda_z$: the elimination (terminal) rate constant.
4. $t_{1/2}$: the elimination (terminal) half-life.

5. $AUC_{(0 \to last)}$: the area under the serum drug concentration-time curve from the time zero to that of the last sample assayed.
6. $AUC_{(0 \to \infty)}$: the area under the serum drug concentration-time curve from the time zero to infinity.
7. CL: the serum clearance of the drug from the body.
8. $V_\beta$: the volume of distribution at the elimination phase.
9. $V_{SS}$: the volume of distribution at steady-state.
10. $MRT_{(0 \to \infty)}$: the mean residence time ($MRT_{(0 \to t)}$) extrapolated to infinity.

10. Statistical Methods:
   10.1 Primary Safety Endpoints
   1. Physical examination: Physical abnormalities were summarized using descriptive statistics by center, day, cohort, and overall. Transition Tables from baseline to the final visit were also presented.
   2. Vital signs: Vital signs were summarized using descriptive statistics by each visit. Changes from baseline values were also presented by center, day, cohort and overall.
   3. Clinical chemistry & hematology tests: Results of clinical chemistry and hematology tests were summarized at applicable visits using descriptive statistics. Based on the investigators' professional judgments and the normal range standards at each study site, the test results were classified into one of the four categories: normal, abnormal without clinical significance (NCS), abnormal with clinical significance (CS), and abnormal with typically clinical significance (CST). The changes in abnormalities of laboratory test results from baseline to the final visit were also shown in transition Tables.
   4. Incidence of Adverse Events (AEs): pre-treatment AEs, treatment-emergent AEs (TEAEs), and drug-related AEs were summarized in frequency distributions. Each reported AE was associated to one Medical Dictionary for Regulatory Affairs (MedDRA) code and one body system class. National Institute of Allergy and Infectious Diseases, Division of AIDS (DAIDS) AE grading Table v1.0 was utilized for severity grading.
   5. ECG: The ECG recording data obtained at applicable visits were summarized by descriptive statistics.
   10.2 Secondary Safety Endpoints
   1. Serum concentration of anti-UB-421 antibody: The antibody concentrations were summarized by applicable visits.
   2. CD4+ T cell count: The cell counts and cell percentages were summarized for applicable visits using distribution statistics. The change from baseline to final visit in both CD4+ T cell count and percentage were also summarized.
   10.3 Efficacy Endpoint.
   1. HIV-1 viral load: The HIV-1 viral loads were summarized using descriptive statistics at each visit. Change from baseline values=(value at post treatment visit –value at baseline visit) were also presented by center, day, treatment cohort and overall.
   10.4 Pharmacokinetic Evaluation Pharmacokinetic parameters were summarized using descriptive statistics at each visit.

According to the protocol and the statistical analyses plan (SAP), safety endpoints were analyzed on the intent-to-treat (ITT) population, while efficacy analyses would be performed on both ITT and efficacy populations. As for PK evaluation, since only subjects at TVGH had samples collected for PK data analyses available, these subjects were defined as PK population. The evaluations of PK were only performed on TVGH subjects.

11. Summary of Conclusions
   11.1 Efficacy, Pharmacokinetics and Safety Results
   11.1.1 Efficacy Results.

The efficacy of UB-421 was evaluated by measuring the changes in HIV-1 viral load at various time points throughout the study as shown in FIG. 22a. The efficacy analyses show that remarkable net changes in mean HIV-1 viral load were found in subjects from Cohort 2 (5 mg/kg), Cohort 3 (10 mg/kg), and Cohort 4 (25 mg/kg) after UB-421 infusion, but not in subjects of Cohort 1 (1 mg/kg).

Efficacy of antibody drug UB-421 (mAb dB4C7) is demonstrated by viral load reduction up to 2.25 log 10 (from the 10 mg/kg group) after single administration (FIG. 22b). The maximum mean decrease in HIV-1 viral load for each cohort is summarized below and shown in FIG. 22b:

Cohort 1 (1 mg/kg): 0.29 $\log_{10}$ copies/mL on day 6 (V5)
Cohort 2 (5 mg/kg): 0.97 $\log_{10}$ copies/mL on day 6 (V5)
Cohort 3 (10 mg/kg): 1.58 $\log_{10}$ copies/mL on day 10 (V6)
Cohort 4 (25 mg/kg): 1.63 $\log_{10}$ copies/mL on day 14 (V7)

The duration of HIV-1 suppression was correlated with dose level, where subjects in the higher dose cohorts showed a longer duration of HIV-1 viral load reduction compared to subjects in lower dose cohorts (FIG. 22a). The duration of HIV-1 viral load suppression for subjects infused with the highest dose of UB-421 (Cohort 4, 25 mg/kg) was maintained for the longest time, about 28 days.

In summary, UB-421 antibody was found to have strong anti-viral effects in a dose-dependent relationship at 5, 10 and 25 mg/kg dose levels. That is, a higher % of patients achieved >1 $Log_{10}$ decrease in serum HIV-1 RNA levels with UB-421 treatment compared to TMB-355 under comparable dosing.

A theoretical comparison of the efficacy data from this study using UB-421 was evaluated against efficacy data previously reported for TMB-355 (previously known as TNX-355; Kuritzkes, D. R., et al., 2004, FIG. 1), as shown in FIGS. 23a to 23c. Based on this comparison, UB-421 achieved a 10 fold reduction in viral load upon receiving single administration of 10 mg/kg or 25 mg/kg in 100% of the subjects evaluated; whereas TMB-355 was only able to achieved a 10 fold reduction in viral load in only 83% of the subjects using the same dosages.

11.1.2 Pharmacokinetics Results.

The pharmacokinetic (PK) parameters listed above were assessed for each dose of UB-421 used in this study (1, 5, 10, and 25 mg/kg). Table 19 summarizes the results of several PK parameters ($C_{max}$, $AUC_{(0 \to \infty)}$, $T_{1/2}$, and MRT) evaluated from 3 subjects in each cohort. The results showed a correlation between the data values for each PK parameter and the dosage of UB-421 administered. That is, increasing the dose of UB-421 from 1 mg/kg to 25 mg/kg corresponded to an increase in the PK parameter evaluated. Specifically, $C_{max}$ increased from 28.6 μg/mL to 462.5 μg/mL; $AUC_{(0 \to \infty)}$ increased from 201 μg-hr/mL to 51367 μg-hr/mL; $T_{1/2}$ increased from 14.4 hrs to 85.4 hrs; and $MRT_{(0 \to \infty)}$ increased from 21.6 hrs to 97.4 hrs.

11.1.3 Safety Results.

The safety features of UB-421 were evaluated by physical examination, vital signs, clinical chemistry & hematology tests, incidences of AE/SAE, and ECG. The CD4+ T cell count and anti-UB-421 antibody concentration were also measured to provide further safety assessment.

The overall incidence of TEAEs with severity grading was 65.0% (13 of 20 subjects) for a total of 30 events. Three subjects were reported with six treatment-related AEs with severity grading: grade 1 (mild) "pruritus" and "furuncle" in subject B-001-001 (dosed with 1 mg/kg of UB-421); grade 1 (mild) "lymphocyte count increased", "neutrophil count decreased" and "platelet count decreased" in subject A-015-009 (dosed with 10 mg/kg of UB-421); and grade 2 (moderate) "rash morbilliform" in subject B-015-008 (dosed with 25 mg/kg of UB-421). The incident of rash morbilliform in subject B-015-008 was a Suspected Unexpected Serious Adverse Reaction (SUSAR); the subject was discharged from hospital after 5 days of care. One subject was reported with another SAE, not related to UB-421, of anal fistula and hemorrhoid in subject A-012-005 (dosed with 5 mg/kg of UB-421); no treatment-related abnormalities were found in vital signs or ECG results. There was only one dose in the treatment; hence, no treatment interruption or change of dose had taken place.

Anti-UB-421 antibodies were detected in three subjects (one from each Cohort 2, 3, and 4) on day 14 (V7) at levels just slightly above the assay detection limit of 0.4 µg/mL. Anti-UB-421 antibodies were not detected at any subsequent visits through day 60 (end of study). No relevant AEs or other physical abnormalities were associated with the appearance of anti-UB-421 antibodies.

Also, the CD4+ T cell count and cell percentage were relatively stable during the 60-day treatment period and also the no-treatment follow-up period.

In summary, UB-421 was safe and well-tolerated for HIV-1 infected adults when a single dose was administered between 1 and 25 mg/kg dose range via intravenous (IV) infusion.

12. Conclusion

This phase I study, with a single intravenous infusion of UB-421 at dosages ranging from 1 to 25 mg/kg, demonstrated that UB-421 was safe and well-tolerated for HIV-1 infected adults. Most of the AEs were mild and unrelated to the study drug. Only one incidence of SUSAR of morbilliform skin rash occurred in Cohort 4 (25 mg/kg dose), but it was unclear whether this incident was related to the study drug. Transient immune reactions to UB-421 were detected only on day 14 (V7) in three subjects with antibody levels only slightly above the assay detection limit of 0.4 µg/mL, suggesting that the appearance of the antibody was of minor clinical significance. Regarding the pharmacokinetic profile of the study drug, the trending of major parameters correlated with the dose level. Moreover, the extent and duration of HIV-1 viral load suppression were significantly and positively associated with UB-421 dose levels at 5, 10, and 25 mg/kg, but were not as obvious in the 1 mg/kg dose cohort.

Considering both safety and efficacy results obtained from this trial, UB-421 at the dose level of at least 5 mg/kg was warranted to be further developed in treating asymptomatic HIV-1 infected adults.

Example 14

A Phase IIa, Open-Label, Multiple-Administration, Dose-Dependent Trial to Investigate the Safety and Efficacy of the UB-421 in Asymptomatic HIV-1 Infected Adults 1. Study Objectives:
1. To evaluate the safety and tolerability of multiple-administrations of two dose regimens of UB-421 in asymptomatic HIV-1 infected subjects.
2. To obtain evidence of antiviral activity of multi-administration of two dose regimens of UB-421 in these subjects.
3. To evaluate the antiviral activity and safety profiles in order to determine the optimal UB-421 administration and dose regimen.
(Clinical Trial Identifier: NCT01668043).

2. Study Design

This was an open-label study with repeated intravenous administrations of UB-421. Subjects who were seropositive for HIV-1 and asymptomatic were screened for eligibility. Twenty-nine (29) enrolled subjects received multiple intravenous infusions of the study drug (UB-421) at one of the two dose levels, 10 mg/kg weekly (Cohort 1) or 25 mg/kg bi-weekly (Cohort 2), for an eight-week treatment period. Subjects were assigned to one of the two study cohorts by site and by turns based on the enrollment sequence. Subjects were followed for an additional eight-week period after the eight-week treatment period. The study ended at week 16.

3. Criteria for Inclusion

Subjects were required to meet the following criteria to be eligible for the phase IIa trial:
1. Asymptomatic, antiretroviral therapy (ART)-naïve, HIV-1 seropositive
2. CD4+ T cell count >350 cells/mm$^3$
3. HIV-1 viral load >5,000 copies/mL
4. No active infection requiring immediate therapy (except HIV-1)
5. No use of immunomodulating drugs or systemic chemotherapy
6. No need for Highly Active Antiretroviral Treatment (HAART).

After completion of this study, subjects followed the routine monitoring schedule (with no antiretroviral agents) at outpatient clinics or received a standard-of-care antiretroviral therapy (e.g. HAART) when deemed necessary by the principal investigator according to current Guidelines for diagnosis and treatment of HIV/AIDS. Individuals who were enrolled in the phase I trial with UB-421 and met the entry criteria of the phase IIa trial were allowed to join this study.

4. Investigational Product(s)

The UB-421 (dB4C7 mAb) were supplied at a concentration of 10 mg/mL (100 mg in 10 mL vial).

Each enrolled subject received multiple intravenous infusions of UB-421 at one of the following dosage levels: 10 mg/kg weekly (Cohort 1) or 25 mg/kg bi-weekly (Cohort 2) for eight weeks. The appropriate volume of UB-421 was based on the specified dose and the subject's body weight. The volume of each individual dose was adjusted using sterile saline so that each individual subject within a cohort was infused with an equivalent infusion volume of drug. The total volume of infusion was approximately 100 mL for 10 mg/kg and 200 mL for 25 mg/kg dose cohorts. The infusion time for each administration was approximately one to two hours.

5. Criteria for Evaluation:

5.1 Primary Safety and Efficacy Endpoints:

The following safety and tolerability parameters of UB-421 were evaluated through week 16 (end of study):
1. Physical examination (PE)
2. Vital signs
3. Clinical Chemistry & Hematology Tests
4. Incidence of adverse event (AE)/serious adverse event (SAE)

The following efficacy parameters of UB-421 were evaluated for each study cohort during the study period (from V2 to V12):
1. Individual maximal viral load reduction
2. Mean maximal viral load reduction 5.2 Secondary Virologic Endpoints The following virologic responses were evaluated during the study period (from V2 to V12):
1. Individual maximal viral load reduction and mean maximal viral load reduction by subgroup within and between each study cohort.
2. The proportion of subjects with viral load <50 copies/mL;
3. The proportion of subjects with viral load <200 copies/mL;
4. The proportion of subjects with viral load reduction >0.5 $\log_{10}$ copies/mL;
5. The proportion of subjects with viral load reduction >1 $\log_{10}$ copies/mL;
6. The proportion of subjects with viral rebound (over 0.5 $\log_{10}$ increase in viral load from the nadir) up to 7 days and 14 days after the last completed study drug administration for cohort 1 and for cohort 2, respectively;
7. Serum concentrations of anti-UB-421 antibodies (immunogenicity of UB-421);
8. Changes in CD4+ and CD8+ T cell counts;
9. Pharmacokinetic parameters of UB-421 ($C_{max}$, $AUC_{(0\to\infty)}$ and $AUC_{(0\to last)}$.

6. Analysis Population:

Intent-to-treat (ITT) population: 29 subjects who received at least one administration of the study drug. The ITT population for Cohort 1 and Cohort 2 was 14 subjects and 15 subjects, respectively.

Per-protocol (PP) population: 18 subjects who received all administration of the study drug, with a valid baseline and at least one valid post-treatment efficacy measurement (HIV-1 viral load test), and lack major protocol violations. The PP population for Cohort 1 and Cohort 2 was 7 subjects and 11 subjects, respectively.

Safety and Immunogenicity population: 29 subjects included in the Intent-to-Treat population.

Pharmacokinetic population: was based on a subset population within the safety and immunogenicity populations.

Baseline data and safety endpoints were analyzed on safety and immunogenicity populations, while efficacy analysis was performed on both ITT and PP populations. Pharmacokinetic analysis was conducted on pharmacokinetic population.

7. Duration of Study Period

Screening period: <4 weeks

Treatment period: 8 weeks

Follow-up period: 8 weeks following the end of the Treatment Period

Visit 0 represented the initial screening and each visit during the study represents a 1 week period. The Follow-up period was generally performed in weekly intervals.

8. Summary of Results:

8.1 Study Population.

A total of 33 asymptomatic HIV infected adults were screened in two study sites in Taiwan. Of those, 29 subjects passed the screening criteria and were selected for the trial. All 29 eligible subjects were male.

8.2 Safety and Tolerability Results:

All 29 subjects experienced at least 1 AE during the study, totaling 128 AEs. Among which, 114 (89.06% in all 29 subjects) were treatment-emergent adverse event (TEAEs) and 14 (10.94% in 5 subjects) were pre-treatment AEs. No serious adverse events (SAEs) were observed in the 29 subjects. All pre-treatment AEs were unrelated to UB-421 and none of these events were considered SAEs. Most (78.95%) of the TEAEs reported were mild, 17.54% were moderate, and 3.51% (in 1 subject) were severe.

The most frequently observed (>10%) TEAE was skin rash and urticarial. Other than adverse events, abnormalities in hematology (154 events in 22 subjects) and biochemistry (32 events in 6 subjects) laboratory test results were observed in 22 subjects. However, most of the changes were minor and were not clinically significant. Physical examination results and vital signs were mostly normal or non-clinically significant during the study period.

UB-421 was well tolerated during the study period with an overall treatment tolerability for the 8-week Treatment period of 73.84% as specified by the clinical trial protocol.

8.3 Pharmacodynamics 8.3.1 CD4+T and CD8+ T Cell Counts.

After the 8-week Treatment period and 8-week Follow-up period, mean CD4$^+$ T cell counts decreased slightly from baseline by 55.10±117.97 cells/mm$^3$ while mean CD8$^+$ T cell counts increased from baseline by 193.31±459.34 cells/mm$^3$. Representative CD4$^+$ T cell counts for subjects in Cohort 1 and mean CD4 T cell count are shown in Table 22a and FIG. 24a. Representative CD4$^+$ T cell counts for subjects in Cohort 2 and mean CD4 T cell count are shown in Table 22b and FIG. 24b.

8.3.2 Coating of CD4 Receptors with UB-421.

The extent of CD4 receptor coating was detected by flow cytometry with fluorescence-conjugated UB-421. The results obtained from four representative subjects, two from Cohort 1 and two from Cohort 2, are shown in FIGS. 25*a*-25*b* and FIGS. 25*c*-25*d*, respectively. The assay's sensitivity is 0.15 μg/mL. Clinical efficacy of UB-421 upon repeated dosing at 10 mg/kg weekly or 25 mg/kg biweekly revealed viral reduction down to non-detectable level in the presence of >10 μg/mL. UB-421 serum level when used as a monotherapy. There is no viral rebound as long as the PBMC CD4+ cells are fully coated (i.e. % dB4C7-Alexa binding approaching 0).

Full coating of CD4 receptors on PBMC with UB-421 was achieved after two to three administrations of UB-421 at both dosage levels. Additionally, full coating of CD4+ T cells with UB-421 was maintained throughout the entire treatment period (FIGS. 25*a*-25*d*, upper panel). In most of the subjects, UB-421 binding to CD4 receptors diminished and returned to baseline values within three weeks of the last UB-421 infusion, as determined by binding of fluorescent dB4C7 mAb (dB4C7-Alexa).

The concentration of UB-421 present in the serum of the subjects during the study was evaluated to determine the serum concentration of UB-421 sufficient to achieve full CD4 coating and HIV-1 viral suppression. Based on the data obtained, constant full coating of CD4+ T cells and HIV-1 viral suppression by UB-421 was achieved as long as the serum concentration of UB-421 was maintained above 10 μg/mL (FIG. 25*a*-25*d*, lower panel).

8.4 Pharmacokinetics:

The mean AUC observed in Cohort 1 increased from 17300±10000 μg×hr/mL (Visit 1-2) to 23900±10700 μg×hr/mL (Visit 8-9) then returned to baseline at Visit 11-12. The mean $AUC_{(0\to last)}$ observed in Cohort 1 was 171000±70300 μg×hr/mL.

The mean AUC observed in Cohort 2 increased from 56500±19500 μg×hr/mL (Visit 1-3) to 61100±20700 μg×hr/mL (Visit 7-9) then returned to baseline at Visit 11-12. The mean $AUC_{(0\to last)}$ observed in Cohort 2 was 239000±73900 μg×hr/mL.

These data demonstrate that the mean serum drug concentration, as assessed by $AUC_{(0\to last)}$, was higher among subjects administered 25 mg/kg bi-weekly UB-421 infusion (Cohort 2, 239000±73900 μg×hr/mL) as compared to those received 10 mg/kg weekly UB-421 infusion (Cohort 1, 171000±70300 μg×hr/mL).

8.5 Efficacy Results:

Twenty-nine (29) HIV-1 infected subjects were recruited in this study and received at least one dose of UB-421 (ITT population). Of the twenty-nine (29) subjects recruited, a total of eighteen (18) subjects completed the 8-week Treatment period, receiving all administrations of the study drug (PP population). The efficacy of the multi-administration of UB-421 was evaluated by assessing individual and mean maximal viral load reduction of the enrolled asymptomatic HIV-1 infected subjects during the study and the results for the ITT and PP populations for Cohorts 1 and 2 are summarized in Table 20.

It was found that the mean maximal viral load reduction did not differ significantly between the two dosage levels in either the ITT or the PP populations. Specifically, viral loads were reduced in the ITT population by 2.27±0.60 $\log_{10}$ copies/mL in Cohort 1 and 2.45±0.46 $\log_{10}$ copies/mL in Cohort 2. In the PP population, viral loads were reduced by 2.73±0.34 $\log_{10}$ copies/mL in Cohort 1 and 2.47±0.45 $\log_{10}$ copies/mL in Cohort 2.

During the treatment period, ≥0.5 $\log_{10}$ copies/mL of viral load reduction was observed in all (n=29, 100.00%) study subjects; and ≥1 $\log_{10}$ copies/mL of viral load reduction was also observed in all (n=29, 100.00%) study subjects.

Further evaluation of the data obtained during the Treatment period revealed the following:

In Cohort 1, 8/14 (57.14%) of subjects in ITT and 5/7 (71.43%) subjects in PP had viral load ≤200 copies/mL; moreover, 3/14 (21.43%) of subjects in ITT and 3/7 (42.86%) of subjects in PP had viral load <50 copies/mL.

In Cohort 2, 10/15 (66.67%) subjects in ITT and 7/11 (63.64%) subjects in PP had viral load ≤200 copies/mL; and 3/15 (20.00%) subjects in ITT and 2/11 (18.18%) of subjects in PP had viral load <50 copies/mL.

Representative viral load reduction data from subjects in Cohorts 1 and 2 are shown in Tables 21a-21c and FIGS. 25a-25d (upper panels). There were no statistically significant differences in the proportion of subjects with viral load reduction within each cohort, between cohorts, or between sub-populations within each cohort. Furthermore, viral loads were reduced to levels below the current assay detection limit (20 copies/mL) in 43% and 18% of the subjects in Cohort 1 and 2, respectively, during the eight-week Treatment period. In all subjects, the viral load reduction persisted while the CD4+ T cells were completely coated by UB-421. Viral loads returned to the baseline levels in both cohorts by the end of the Follow-up period. In addition, no viral rebound was observed in any of the study subjects during the Treatment period. No quantitatable anti-UB-421 antibodies was detected throughout the treatment period from patient in both cohorts (Table 21a to 21c).

8.6 Comparison of UB-421 with TMB-355:

The results obtained in this study for UB-421 were evaluated against results obtained in similar studies for TMB-355 (ibalizumab, formerly TNX-355) performed by others (Jacobson, J. L., et al., 2009; Toma, J., et al., 2011; and Pace, C. S., et al., 2013). FIG. 26a show superior viral load reduction up to >3 $\log_{10}$ with no viral load rebound in the presence of UB-421 with full coating of CD4+ cells. In contrast, patients undergoing treatment with TMB-355 encountered viral rebound after only one week from treatment even in the presence of full coating of CD4+ cells, indicative of development of resistant viral mutants (FIG. 26b).

A comparison of these two treatment regimens, as illustrated in the figures, demonstrates that treating HIV infected subjects with UB-421 has distinct advantages over TMB-355 treatment. Specifically, UB-421 provides a continual decrease in HIV viral load throughout out the Treatment period and even one or two weeks into the Follow-up period with maximal viral load reduction >3 $\log_{10}$. In contrast, TMB-355 provides only a temporary viral load reduction with the first administration and maximal viral load reduction of approximately 1 $\log_{10}$.

Also, prior studies using TMB-355 found that, despite the presence of serum TMB-355 and full coating of CD4 positive T cells, HIV viral rebound occurred after one week into the treatment (Jacobson, J. L., et al., 2009). This result is consistent with the earlier prediction in Example 4 above that a non-competitive entry inhibition mechanism, as mediated by TMB-355 (ibalizumab), would afford a high likelihood for development of resistant HIV mutants during the antibody treatment period. Indeed, viral resistant mutants were found with mutations identified at V5 region of gp120 (Toma, J., et al., 2011; Pace, C. S., et al., 2013) from patients receiving TMB-355 treatment for viral load reduction.

9. Conclusion

Eight-week treatment with UB-421 in asymptomatic HIV-1 infected subjects was found to be well tolerated. In addition, representative CD4+ T cell counts for individual subjects (Tables 22a and 22b) and mean CD4 T cell counts (FIGS. 24a and 24b) from both cohorts 1 and 2, respectively, remained stable throughout the two-month period monitored.

More importantly, treatment with UB-421 resulted in significant viral load reduction in all subjects (100% of the treated subjects responded with a maximal reduction of ≥1 $\log_{10}$ copies/mL. Both regimens, 10 mg/kg weekly (Cohort 1) and 25 mg/kg bi-weekly (Cohort 2) infusions, showed similar efficacy in viral load reduction. The mean maximal viral reduction in ITT population reached to 2.27±0.60 $\log_{10}$ copies/mL in Cohort 1 and 2.45±0.46 $\log_{10}$ copies/mL in Cohort 2). The observed viral reduction efficacy with UB-421 is superior than any other small molecule anti HIV drugs tested thus far.

The clinical trial results from this carefully executed multiple-dose phase IIa trial of UB-421 demonstrated high tolerability, safety, and an unprecedented efficacy in viral load reduction as a monotherapy without viral rebound during the Treatment period. The results obtained in this study are unexpected and contradict the long-held suspicion in the field that anti-CD4 monoclonal antibodies that bind to domain 1 of CD4 would be immunosuppressive because of interference with major histocompatibility complex class II-mediated immune functions and such therapies would be unsuitable for the treatment of HIV disease (Jacobson, J. L., et al., 2009). These results further suggest that additional modalities of HIV therapy using UB-421 in combination with orthogonal HAART and/or other HIV reservoir activating agents, such as HDACi, could achieve a functional cure for HIV infection.

Example 15

Treatment Modality Employing UB-421 Monotherapy as a Substitute for Antiretroviral Therapy in HIV-1 Infected Adults FIG. 27 illustrates a treatment modality for various HIV patient populations employing UB-421 monotherapy as a substitute for antiretroviral. Detailed objectives and protocol are described below.

1. Patient Populations Applied

Subjects who are seropositive for HIV-1 with viral suppression by stable highly active antiretroviral therapy (HAART) would be eligible for such treatment.

The eligible patients will receive UB-421 administered through either IV or SC route for an initial period of 4 months followed by another cycle of HAART treatment. A "HAART-UB-421" alternating treatment cycle can be repeated several times until viral rebound is no longer observed upon withdrawing both UB-421 and HAART therapies, thereby resulting in a functional cure for HIV infection.

More specifically, these subjects would receive multiple intravenous infusions of the study drug (UB-421) at one of the two dose levels, 10 mg/kg weekly or 25 mg/kg bi-weekly, for eight-week and sixteen-week treatment periods, respectively. The HAART regimens will be withdrawn on the day before the first UB-421 infusion. Prior to UB-421 administration, the subjects will be given prophylactic medication (pre-medication), including steroid and anti-histamine drugs as judged by principal investigator, to prevent infusion reactions. After completing the last scheduled UB-421 administration, all subjects will restart their original or other appropriate virus-sensitive antiretroviral therapies on the same day. The use of HAART regimens will be judged by the principal investigators. Viral load and CD4 cell counts from all patients will be monitored during the treatment period and 6 months after the treatment period ends.

2. Inclusion Criteria

Subjects may be included in this treatment modality if they meet all of the following criteria:
1. HIV-1 seropositive;
2. Aged 20 years or older;
3. Have received HAART treatment, defined as at least 2 nucleoside/nucleotide reverse transcriptase inhibitors (NRTIs) plus a non-nucleoside reverse transcriptase inhibitor (NNRTI), integrase inhibitor, or a protease inhibitor, for at least 2 years; the treatment is ongoing and without changes of drugs within one year prior to entry of the study;
4. With two measurements of CD4+ T cell count ≥500 cells/mm$^3$ or CD4 percentage ≥28% within 1 year prior to the screening visit;
5. With a CD4+ T cell count ≥500 cells/mm$^3$ obtained within 4 weeks prior to the screening visit or at the screening visit;
6. HIV-1 plasma RNA remains undetectable for at least 1 year prior to the screening visit, with at least 2 viral load measures per year. The viral load is also undetectable within 4 weeks prior to the screening visit or at the screening visit; single episode of detectable HIV plasma RNA prior to 4 weeks before the screening visit will not exclude participation.

3. Exclusion Criteria

Subjects will be excluded from the treatment modality for any of the following reasons:
1. Any active infection (except for HIV) requiring immediate therapy;
2. Any previously diagnosed or active AIDS-defining illness per Category B and Category C conditions according to the U.S. Centers for Disease Control and Prevention (CDC) Classification System for HIV Infection;
3. Body weight >80 kg;
4. Any documented CD4+ T cell count <250 cells/mm$^3$ or CD4+ T cell percentage ≤14% within 12 weeks before screening;
5. Previously enrolled in either phase I or phase IIa trials of UB-421 or any history of the presence of anti-UB-421 antibody;
6. Any previous exposure to a monoclonal antibody within 12 weeks prior to first dose of study drug UB-421;
7. Any significant diseases (other than HIV-1 infection) or clinically significant findings, including psychiatric and behavioral problems, determined from screening, medical history and/or physical examination that, in the investigator's opinion, would preclude the subject from participating in this study;
8. Any vaccination within 8 weeks prior to first dose of study drug;
9. Any immunomodulating therapy (including interferon), systemic chemotherapy within 12 weeks prior to first dose of study drug;
10. Life expectancy of less than 12 months;
11. Any illicit intravenous drugs within 12 weeks prior to first dose of study drug;
12. More than one change of HAART regimen because of virologic failure, and prior non-Hodgkin's lymphoma or Kaposi's sarcoma;
13. Any current alcohol or illicit drug use that, in the investigator's opinion, will interfere with the subject's ability to comply with the dosing and visit schedules and protocol evaluations.

4. Drug Product

Drug Product UB-421 (dB4C7 mAb) will be supplied at a concentration of 10 mg/mL (100 mg in 10 mL vial). Subjects will receive either eight weekly doses of 10 mg/kg UB-421 or eight bi-weekly doses of 25 mg/kg UB-421 by intravenous infusion.

The appropriate volume of UB-421 will be based on the specified dose and the subject's body weight. The volume of each individual dose was adjusted using sterile saline so that each individual subject within a cohort was infused with an equivalent infusion volume of drug. The total volume of infusion was approximately 100 mL for 10 mg/kg and 200 mL for 25 mg/kg dose cohorts. The infusion time for each administration was approximately one to two hours.

Example 16

Treatment Modality Employing UB-421 in Combination with HAART for Functional Cure of HIV Infection FIG. 28 illustrates the treatment modality for various HIV patient populations employing antibody UB-421 in combination with HAART for functional cure of HIV infection. Patient populations applied: (1) Treatment naïve HIV patients; (2) HAART treatment stabilized HIV patients; and (3) HIV Patients who failed HAART treatment.

More specifically, the clinical protocol for the functional cure of HIV in infected subjects can be achieved by administering UB-421 through either the IV or SC route for an initial period of 4 months followed by 2 months of treatment holiday as one treatment cycle (6 months) for two complete cycles (one year). These same subjects will also begin and continue HAART treatment during the two complete cycles of UB-421 treatment. At the end of two complete cycles, both HAART and UB-421 will be withdrawn (Arm A) to assess the amount of time for viral rebound to occur, if any. A control group, containing subjects that are treated with HAART alone through the same 12 month period before HAART treatment is withdrawn, will also be evaluated to assess the time to viral rebound to occur, if any (Arm B).

Viral load and CD4 cell counts from all patients will be monitored during the two cycles of concurrent UB-421 and HAART treatment and 6 months after the treatment period for a total of 18 months.

Arm A: HAART treatment in combination with UB-421 administration at 10 mg/kg weekly or 25 mg/kg biweekly.
Arm B: HAART treatment alone.

2. Design of UB-421 Treatment in Functional Cure (Table 23)

Potential Advantage of UB-421 over HAART drugs:
1. UB-421 blocks cell-to-cell transmission of HIV-1 viruses
2. UB-421 cross-links CDR2-like loop of CD4 and activates cells and, thus, induces and releases HIV-1 from latency
3. Goals:
1. To provide an effective treatment and protection to HIV infected subjects, using UB-421 in combination with HAART, by blocking both cell-free and cell-to-cell transmission of HIV.
2. To provide a functional cure for HIV in HIV-infected subjects.
4. Patient Populations Applied:
(1) HAART treatment stabilized HIV patients; (2) HAART treatment naïve HIV patients, and (3) HIV patients failed HAART treatment.
5. Drug Product UB-421

Drug Product UB-421 (dB4C7 mAb) will be supplied at a concentration of 10 mg/mL (100 mg in 10 mL vial). Subjects will receive either eight weekly doses of 10 mg/kg UB-421 or eight bi-weekly doses of 25 mg/kg UB-421 by intravenous infusion.

The appropriate volume of UB-421 will be based on the specified dose and the subject's body weight. The volume of each individual dose was adjusted using sterile saline so that each individual subject within a cohort was infused with an equivalent infusion volume of drug. The total volume of infusion was approximately 100 mL for 10 mg/kg and 200 mL for 25 mg/kg dose cohorts. The infusion time for each administration was approximately one to two hours.

6. Assigned Interventions:
The following interventions will be assigned:
6.1 Arm A—Combination of UB-421 and HAART Treatment Subjects will be continuously treated with the appropriate HAART therapy and also be treated with UB-421 for two complete cycles lasting one year. Each cycle of UB-421 treatment will include an administration of 10 mg/kg UB-421 each week or an administration of 25 mg/kg UB-421 every other week over a period of 4 months followed by two months without UB-421 treatment.

After completion of the 1 year treatment period, both HAART and UB-421 therapies will be withdrawn. Additional observational study will be conducted to assure functional cure of HIV infection by not seeing any viral rebound in the absence of HAART and UB-421.

6.1 Arm B—HAART Treatment Alone

As a control group, a separate set of subjects will be continuously treated with the appropriate HAART therapy without being treated with UB-421 during the same period.

After completion of the 1 year treatment period, HAART therapy will be withdrawn and the subjects will be monitored for viral rebound.

TABLE 1

Unmet Medical Needs in HIV Treatment: Functional Cure & Eradication

| Sterilizing Cure (Eradication) | Functional Cure |
|---|---|
| Elimination of all HIV-infected cells | Long term viral suppression in absence of HAART |
| HIV RNA <1 copy/ml | HIV RNA <50 copies/ml (or below assay detection limit) |
| Cure | Remission |

TABLE 2

List of HDAC Inhibitors for Reactivation of HIV Infected Resting T cells Currently under Development

| Drug Name | Information |
|---|---|
| Vorinostat (SAHA) | Vorinostat (suberoylanilide hydroxamic acid, SAHA, ZOLINZA ®) is a HDAC inhibitor with $IC_{50}$ of ~10 nM. |
| Entinostat (MS-275, SNDX-275) | MS-275 is a HDAC inhibitor of HDAC1 and HDAC3 with $IC_{50}$ of 0.51 μM and 1.7 μM, respectively. |
| Panobinostat (LBH589) | LBH589 (Panobinostat) is a novel broad-spectrum HDAC inhibitor for MOLT-4 and Reh cells with $IC_{50}$ of 5 and 20 nM, respectively. |
| Trichostatin A (TSA) | Trichostatin A (TSA) is a HDAC inhibitor with $IC_{50}$ of ~1.8 nM. |
| Belinostat (PDX101) | Belinostat (PXD101) is a novel HDAC inhibitor with $IC_{50}$ of 27 nM in HeLa cell extracts. |
| Mocetinostat (MGCD0103) | MGCD0103 (Mocetinostat) is a potent histone deacetylases (HDAC), class I inhibitor for HDAC, HDAC 2 and HDAC 3 with $IC_{50}$ of 0.15 μM, 0.29 μM and 1.66 μM, respectively. |
| MC1568 | MC1568 is a class II (IIa) selective HDAC inhibitor with $IC_{50}$ of 220 nM. |
| Romidepsin (FK228, depsipeptide) | Romidepsin (FK228, depsipeptide) is a potent histone deacetylase 1 and 2 (HDAC1 and HDAC2) inhibitor with $IC_{50}$ of 36 nM and 47 nM, respectively. |
| M344 | M344 is a potent HDAC inhibitor with $IC_{50}$ of 100 nM |
| PCI-34051 | PCI-34051 is a potent and specific histone deacetylase 8 (HDAC8) inhibitor with $IC_{50}$ of 10 nM. |
| Tubastatin A HCl | Tubastatin A is a potent HDAC6 inhibitor with $IC_{50}$ of 15 nM. |
| AR-42 (HDAC-42) | AR-42 is a novel HDAC inhibitor with an $IC_{50}$ of 0.61 μM for acute lymphoblastic leukemia (697) cell lines. |
| ITF2357 (Givinostat) | ITF2357 (Givinostat) is an orally active, potent inhibitor of histone deacetylases (HDACs) with $IC_{50}$ values of 7.5-16 nM. |
| SB939 (Pracinostat) | SB939 is a potent small-molecule; an inhibitor of histone deacetylase with $IC_{50}$ values ranging from 40 nM to 140 nM for HDAC class I, class II and class IV isoenzymes. |

TABLE 2-continued

List of HDAC Inhibitors for Reactivation of HIV Infected Resting T cells Currently under Development

| Drug Name | Information |
|---|---|
| Droxinostat | Droxinostat (CMH, 5809354) is a selective inhibitor of HDAC3, HDAC6, and HDAC8, with $IC_{50}$ of 1.46 µM to 16.9 µM. |
| CUDC-01 | CUDC-101 is a potent multitargeted HDAC, EGFR and HER2 inhibitor with $IC_{50}$ of 4.4, 2.4, and 15.7 nM, respectively. |
| Valproic acid sodium salt (Sodium valproate) | Valproic acid sodium salt (Sodium valproate) is a histone deacetylase inhibitor with an $IC_{50}$ of 0.4 mM and exhibits anticancer, anti-inflammatory and neuroprotective effects. |
| JNJ-26481585 | JNJ-26481585 (Quisinostat) is an orally bioavailable, second-generation, hydroxamic acid-based HDAC inhibitor with $IC_{50}$ of 0.11 nM for HDAC1. |
| LAQ824 (NVP-LAQ824, Dacinostat) | LAQ824 (NVP-LAQ824) is a novel HDAC inhibitor with $IC_{50}$ of 32 nM. |
| PCI-24781 | HDAC inhibitor with Ki of 7 µM. |

TABLE 3

HIV Entry Inhibition Activities of monoclonal antibody B4 (MONOGRAM BIOSCIENCE PHENOSENSE ™ Assay) B4 MAb: non-B Clade Viruses

| Clade | Isolate Name | IC50 | IC90 |
|---|---|---|---|
| | B4 Mab (µg/mL) | | |
| A | 92/RW/008 | 0.026 | 0.082 |
| A | 92/RW/024 | 0.055 | 0.105 |
| A | 93/RW/029 | 0.019 | 0.063 |
| A | 93/UG/077 | 0.012 | 0.109 |
| A | 94/UG/103 | 0.021 | 0.082 |
| A | CA1 | 0.011 | 0.062 |
| A | CA2 | 0.018 | 0.055 |
| A | CA3 | 0.019 | 0.052 |
| BF | 93/BR/019 | 0.013 | 0.046 |
| C | 10362 | 0.020 | 0.065 |
| C | 21068 | 0.011 | 0.053 |
| C | 10215-6 | 0.018 | 0.063 |
| C | 11657-3 | 0.025 | 0.067 |
| C | 20635-4 | 0.020 | 0.090 |
| C | 93/IN/101 | 0.016 | 0.047 |
| C | CC1 | 0.016 | 0.052 |
| C | CC10 | 0.015 | 0.053 |
| C | CC2 | 0.021 | 0.065 |
| C | CC3 | 0.012 | 0.049 |
| C | CC4 | 0.013 | 0.044 |
| C | CC5 | 0.019 | 0.062 |
| C | CC6 | 0.018 | 0.061 |
| C | CC7 | 0.013 | 0.050 |
| C | CC8 | 0.019 | 0.053 |
| C | CC9 | 0.020 | 0.071 |
| C | MW/93/959 | 0.019 | 0.050 |
| C | MW/93/960 | 0.010 | 0.056 |
| D | 92/UG/001 | 0.018 | 0.056 |
| D | 92/UG/005 | 0.019 | 0.073 |
| D | 92/UG/021 | 0.017 | 0.054 |
| D | 92/UG/024 | 0.040 | 0.085 |
| D | 92/UG/035 | 0.011 | 0.025 |
| D | 92/UG/038 | 0.014 | 0.039 |
| D | 92/UG/046 | 0.015 | 0.042 |
| D | 93/UG/053 | 0.020 | 0.049 |
| D | 93/UG/065 | 0.015 | 0.044 |
| D | 93/UG/067 | 0.016 | 0.080 |
| D | 93/UG/070 | 0.011 | 0.053 |
| D | 93/UG/082 | 0.016 | 0.059 |
| | B4 Mab (µg/mL) | | |
| D | 93/UG/086 | 0.015 | 0.052 |
| D | 94/UG/105 | 0.021 | 0.073 |
| D | 94/UG/114 | 0.015 | 0.054 |
| D | 94/UG/117 | 0.017 | 0.063 |
| D | 94/UG/118 | 0.020 | 0.066 |
| D | CD1 | 0.016 | 0.047 |
| E | 93/TH/057 | 0.023 | 0.079 |
| E | 93/TH/305 | 0.021 | 0.069 |
| E | CMU06 | 0.026 | 0.088 |
| E? | QZ4589 | 0.036 | 0.170 |
| EA | 92/TH/005 | 0.012 | 0.054 |
| EA | 92/TH/006 | 0.022 | 0.073 |
| EA | 92/TH/007 | 0.013 | 0.061 |
| EA | 92/TH/009 | 0.021 | 0.052 |
| EA | 92/TH/019 | 0.022 | 0.063 |
| EA | 92/TH/020 | 0.015 | 0.051 |
| EA | 92/TH/021 | 0.017 | 0.052 |
| EA | 92/TH/022 | 0.012 | 0.035 |
| EA | 92/TH/024 | 0.010 | 0.048 |
| EA | CMU02 | 0.011 | 0.041 |
| F | 93/BR/020 | 0.024 | 0.069 |
| F | CF2 | 0.016 | 0.053 |
| F | CF3 | 0.024 | 0.081 |
| F | CF4 | 0.019 | 0.055 |
| F | CF5 | 0.018 | 0.060 |
| F | CF6 | 0.018 | 0.064 |
| F | CF7 | 0.019 | 0.064 |
| F | CF8 | 0.017 | 0.079 |
| G | CG1 | 0.018 | 0.071 |
| G | CG2 | 0.027 | 0.081 |
| G | CG3 | 0.016 | 0.045 |
| G | CG4 | 0.013 | 0.037 |
| J | CJ1 | 0.018 | 0.056 |
| J | CJ2 | 0.019 | 0.063 |
| CONTROLS | 92HT594 | 0.021 | 0.062 |
| CONTROLS | JRCSF | 0.034 | 0.077 |
| CONTROLS | JRFL | 0.074 | 0.152 |

Average: IC50 = 0.018 µg/mL
IC90 = 0.062 µg/mL

TABLE 4

Corresponding CDR 1, 2, 3 Sequences from the Heavy and Light Chain Sequences of Murine Antibody B4

| Description | Seq ID No. | Sequence |
|---|---|---|
| CDR1 of Heavy Chain of murine antibody B4 | 1 | DYVIH |
| CDR2 of Heavy Chain of murine antibody B4 | 2 | EIYPGSGSAYSNAKFKD |
| CDR3 of Heavy Chain of murine antibody B4 | 3 | RGNGTGFAY |

TABLE 4-continued

Corresponding CDR 1, 2, 3 Sequences from the Heavy and Light Chain Sequences of Murine Antibody B4

| Description | Seq ID No. | Sequence |
|---|---|---|
| CDR1 of Light Chain of murine antibody B4 | 4 | KAGQSVDYDGDSYMN |
| CDR2 of Light Chain of murine antibody B4 | 5 | VASNLES |
| CDR3 of Light Chain of murine antibody B4 | 6 | QQSYKDPLT |

TABLE 5

Neutralizing Activities of Deimmunized B4 (dB4C7) in Comparison to Parental B4 (MT-2 Microplaque Assay)

| HIV-1 Isolate | Clade | B4 Antibody* | Antibody Conc (μg/mL) at 50% Inhibition | Antibody Conc (μg/mL) at 90% Inhibition |
|---|---|---|---|---|
| VL 135 | B | mAb dB4C7 | 0.06 | 0.19 |
|  |  | murine mAb B4 | 0.12 | 0.29 |
| UG 029 | A | mAb dB4C7 | 0.5 | 1.88 |
|  |  | murine mAb B4 | 0.31 | 0.94 |
| UG 046 | D | mAb dB4C7 | 0.44 | 11 |
|  |  | murine mAb B4 | 0.43 | 5.7 |
| TH 036 | E | mAb dB4C7 | 0.19 | 0.56 |
|  |  | murine mAb B4 | 0.25 | 0.74 |
| USNG/98/31 | C | mAb dB4C7 | 0.08 | 0.22 |
|  |  | murine mAb B4 | 0.19 | 0.36 |

TABLE 6

Neutralizing Activities of Deimmunized B4 (dB4C7) in Comparison to Parental B4 (PBMC Assay)

| HIV-1 Isolate | Clade | B4 Antibody* | Antibody Conc (μg/mL) at 50% Inhibition | Antibody Conc (μg/mL) at 90% Inhibition |
|---|---|---|---|---|
| ZA/98/009 | C | mAb dB4C7 | 0.04 | 0.08 |
|  |  | murine mAb B4 | 0.03 | 0.13 |
| CM 235 | E | mAb dB4C7 | 0.04 | 0.07 |
|  |  | murine mAb B4 | 0.02 | 0.1 |

TABLE 7

Inhibition of HIV isolates (R5, X4 or R5/X4) from entry into CD4 positive PBMC cells in a cell-free system by monoclonal antibody B4 or dB4 measured by $IC_{50}$ (μg/mL) in neutralization of viral replication. Broadly neutralizing monoclonal antibodies 2F5 and 2G12 directed against HIV gp120 are included for comparison.

| | $IC_{50}$ (μg/mL) | | | | | |
|---|---|---|---|---|---|---|
| Antibody | JRCSF (R5) | HXB2 (X4) | 92TH594 (R5/X4) | Primary Isolate #5 (R5) | Primary Isolate #6 (R5) | Primary Isolate #7 (R5) |
| 2F5 | 4 | 0.07 | 3 | 50 | 2 | >100 |
| 2G12 | 0.8 | 0.5 | 1.3 | 20 | 3 | 2 |
| mAb dB4C7 | 0.04 | 0.4 | 0.05 | 0.05 | 0.05 | 0.03 |
| mAb B4 | 0.04 | 0.4 | 0.05 | 0.05 | 0.05 | 0.03 |

TABLE 8

Binding Activity ($EC_{50}$) of dB4C7 to HPB-ALL cells

| Exp. (no.) | $EC_{50}$ by MFI (ng/mL) | $EC_{50}$ by % MFI (ng/mL) |
|---|---|---|
| 1 | 42.1 | 42.4 |
| 2 | 43.7 | 45.7 |
| 3 | 40.7 | 40.7 |
| Mean | 42.2 | 42.9 |
| SD | 1.5 | 2.5 |
| % CV | 3.6 | 5.9 |

TABLE 9

Absolute Binding Affinity (Kd) and Capacity (Bmax) of dB4C7 to HPB-ALL cells

| Exp. (no.) | Kd (ng/mL) | Kd ($10^{-11}$ M) | Bmax (ng/mL) | Bmax ($10^{-11}$ M) | Bmax ($10^6$ Ab/cell) |
|---|---|---|---|---|---|
| 1 | 8.6 | 5.7 | 65.4 | 43.6 | 1.3 |
| 2 | 12.1 | 8.1 | 70.4 | 47.0 | 1.4 |
| 3 | 4.7 | 3.1 | 46.4 | 31.1 | 0.93 |
| Mean | 8.5 | 5.6 | 60.7 | 40.6 | 1.2 |
| SD | 3.7 | 2.5 | 12.7 | 8.4 | 0.25 |
| % CV | 43.7 | 44.4 | 20.9 | 20.6 | 20.5 |

TABLE 10

Binding Activities ($EC_{50}$) of dB4C7 Detected by (1) Goat anti-huIgG-FITC and (2) dB4C7-Alexa Binding to Blood CD4+ T cells

| | Goat anti-hIgG | | dB4C7-Alexa | |
|---|---|---|---|---|
| Subjects (gender) | $EC_{50}$ (ng/mL) | Max. (%) | $EC_{50}$ (ng/mL) | Max. (%) |
| M1 | 3.7 | 93.0 | 4.8 | 67.3 |
| M2 | 4.2 | 68.9 | 4.6 | 62.6 |
| M3 | 2.6 | 67.6 | 3.3 | 63.7 |
| F1 | 4.7 | 91.3 | 4.3 | 65.6 |
| F2 | 5.7 | 71.5 | 6.6 | 68.3 |
| F3 | 3.7 | 74.6 | 4.3 | 61.0 |
| Mean | 4.1 | 77.8 | 4.7 | 64.7 |
| SD | 1.1 | 11.4 | 1.1 | 2.8 |
| % CV | 25.5 | 14.6 | 23.4 | 4.3 |

TABLE 11

Monoclonal Antibody B4 Blocks Both Cell-free and Cell-to-cell Transmission of HIV

| | Titer for fusion inhibition (cell-to-cell) | | Titer for neutralization (cell-free) | |
|---|---|---|---|---|
| Virus strain | 50% | 90% | 50% | 90% |
| UG266 | 1:1060 | 1:140 | 1:280 | 1:136 |
| UG046 | 1:1479 | 1:245 | 1:628 | 1:234 |

TABLE 12

Sequential Staining by FACS Analysis - Percent Positive PBMC

| Single Label | | 1st - Leu3a binding 2nd - B4 exposure | | | 1st - B4 binding 2nd - Leu3a exposure | | |
|---|---|---|---|---|---|---|---|
| Control | | Leu3a+ | Leu3a− | Leu3a+ | Leu3a+ | Leu3a− | Leu3a+ |
| Leu3a+ | B4+ | B4− | B4+ | B4+ | B4− | B4+ | B4+ |
| X282 25.5 | 26.1 | 0.1 | 0.8 | 24.5 | 0.0 | 21.9 | 1.2 |
| X301 44.0 | 45.5 | 0.3 | 0.6 | 46.7 | 0.0 | 42.7 | 3.0 |

TABLE 13

TNF-α Levels and HIV-1 Viral Load in PBMC Culture

| Stimulator | TNF-α conc. (pg/ml) | | | Viral load (copies/ml) | | | Viral load % change (Normalized to Medium) | | | Cell count (×10$^6$)/ Viability (%) | | |
|---|---|---|---|---|---|---|---|---|---|---|---|---|
| | D0 | D2 | D7 | D0 | D2 | D7 | D0 | D2 | D7 | D0 | D2 | D7 |
| Medium only (control) | ND | ND | ND | 82 | 37731 | 24905 | 100 | 100 | 100 | 11.86/ 92.4 | 2.13/ 94.4 | 0.84/ 98.4 |
| mAb dB4 | ND | 546.7 | 349.5 | 99 | 57162 | 54797 | 121 | 151 | 220 | 11.98/ 89.2 | 2.00/ 91.7 | 1.02/ 77.1 |
| PMA + PHA | ND | 2593.1 | 1030 | 344 | 20738 | 19465 | 420 | 55 | 78 | 11.71/ 93.4 | 1.32/ 85.2 | 5.20/ 92.0 |

ND: Non-Detectable

TABLE 14a

Study A: Single Administration Pre-Clinical Study in Baboons

| Group | Dose (100 mL) | Administration interval | No. of Animals | |
|---|---|---|---|---|
| | | | Male | Female |
| 1A (Control) | None (saline) | Single dose | 1 | 1 |
| 2A (Low dose) | 5 mg/kg BW | Single dose | 1 | 1 |
| 3A (High dose) | 25 mg/kg BW | Single dose | 1 | 1 |

TABLE 14b

Study B: Multiple Administration Pre-Clinical Study in Baboons

| | Group | Dose$^{1,2}$ (100 mL) | No. of Animals | |
|---|---|---|---|---|
| | | | Male | Female |
| Part 1 Treatment Phase Only | 1B Control | Saline | 1 | 1 |
| | 2B UB-421 - Low dose | 5 mg/kg | 2 | 2 |
| | 3B UB-421 - Low dose | 25 mg/kg | 2 | 2 |

TABLE 14b-continued

Study B: Multiple Administration Pre-Clinical Study in Baboons

| | Group | Dose$^{1,2}$ (100 mL) | No. of Animals | |
|---|---|---|---|---|
| | | | Male | Female |
| Part 2 Treatment Phase & Recovery Phase | 1B Control | Saline | 1 | 1 |
| | 2B UB-421 - Low dose | 5 mg/kg | 2 | 2 |
| | 3B UB-421 - Low dose | 25 mg/kg | 2 | 2 |

$^1$Administered weekly for 8 weeks
$^2$Dosage: mg (UB-421)/kg (body weight)

TABLE 15

Blood and Biopsy Results in Baboons

| Item | Result |
|---|---|
| Clinical Hematology | Normal |
| Clinical Chemistry | Normal |
| Coagulation Tests | Normal |
| UB-421 Analysis: Serum & CD4+ Cells | Dose dependent kinetics |
| Baboon Antibody Response to UB-421 | No detectable antibodies against UB-421 |
| Minimum conc. of UB-421 detected in serum of samples with UB-421 bound to CD4+ cells | ~10 μg/mL |
| Lymphocyte & Monocyte Subpopulations | No depletion of CD4+ cells noted |
| Effect of UB-421 on HBV immunization | Hypo-responsiveness to HBV observed in 6 of 8 animals treated with low dose UB-421 3 of 8 animals treated with high dose UB-421 |
| Cytokine Analysis (IL-2, IL-6, IFN-γ, TNF-α) | No change in cytokine production observed in mitogen stimulated PBMC cultures |
| Flow Cytometry of lymph node (T cells & monocytes) | Dose dependent kinetics |

TABLE 16

Observations & Necropsy Results in Baboons

| Item | Result |
|---|---|
| Ophthalmic (eye) Observations | Normal - no change noted after 8 weekly administrations of high dose UB-421 (Group 3B) |
| Electrocardiogram (ECG) Observations during each infusion | Changes in ECG recordings were identified as normal day-to-day variations & not related to UB-421 |
| Age Range | 7 to 18 years |
| Body Weight | Females: 17-23 kgs<br>Males: 24-35 kgs |
| Organ Weight | Within normal limits |
| Gross & Microscopic Diagnosis | Some animals had age-related, abnormal features (osteoarthritis, amyloidosis, and/or endocrine cysts) not related to UB-421 treatment |
| Histopathology (H&E staining) Bone Marrow samples | No significant lesions - Over 50 organs & tissue samples examined per animal |

TABLE 17

Pre-clinical Summary of UB-421: IND-enabling Toxicology Study in Baboons

No abnormal observations in body weight or temperature, food consumption, hematology, clinical chemistry, electrocardiograms, ophthalmoscopic exams, organ weight, or histopathology were found after 8 weekly infusions of low dose (5 mg/kg) or high dose (25 mg/kg) UB-421.
No significant changes in relative numbers of CD4+ and CD8+ T cells were found after UB-421 infusions; transient (slightly elevated) monocytosis was noted in a few blood samples from both control and UB-421 treated animals.
Duration of UB-421 "coating" of baboon CD4+ T-cells by flow cytometry:
5 mg/kg BW (low dose)~between 3 to 7+ days.
25 mg/kg BW (high dose)~greater than 7 to 21+ days.
None of the baboons developed antibodies against UB-421 (BAHA) after multiple infusions.
Expression of cytokines (IL2, IL6, IFN-γ, TNF-α) were not affected by UB-421 treatments and were not elevated or significantly suppressed.
No suppression of lymphocyte proliferative responses to mitogens Con-A, PHA or PWM was observed in low- or high-dose UB-421 treated animals when compared to the responses of control animals to the same mitogens.
Although completely coated with UB-421 for 8 weeks, some baboons treated with high dose UB-421 (Group 3B) generated anti-HBsAg antibodies after 2 immunizations of the Merck Hepatitis B Vaccine (Recombivax HB ®).
Multiple infusions with both low- and high-dose UB-421 were found to be safe and well tolerated in all baboons examined (n = 16).

TABLE 18

Tissues evaluated for cross-reactivity analysis using biotinylated mAb dB4C7

| | |
|---|---|
| Adult human tissues tested; three or more donors were evaluated, except eye (n = 1) | Adrenal, Bone Marrow, Breast (mammary gland), Brain (cerebrum, cerebellum), Cervix, Esophagus, Eye, Heart (cardiac muscle), Intestine (small, large, colon), Kidney, Liver[5], Lung (mesothelial), mononuclear cells (lymphocytes and macrophages in tissues)[4], Ovary, Pancreas, Peripheral Nerve, Pituitary, Placenta, Prostate, Salivary gland, Skin, Spinal cord, Spleen[3], Stomach, Striated muscle, Testis, Thymus[1], Thyroid, Tonsil (and lymph nodes)[1,2], Urinary Bladder (ureter), Uterus (endometrium & myometrium), Vascular endothelium,. |

[1]Strong positive surface membrane staining observed
[2]Pre-incubation with unlabeled mAb dB4C7 blocked staining
[3]Weak positive reactivity observed
[4]Occasional positive staining observed
[5]Focal weak Kupffer cell staining

TABLE 19

PK Parameters for Single-Dose UB-421 in Phase I Trial

| Parameters | UB-421 (single dose, iv)[1] | |
|---|---|---|
| $C_{MAX}$ (μg/ml) | 1 mg/Kg | 28.6 |
| | 5 mg/Kg | 81.7 |
| | 10 mg/Kg | 164.5 |
| | 25 mg/Kg | 462.5 |
| $AUC_{0-\infty}$ (μg · hr/ml) | 1 mg/Kg | 201 |
| | 5 mg/Kg | 4739 |
| | 10 mg/Kg | 12785 |
| | 25 mg/Kg | 51367 |

TABLE 19-continued

PK Parameters for Single-Dose UB-421 in Phase I Trial

| Parameters | | UB-421 (single dose, iv)[1] |
|---|---|---|
| $T_{1/2}$ (hr) | 1 mg/Kg | 14.4 |
| | 5 mg/Kg | 25.2 |
| | 10 mg/Kg | 37.0 |
| | 25 mg/Kg | 85.4 |
| MRT (hr) | 1 mg/Kg | 21.6 |
| | 5 mg/Kg | 45.3 |
| | 10 mg/Kg | 62.6 |
| | 25 mg/Kg | 97.4 |

[1]Results are an average from 3 subjects

TABLE 20

Viral Load Reduction After Multiple Administrations of UB-421 in Phase IIa Trial

| Endpoint | Cohort 1 (10 mg/kg weekly) | | Cohort 2 (25 mg/kg bi-weekly) | |
|---|---|---|---|---|
| | ITT N = 14 | PP N = 7 | ITT N = 15 | PP N = 11 |
| Mean (SD) max. VL reduction Log$_{10}$ copies/ml | −2.27 (0.60) | −2.73 (0.34) | 2.45 (0.46) | −2.47 (0.45) |
| Maximal individual VL reduction Log$_{10}$ copies/ml | | −3.23 | | −3.28 |
| n (%) >1 Log$_{10}$ VL reduction | 14 (100%) | 7 (100%) | 15 (100%) | 11 (100%) |
| n (%) <200 copies/ml | 8 (57.1%) | 5 (71.4%) | 10 (66.7%) | 7 (63.6%) |
| n (%) <50 copies/ml | 3 (21.4%) | 3 (42.9%) | 3 (20.0%) | 2 (18.2%) |
| n (%) <20 copies/ml | | 3 (42.9%) | | 2 (18.2%) |

ITT: Intent-to-Treat Population
PP: Per-Protocol Population
VL: Viral Load

TABLE 21a

Phase IIa clinical efficacy data showing viral reduction down to nondetectable level: Patient 1-1-01 (Cohort 1: 10 mg/kg weekly)

| Visit | Viral load (copies/mL) | Anti-UB-421 (μg/mL) |
|---|---|---|
| 1 | 9,570 | NQ |
| 2 | 392 | |
| 3 | 185 | NQ |
| 4 | 27 | |
| 5 | <20 | NQ |
| 6 | <20 | |
| 7 | <20 | NQ |
| 8 | <20 | |
| 9 | <20 | |
| 10 | <20 | NQ |
| 11 | 1,730 | NQ |

NQ: Not Quantitatable
Slash: Not evaluated

TABLE 21b

Phase IIa clinical efficacy data showing viral reduction down to nondetectable level: Patient 1-1-02 (Cohort 1: 10 mg/kg weekly)

| Visit | Viral load (copies/mL) | Anti-UB-421 (μg/mL) |
|---|---|---|
| 1 | 34,200 | NQ |
| 2 | 817 | |
| 3 | 143 | NQ |
| 4 | 187 | |
| 5 | 76 | NQ |
| 6 | 63 | |
| 7 | 27 | NQ |
| 8 | 69 | |
| 9 | <20 | |
| 10 | 30 | NQ |
| 11 | 98,800 | NQ |

NQ: Not Quantitatable
Slash: Not evaluated

TABLE 21c

Phase IIa clinical efficacy data showing viral reduction down to nondetectable level: 1-2-03 (Cohort 2: 25 mg/kg bi-weekly)

| Visit | Viral load (copies/mL) | Anti-UB-421 (μg/mL) |
|---|---|---|
| 1 | 2,990 | NQ |
| 2 | 393 | |
| 3 | 31 | NQ |
| 4 | 71 | |
| 5 | 60 | NQ |
| 6 | 20 | |
| 7 | <20 | NQ |
| 8 | <20 | |
| 9 | <20 | |
| 10 | <20 | NQ |
| 11 | 4,010 | NQ |

NQ: Not Quantitatable
Slash: Not evaluated

TABLE 22a

Mean CD4 T Cell Count of UB-421 Treated Patients from Cohort 1 (10 mg/kg weekly)

| Visit | T 1-1-01 (PP) | T 1-1-02 (PP) | K 2-1-03 (PP) | K 2-1-04 (PP) | K 2-1-05 (PP) | Mean CD4 count |
|---|---|---|---|---|---|---|
| 1 | 509 | 867 | 526 | 512 | 466 | 561 |
| 2 | 1101 | 655 | 646 | 811 | 455 | 703 |
| 3 | 890 | 429 | 619 | 566 | 552 | 594 |
| 4 | 890 | 534 | 585 | 735 | 649 | 668 |
| 5 | 754 | 304 | 658 | 531 | 592 | 543 |
| 6 | 821 | 734 | 617 | 606 | 512 | 649 |
| 7 | 877 | 559 | 653 | 600 | 563 | 641 |
| 8 | 804 | 650 | 765 | 741 | 685 | 727 |
| 9 | 756 | 810 | 657 | 632 | 539 | 672 |
| 10 | 918 | 511 | 402 | 377 | 659 | 542 |
| 11 | 461 | 622 | 725 | 667 | 381 | 555 |
| 12 | 507 | 637 | 606 | 589 | 480 | 561 |

TABLE 22b

Mean CD4 T cell count of UB-421 Treated Patients from Cohort 2 (25 mg/kg weekly)

| Visit | T 1-2-01 (PP) | T 1-2-02 (PP) | T 1-2-03 (PP) | T 1-2-04 (PP) | K 2-2-01 (PP) | K 2-2-02 (PP) | T 1-2-06 (PP) | Mean CD4 count |
|---|---|---|---|---|---|---|---|---|
| 1 | 310 | 466 | 756 | 430 | 806 | 618 | 425 | 518 |
| 2 | 458 | 548 | 766 | 600 | 811 | 672 | 558 | 620 |
| 3 | 533 | 581 | 569 | 610 | 701 | 662 | 445 | 580 |
| 4 | 459 | 591 | 699 | 409 | 902 | 648 | 629 | 602 |
| 5 | 392 | 608 | 670 | 506 | 665 | 776 | 539 | 581 |
| 6 | 396 | 462 | 640 | 532 | 999 | 646 | 128 | 471 |
| 7 | 365 | 388 | 552 | 598 | 756 | 653 | 548 | 536 |
| 8 | 397 | 606 | 451 | 557 | 666 | 697 | 662 | 566 |
| 9 | 415 | 466 | 481 | 653 | 690 | 619 | 483 | 535 |
| 10 | 287 | 470 | 584 | 281 | 784 | 550 | 493 | 465 |
| 11 | 379 | 404 | 521 | 375 | 771 | 470 | 548 | 481 |
| 12 | 345 | 367 | 729 | 393 | 705 | 534 | 511 | 492 |

TABLE 23

Design of UB-421 Treatment in Functional Cure

Potential Advantage of UB-421 over HAART drugs:

UB-421 blocks cell-to-cell transmission of HIV-1 viruses
UB-421 cross-links CDR2-like loop of CD4 and activates cells and thus the HIV-1 in latency
Goals:

To provide an effective protection, in addition to HAART, by blocking both cell-free and cell-to-cell transmission
To develop a functional cure strategy for HIV-infected patients either with no previous treatment or who are currently on stable antiretroviral therapy
Objectives:

To evaluate the potency of cycling treatment of UB-421 with continuous HAART in reducing the size of the latent viral reservoir and curing HIV-1-infected patients
Study type:

Interventional
Study Design:

Single group assessment; open-label
Assigned interventions:

Two cycles of 8 doses of 25 mg/kg UB-421 administered bi-weekly by intravenous infusion on days 1, 15, 29, 43, 57, 71, 85 and 99 for a period of 4 months followed by 2 months of background HAART alone will be provided to HIV-1 infected patients. Upon completion of one year study period, additional observational study will be conducted and conditioned by:
   Completion of 2 cycles of UB-421 in combination with HAART in one year study
   Significant reduction in viral reservoir
   CD4+ T-cell count >500/mm$^3$
In the additional observational study, the background HAART will be interrupted to evaluate:
   time to viremia >1,000 copies/ml
   time to meet criteria to restart HAART

The invention claimed is:

1. An antibody directed against a CD4 molecule, wherein the antibody comprises:
   a heavy chain variable region amino acid sequence comprising:
   CDR1 of SEQ ID NO: 1,
   CDR2 of SEQ ID NO: 2, and
   CDR3 of SEQ ID NO: 3; and
   a heavy chain constant region amino acid sequence of SEQ ID NO: 12;
   a light chain variable region amino acid sequence comprising:
   CDR1 of SEQ ID NO: 4,
   CDR2 of SEQ ID NO: 5, and
   CDR3 of SEQ ID NO: 6; and
   a light chain constant region amino acid sequence of SEQ ID NO: 14.

2. The antibody of claim 1, wherein the antibody;
   a) binds to an extracellular region of the CD4 molecule;
   b) competitively inhibits HIV entry into a cell;
   c) reduces HIV viral load in an HIV positive patient to less than 50 copies per milliliter of blood without viral load rebound, when the antibody is administered to the HIV positive patient in an amount sufficient to fully coat CD4+ cells; and
   d) activates a resting CD4+ cells upon crosslinking.

3. The antibody of claim 1, wherein the antibody binds to a region around domain 1 of the CD4 molecule.

4. The antibody of claim 1, wherein the antibody binds to a region around the CDR2 region in domain 1 of CD4.

5. The antibody of claim 1, wherein the antibody comprises an N-glycosylation site in the Fv region.

6. The antibody of claim 1, wherein the antibody comprises an N-glycosylation site in the heavy chain variable region.

7. The antibody of claim 1, wherein the antibody comprises an asparagine (Asn) residue located in a CDR of the heavy chain variable region that is bound to a sugar molecule.

8. The antibody of claim 1, wherein the heavy chain constant region amino acid sequence of SEQ ID NO: 12 has amino acids Tyr (Y), Thr (T), Glu (E), and His (H) at positions 135, 137, 139, and 180, respectively.

9. The antibody of claim 1, wherein the heavy chain constant region amino acid sequence of SEQ ID NO: 12 has amino acids Met (M), Ser (S), Thr (T), and His (H) at positions 135, 137, 139, and 180, respectively.

10. The antibody of claim 9, wherein the antibody comprises an N-glycosylation site in the heavy chain variable region.

11. The antibody of claim 10, wherein the N-glycosylation site is the asparagine (Asn) residue located in the CDR3 of the heavy chain variable region.

12. The antibody of claim 1, wherein the antibody is a monoclonal antibody.

13. The antibody of claim 1, wherein the antibody is a humanized monoclonal antibody.

14. The antibody of claim 1, wherein the antibody is a humanized monoclonal antibody comprising:
   a heavy chain variable region comprising the amino acid sequence of SEQ ID NO: 11; and
   a light chain variable region comprising the amino acid sequence of SEQ ID NO: 13.

15. The antibody of claim 1, wherein the antibody is a humanized monoclonal antibody comprising:
   a heavy chain comprising the amino acid sequence of SEQ ID NO: 10; and
   a light chain comprising the amino acid sequence of SEQ ID NO: 8.

16. The antibody of claim 1, wherein the antibody is a humanized monoclonal antibody comprising:
   a heavy chain comprising the amino acid sequence of SEQ ID NO: 9; and
   a light chain comprising the amino acid sequence of SEQ ID NO: 8.

17. The antibody of claim 1, wherein the antibody is a humanized monoclonal antibody comprising:
   a heavy chain comprising the amino acid sequence of SEQ ID NO: 7; and
   a light chain comprising the amino acid sequence of SEQ ID NO: 8.

18. The antibody of claim 1 having an absolute binding affinity (Kd) to membrane-bound CD4 on HPB-ALL cells between about $3.1 \times 10^{-11}$ M to about $8.1 \times 10^{-11}$ M.

19. The antibody of claim 1 bound to a CD4 molecule.

20. The antibody of claim 1 bound to a CD4 molecule on the surface of a T cell.

21. A composition comprising the antibody of claim 1.

22. A pharmaceutical composition comprising the antibody of claim 1 and a pharmaceutically acceptable carrier.

23. A pharmaceutical composition comprising the antibody of claim 1 in phosphate buffer saline (PBS), 20 mM glycine, and 0.05% (v/v) polysorbate 20.

24. A pharmaceutical composition comprising the antibody of claim 1 in phosphate buffer saline (PBS), 20 mM glycine, 0.05% (v/v) polysorbate 20, and 10 mM histidine.

25. A pharmaceutical composition comprising about 1.0 mg/mL to about 200.0 mg/mL of the antibody of claim 1 in phosphate buffer saline (PBS), 20 mM glycine, and 0.05% (v/v) polysorbate 20.

26. A pharmaceutical composition comprising about 1.0 mg/mL to about 200.0 mg/mL of the antibody of claim 1 in phosphate buffer saline (PBS), 20 mM glycine, 0.05% (v/v) polysorbate 20, and 10 mM histidine.

27. A pharmaceutical composition comprising about 10.0 mg/mL of the antibody of claim 1 in phosphate buffer saline (PBS), 20 mM glycine, and 0.05% (v/v) polysorbate 20.

28. A pharmaceutical composition comprising about 10.0 mg/mL of the antibody of claim 1 in phosphate buffer saline (PBS), 20 mM glycine, 0.05% (v/v) polysorbate 20, and 10 mM histidine.

29. A pharmaceutical composition comprising the antibody of claim 15 and a pharmaceutically acceptable carrier.

30. A pharmaceutical composition comprising the antibody of claim 17 and a pharmaceutically acceptable carrier.

31. A method for treating a subject exposed to HIV comprising:
administering to the subject a pharmacologically effective amount of the antibody of claim 1.

32. The method of claim 31, wherein the antibody is administered to the subject prior to exposure to HIV.

33. The method according to claim 31, wherein the antibody is administered to the subject after exposure to HIV.

34. The method according to claim 31, wherein the antibody is administered within 48 hours after exposure to HIV.

35. The method according to claim 31, wherein the antibody is administered to the subject at a dosage of at least about 5 mg/kg body weight.

36. The method according to claim 35, wherein the antibody is administered to the subject multiple times.

37. The method according to claim 36, wherein the antibody is administered to the subject in a weekly, bi-weekly, or monthly interval.

38. The method according to claim 36, further comprising a step of administering an antiviral agent to the subject.

39. The method according to claim 38, wherein the antiviral agent is a highly active antiretroviral therapy (HAART).

40. The method according to claim 39, wherein HAART comprises a nucleoside analogue reverse transcriptase inhibitor in combination with a protease inhibitor or a non-nucleoside reverse transcriptase inhibitor.

41. The method according to claim 39, wherein the antibody is administered concurrently with HAART.

42. The method according to claim 39, wherein the antibody and HAART are administered to the subject over the course of a cycle, wherein the cycle comprises:
i) administering the antibody to the subject for a first period of time followed by a treatment holiday for a second period of time; and
ii) administering HAART to the subject continuously during the first period of time and the second period of time in (i).

43. The method according to claim 39, wherein the antibody and HAART are administered to the subject over the course of a cycle, wherein the cycle comprises:
i) administering the antibody to the subject for a period of four months in a weekly, bi-weekly, or monthly interval followed by a two month treatment holiday; and
ii) administering HAART to the subject continuously during the six-month period in (i).

44. The method according to claim 42, wherein the subject is treated over the course of two cycles.

45. The method according to claim 43, wherein the subject is treated over the course of two cycles.

46. The method according to claim 39, wherein the antibody is administered at a time that is not concurrent with HAART.

47. The method according to claim 39, wherein the antibody and HAART are administered to the subject over the course of a cycle, wherein the cycle comprises:
i) administering the antibody to the subject for a first period of time followed by a treatment holiday for a second period of time; and
ii) administering HAART to the subject during the second period of time and not during the first period of time.

48. The method according to claim 47, wherein the antibody is administered in regular intervals during the first time period.

49. The method according to claim 47, wherein the antibody is administered in weekly, bi-weekly, or monthly intervals during the first time period.

50. A method for treating a subject with HIV infection, comprising administering to the subject a treatment regimen comprising:
a) a pharmacologically effective amount of the antibody of claim 1; and
b) a highly active antiretroviral therapy (HAART).

51. The method of claim 50, wherein the antibody is administered to the subject at a dosage of at least about 5 mg/kg body weight.

52. The method according to claim 50, wherein the antibody and HAART are administered to the subject over the course of a cycle, wherein the cycle comprises:
i) administering the antibody to the subject for a first period of time followed by a treatment holiday for a second period of time; and
ii) administering HAART to the subject continuously during the first period of time and the second period of time in (i).

53. The method according to claim 50, wherein the antibody and HAART are administered to the subject over the course of a cycle, wherein the cycle comprises:
i) administering the antibody to the subject for a period of four months in a weekly, bi-weekly, or monthly interval followed by a two-month treatment holiday; and
ii) administering HAART to the subject continuously during the six-month period in (i).

54. The method according to claim 52, wherein the subject is treated over the course of two or more cycles.

55. The method according to claim 53, wherein the subject is treated over the course of two or more cycles.

56. The method according to claim 53, wherein the antibody and HAART are administered to the subject over the course of a cycle, wherein the cycle comprises:
i) administering the antibody to the subject for a period of four months in a weekly, bi-weekly, or monthly interval followed by a two-month treatment holiday; and
ii) administering HAART to the subject continuously during the six-month period in (i).

57. The method according to claim 50, wherein the antibody in (a) is administered at a time that is not concurrent with HAART in (b).

58. The method according to claim 50, wherein the antibody in (a) and HAART in (b) are administered to the subject over the course of a cycle, wherein the cycle comprises:
   i) administering the antibody to the subject for a first period of time followed by a treatment holiday for a second period of time; and
   ii) administering HAART to the subject during the second period of time and not during the first period of time.

59. The method according to claim 58, wherein the antibody is administered in regular intervals during the first time period.

60. The method according to claim 58, wherein the antibody is administered in weekly, bi-weekly, or monthly intervals during the first time period.

61. A method for inhibiting HIV entry into a CD4+ cell, comprising exposing the antibody of claim 1 to the cell.

62. A method for inhibiting gp120 binding to a CD4+ cell, comprising exposing the antibody of claim 1 to the cell.

63. A method for activating a resting CD4+ T cell upon crosslinking, comprising exposing the antibody of claim 1 to the cell.

64. A method for activating a latent reservoir of HIV in a resting T cell upon crosslinking, comprising
exposing the antibody of claim 1 to the cell.

65. A method for reducing latent HIV reservoirs in a sample of cells infected with HIV, comprising
   a) exposing the antibody of claim 1 to the sample of cells; and
   b) exposing HAART to the sample of cells.

* * * * *

SEQUENCE LISTING

<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: Murine Antibody
<220> FEATURE:
<221> NAME/KEY: DOMAIN
<222> LOCATION: (1)..(5)
<223> OTHER INFORMATION: CDR1 of heavy chain of murine antibody B4

```
<400> SEQUENCE: 1

Asp Tyr Val Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Murine Antibody
<220> FEATURE:
<221> NAME/KEY: DOMAIN
<222> LOCATION: (1)..(17)
<223> OTHER INFORMATION: CDR2 of heavy chain of murine antibody B4

<400> SEQUENCE: 2

Glu Ile Tyr Pro Gly Ser Gly Ser Ala Tyr Ser Asn Ala Lys Phe Lys
1               5                   10                  15

Asp

<210> SEQ ID NO 3
<211> LENGTH: 9
<212> TYPE: PRT
<213> ORGANISM: Artificial Sequence
<220> FEATURE:
<223> OTHER INFORMATION: Murine Antibody
<220> FEATURE:
<221> NAME/KEY: DOMAIN
<222> LOCATION: (1)..(9)
<223> OTHER INFORMATION: CDR3 of heavy chain of murie antibody B4

<400> SEQUENCE: 3

Arg Gly Asn Gly Thr Gly Phe Ala Tyr
1               5

<210> SEQ ID NO 4
<211> LENGTH: 15
<212> TYPE: PRT
<213> ORGANISM: Artificial Sequence
<220> FEATURE:
<223> OTHER INFORMATION: Murine Antibody
<220> FEATURE:
<221> NAME/KEY: DOMAIN
<222> LOCATION: (1)..(15)
<223> OTHER INFORMATION: CDR1 of light chain of murine antibody B4

<400> SEQUENCE: 4

Lys Ala Gly Gln Ser Val Asp Tyr Asp Gly Asp Ser Tyr Met Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Murine Antibody
<220> FEATURE:
<221> NAME/KEY: DOMAIN
<222> LOCATION: (1)..(7)
<223> OTHER INFORMATION: CDR2 of light chain of murine antibody B4

<400> SEQUENCE: 5

Val Ala Ser Asn Leu Glu Ser
1               5
```

```
<210> SEQ ID NO 6
<211> LENGTH: 9
<212> TYPE: PRT
<213> ORGANISM: Artificial Sequence
<220> FEATURE:
<223> OTHER INFORMATION: Murine Antibody
<220> FEATURE:
<221> NAME/KEY: DOMAIN
<222> LOCATION: (1)..(9)
<223> OTHER INFORMATION: CDR3 of light chain of murine antibody B4

<400> SEQUENCE: 6

Gln Gln Ser Tyr Lys Asp Pro Leu Thr
1               5

<210> SEQ ID NO 7
<211> LENGTH: 448
<212> TYPE: PRT
<213> ORGANISM: Artificial Sequence
<220> FEATURE:
<223> OTHER INFORMATION: Humanized Antibody
<220> FEATURE:
<221> NAME/KEY: DOMAIN
<222> LOCATION: (1)..(448)
<223> OTHER INFORMATION: Heavy Chain of deimmunized human antibody B4
      [UB421] with identical CDRs1, 2 and 3 derived from the
      corresponding CDRs1, 2 and 3 from the heavy chain sequence of the
      parental murine B4 antibody

<400> SEQUENCE: 7

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Val Ile His Trp Val Lys Gln Ala Thr Gly Gln Gly Leu Glu Trp Ile
        35                  40                  45

Gly Glu Ile Tyr Pro Gly Ser Gly Ser Ala Tyr Ser Asn Ala Lys Phe
    50                  55                  60

Lys Asp Arg Val Thr Met Thr Ala Asp Lys Ser Ser Asn Thr Ala Tyr
65                  70                  75                  80

Met Glu Leu Ser Ser Leu Thr Ser Asp Asp Thr Ala Val Tyr Phe Cys
                85                  90                  95

Ala Arg Arg Gly Asn Gly Thr Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240
```

-continued

```
Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Gln Tyr His Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 8
<211> LENGTH: 218
<212> TYPE: PRT
<213> ORGANISM: Artificial Sequence
<220> FEATURE:
<223> OTHER INFORMATION: Humanized Antibody
<220> FEATURE:
<221> NAME/KEY: DOMAIN
<222> LOCATION: (1)..(218)
<223> OTHER INFORMATION: Light Chain of deimmuized human antibody B4
      [UB421] with identical CDRs1, 2 and 3 derived from the
      corresponding CDRs1, 2,and 3 from the light chain sequence of the
      parental murine B4 antibody

<400> SEQUENCE: 8

```
Asp Ile Val Leu Thr Gln Ser Pro Ala Ser Leu Ala Val Ser Leu Gly
1               5                   10                  15

Gln Arg Ala Thr Ile Thr Cys Lys Ala Gly Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Val Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Asn Asp Ala Ala Thr Tyr Tyr Cys Gln Gln Ser Tyr
                85                  90                  95

Lys Asp Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Leu Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 9
<211> LENGTH: 448
<212> TYPE: PRT
<213> ORGANISM: Artificial Sequence
<220> FEATURE:
<223> OTHER INFORMATION: Humanized Antibody
<220> FEATURE:
<221> NAME/KEY: DOMAIN
<222> LOCATION: (1)..(448)
<223> OTHER INFORMATION: Heavy Chain of the deimmunized human antibody
      B4 [UB421] with M253Y/S255T/T257E substitutions

<400> SEQUENCE: 9

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Val Ile His Trp Val Lys Gln Ala Thr Gly Gln Gly Leu Glu Trp Ile
            35                  40                  45

Gly Glu Ile Tyr Pro Gly Ser Gly Ser Ala Tyr Ser Asn Ala Lys Phe
    50                  55                  60

Lys Asp Arg Val Thr Met Thr Ala Asp Lys Ser Ser Asn Thr Ala Tyr
65                  70                  75                  80

Met Glu Leu Ser Ser Leu Thr Ser Asp Asp Thr Ala Val Tyr Phe Cys
                85                  90                  95

Ala Arg Arg Gly Asn Gly Thr Gly Phe Ala Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Tyr Ile Thr Arg
                245                 250                 255

Glu Pro Glu Val Thr Cys Val Val Asp Val Ser His Glu Asp Pro
        260                 265                 270

Glu Val Lys Phe Asn Trp Tyr Val Asp Gly Val Glu Val His Asn Ala
            275                 280                 285

Lys Thr Lys Pro Arg Glu Glu Gln Tyr His Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 10
<211> LENGTH: 448
<212> TYPE: PRT
<213> ORGANISM: Artificial Sequence
<220> FEATURE:
<223> OTHER INFORMATION: Humanized Antibody
<220> FEATURE:
<221> NAME/KEY: SITE
<222> LOCATION: (253)..(253)
<223> OTHER INFORMATION: M or Y
<220> FEATURE:
<221> NAME/KEY: SITE
<222> LOCATION: (255)..(255)
<223> OTHER INFORMATION: S or T
<220> FEATURE:
<221> NAME/KEY: SITE
<222> LOCATION: (257)..(257)
<223> OTHER INFORMATION: T or E
<220> FEATURE:
<221> NAME/KEY: SITE
<222> LOCATION: (298)..(298)
<223> OTHER INFORMATION: N or H

<400> SEQUENCE: 10

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Val Ile His Trp Val Lys Gln Ala Thr Gly Gln Gly Leu Glu Trp Ile
            35                  40                  45

Gly Glu Ile Tyr Pro Gly Ser Gly Ser Ala Tyr Ser Asn Ala Lys Phe
        50                  55                  60

Lys Asp Arg Val Thr Met Thr Ala Asp Lys Ser Ser Asn Thr Ala Tyr
65                  70                  75                  80
```

```
Met Glu Leu Ser Ser Leu Thr Ser Asp Asp Thr Ala Val Tyr Phe Cys
             85                  90                  95

Ala Arg Arg Gly Asn Gly Thr Gly Phe Ala Tyr Trp Gly Gln Gly Thr
        100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Xaa Ile Xaa Arg
                245                 250                 255

Xaa Pro Glu Val Thr Cys Val Val Asp Val Ser His Glu Asp Pro
                260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Xaa Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
        435                 440                 445

<210> SEQ ID NO 11
<211> LENGTH: 118
<212> TYPE: PRT
<213> ORGANISM: Artificial Sequence
<220> FEATURE:
<223> OTHER INFORMATION: Humanized Antibody
```

<400> SEQUENCE: 11

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Val Ile His Trp Val Lys Gln Ala Thr Gly Gln Gly Leu Glu Trp Ile
        35                  40                  45

Gly Glu Ile Tyr Pro Gly Ser Gly Ser Ala Tyr Ser Asn Ala Lys Phe
    50                  55                  60

Lys Asp Arg Val Thr Met Thr Ala Asp Lys Ser Ser Asn Thr Ala Tyr
65                  70                  75                  80

Met Glu Leu Ser Ser Leu Thr Ser Asp Asp Thr Ala Val Tyr Phe Cys
                85                  90                  95

Ala Arg Arg Gly Asn Gly Thr Gly Phe Ala Tyr Trp Gly Gln Gly Thr
            100                 105                 110

Leu Val Thr Val Ser Ser
        115

<210> SEQ ID NO 12
<211> LENGTH: 330
<212> TYPE: PRT
<213> ORGANISM: Artificial Sequence
<220> FEATURE:
<223> OTHER INFORMATION: Humanized Antibody
<220> FEATURE:
<221> NAME/KEY: SITE
<222> LOCATION: (135)..(135)
<223> OTHER INFORMATION: M or Y
<220> FEATURE:
<221> NAME/KEY: SITE
<222> LOCATION: (137)..(137)
<223> OTHER INFORMATION: S or T
<220> FEATURE:
<221> NAME/KEY: SITE
<222> LOCATION: (139)..(139)
<223> OTHER INFORMATION: T or E
<220> FEATURE:
<221> NAME/KEY: SITE
<222> LOCATION: (180)..(180)
<223> OTHER INFORMATION: N or H

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Xaa Ile Xaa Arg Xaa Pro Glu Val Thr Cys
    130                 135                 140

-continued

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Xaa Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 13
<211> LENGTH: 111
<212> TYPE: PRT
<213> ORGANISM: Artificial Sequence
<220> FEATURE:
<223> OTHER INFORMATION: Humanized Antibody

<400> SEQUENCE: 13

Asp Ile Val Leu Thr Gln Ser Pro Ala Ser Leu Ala Val Ser Leu Gly
1               5                   10                  15

Gln Arg Ala Thr Ile Thr Cys Lys Ala Gly Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Val Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Asn Asp Ala Ala Thr Tyr Tyr Cys Gln Gln Ser Tyr
                85                  90                  95

Lys Asp Pro Leu Thr Phe Gly Gln Gly Thr Lys Leu Glu Ile Lys
            100                 105                 110

<210> SEQ ID NO 14
<211> LENGTH: 107
<212> TYPE: PRT
<213> ORGANISM: Artificial Sequence
<220> FEATURE:
<223> OTHER INFORMATION: Humanized Antibody -continued

```
<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105
```